(12) United States Patent
Zhang et al.

(10) Patent No.: US 12,559,537 B2
(45) Date of Patent: *Feb. 24, 2026

(54) NUCLEIC ACID ENCODING NKP30 RECEPTOR TARGETED THERAPEUTICS

(71) Applicant: THE TRUSTEES OF DARTMOUTH COLLEGE, Hanover, NH (US)

(72) Inventors: Tong Zhang, Lebanon, NH (US); Charles L. Sentman, Grantham, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/513,960

(22) Filed: Nov. 20, 2023

(65) Prior Publication Data

US 2024/0200029 A1     Jun. 20, 2024

Related U.S. Application Data

(62) Division of application No. 16/882,800, filed on May 26, 2020, now Pat. No. 11,872,248, which is a
(Continued)

(51) Int. Cl.
*C12N 15/62* (2006.01)
*A61K 40/11* (2025.01)
(Continued)

(52) U.S. Cl.
CPC ........ *C07K 14/70503* (2013.01); *A61K 40/11* (2025.01); *A61K 40/31* (2025.01);
(Continued)

(58) Field of Classification Search
None
See application file for complete search history.

(56) References Cited

U.S. PATENT DOCUMENTS

| 5,415,874 A | 5/1995 | Bender et al. |
| 5,552,300 A | 9/1996 | Makrides et al. |
| | (Continued) | |

FOREIGN PATENT DOCUMENTS

| DE | 4408999 | 9/1995 |
| DE | 19540515 | 6/1997 |
| | (Continued) | |

OTHER PUBLICATIONS

Pule' et al., A Chimeric T Cell Antigen Receptor That Augments Cytokine Release and Supports Clonal Expansion of Primary Human T Cells, Mol. Ther. 12(5):934-941, Nov. 2005.*
(Continued)

*Primary Examiner* — Claire Kaufman
(74) *Attorney, Agent, or Firm* — Robin L. Teskin; Baker, Donelson, Bearman, Caldwell & Berkowitz PC

(57) ABSTRACT

The invention is directed to T cells and other cells that express chimeric NK-p30 receptors ("chimeric NKp30 T cells"), methods of making and using chimeric NKp30 T cells, and methods of using these chimeric NKp30 T cells to address diseases and disorders. In one aspect, the disclosure broadly relates to chimeric NKp30 T cells, isolated populations thereof, and compositions comprising the same. In another aspect, said chimeric NKp30 T cells are further designed to express a functional non-TCR receptor. The disclosure also pertains to methods of making said chimeric NKp30 T cells, and methods of reducing or ameliorating, or preventing or treating, diseases and disorders using said chimeric NKp30 T cells, populations thereof, or compositions comprising the same.

11 Claims, 23 Drawing Sheets

Specification includes a Sequence Listing.

EX     TM     CYP wtNKp30

NKp30-CD3ζ

NKp30-CD28-CD3ζ

EX: extracellular domain
TM: transmembrane domain
CYP: cytoplasmic domain

Related U.S. Application Data division of application No. 15/830,605, filed on Dec. 4, 2017, now Pat. No. 10,682,378, which is a division of application No. 14/342,060, filed as application No. PCT/US2012/053511 on Aug. 31, 2012, now Pat. No. 9,833,476.

(60) Provisional application No. 61/529,410, filed on Aug. 31, 2011.

(51) Int. Cl.

| | |
|---|---|
| *A61K 40/31* | (2025.01) |
| *A61K 40/42* | (2025.01) |
| *C07K 14/705* | (2006.01) |
| *C07K 16/28* | (2006.01) |
| *C12N 5/0783* | (2010.01) |
| *C12N 15/00* | (2006.01) |

(52) U.S. Cl.
CPC .... *A61K 40/4202* (2025.01); *C07K 14/70521* (2013.01); *C07K 14/70575* (2013.01); *C07K 14/70578* (2013.01); *C07K 14/70596* (2013.01); *C07K 16/2803* (2013.01); *C12N 5/0636* (2013.01); *C12N 15/00* (2013.01); *C12N 15/62* (2013.01); *A61K 2239/48* (2023.05); *C07K 2319/00* (2013.01); *C07K 2319/03* (2013.01); *C12N 2800/22* (2013.01)

(56) References Cited

U.S. PATENT DOCUMENTS

| | | | |
|---|---|---|---|
| 5,667,967 | A | 9/1997 | Steinman et al. |
| 5,686,281 | A | 11/1997 | Roberts |
| 5,830,755 | A | 11/1998 | Nishimura et al. |
| 5,851,828 | A | 12/1998 | Seed et al. |
| 6,103,521 | A | 8/2000 | Capon et al. |
| 6,133,433 | A | 10/2000 | Pande et al. |
| 6,190,656 | B1 | 2/2001 | Lane |
| 6,242,567 | B1 | 6/2001 | Pande et al. |
| 6,284,240 | B1 | 9/2001 | Seed et al. |
| 6,407,221 | B1 | 6/2002 | Capon et al. |
| 6,410,319 | B1 | 6/2002 | Raubitschek et al. |
| 6,464,978 | B1 | 10/2002 | Brostoff et al. |
| 6,753,162 | B1 | 6/2004 | Seed et al. |
| 6,770,749 | B2 | 8/2004 | Ellenhorn et al. |
| 6,984,382 | B1 | 1/2006 | Groner et al. |
| 7,049,136 | B2 | 5/2006 | Seed et al. |
| 7,052,906 | B1 | 5/2006 | Lawson et al. |
| 7,070,995 | B2 | 7/2006 | Jensen |
| 7,094,599 | B2 | 8/2006 | Seed et al. |
| 7,435,596 | B2 | 10/2008 | Campana et al. |
| 7,446,179 | B2 | 11/2008 | Jensen et al. |
| 7,446,190 | B2 | 11/2008 | Sadelain et al. |
| 7,456,263 | B2 | 11/2008 | Sherman et al. |
| 7,514,537 | B2 | 4/2009 | Jensen |
| 7,569,357 | B2 | 8/2009 | Kranz et al. |
| 7,608,410 | B2 | 10/2009 | Dunn et al. |
| 7,618,817 | B2 | 11/2009 | Campbell |
| 7,655,461 | B2 | 2/2010 | Finn et al. |
| 7,763,243 | B2 | 7/2010 | Lum et al. |
| 7,820,174 | B2 | 10/2010 | Wang et al. |
| 7,994,298 | B2 | 8/2011 | Zhang et al. |
| 8,026,097 | B2 | 9/2011 | Campana et al. |
| 8,252,914 | B2 | 8/2012 | Zhang et al. |
| 8,283,446 | B2 | 10/2012 | Jakobsen et al. |
| 8,399,645 | B2 | 3/2013 | Campana et al. |
| 8,465,743 | B2 | 6/2013 | Rosenberg et al. |
| 8,519,100 | B2 | 8/2013 | Jakobsen et al. |
| 8,835,617 | B2 | 9/2014 | Luban et al. |
| 8,945,868 | B2 | 2/2015 | Collingwood et al. |
| 8,956,828 | B2 | 2/2015 | Bonini et al. |
| 9,051,391 | B2 | 6/2015 | Mineno et al. |
| 2001/0007152 | A1 | 7/2001 | Sherman et al. |

| | | | |
|---|---|---|---|
| 2002/0045241 | A1 | 4/2002 | Schendel |
| 2002/0137697 | A1 | 9/2002 | Eshhar et al. |
| 2003/0060444 | A1 | 3/2003 | Finney et al. |
| 2003/0077249 | A1 | 4/2003 | Bebbington et al. |
| 2003/0082719 | A1 | 5/2003 | Schumacher et al. |
| 2003/0093818 | A1 | 5/2003 | Belmont et al. |
| 2003/0219463 | A1 | 11/2003 | Falkenburg et al. |
| 2004/0038886 | A1 | 2/2004 | Finney et al. |
| 2004/0115198 | A1 | 6/2004 | Spies et al. |
| 2004/0259196 | A1 | 12/2004 | Zipori et al. |
| 2005/0048055 | A1 | 3/2005 | Newell et al. |
| 2005/0113564 | A1 | 5/2005 | Campana et al. |
| 2005/0129671 | A1 | 6/2005 | Cooper et al. |
| 2005/0238626 | A1 | 10/2005 | Yang et al. |
| 2006/0093605 | A1 | 5/2006 | Campana et al. |
| 2006/0166314 | A1 | 7/2006 | Voss et al. |
| 2006/0247420 | A1 | 11/2006 | Coukos et al. |
| 2006/0263334 | A1 | 11/2006 | Finn et al. |
| 2006/0269529 | A1 | 11/2006 | Niederman et al. |
| 2007/0066802 | A1 | 3/2007 | Geiger |
| 2007/0077241 | A1 | 4/2007 | Spies et al. |
| 2007/0116690 | A1 | 5/2007 | Yang et al. |
| 2008/0153029 | A1 | 6/2008 | Henzel et al. |
| 2008/0199424 | A1 | 8/2008 | Yang et al. |
| 2008/0292549 | A1 | 11/2008 | Jakobsen et al. |
| 2008/0292602 | A1 | 11/2008 | Jakobsen et al. |
| 2009/0053184 | A1 | 2/2009 | Morgan et al. |
| 2009/0202501 | A1 | 8/2009 | Zhang et al. |
| 2009/0226404 | A1 | 9/2009 | Schuler et al. |
| 2009/0304657 | A1 | 12/2009 | Morgan et al. |
| 2009/0324566 | A1 | 12/2009 | Shiku et al. |
| 2010/0009863 | A1 | 1/2010 | Himmler et al. |
| 2010/0015113 | A1 | 1/2010 | Restifo et al. |
| 2010/0029749 | A1 | 2/2010 | Zhang et al. |
| 2010/0055117 | A1 | 3/2010 | Krackhardt et al. |
| 2010/0104556 | A1 | 4/2010 | Blankenstein et al. |
| 2010/0105136 | A1 | 4/2010 | Carter et al. |
| 2010/0135974 | A1 | 6/2010 | Eshhar et al. |
| 2010/0143315 | A1 | 6/2010 | Voss et al. |
| 2010/0178276 | A1 | 7/2010 | Sadelain et al. |
| 2010/0189728 | A1 | 7/2010 | Schendel et al. |
| 2010/0273213 | A1 | 10/2010 | Mineno et al. |
| 2011/0158957 | A1 | 6/2011 | Bonini et al. |
| 2011/0213288 | A1 | 9/2011 | Choi et al. |
| 2012/0015434 | A1 | 1/2012 | Campana et al. |
| 2012/0252742 | A1 | 10/2012 | Kranz et al. |
| 2012/0294857 | A1 | 11/2012 | Sentman et al. |
| 2012/0302466 | A1 | 11/2012 | Sentman et al. |
| 2013/0011375 | A1 | 1/2013 | Chen |
| 2013/0216509 | A1 | 8/2013 | Campana et al. |
| 2013/0266551 | A1 | 10/2013 | Campana et al. |
| 2013/0323214 | A1 | 12/2013 | Gottschalk et al. |
| 2014/0004132 | A1 | 1/2014 | Brenner et al. |
| 2014/0148354 | A1 | 5/2014 | Campana et al. |
| 2014/0328812 | A1 | 11/2014 | Campana et al. |
| 2015/0139943 | A1 | 5/2015 | Campana et al. |
| 2016/0194375 | A1 | 7/2016 | Kitchen et al. |

FOREIGN PATENT DOCUMENTS

| | | |
|---|---|---|
| DE | 10259713 | 8/2004 |
| EP | 0340793 | 8/1995 |
| EP | 0499555 | 5/2000 |
| EP | 0574512 | 5/2003 |
| EP | 1226244 | 7/2004 |
| EP | 0871495 | 6/2005 |
| EP | 1075517 | 7/2006 |
| EP | 1932537 | 6/2008 |
| EP | 1765860 | 10/2008 |
| EP | 2186825 | 5/2010 |
| EP | 1791865 | 7/2010 |
| JP | H05176760 | 7/1993 |
| JP | H11243955 | 9/1999 |
| JP | 2008523783 | 7/2008 |
| JP | 2011512786 | 4/2011 |
| WO | WO 1991018019 | 11/1991 |
| WO | WO 1992015322 | 9/1992 |
| WO | WO 1994024282 | 10/1994 |
| WO | WO 1996015238 | 5/1996 |

(56)        References Cited

FOREIGN PATENT DOCUMENTS

| | | |
|---|---|---|
| WO | WO 1996013584 | 9/1996 |
| WO | WO 1998018809 | 7/1998 |
| WO | WO 1998041613 | 9/1998 |
| WO | WO 2000031239 | 2/2000 |
| WO | WO 2000014257 | 3/2000 |
| WO | WO 2001092291 | 6/2001 |
| WO | WO 2004056845 | 8/2004 |
| WO | WO 2006036445 | 4/2006 |
| WO | WO 2006103429 | 5/2006 |
| WO | WO 2006060878 | 6/2006 |
| WO | WO 2008153029 | 12/2008 |
| WO | WO 2009059804 | 5/2009 |
| WO | WO 2009091826 | 7/2009 |
| WO | WO 2010012829 | 4/2010 |
| WO | WO 2010025177 | 4/2010 |
| WO | WO 2010058023 | 5/2010 |
| WO | WO 2010088160 | 5/2010 |
| WO | WO 2010037395 | 8/2010 |
| WO | WO 2010107400 | 9/2010 |
| WO | WO 2011059836 | 5/2011 |
| WO | WO 2011070443 | 6/2011 |
| WO | WO 2012050374 | 4/2012 |
| WO | WO 2013166051 | 11/2013 |

OTHER PUBLICATIONS

Schleinitz, Nicolas, et al. "Expression of the CD85j (leukocyte Ig-like receptor 1, Ig-like transcript 2) receptor for class I major histocompatibility complex molecules in idiopathic inflammatory myopathies." Arthritis & Rheumatism: Official Journal of the American College of Rheumatology 58.10 (2008): 3216-3223.

Kieback, Elisa, and Wolfgang Uckert. "Enhanced T cell receptor gene therapy for cancer." Expert opinion on biological therapy 10.5 (2010): 749-762.

Motmans, Kris, Jef Raus, and Caroline Vandevyver. "Enhancing the tumor-specifity of human T cells by the expression of chimeric immunoglobulin/T cell receptor genes." Immunotechnology 4.2 (1996): 303-304.

von Laer, D., C. Baum, and U. Protzer. "Antiviral gene therapy." Antiviral Strategies (2009): 265-297.

Walker, B. D. "Immunotherapy with immune reconstitution and HIV. 2001; 1-40." Retrieved from aids-chushi. or. jp on Oct. 13 (2016); Learning materials in Chuo Shikoku AIDS Center Department Feb. 1, 2001.

Zhu, Y., et al. "Screening of Jurkat cells expressing FLT1-CAR and their chemotaxis to VEGF." Chinese J Cancer Biother 20.5 (2013): 559-64. [English Abstract Only].

Kudo, Ko, et al. "T lymphocytes expressing a CD16 signaling receptor exert antibody-dependent cancer cell killing." Cancer research 74.1 (2014): 93-103.

Gilman, Alfred and Goodman, Louis S. "Goodman and Gilman's the pharmacological basis of therapeutics. Twelfth." (2011): pp. 52-76.

Pfeifer A, Verma IM. Gene therapy: promises and problems. Annual review of genomics and human genetics. Sep. 2001;2(1):177-211.

Kelland LR. "Of mice and men": values and liabilities of the athymic nude mouse model in anticancer drug development. European journal of cancer. Apr. 1, 2004;40(6):827-36.

Vile RG, Russell SJ, Lemoine NR. Cancer gene therapy: hard lessons and new courses. Gene therapy. Jan. 2000;7(1):2-8.

Verma IM, Naldini L, Kafri T, Miyoshi H, Takahashi M, Blömer U, Somia N, Wang L, Gage FH. Gene therapy: promises, problems and prospects. InGenes and resistance to disease 2000 (pp. 147-157). Springer Berlin Heidelberg.

Alajez NM 'MHC-Unrestricted MUC1-Specific T Cell Receptor for Cancer Immunotherapy/Gene Therapy' (2003) MHC-Unrestricted MUC1-Specific T Cell Receptor for Cancer Immunotherapy/Gene Therapy.Doctoral Dissertation, University of Pittsburgh.

Alajez NM, et al. "Therapeutic potential of a tumor-specific, MHC-unrestricted T-cell receptor expressed on effector cells of the innate and the adaptive immune system through bone marrow transduction and immune reconstitution," Blood. Jun. 15, 2005;105(12):4583-9. Epub Mar. 3, 2005.

Alli R, et al. "Retrogenic Modeling of Experimental Allergic Encephalomyelitis Associates T Cell Frequency but Not TCR Functional Affinity with Pathogenicity," J Immunol. Jul. 1, 2008;181(1):136-45.

Almåsbak H, et al. "Non-MHC-dependent redirected T cells against tumor cells," Methods Mol Biol. 2010;629:453-93. doi: 10.1007/978-1-60761-657-3_28.

Beecham EJ, et al. "Dynamics of tumor cell killing by human T lymphocytes armed with an anti-carcinoembryonic antigen chimeric immunoglobulin T-cell receptor," J Immunother. May-Jun. 2000 23(3):332-43.

Bell LM, et al. "Cytoplasmic tail deletion of T cell receptor (TCR) beta-chain results in its surface expression as glycosylphosphatidylinositol-anchored polypeptide on mature T cells in the absence of TCR-alpha," J Biol Chem. Sep. 9, 1994;269(36):22758-63.

Berry LJ, et al. "Adoptive immunotherapy for cancer: the next generation of gene-engineered immune cells," Tissue Antigens. Oct. 2009;74(4):277-89. doi: 10.1111/j.1399-0039.2009.01336.x.

Bialer G, et al. "Selected murine residues endow human TCR with enhanced tumor recognition," J Immunol. Jun. 1, 2010;184(11):6232-41. doi: 10.4049/jimmunol.0902047. Epub Apr. 28, 2010.

Billadeau DD, et al. "NKG2D-DAP10 triggers human NK cell-mediated killing via a Syk-independent regulatory pathway," Nat Immunol. Jun. 2003;4(6):557-64. Epub May 11, 2003.

Bridgeman JS, et al. "The optimal antigen response of chimeric antigen receptors harboring the CD3zeta transmembrane domain is dependent upon incorporation of the receptor into the endogenous TCR/CD3 complex," J Immunol. Jun. 15, 2010;184(12):6938-49. doi: 10.4049/jimmunol.0901766. Epub May 17, 2010.

Chmielewski M, et al. "CD28 cosignalling does not affect the activation threshold in a chimeric antigen receptor-redirected T-cell attack," Gene Ther. Jan. 2011;18(1):62-72. doi: 10.1038/gt.2010. 127. Epub Oct. 14, 2010.

Cohen CJ, et al. "Enhanced Antitumor Activity of Murine-Human Hybrid T-Cell Receptor (TCR) in Human Lymphocytes Is Associated with Improved Pairing and TCR/CD3 Stability," Cancer Res. Sep. 1, 2006;66(17):8878-86.

Cooper LJ, et al. "Manufacturing of gene-modified cytotoxic T lymphocytes for autologous cellular therapy for lymphoma," Cytotherapy. 2006;8(2):105-17.

Dall P, et al. "In vivo cervical cancer growth inhibition by genetically engineered cytotoxic T cell," Cancer Immunol Immunother. Jan. 2005;54(1):51-60.

Danielian S, et al. "Both T cell receptor (TcR)-CD3 complex and CD2 increase the tyrosine kinase activity of p56lck. CD2 can mediate TcR-CD3-independent and CD45-dependent activation of p56lck," Eur J Immunol. Nov. 1992;22(11):2915-21.

Donnadieu et al., "Reconstitution of CD3 zeta coupling to calcium mobilization via genetic complementation," J Biol. Chem. 269:32828-34 (1994).

Dennehy KM, et al. "Mitogenic CD28 Signals Require the Exchange Factor Vav1 to Enhance TCR Signaling at the SLP-76-Vav-Itk Signalosome," J Immunol. Feb. 1, 2007;178(3):1363-71.

D'Oro U, et al. "Regulation of constitutive TCR internalization by the zeta-chain," J Immunol. Dec. 1, 2002;169(11):6269-78.

Duplay P, et al. "An activated epidermal growth factor receptor/Lck chimera restores early T cell receptor-mediated calcium response in a CD45-deficient T cell line," J Biol Chem. Jul. 26, 1996;271(30):17896-902.

Eshhar Z, et al. "Specific activation and targeting of cytotoxic lymphocytes through chimeric single chains consisting of antibody-binding domains and the gamma or zeta subunits of the immunoglobulin and T-cell receptors," Proc Natl Acad Sci U S A. Jan. 15, 1993;90(2):720-4.

Favier B, et al. "TCR dynamics on the surface of living T cells," Int Immunol. Dec. 2001;13(12):1525-32.

Finney HM, et al. "Chimeric receptors providing both primary and costimulatory signaling in T cells from a single gene product," J Immunol. Sep. 15, 1998;161(6):2791-7.

(56)                    References Cited

OTHER PUBLICATIONS

Frankel TL, et al. "Both CD4 and CD8 T Cells Mediate Equally Effective in Vivo Tumor Treatment When Engineered with a Highly Avid TCR Targeting Tyrosinase," J Immunol. Jun. 1, 2010;184(11):5988-98. doi: 10.4049/jimmunol.1000189. Epub Apr. 28, 2010.

Fujihashi K, et al. "gamma/delta T cell-deficient mice have impaired mucosal immunoglobulin A response," J Exp Med. Apr. 1, 1996;183(4):1929-35.

Garrity D, et al. "The activating NKG2D receptor assembles in the membrane with two signaling dimers into a hexameric structure," Proc Natl Acad Sci U S A. May 24, 2005; 102(21):7641-6. Epub May 13, 2005.

Geiger TL, et al. "The TCR zeta-chain immunoreceptor tyrosine-based activation motifs are sufficient for the activation and differentiation of primary T lymphocytes," J Immunol. May 15, 1999;162(10):5931-9.

Geiger TL, et al. "Integrated src kinase and costimulatory activity enhances signal transduction through single-chain chimeric receptors in T lymphocytes," Blood. Oct. 15, 2001;98(8):2364-71.

Gouaillard C, et al. "Evolution of T cell receptor (TCR) α β heterodimer assembly with the CD3 complex," Eur J Immunol. Dec. 2001;31(12):3798-805.

Hawkins RE, et al. "Development of adoptive cell therapy for cancer: a clinical perspective," Hum Gene Ther. Jun. 2010;21(6):665-72. doi: 10.1089/hum.2010.086.

Haynes NM, et al. "Redirecting Mouse CTL Against Colon Carcinoma: Superior Signaling Efficacy of Single-Chain Variable Domain Chimeras Containing TCR-ξ vs FcεRI-γ," J Immunol. Jan. 1, 2001;166(1):182-7.

Horng T, et al. "NKG2D signaling is coupled to the interleukin 15 receptor signaling pathway," Nat Immunol. Dec. 2007;8(12):1345-52. Epub Oct. 21, 2007.

Imai C, et al. 'Chimeric receptors with 4-1BB signaling capacity provoke potent cytotoxicity against acute lymphoblastic leukemia.' Leukemia. Apr. 2004;18(4):676-84.

Irles C, et al. "CD45 ectodomain controls interaction with GEMs and Lck activity for optimal TCR signaling," Nat Immunol. Feb. 2003;4(2):189-97. Epub Dec. 23, 2002.

Itohara S, et al. "T cell receptor delta gene mutant mice: independent generation of alpha beta T cells and programmed rearrangements of gamma delta TCR genes," Cell. Feb. 12, 1993;72(3):337-48.

Joyce DE, et al. "Functional interactions between the thrombin receptor and the T-cell antigen receptor in human T-cell lines," Blood. Sep. 1, 1997;90(5):1893-901.

Kieback E, et al. "A safeguard eliminates T cell receptor gene-modified autoreactive T cells after adoptive transfer," Proc Natl Acad Sci U S A. Jan. 15, 2008;105(2):623-8. doi: 10.1073/pnas.0710198105. Epub Jan. 8, 2008.

Kreiβ et al., "Contrasting contributions of complementarity-determining region 2 and hypervariable region 4 of rat BV8S2+ (Vbeta8.2) TCR to the recognition of myelin basic protein and different types of bacterial superantigens," Int Immunol. 16(5):655-663 (2004).

Koya RC, et al. "Kinetic phases of distribution and tumor targeting by T cell receptor engineered lymphocytes inducing robust antitumor responses," Proc Natl Acad Sci U S A. Aug. 10, 2010;107(32):14286-91. doi: 10.1073/pnas.1008300107. Epub Jul. 12, 2010.

Leisegang M, et al. "T-Cell Receptor Gene-Modified T Cells with Shared Renal Cell Carcinoma Specificity for Adoptive T-Cell Therapy," Clin Cancer Res. Apr. 15, 2010;16(8):2333-43. doi: 10.1158/1078-0432.CCR-09-2897. Epub Apr. 6, 2010.

Liang X, et al. "A Single TCRa-Chain with Dominant Peptide Recognition in the Allorestricted HER2/neu-Specific T Cell Repertoire," J Immunol. Feb. 1, 2010;184(3):1617-29. doi: 10.4049/jimmunol.0902155. Epub Dec. 30, 2009.

Lin WY, et al. "Developmental dissociation of T cells from B, NK, and myeloid cells revealed by MHC class II-specific chimeric immune receptors bearing TCR-zeta or FcR-gamma chain signaling domains," Blood. Oct. 15, 2002;100(8):3045-8.

Losch FO, et al. "Activation of T cells via tumor antigen specific chimeric receptors: the role of the intracellular signaling domain," Int J Cancer. Jan. 20, 2003;103(3):399-407.

Maher J, et al. "Human T-lymphocyte cytotoxicity and proliferation directed by a single chimeric TCRzeta /CD28 receptor," Nat Biotechnol. Jan. 2002;20(1):70-5.

Mallevaey T, et al. "T Cell Receptor CDR2b and CDR3b Loops Collaborate Functionally to Shape the iNKT Cell Repertoire," Immunity. Jul. 17, 2009;31(1):60-71. doi: 10.1016/j.immuni.2009.05.010.

Marie-Cardine A, et al. "SHP2-interacting Transmembrane Adaptor Protein (SIT), A Novel Disulfide-linked Dimer Regulating Human T Cell Activation," J Exp Med. Apr. 19, 1999;189(8):1181-94.

McFarland HI, et al. "Signaling through MHC in transgenic mice generates a population of memory phenotype cytolytic cells that lack TCR," Blood. Jun. 1, 2003;101(11):4520-8. Epub Feb. 13, 2003.

Mekala DJ, et al. "IL-10-dependent suppression of experimental allergic encephalomyelitis by Th2-differentiated, anti-TCRredirected T lymphocytes," J Immunol. Mar. 15, 2005;174(6):3789-97.

Meresse B, et al. "Coordinated induction by IL15 of a TCR-independent NKG2D signaling pathway converts CTL into lymphokine-activated killer cells in celiac disease," Immunity. Sep. 2004;21(3):357-66.

Milone MC, et al. "Chimeric receptors containing CD137 signal transduction domains mediate enhanced survival of T cells and increased antileukemic efficacy in vivo," Mol Ther. Aug. 2009; 17(8):1453-64. doi: 10.1038/mt.2009.83. Epub Apr. 21, 2009.

Mizoguchi A, et al. "Role of appendix in the development of inflammatory bowel disease in TCR-alpha mutant mice," J Exp Med. Aug. 1, 1996;184(2):707-15.

Moeller M, et al. "A functional role for CD28 costimulation in tumor recognition by single-chain receptor-modified T cells," Cancer Gene Ther. May 2004;11(5):371-9.

Moisini I, et al. "Redirecting Therapeutic T Cells against Myelin-Specific T Lymphocytes Using a Humanized Myelin Basic Protein-HLA-DR2-ξ Chimeric Receptor," J Immunol. Mar. 1, 2008;180(5):3601-11.

Mombaerts P, et al. "Mutations in T-cell antigen receptor genes alpha and beta block thymocyte development at different stages," Nature. Nov. 19, 1992;360(6401):225-31.

Nguyen P, et al. "Antigen-specific targeting of CD8+ T cells with receptor-modified T lymphocytes," Gene Ther. Apr. 2003;10(7):594-604.

Nguyen P, et al. "Discrete TCR repertoires and CDR3 features distinguish effector and Foxp3+ regulatory T lymphocytes in myelin oligodendrocyte glycoprotein-induced experimental allergic encephalomyelitis," J Immunol. Oct. 1, 2010;185(7):3895-904. doi: 10.4049/jimmunol.1001550. Epub Sep. 1, 2010.

Okamoto et al., "Improved expression and reactivity of transduced tumor-specific TCRs in human lymphocytes by specific silencing of endogenous TCR," Cancer Res 69:9003-11 (2009).

Nguyen P, et al. 'Identification of a murine CD28 dileucine motif that suppresses single-chain chimeric T-cell receptor expression and function.' Blood. Dec. 15, 2003;102(13):4320-5. Epub Aug. 28, 2003.

Polic B, et al. "How alpha beta T cells deal with induced TCR alpha ablation," Proc Natl Acad Sci U S A. Jul. 17, 2001;98(15):8744-9. Epub Jul. 10, 2001.

Qian D, et al. "Dominant-negative zeta-associated protein 70 inhibits T cell antigen receptor signaling," J Exp Med. Feb. 1, 1996;183(2):611-20.

Rivera A, et al. "Host stem cells can selectively reconstitute missing lymphoid lineages in irradiation bone marrow chimeras," Blood. Jun. 1, 2003;101(11):4347-54. Epub Feb. 13, 2003.

Rossig C, et al. "Targeting of G(D2)-positive tumor cells by human T lymphocytes engineered to express chimeric T-cell receptor genes," Int J Cancer. Oct. 15, 2001;94(2):228-36.

(56)         References Cited

OTHER PUBLICATIONS

Sadelain M. "T-cell engineering for cancer immunotherapy," Cancer J. Nov.-Dec. 2009;15(6):451-5. doi: 10.1097/PPO.0b013e3181c51f37.

Schirrmann T, et al. "Human natural killer cell line modified with a chimeric immunoglobulin T-cell receptor gene leads to tumor growth inhibition in vivo," Cancer Gene Ther. Apr. 2002;9(4):390-8.

Schmitt TM, et al. "T cell receptor gene therapy for cancer," Hum Gene Ther. Nov. 2009;20(11):1240-8. doi: 10.1089/hum.2009.146.

Sommermeyer D, et al. "Designer T cells by T cell receptor replacement," Eur J Immunol. Nov. 2006;36(11):3052-9.

Spaapen R, "Rebuilding human leukocyte antigen class II-restricted," Novel strategies for identification and therapeutic application of minor histocompatibility antigens 13 (2009):79.

Spaapen R, et al. "Rebuilding Human Leukocyte Antigen Class II—Restricted Minor Histocompatibility Antigen Specificity in Recall Antigen-Specific T Cells by Adoptive T Cell Receptor Transfer: Implications for Adoptive Immunotherapy," Clin Cancer Res. Jul. 1, 2007;13(13):4009-15.

Sturmhöfel K, et al. "Antigen-independent, integrin-mediated T cell activation," J Immunol. Mar. 1, 1995;154(5):2104-11.

Sugita M, et al. "Failure of Trafficking and Antigen Presentation by CD1 in AP-3-Deficient Cells," Immunity. May 2002;16(5):697-706.

Symes J, et al. "Genetic Modification of T Lymphocytes for Cancer Therapy," Gene Therapy and Cancer Research Focus (2008):163.

Udyavar A, et al. "Rebalancing immune specificity and function in cancer by T-cell receptor gene therapy," Arch Immunol Ther Exp (Warsz). Oct. 2010;58(5):335-46. doi: 10.1007/s00005-010-0090-1. Epub Aug. 1, 2010.

Udyavar A, et al. "Subtle affinity-enhancing mutations in a myelin oligodendrocyte glycoprotein-specific TCR alter specificity and generate new self-reactivity," J Immunol. Apr. 1, 2009;182(7):4439-47. doi: 10.4049/jimmunol.0804377.

Verneris MR, et al. "Role of NKG2D signaling in the cytotoxicity of activated and expanded CD8+ T cells," Blood. Apr. 15, 2004;103(8):3065-72. Epub Nov. 20, 2003.

Voss RH, et al. "Molecular design of the $C\alpha\beta$ interface favors specific pairing of introduced $TCR\alpha\beta$ in human T cells," J Immunol. Jan. 1, 2008;180(1):391-401.

Wang J, et al. Optimizing adoptive polyclonal T cell immunotherapy of lymphomas, using a chimeric T cell receptor possessing CD28 and CD137 costimulatory domains. Hum Gene Ther. Aug. 2007;18(8):712-25.

Weiss A, et al. "Regulation of protein tyrosine kinase activation by the T-cell antigen receptor zeta chain," Cold Spring Harb Symp Quant Biol. 1992;57:107-16.

Williams BL, et al. "Genetic evidence for differential coupling of Syk family kinases to the T-cell receptor: reconstitution studies in a ZAP-70-deficient Jurkat T-cell line," Mol Cell Biol. Mar. 1998;18(3):1388-99.

Wu J, et al. "An activating immunoreceptor complex formed by NKG2D and DAP10," Science. Jul. 30, 1999;285(5428):730-2.

Xu H, et al. "A kinase-independent function of Lck in potentiating antigen-specific T cell activation," Cell. Aug. 27, 1993;74(4):633-43.

Yachi PP, et al. "Altered Peptide Ligands Induce Delayed CD8-T Cell Receptor Interaction—a Role for CD8 in Distinguishing Antigen Quality," Immunity. Aug. 2006;25(2):203-11. Epub Jul. 27, 2006.

Zhang T, et al. "Generation of antitumor responses by genetic modification of primary human T cells with a chimeric NKG2D receptor," Cancer Res. Jun. 1, 2006;66(11):5927-33.

Zhao Y, et al. "A Herceptin-Based Chimeric Antigen Receptor with Modified Signaling Domains Leads to Enhanced Survival of Transduced T Lymphocytes and Antitumor Activity," J Immunol. Nov. 1, 2009;183(9):5563-74. doi: 10.4049/jimmunol.0900447.

Yu C, et al. "Inhibitory signaling potential of a TCR-like molecule in lamprey," Eur J Immunol. Feb. 2009;39(2):571-9. doi: 10.1002/eji.200838846.

Lustgarten J, et al. "Specific elimination of IgE production using T cell lines expressing chimeric T cell receptor genes," Eur J Immunol. Oct. 1995;25(10):2985-91.

Surh CD, et al. "Homeostasis of memory T cells," Immunol Rev. Jun. 2006;211:154-63.

Schneider MA, et al. "CCR7 is required for the in vivo function of CD4+ CD25+ regulatory T cells," J Exp Med. Apr. 16, 2007;204(4):735-45.

Maloy KJ, et al. "Fueling regulation: IL-2 keeps CD4+ Treg cells fit," Nat Immunol. Nov. 2005;6(11):1071-2.

Call ME, et al. "Molecular mechanisms for the assembly of the T cell receptor-CD3 complex," Mol Immunol. Apr. 2004;40(18):1295-305.

Cooper TA, "Use of minigene systems to dissect alternative splicing elements," Methods. Dec. 2005;37(4):331-40.

Ehlers S, et al. "Alphabeta T cell receptor-positive cells and interferon-gamma, but not inducible nitric oxide synthase, are critical for granuloma necrosis in a mouse model of mycobacteria-induced pulmonary immunopathology," J Exp Med. Dec. 17, 2001;194(12):1847-59.

Madrenas, J. et al., "Thymus-independent Expression of Truncated T Cell Receptor-a mRNA in Murine Kidney," J Immunol. Jan. 15, 1992:148(2):612-9. Abstract.

Roberts S, et al., "T-Cell a~+ and yo+ Deficient Mice Display Abnormal but Distinct Phenotypes Toward a Natural, Widespread Infection of the Intestinal Epithelium," PNAS, Oct. 15, 1996;93(21):11174-79.

Stoss O, et al., "The in vivo minigene approach to analyze tissue-specific splicing," Brain Research Protocols. Dec. 1999;4(3):383-94.

Szczepanik M, et al., "Gamma.delta. T Cells from Tolerized a~ T Cell Receptor (TCR)-deficient Mice Inhibit Contact Sensitivity-effector T Cells in Vivo, and Their Interferon-y Production in Vitro," The J Exp Med. Dec. 1, 1996;184(6)2129-39.

Trickett A, et al., "T cell stimulation and expansion using anti-CD3/CD28 beads," J Immunol Methods. Apr. 1, 2003;275(1-2):251-5.

Wormley F, et al., "Resistance of T-Cell Receptor o-Chain-Deficient Mice to Experimental Candida Albicans Vaginitis," Infect Immun. Nov. 2001; 69(11):7162-4.

Wilson AM, et al., "A minigene approach for analysis of ATP7B splice variants in patients with Wilson disease," Biochimie. Oct. 1, 2009;91(10):1342-5.

Sigma-Aldrich, Cook Book of Sep. 2010, vol. 12, Fundamental Techniques in Cell Culture Laboratory Handbook, 2nd Edition, pp. 1-4.

Bisset LR, et al. "Reference values for peripheral blood lymphocyte phenotypes applicable to the healthy adult population in Switzerland," Eur J Haematol. Mar. 2004;72(3):203-12.

Groh V, et al. "Costimulation of CD8alphabeta T cells by NKG2D via engagement by MIC induced on virus-infected cells," Nat Immunol. Mar. 2001;2(3):255-60.

Kowolik CM, et al. "CD28 costimulation provided through a CD19-specific chimeric antigen receptor enhances in vivo persistence and antitumor efficacy of adoptively transferred T cells," Cancer Res. Nov. 15, 2006;66(22):10995-1004.

Yang W, et al. "Chimeric immune receptors (CIRs) specific to JC virus for immunotherapy in progressive multifocal leukoencephalopathy (PML)," Int Immunol. Sep. 2007;19(9):1083-93.

Cooper LJ, et al. "Enhanced antilymphoma efficacy of CD19-redirected influenza MP1-specific CTLs by cotransfer of T cells modified to present influenza MP1," Blood. Feb. 15, 2005;105(4):1622-31.

Pardoll DM, "Tumor reactive T cells get a boost," Nat Biotechnol. Dec. 2002;20(12):1207-8.

Merriam-Webster dictionary definition for "isolated," http://www.meriam-webster.com/dictionary/isolated downloaded Oct. 14, 2014, pp. 1-2.

Pamela Stanley lab wiki, "Transfection of Cells with DNA," http://stanxterm.aecom.yu.edu/wik/index.php?page=Transfection Aug. 13, 2009, pp. 1-4.

Schwab R, et al. "Requirements for T cell activation by OKT3 monoclonal antibody: role of modulation of T3 molecules and interleukin 1," J Immunol. Sep. 1985;135(3):1714-8.

(56) References Cited

OTHER PUBLICATIONS

Alegre ML, et al. "Effect of a single amino acid mutation on the activating and immunosuppressive properties of a "humanized" OKT3 monoclonal antibody," J Immunol. Jun. 1, 1992;148(11):3461-8.

Barber A, et al. "Chimeric NKG2D receptor-expressing T cells as an immunotherapy for multiple myeloma," Exp Hematol. Oct. 2008;36(10):1318-28.

Schumacher TN, "T-cell-receptor gene therapy," Nat Rev Immunol. Jul. 2002;2(7):512-9.

Eagle RA, et al., "Beyond Stressed Self: Evidence for NKG2D Ligand Expression on Healthy Cells," Curr Immunol Rev. Feb. 2009;5(1):22-34.

Basu S, et al., "Estradiol regulates MICA expression in human endometrial cells," Clin Immunol. Nov. 2008;129(2):325-32.

Scheer M, et al., "Knock-down of gene expression in hematopoietic cells," Methods Mol Biol. 2009;506:207-19.

Llano M, et al., "Rapid, controlled and intensive lentiviral vector-based RNAi," Methods Mol Biol. 2009;485:257-70.

Gascoigne NR., "Transport and secretion of truncated T cell receptor beta-chain occurs in the absence of association with CD3," J Biol Chem. Jun. 5, 1990;265(16):9296-301.

Rubin DC, et al., "Altered enteroendocrine cell expression in T cell receptor alpha chain knock-out mice," Microsc Res Tech. Oct. 15, 2000;51(2):112-20.

Database GenBank [online], Accession No. BC025703, Jul. 15, 2006.

Database GenBank [online], Accession No. P20963, Oct. 10, 2002.

Pui CH, et al., Education Session 1; Treatment of Acute Leukemia, Oct. 1999, Retrieved from: http://citeseerx.ist.psu.edu/viewdoc/download?doi=10.1.1.622.3615&rep=rep1&type=pdf on Sep. 15, 2016.

Pule M, et al., "Artificial T-cell receptors," Cytotherapy. 2003;5(3):211-26.

Quinn ER, et al., "T cell activation modulates retrovirus-mediated gene expression," Hum Gene Ther. 1998;9(10):1457-67.

Rabinovich PM, et al., "Synthetic messenger RNA as a tool for gene therapy," Hum Gene Ther. Oct. 2006;17(10):1027-35.

Regueiro JR, et al., "Immunity and gene therapy: benefits and risks," Inmunologia. 2004;23(1):56-62.

Riley JL, et al., "16 Genetically Modified T Cells for Human Gene Therapy," In; Dropulic B, Carter, editors. Concepts in Genetic Medicine. Hoboken, New Jersey: John Wiley & Sons, Inc; Jan. 3, 2008:193-205.

Roberts MR, et al., "Antigen-specific cytolysis by neutrophils and NK cells expressing chimeric immune receptors bearing ζ or γ signaling domains," J Immunol. Jul. 1998;161(1):375-84.

Roberts MR, et al., "Targeting of human immunodeficiency virus-infected cells by CD8+ T lymphocytes armed with universal T-cell receptors," Blood. Nov. 1, 1994;84(9):2878-89.

Rondon IJ, et al., "Gene Therapy for HIV-1 Using Intracellular Antibodies Against HIV-1 Gag Proteins," In Intrabodies: Basic Research and Clinical Gene Therapy Applications. Springer, Berlin, Heidelberg. 1998;163-181.

Rondon IJ, et al., "Intracellular antibodies (intrabodies) for gene therapy of infectious diseases," Annu Rev in Microbiol. Oct. 1997;51(1):257-83.

Rossi JJ, et al., "Genetic therapies against HIV," Nat Biotechnol. Dec. 2007;25(12):1444-54.

Rossig C, et al., "Epstein-Barr virus-specific human T lymphocytes expressing antitumor chimeric T-cell receptors: potential for improved immunotherapy," Blood. Mar. 15, 2002,99(6):2009-16.

Rossig C et al., "Chimeric T-cell receptors for the targeting of cancer cells," Acta Haematol. 2003;110(2-3):154-9.

Rossig C, et al., "Genetic modification of T lymphocytes for adoptive immunotherapy," Mol Ther. Jul. 2004;10(1):5-18.

Roszkowski JJ, et al., "Retroviral-Mediated Gene Transfer for Engineering Tumor-Reactive T-Cells," *Immunotherapy of Cancer*. Humana Press, 2006. 213-33.

Sahu GK, et al., "Anti-HIV designer T cells progressively eradicate a latently infected cell line by sequentially inducing HIV reactivation then killing the newly gp120-positive cells," Virology. Nov. 1, 2013;446(1-2):268-75.

Schirrmann T, et al., "Emerging Therapeutic Concepts III: Chimeric Immunoglobulin T Cell Receptors, T-Bodies," Handbook of Therapeutic Antibodies. Jan. 26, 2007:533-71.

Scholler J, et al., "Decade-long safety and function of retroviral-modified chimeric antigen receptor T cells," Sci Transl Med. May 2, 2012;4(132):132ra53.

Seow SV, et al., Expansion and activation of allogeneic NK cells for adoptive immunotherapy of advanced leukemia/lymphoma. In International Immunology Meeting Abstracts Aug. 1, 2010 (vol. 22 No. Suppl. 1 Pt 2. pp. ii21-ii123). Oxford University Press.

Severino et al., "Chimeric immune receptor T cells bypass class I requirements and recognize multiple cell types relevant in HIV-1 infection," Virology. Feb. 15, 2003;306(2):371-5.

Shi J, et al., "Activation and Expansion of Natural Killer (NK) Cells with Potent Cytotoxicity for Multiple Myeloma," Blood. Nov. 16, 2008;112(11):2758.

Shibaguchi H, et al., "A fully human chimeric immune receptor for retargeting T-cells to CEA-expressing tumor cells," Anticancer Res. Nov.-Dec 1, 2006;26(6A):4067-72.

Shimasaki N, et al., "Expanded and armed natural killer cells for cancer treatment," Cytotherapy. Nov. 18, 2016(11):1422-34.

Sorg T, et al., "Gene therapy for AIDS," Transfus Sci. Jun. 1997;18(2):277-89.

Sprent J., "T cell memory," Annu Rev Immunol. 2002;20:551-79. Epub Oct. 4, 2001.

Starr TK, et al., "Positive and negative selection of T cells," Annu Rev Immunol. Apr. 2003; 21(1):139-76.

Surh CD, et al., "Homeostasis of naive and memory T cells," Immunity. Dec. 19, 2008;29(6):848-62.

Surh CD, et al., "Regulation of mature T cell homeostasis," Semin Immunol. Jun. 2005; 17(3):183-191.

Szmania S, et al., "Fresh ex vivo expanded natural killer cells demonstrate robust proliferation in vivo in high-risk relapsed multiple myeloma (MM) patients," Blood (2012):579.

Szmania S, et al., "Ex vivo expanded natural killer cells demonstrate robust proliferation in vivo in high-risk relapsed multiple myeloma patients," J Immunother. (Hagerstown, Md.: 1997). Jan. 2015;38(1):24-36.

Szmania S, et al., Expanded natural killer (NK) cells for immunotherapy: fresh and made to order. Blood 2012:1912.

Takachi T, et al., "Lymphoblastic lymphoma with mature b-cell immunophenotype and MLL-5AF9 in a child," Pediatr Blood & Cancer. Dec. 15, 2011;57(7):1251-2.

Todisco E, et al., "CD38 ligation inhibits normal and leukemic myelopoiesis," Blood. Jan. 15, 2000;95(2):535-42.

Tsui LV, et al., "Production of human clotting Factor IX without toxicity in mice after vascular delivery of a lentiviral vector," Nat Biotechnol. Jan. 2002;20(1):53-7.

Uherek C, et al., "Chimeric antigen receptors for the retargeting of cytotoxic effector cells," J HematotherStem Cell Res. Aug. 2001:10(4):523-34.

von Boehmer et al., "Self-nonself discrimination by T cells," Science. Jun. 15, 1990;248(4961):1369-73.

Voskens CJ, et al., "Ex-vivo expanded human NK cells express activating receptors that mediate cytotoxicity of allogeneic and autologous cancer cell lines by direct recognition and antibody directed cellular cytotoxicity," J Exp Clin Cancer Res. Oct. 11, 2010;29(1):134.

Walker RE, et al., "long-term in vivo survival of receptor-modified syngeneic T cells in patients with human immunodeficiency virus infection," Blood. Jul. 15, 2000;96(2):467-74.

Wang G, et al., "AT cell-independent antitumor response in mice with bone marrow cells retrovirally transduced with an antibody/Fc-γ chain chimeric receptor gene recognizing a human ovarian cancer antigen," Nat Med. Feb. 1998;4(2):168-72.

Wang W, et al., "Human NK cells maintain licensing status and are subject to killer immunoglobulin-like receptor (KIR) and KIR-ligand inhibition following ex vivo expansion," Cancer Immunology, Immunother. Sep. 2016:;65(9):1047-59.

(56)　　　　References Cited

OTHER PUBLICATIONS

Weijtens et al., "Functional balance between T cell chimeric receptor density and tumor associated antigen density: CTL mediated cytolysis and lymphokine production," Gene Ther. Jan. 2000;7(1):35-42.

Weijtens ME, et al,. "A retroviral vector system 'STITCH' in combination with an optimized single chain antibody chimeric receptor gene structure allows efficient gene transduction and expression in human T lymphocytes," Gene Ther. Sep. 1998;5(9):1195-203.

Weijtens Mo, "Immune-gene therapy for renal cancer: chimeric receptor-mediated lysis of tumor cells," Erasmus MC: University Medical Center Rotterdam; 2001.

Wickremasinghe RG, et al., "Rapid down-regulation of protein kinase C and membrane association in phorbol ester-treated leukemia cells," FEBS letters. Oct. 7, 1985;190(1):50-4.

Willcox N, et al., "Variable corticosteroid sensitivity of thymic cortex and medullary peripheral-type lymphoid tissue in myasthenia gravis patients: structural and functional effects," QJ Med. Nov. 1989;73(2):1071-87.

Willemsen RA, et al., "Genetic engineering of T cell specificity for immunotherapy of cancer," Hum Immunol. Jan. 2003;64(1):56-68.

Willemsen RA, et al., "A phage display selected fab fragment with MHC class I-restricted specificity for MAGE-A1 allows for retargeting of primary human T lymphocytes," Gene Ther. Nov. 2001;8(21):1601-8.

Wong KK, et al., "Adeno-associated virus based vectors as antivirals," Curr Top Microbiol Immunol. 1996;218:145-170.

Liu L, et al., "Adoptive T-cell therapy of B-cell malignancies: conventional and physiological chimeric antigen receptors," Cancer Lett. Mar. 2012;316(1):1-5.

Nagorsen D, et al., "Immunomodulatory therapy of cancer with T cell-engaging BiTE antibody blinatumomab," Exp Cell Res. May 15, 2011;317(9):1255-60.

Wu AM, et al., "Multimerization of a chimeric anti-CD20 single-chain Fv-Fc fusion protein is mediated through variable domain exchange," Protein Eng. Dec. 1, 2001;14(12):1025-33.

Wu CY, et al., "Remote control of therapeutic T cells through a small molecule-gated chimeric receptor," Science. Oct. 16, 2015;350(6258):aab4077.

Yang OO, et al., "Nef-mediated resistance of human immunodeficiency virus type 1 to antiviral cytotoxic T lymphocytes," J Virol. Feb. 2002;76(4):1626-31.

Yang OO, et al., "Lysis of HIV-1-infected cells and inhibition of viral replication by universal receptor T cells," Proc Natl Acad Sci USA. Oct. 14, 1997;94(21):11478-83.

Yang OO, et al., "CD8+ cells in human immunodeficiency virus type I pathogenesis: cytolytic and noncytolytic inhibition of viral replication," Adv Immunol. 1997;66:273-311.

Yel L, et al., "Mutations in the mu heavy-chain gene in patients with agammaglobulinemia," N Engl J Med. Nov. 14, 1996;335(20):1486-93.

Yun CO, et al., "Targeting of T lymphocytes to melanoma cells through chimeric anti-GD3 immunoglobulin T-cell receptors," Neoplasia, Sep.-Oct 2000;2(5):449-59.

Zhu Y, et al., "Screening and Functional Research on Jurkat Cell Strain of Stable Chimeric Antigen Receptor Expression," Sci online. 2013. Retrived from http://www.paper.edu.cn/download/downPaper/201302-359 on Oct. 13, 2016.

Kumagai MA, et al., "Ligation of CD38 suppresses human B lymphopoiesis," J Exp Med. Mar. 1, 1995;181(3):1101-10.

Labrecque N, et al., "How much TCR does a T cell need?," Immunity. Jul. 1, 2001;15(1):71-82.

Lake DF, et al., "Construction and binding analysis of recombinant single-chain TCR derived from tumor-infiltrating lymphocytes and a cytotoxic T lymphocyte clone directed against MAGE-1," Int Immunol. May 1, 1999;11(5):745-51.

Lamers CH, et al., "Protocol for gene transduction and expansion of human T lymphocytes for clinical immunogene therapy of cancer," Cancer Gene Ther.Jul. 2002;9(7):613-23.

Lampson LA, "Beyond inflammation: site-directed immunotherapy," Immunol. Today. Jan. 1, 1998;19(1):17-22.

Lapteva N, et al., "Large-scale ex vivo expansion and characterization of natural killer cells for clinical applications," Cytotherapy. Oct. 1, 2012;14(9):1131-43.

Lee DA, et al., "Acquisition, preparation, and functional assessment of human NK cells for adoptive immunotherapy," In: Immunotherapy of Cancer: Methods Mol Biol. 2010;651:61-77.

Leibman RS, et al., "Engineering T cells to functionally cure HIV-1 infection," Mol Ther. Jul. 1, 2015;23(7):1149-59.

Leivas Alejandra, et al., "Autologous Activated and Expanded Natural Killer Cells Are Safe and Clinically Actives in Multiple Myeloma." (2015): 1856-1856.

Leivas A, et al., "Multiple Infusions of Autologous Activated and Expanded Natural Killer Cells: A New Therapeutic Option for Multiple Myeloma," Clinical Lymphoma, Myeloma and Leukemia. Sep. 1, 2015;15:e297-8.

Leivas A, et al., "Autologous Activated and Expanded Natural Killer Cells Destroy Multiple Myeloma Clonogenic Tumor Cells through NKG2D and Its Ligands," Clinical Lymphoma, Myeloma and Leukemia. Sep. 1, 2015;15:e245-6.

Leung W, et al., "High success of hematopoietic cell transplantation regardless of donor source in children with very high-risk leukemia," Blood. Jul. 14, 2011;118(2):223-30.

Li Linhong, et al., "A Highly Efficient, Clinically Applicable Transfection Method to Redirect the Specificity of Immune Cells and Enhance Their Anti-Tumor Capacity." (2008): 3894.

Liao KW, et al., "Design of transgenes for efficient expression of active chimeric proteins on mammalian cells," Biotechnol Bioeng, May 20, 2001;73(4):313-23.

Lim KS, et al., "Implication of highly cytotoxic natural killer cells for esophageal cancer treatment," Cancer Res. Aug. 1, 2015:75:3148.

Liu C, et al., "HIV-1 functional cure: will the dream come true?" BMC Med. 2015;13(1):284.

Liu L, et al., "Novel CD4-based bispecific chimeric antigen receptor designed for enhanced anti-HIV potency and absence of HIV entry receptor activity," J Virol. Jul. 2015;89(13):6685-94, Apr. 15,:JVI-00474.

Lund JA, et al., "Future Anti-HIV therapy. In: Spach DH, Hooton TM. Editors. The HIV Manual: A Guide to Dianosis and Treatment," Oxford University Press; 1996:89-104.

Lund O, et al., "Gene Therapy of T helper cells HIV infection: mathematical model of the criteria for clinical effect," Bull Math Biol. 1997;59(4):725-45.

Luszczek W, et al., "Expanded human regulatory iNKT cells exhibit direct cytotoxicity against hematolymphoid tumor targets," Cancer Res. 2012:3512.

Ma Q, et al., "Anti-prostate specific membrane antigen designer T cells for prostate cancer therapy," Prostate. 2004 61(1):12-25.

Marathe JG, et al., "Is gene therapy a good therapeutic approach for HIV-positive patients?" Genet Vaccines Ther. 2007:5:5.

Marin V, et al., "Enhancement of the anti-leukemic activity of cytokine induced killer cells with an anti-CD19 chimeric receptor delivering a 4-1BB-ζ activating signal," Exp hematol. Sep. 1, 2007;35(9):1388-97.

Ma Q, et al., Genetically engineered T cells as adoptive immunotherapy of cancer, Cancer Chemother. Biol. Response Modif. 2002;20:315-41.

Masiero S, et al., "T-cell engineering by a chimeric T-cell receptor with antibody-type specificity for the HIV-1 gp120," Gene Ther. Feb. 2005;12(4):299-310.

McGuinness RP, et al., "Anti-tumor activity of human T cells expressing the CC49-zeta chimeric immune receptor," Hum Gene Ther. Jan. 20, 1999;10(2):165-73.

Mihara K, et al., "Development and functional characterization of human bone marrow mesenchymal cells immortalized by enforced expression of telomerase," Br J Haematol. Mar. 2003;120(5):846-9.

Mihara K, et al., "Development of Effective Immunotherapy for B-Cell Non-Hodgkin's Lymphoma with CD19-Specific Cytotoxic T Cells." Blood 2004:3277.

Mihara K, et al., "Activated T—cell-mediated Immunotherapy With a Chimeric Receptor Against CD38 in B-cell Non-Hodgkin Lymphoma," J Immunother. Sep. 1, 2009;32(7):737-43.

(56)                    References Cited

OTHER PUBLICATIONS

Mihara K, et al., "Synergistic and persistent effect of T-cell immunotherapy with anti-CD19 or anti-CD38 chimeric receptor in conjunction with rituximab on B-cell non-Hodgkin lymphoma," Br J Haematol. Oct. 2010;151(1):37-46.

Milone MC, et al., "Chimeric receptors containing CD137 signal transduction domains mediate enhanced survival of T cells and increased antileukemic efficacy in vivo," Mol Ther. Aug. 1, 2009;17(8):1453-64.

Mimura K, et al., "Therapeutic potential of highly cytotoxic natural killer cells for gastric cancer. Int J Cancer," Sep. 15, 2014;135(6):1390-8.

Mitra AK, et al., "Genetic variants in cytosolic 5'-nucleotidase II are associated with its expression and cytarabine sensitivity in HapMap cell lines and in patients with acute myeloid leukemia," J Pharmacol Exp Ther. Oct. 2011;339(1):9-23.

Mitsuyasu RT, et al., "Prolonged survival and tissue trafficking following adoptive transfer of CD4ζ gene-modified autologous CD4+ and CD8+ T cells in human immunodeficiency virus—infected subjects," Blood. Aug. 1, 2000;96(3):785-93.

Muniappan A, et al., "Ligand-mediated cytolysis of tumor cells: use of heregulin-ζ chimeras to redirect cytotoxic T lymphocytes," Cancer Gene Ther. Jan. 2000;7(1):128-34.

Nešić D, et al., "MHC class I is required for peripheral accumulation of CD8+ thymic emigrants," J Immunol. Apr. 15, 1998;160(8):3705-12.

Nguyen P, et al., "Induction of tolerance and immunity by redirected B cell-specific cytolytic T lymphocytes," Gene Ther. Dec. 2007;14(24):1739-49.

Ni Z, et al., "Expression of chimeric receptor CD4ζ by natural killer cells derived from human pluripotent stem cells improves in vitro activity but does not enhance suppression of HIV infection in vivo," Stem Cells. Apr. 1, 2014;32(4):1021-31.

Palu G, et al., "Genetically modified immunocompetent cells in HIV infection," Gene Ther. Nov. 2001;8(21):1593-600.

Patel SD, et al., "Impact of chimeric immune receptor extracellular protein domains on T cell function," Gene Ther. Mar. 1999;6(3):412-9.

Patel SD, et al., T-cell killing of heterogenous tumor or viral targets with bispecific chimeric immune receptors. Cancer Gene Ther. Aug. 2000;7(8):1127-34.

Petrausch U, et al., Chimeric Antigen Receptors—"CARs." In: Dubel S, Reichert JM, editors. Handbook of Therapeutic Antibodies. Weinheim, Germany: Wiley-VCH Verlag GmbH & Co; 2014; 519-60.

Pinthus JH, et al., "The T-body approach: towards cancer immuno-gene therapy," Cancer Immune Therapy—Current and Future Strategies. Weinheim, Germany: Wiley-VCH. Aug. 27, 2002:287-98.

Pircher M et al., "T Cell Engineering," Prog Tumor Res. 2015;42:110-35.

Poeschia EM, et al., "Advances in Gene Therapy for HIV and Other Viral Infections," In: The Development of Human Gene Therapy. Cold Spring Harbor Laboratory Press; 1999;573-606.

Prapa M, et al., "A novel anti-GD2/4-1BB chimerio antigen receptor triggers neuroblastoma cell killing," Oncotarget. Sep. 22, 2015;6(28):24884.

Prapa M, et al., "Adoptive Car T Cell Therapy Targeting GD2-Positive Cancers," Cytotherapy. Jun. 1, 2016;18(6):S101.

Protzer U, et al., "Can engineered "designer" T cells outsmart chronic hepatitis B?" Hepat Res Treat. 2010.

Fujisaki H, et al., "Expanded Natural Killer Cells for Cellular Therapy of Acute Myeloid Leukemia." (2007):2743.

Fujisaki H, et al., "Expansion of highly cytotoxic human natural killer cells for cancer cell therapy," Cancer Res. May 1, 2009;69(9):4010-7.

Garg, Tarun K., et al., "Ex vivo activated natural killer (NK) cells from myeloma patients kill autologous myeloma and killing is enhanced by elotuzumab." Blood (2008) Nov.;112:3666.

Garg TK, et al., "Highly activated and expanded natural killer cells for multiple myeloma immunotherapy," Haematologica. Sep. 2012;97(9):1348-56.

Gilham DE, et al., "Primary polyclonal human T lymphocytes targeted to carcino-embryonic antigens and neural cell adhesion molecule tumor antigens by CD3ζ-based chimeric immune receptors," J Immunother. Mar.-Apr. 2002;25(2):139-51.

Gray D, "A role for antigen in the maintenance of immunological memory," Nat Rev Immunol Jan. 2002;2(1):60-5.

Grossman Z, et al., "Adaptive cellular interactions in the immune system: the tunable activation threshold and the significance of subthreshold responses," Proc Natl Acad Sci U S A. Nov. 1, 1992;89(21):10365-9.

Grossman Z, et al., "Autoreactivity, dynamic tuning and selectivity," Curr Opin Immunol. Dec. 1, 2001;13(6):687-98.

Grossman Z, et al., "Self-tolerance: context dependent tuning of T cell antigen recognition," Semin Immunol. Jun. 2000;12(3):197-203).

Guest RD, et al., "The role of extracellular spacer regions in the optimal design of chimeric immune receptors: evaluation of four different scFvs and antigens," J Immunother. May-Jun.2005;28(3):203-11.

Hamer DH, Can HIV be cured? Mechanisms of HIV persistence and strategies to combat it, Curr HIV Res. Apr. 2004 ;2(2):99-111.

Hege KM, et al., "Systemic T Cell-independent Tumor Immunity after Transplantation of Universal Receptor—modified Bone Marrow into SCID Mice," J Exp Med. Dec. 1, 1996;184(6):2261-9.

Hege KM et al., "T-cell gene therapy," Curr Opin Biotechnol. Dec. 1996;7(6);629-34.

Ho WY, et al., "Adoptive immunotherapy: engineering T cell responses as biologic weapons for tumor mass destruction," Cancer Cell. May 2003;3(5):431-7.

Hochberg, Jessica, et al., "Genetic engineering and significant ex-vivo expansion of cord blood natural killer cells: implications for post-transplant adoptive cellular immunotherapy," Blood; Nov. 16, 2008; 112(11):209.

Hochberg et al., "Genetically Reengineered K562 Cells (antigen Presenting Cells, Apc) Significantly Expand Cord Blood (CB) Natural Killer (NK) Cells for Use in Adoptive Cellular Immunotherapy:(poster 100)," Pediatric Blood & Cancer. Jun. 1, 2009;52(6):698.

Hombach A, et al., "Characterization of a chimeric T-cell receptor with specificity for the Hodgkin's lymphoma-associated CD30 antigen," J Immunother. Nov. 1999;22(6):473-80.

Hombach A, et al., "Grafting T cells with tumor specificity: the chimeric receptor strategy for use in immunotherapy of malignant diseases," Hybridoma. Feb. 1999;18(1):57-61.

Hombach A, et al., Chimeric anti-TAG72 receptors with Immunoglobulin constant Fc domains and gamma or zeta signalling chains. Int J Mol Med. Jul. 1, 1998;2(1):99-103.

Hua CK, et al., "Engineering broadly neutralizing antibodies for HIV prevention and therapy." Adv Drug Deliv Rev. Aug. 1, 2016;103:157-73.

Imai C, et al., "Acute suppurative thyroiditis as a rare complication of aggressive chemotherapy in children with acute myelogeneous leukemia," Pediatr Hematol Oncol. Jan. 1, 2002;19(4):247-53.

Imai C, et al., "T-Cell immunotherapy for B-lineage acute lymphoblastic leukemia using chimeric antigen receptors that deliver 4-1BB-mediated costimulatory signals," Blood Nov. 16, 2003;102 (11):66A-67A.

Imal C, et al., "Expression of the adaptor protein BLNK/SLP-65 in childhood acute lymphoblastic leukemia," Leukemia. May 1, 2004;18(5):922-5.

Imai C, et al., "Interleukin-2 Gene Transduction in Human Natural Killer Cells Augments Their Survival and Anti-Leukemic Capacity," (2008): 5437.

Imami N, et al., "Prospects for immune reconstitution in HIV-1 infection," Clin Exp Immunol. Mar. 2002;127(3):402-11.

Imamura M, et al., "Juvenile myelomonocytic leukemia with less aggressive clinical course and KRAS mutation," Pediatr Blood Cancer. Oct. 2008;51(4):569.

(56)        References Cited

OTHER PUBLICATIONS

Imamura M, et al., "Anticancer Drugs Overexpress Fas-associated Phosphatase-1 in Some Leukemic Cells," Acta Medica et Biologica; 2004;52(3):81-9.

Imamura M, et al., "Autonomous growth and increased cytotoxicity of natural killer cells expressing membrane-bound interleukin-15," Blood 2014 14;124(7);1081-8.

Irving B. et al., "Surface chimeric receptors as tools in study of lymphocyte activation," Methods Enzymol. 2000;327:210-28.

Iwabuchi H, et al., "A gene homologous to human endogenous retrovirus overexpressed in childhood acute lymphoblastic leukemia," Leuk Lymphoma. Nov. 2004;45(11):2303-6.

Jameson SC, et al., "Diversity in T cell memory: an embarrassment of riches," Immunity. Dec. 18, 2009;31(6):859-71.

Jameson SC et al., "T cell homeostasis," Nat Rev Immunol. Aug. 2002;2(8):547-56.

Janossy G, et al., "Development of B cell subpopulations in humans and its relevance to malignancy," In Modern Trends in Human Leukemia VI New Results in Clinical and Biological Research Including Pediatric Oncology 1985 (pp. 461-470). Springer, Berlin, Heidelberg.

Janossy G, et al., "Kinetics of T lymphocyte development," Curr Top Pathol. 1989;79:59-99.

Janossy G, et al., "Leukaemia and lymphoma treatment with autologous bone marrow transplantation: preclinical studies," Cancer Detect Prev 1988;12(1-6):597-604.

Janossy G,et al., "T lymphocyte regeneration after transplantation of T cell depleted allogeneic bone marrow," Clin Exp Immmunol. Mar. 1986;63(3):577.

Jensen M, et al., "CD20 is a molecular target for scFvFc: zeta receptor redirected T cells: implications for cellular immunotherapy of CD20+ malignancy." Biol Blood and Marrow Transplantat. Aug. 1, 1998:4(2):75-83.

June CH et al., Pilot study of redirected autologous T cells engineered to contain anti-CD19 attached to TCRζ and 4-1BB signaling domains in patients with chemotherapy-resistant or-refractory CD19+ leukemia and lymphoma. 2009. Retrivied from http://www.med.upenn.edu/junelab/docs/June_protocol_OLF.PDF on Oct. 13, 2016.

Junghans RP. Designer T Cells for Breast Cancer Therapy: Phase I Studies. Beth Israel Deaconess Medical Center Boston MA; Jul. 2001. Retrieved from http://oai.dtic.mil/oai/oai?verb=getRecord &metadataPrefix=html&identifier=ADA398295 on Oct. 11, 2016.

Kanwar VS,et al., "Lack of constitutive activation of Janus kinases and signal transduction and activation of transcription factors in Philadelphia chromosome-positive acute lymphoblastic leukemia," Blood. Jun. 1, 1996;87(11):4911-2.

Kershaw MH, et al., "Redirected Cytotoxic Effector Function Requirements for Expression of Chimeric Single Chain High Affinity Immunoglobulin E Receptors," J Biol Chem. Aug. 30, 1996;271(35):21214-20.

Kitanaka A, et al., "CD38 ligation in human B cell progenitors triggers tyrosine phosphorylation of CD19 and association of CD19 with lyn and phosphatidylinositol 3-kinase," J Immunol. Jul. 1, 1997;159(1):184-92.

Kitanaka A, et al., "Expression and activation of the nonreceptor tyrosine kinase Tec in human B cells," Blood. Feb. 1, 1998;91(3):940-8.

Kitchen SG, et al., "Stem cell-based anti-HIV gene therapy," Virology. Mar. 15, 2011;411(2):260-72.

Kitchen et al., "Stem cell approaches to treating HIV infection," Curr Opin HIV AIDS. Jan. 2011:6(1):68-73.

Koenig S, "A lesson from the HIV patient: The immune response is still the bane (or promise) of gene therapy," Nat Med. Feb. 1996;2(2):165-167.

Koh S, et al., "A practical approach to immunotherapy of hepatocellular carcinoma using T cells redirected against hepatitis B virus," Mol Ther Nucleic Acids. Aug. 13, 2013;2:e114.

Krampera M, et al., "Methodological approach to minimal residual disease detection by flow cytometry in adult B-lineage acute lymphoblastic leukemia," Haematologica. Jan. 1, 2006;91(8):1109-12.

Bohne F, *Specific elimination of hepatitis B virus-infected hepatocytes by modified human T cells expressing a chimeric T cell receptor and establishing a cytotoxic immune response. Diss. Thesis.*) University of Cologne, 2006.

Bolhuis RL, et al., "Targeting of peripheral blood T lymphocytes," Springer Semin Immunopathol. 1996 18(2):211-226.

Bridges SH, "Immune reconstitution for HIV disease," Antibiot Chemother. 1996;48:233-9.

Brocker T, et al., Adoptive tumor immunity mediated by lymphocytes bearing modified antigen-specific receptors. Adv Immunol. 1998;68:257-69.

Bucala R, et al., "Immunosuppressive factors in cancer." *Cancer Immune Therapy. Weinheim, Germany: Wiley-VCH Verlag Gmbh & Co* (2002): 119-54.

Bullain SS, et al., "Genetically engineered T cells to target EGFRvill expressing glioblastoma," J Neurooncol. Sep. 2009;;94(3):373-82.

Buschle M, et al., "Interferon gamma Inhibits Apoptotic Cell Death in B Cell Chronic Lymphocytic Leukemia," J Exp Med. Jan. 1, 1993;177(1):213-8.

Calogero A, et al., Recombinant T-cell receptors: an immunologic link to cancer therapy. J Immunother. 2000;23(4):393-400.

Campana D, et al., "The immunologic detection of minimal residual disease in acute leukemia," Blood Jul. 1, 1990;76(1):163-71.

Campana D, et al., "Human B cell development. I. Phenotypic differences of B lymphocytes in the bone marrow and peripheral lymphoid tissue," J Immunol. Mar. 1, 1985;134(3):1524-30.

Campana D, et al., "Leukemia diagnosis and testing of complement-fixing antibodies for bone marrow purging in acute lymphoid leukemia," Blood. Dec. 1, 1986;68(6):1264-71.

Campana D. et al., "4-1BB chimeric antigen receptors," Cancer J. Mar. 1, 2014;20(2):134-40.

Campana D, "Chimeric antigen receptor technology: a breakthrough in immuno-oncology," Medicographia. 2015;37:280-6.

Campana D, "Making Headway," Asia-Pacific Biotech News Jun. 2008;12(8):20-3.

Campana D, et al., "The expression of T cell receptor-associated proteins during T cell ontogeny in man," J Immunol. Jan. 1, 1989;142(1):57-66.

Cartellieri M, et al., "Chimeric antigen receptor-engineered T cells for immunotherapy of cancer," J Biomed Biotechnol. 2010;2010. :956304.

Cartellieri M, et al., "A novel Ex Vivo isolation and expansion procedure for chimeric antigen receptor engrafted human T cells," PLoS One. Apr. 3, 2014;9(4):e93745.

Cebecauer M, et al., "CD8+ cytotoxic T lymphocyte activation by soluble major histocompatibility complex)-peptide dimers," J Biol Chem. Jun. 24, 2005;280(25):23820-8.

Chamorro LM, *Adverse immune response in previously untreated patients infected with the human immunodeficiency virus initiating highly active antiretroviral therapy (HAART): prevalence factors, predictors, and clinical evolution* (Doctoral dissertation, Thesis.) Complutense University of Madrid School of Medicine; 2010.

Chang YH, et al., "Increasing the antineoplastic potential of natural killer cells with a chimeric receptor activated by NKG2D ligands," Oncoimmunology. Jul. 1, 2013;2(7):e24899.

Chang YH, et al., "A chimeric receptor with NKG2D specificity enhances natural killer cell activation and killing of tumor cells," Cancer Res. Mar. 15, 2013;73(6):1777-86.

Chen Z, et al., "GRB2 interaction with the ecotropic murine leukemia virus receptor, mCAT-1, controls virus entry and is stimulated by virus binding," J Virol. Feb. 1, 2012;86(3):1421-32.

Cheng M, et al., "Natural killer cell lines in tumor immunotherapy," Front Med. Mar. 2012;6(1):56-66.

Cheok MH, et al., "Genetic Polymorphism in the Promoter Region of the beta-2 Adrenergic Receptor Are Associated with the Early Response of Acte Lymphoblastic Leukemia to Chemotherapy," Blood Nov. 16, 2004;104(11):1959.

(56) References Cited

OTHER PUBLICATIONS

Cho D, et al., "Cytotoxicity of activated natural killer cells against pediatric solid tumors," Clin Cancer Res. Aug. 1, 2010;16(15):3901-9.

Conley ME, et al., "Hyper IgM syndrome associated with defective CD40-mediated B cell activation," J Clin Invest. Oct. 1, 1994;94(4):1404-9.

Cooper LJ, et al., "Transfer of specificity for human immunodeficiency virus type 1 into primary human T lymphocytes by introduction of T-cell receptor genes," J Virol. Sep. 1, 2000;74(17):8207-12.

Costa GL, et al., "Targeting rare populations of murine antigen-specific T lymphocytes by retroviral transduction for potential application in gene therapy for autoimmune disease," J Immunol. Apr. 1, 2000;164(7):3581-90.

Coustan-Smith E, Kitanaka A, Pui CH, McNinch L, Evans WE, Raimondi SC, Behm FG, Aricò M, Campana D. Clinical relevance of BCL-2 overexpression in childhood acute lymphoblastic leukemia, Blood. Feb. 1, 1996;87(3):1140-6.

Coustan-Smith E, et al., "Use of peripheral blood instead of bone marrow to monitor residual disease in children with acute lymphoblastic leukemia," Blood. Oct. 1, 2002;100(7):2399-402.

Coustan-Smith E, et al., "Minimal disseminated disease in childhood T-cell lymphoblastic lymphoma: a report from the children's oncology group," J Clin Oncol. Jul. 20, 2009;27(21):3533-9.

Daly T, et al., "Recognition of human colon cancer by T cells transduced with a chimeric receptor gene," Cancer Gene Ther. Feb. 2000;7(2):284-91.

Darcy PK, et al., "Redirected perforin-dependent lysis of colon carcinoma by ex vivo genetically engineered CTL," J Immunol. Apr. 1, 2000;164(7):3705-12.

Davies DM, et al., "Adoptive T-cell immunotherapy of cancer using chimeric antigen receptor-grafted T cells," Arch Immunol Ther Exp (Warsz). Jun. 1, 2010;58(3):165-78.

Deeks SG, et al., "A phase II randomized study of HIV-specific T-cell gene therapy in subjects with undetectable plasma viremia on combination antiretroviral therapy," Mol Ther. Jun. 1, 2002;5(6):788-97.

Dey B, et al., "Toward an HIV Cure Based on Targeted Killing of Infected Cells: Different Approaches Against Acute Versus Chronic Infection," Curr Opin HIV AIDS. May 2015;10(3):207-13.

Didigu C, et al., "Gene Therapy Targeting HIV Entry," Viruses. Mar. 21, 2014;6(3):1395-409.

Didigu CA, "Therapeutic applications and specificity of action of designer nucleases for precision genome engineering," (Thesis) University of Pennsylvania; (2015).

Dorfman JR, et al., "MHC-dependent survival of naive T cells? A complicated answer to a simple question," Microbes Infection. Apr. 1, 2002;4(5):547-54.

Dropulic B, et al., "Gene-based immunotherapy for human immunodeficiency virus infection and acquired immunodeficiency syndrome," Hum Gene Ther. Jun. 1, 2006;17(6):577-88.

Dunbar CE, "Blood's 70th anniversary: CARs on the Blood highway." Blood Jul. 7, 2016;128(1): 1-3.

Egerer L, et al., Gene therapy for HIV-1 infection. In: Tang Y-W, editor. Recent Translational Research in HIV/AIDS. In Tech: 2011; 431-56.

Erst B, et al., "The peptide ligands mediating positive selection in the thymus control T cell survival and homeostatic proliferation in the periphery," Immunity. Aug. 1999;11(2):173-81.

Farson D, et al., "Large-scale manufacturing of safe and efficient retrovirus packaging lines for use in immunotherapy protocols," J Gene Med. May 1999;1(3):195-209.

Farson D, et al., "A new-generation stable inducible packaging cell line for lentiviral vectors," Hum Gene Ther. May 20, 2001;12(8):981-97.

Finney HM, et al., "Activation of Resting Human Primary T Cells with Chimeric Receptors: Costimulation from CD28, Inducible Costimulator, CD134, and CD137 in Series with Signals from the TCRζ chain," J Immunol. Jan. 1, 2004;172(1):104-13.

Fitzer-Attas CJ, et al., "Tyrosine kinase chimeras for antigen-selective T-body therapy," Adv Drug Deliv Rev. Apr. 6, 1998;31(1-2):171-82.

Froelich CJ, et al., "Lymphocyte granule-mediated apoptosis: matters of viral mimicry and deadly proteases," Immunol Today. Jan. 1, 1998;19(1):30-6.

Fujisaki Hiroyuki, et al., "Sustained Expansion of Human Natural Killer Cells for Leukemia Therapy." Blood (2006):3719.

Fujisaki H, et al., "Replicative potential of human natural killer cells," Br J Haematol. Jun. 2009;145(5):606-13.

Imai, C. et al., "A Novel Method for Propagating Primary Natural Killer (NK) Cells Allows Highly Efficient Expression of Anti-CD19 Chimeric Receptors and Generation of Powerful Cytotoxicity Against NK-Resistant Acute Lymphoblastic Leukemia Cells," Blood (2004):306.

Imal C, et al., "Genetic modification of primary natural killer cells overcomes inhibitory signals and induces specific killing of leukemic cells," Blood. Jul. 1, 2005;106(1):376-83.

Cho D, et al., "Expansion and activation of natural killer cells for cancer immunotherapy," The Korean J Lab Med. Apr. 1, 2009;29(2):89-96.

Altvater B et al., 2B4 (CD244) signaling by recombinant antigen-specific chimeric receptors costimulates natural killer cell activation to leukemia and neuroblastoma cells. Clinical Cancer Research. Aug. 1, 2009;15(15):4857-66.

Li L, et al., "Expression of chimeric antigen receptors in natural killer cells with a regulatory-compliant non-viral method," Cancer Gene Ther. Mar. 2010;17(3):147-54.

Shook DR, er al., "Natural killer cell engineering for cellular therapy of cancer. Tissue antigens," Dec. 2011;78(6):409-15.

Shimasaki N, et al., "A clinically adaptable method to enhance the cytotoxicity of natural killer cells against B-cell malignancies," Cytotherapy. Aug. 1, 2012;14(7):830-40.

Shimasaki N, et al., "Natural killer cell reprogramming with chimeric immune receptors," Synthetic Messenger RNA and Cell Metabolism Modulation Methods Mol Biol. 2013;969:203-220.

Kamiya T, et al., "Expanded and activated natural killer cells for immunotherapy of hepatocellular carcinoma," Cancer Immunol Res. Jul. 2016;574-81.

Imai C, et al., "Genetic Modification of Natural Killer Cells for Leukemia Therapies," Anti-Inflammatory & Anti-Allergy Agents in Medicinal Chemistry (Formerly Current Medicinal Chemistry-Anti-Inflammatory and Anti-Allergy Agents). May 1, 2007;6(2):101-8.

Moisini I. "Humanized Chimeric Receptors in the Therapy of Multiple Sclerosis," (Thesis) University of Tennessee; 2007.

Wayne A, et al., "Monoclonal antibodies and immunotoxins as new therapeutic agents for childhood acute lymphoblastic leukemia," Amer Soc Clin Oncol. 2007;596-601.

Tassev D.V., *Generation and use of HLA-A2-restricted, peptide-specific monoclonal antibodies and chimeric antigen receptors.* (Thesis) Gernster Sloan Kettering Graduate School of Biomedical Sciences, 2011.

Xu Jing. *Viral and Plasmid Transduction Systems: Methods to Modify Immune Cells for Cancer Immunotherapy.* (Thesis) Uppsala University, 2011.

Hombach AA, et al., The weal and woe of costimulation in the adoptive therapy of cancer with chimeric antigen receptor (CAR)-redirected T cells. Curr Mol Med. Aug. 1, 2013;13(7):1079-88.

Torikai H, et al., "A foundation for" universal "T-cell based immunotherapy: T-cells engineered to express a CD19-specific chimerio-antigen-receptor and eliminate expression of endogenous TCR," Blood. Jun. 14, 2012;116(24):5697-705.

Markiewicz MA, et al., "Long-term T cell memory requires the surface expression of self-peptide/major histocompatibility complex molecules," Proc Natl Acad Sci USA. Mar. 17, 1998;95(6):3065-70.

Viret C, et al., "Designing and maintaining the mature TCR repertoire: the continuum of self-peptide: self-MHC complex recognition," Immunity. May 1, 1999;10(5):559-68.

Witherden D, et al., "Tetracycline-controllable selection of CD4+ T cells: half-life and survival signals in the absence of major histocompatibility complex class II molecules," J Exp Med. Jan. 17, 2000;191(2):355-64.

(56)                     References Cited

OTHER PUBLICATIONS

Obst R, et al., "Antigen persistence is required throughout the expansion phase of a CD4+ T cell response," J Exp Med. May 16, 2005;201(10):1555-65.

Takada K, et al., "Self—class I MHC molecules support survival of naive CD8 T cells, but depress their functional sensitivity through regulation of CD8 expression levels," J Exp Med. Sep. 28, 2009;206(10):2253-69.

Kirberg J, et al., "Peripheral T cell survival requires continual ligation of the T cell receptor to major histocompatibility complex-encoded molecules," J Exp Med. Oct. 20, 1997;186(8):1269-75.

Seddon B, et al., "Long-term survival but impaired homeostatic proliferation of naive T cells in the absence of.,56lck," Science. Oct. 6, 2000;290(5489):127-31.

Seddon B, et al., "TCR signals mediated by Sro family kinases are essential for the survival of naive T cells," J Immunol. Sep. 15, 2002;169(6):2997-3005.

Tanchot C, et al., "Differential requirements for survival and pro-liferation of CD8 naive or memory T cells," Science. Jun. 27, 1997;276(5321):2057-62.

Markiewicz MA, et al., "Death of peripheral CD8+ T cells in the absence of MHC class I is Fas-dependent and not blocked by Bcl-xL," Eur J Immunol. Oct. 2003;33(10):2917-26.

Boyman O, et al., "A major histocompatibility complex class I—dependent subset of memory phenotype CD8+ cells," J Exp Med. Jul. 10, 2006;203(7):1817-25.

Takeda S, et al., "MHC class II molecules are not required for survival of newly generated CD4+ T cells, but affect their long-term life span," Immunity. Sep. 1, 1996;5(3):217-28.

Brocker T., "Survival of mature CD4 T lymphocytes is dependent on major histocompatibility complex class II—expressing dendritic cells," J Exp Med. Oct. 20, 1997;186(8):1223-32.

Rooke R, et al., "Targeted complementation of MHC class II deficiency by intrathymic delivery of recombinant adenoviruses," Immunity. Jul. 1, 1997;7(1):123-34.

Kassiotis G, et al., "Impairment of immunological memory in the absence of MHC despite survival of memory T cells," Nat Immunol. Mar. 2002;3(3):244-50.

Huppa JB, et al., "Continuous T cell receptor signaling required for synapse maintenance and full effector potential," Nat Immunol. Aug. 2003;4(8):749-55.

Bhandoola A, et al., "Peripheral expression of self-MHC-II influ-ences the reactivity and self-tolerance of mature CD4+ T cells: evidence from a lymphopenic T cell model," Immunity. Oct. 1, 2002;17(4):425-36.

Fischer UB, et al., "MHC class II deprivation impairs CD4 T cell motility and responsiveness to antigen-bearing dendritic cells in vivo," Proc Natl Acad Sci USA. Apr. 24, 2007;104(17):7181-6.

Isaaz S, et al., "Serial killing by cytotoxic T lymphocytes: T cell receptor triggers degranulation, re-filling of the lytic granules and secretion of lytic proteins via a non-granule pathway," Eur J Immunol. Apr. 1995;25(4):1071-9.

Berg NN, et al., "Sustained TCR signaling is required for mitogen-activated protein kinase activation and degranulation by cytotoxic T lymphocytes," J Immunol. Sep. 15, 1998;161(6):2919-24.

Hudrisier D, et al., "Cutting edge: CTLs rapidly capture membrane fragments from target cells in a TCR signaling-dependent manner," J Immunol. Mar. 15, 2001;166(6):3645-9.

Doucey MA, et al., "CTL activation is induced by cross-linking of TCR/MHC-peptide-CD8/p56lck adducts in rafts," Eur J Immunol. May 2001;31(5):1561-70.

Kassiotis G, et al., "Involvement of avidity for major histocompat-ibility complex in homeostasis of naive and memory T cells," J Exp Med. Apr. 21, 2003;197(8):1007-16.

Lee KH, et al., T cell receptor signaling precedes immunological synapse formation. Science. Feb. 22, 2002;295(5559):1539-42.

Abken H, et al., "Immune response manipulation: recombinant immunoreceptors endow T-cells with predefined specificity," Curr Pharm Des. Sep. 1, 2003;9(24):1992-2001.

Bahceci E, et al., "Immunotherapy of B Cell Malignancies Using Transiently Redirected Cytotoxic T Cells," Blood Nov. 16, 2007;110(11):2750.

Beecham EJ, et al., "Coupling CD28 co-stimulation to immuno-globulin T-cell receptor molecules: the dynamics of T-cell prolif-eration and death," J Immunother. Nov. 1, 2000;23(6):631-42.

Berger C, et al., "Genetic modification of T cells for immunotherapy," Expert Opin Biol Ther. Aug. 1, 2007;7(8):1167-82.

Bitton N, et al., "Gene therapy approaches to HIV-infection: immu-nological strategies: use of T bodies and universal receptors to redirect cytolytic T-cells," Front Biosci. Apr. 1, 1999;4:D386-93.

Blankson JN, et al., "The challenge of viral reservoirs in HIV-1 infection," Annu Rev Med. Feb. 2002;53(1):557-93.

Bohne F, et al., "T-cell therapy as a therapeutic option for chronic hepatitis B," J Viral Hepat. Nov. 2007;14:45-50.

Okamoto S, et al., Improved expression and reactivity of transduced tumor-specific TCRs in human lymphocytes by specific silencing of endogenous TCR. Cancer Res. Dec. 1, 2009;69(23):9003-11.

Chan SM, et al., "Single-cell analysis of siRNA-mediated gene silencing using multiparameter flow cytometry," Cytometry Part A: Feb. 2006;69(2):59-65.

Imai C, et al., "Genetic modification of T cells for cancer therapy," J Biol Regul Homeost Agents. Jan. 1, 2004;18:62-71.

Kambayashi T, et al., "IL-2 down-regulates the expression of TCR and TCR-associated surface molecules on CD8+ T cells," Eur J Immunol. Nov. 1, 2001;31(11):3248-54.

Irving BA, et al., "The cytoplasmic domain of the T cell receptor ζ chain is sufficient to couple to receptor-associated signal transduc-tion pathways," Cell. Mar. 8, 1991;64(5):891-901.

Levin SD, et al., "A dominant-negative transgene defines a role for p56lck in thymopoiesis," EMBO J. Apr. 1993;12(4):1671-80.

Wu J et al., "A functional T-cell receptor signaling pathway is required for p95vav activity," Mol Cell Biol. Aug. 1, 1995;15(8):4337-46.

Martinius, H. O. *Präklinische Untersuchungen zur Gentherapie der HIV-Infektion mit dem retroviralen Vektor M87o (Preclinical exami-nations on genetherapy of HIV infection with the retroviral vector M870). Diss. Thesis.)* Goethe University Frankfurt, 2007.

Gobbi M, et al., "Functional behaviour and immunological pheno-type of circulating B lymphocytes in multiple myeloma. Studies with pokeweed mitogen," Clin Exp Immunol. Dec. 1984;58(3):625.

Kitanaka A, et al., "CD38-mediated signaling events in murine pro-B cells expressing human CD38 with or without its cytoplasmic domain," J Immunol. Feb. 15, 1999;162(4):1952-8.

Cheok MH, et al., "Genetic Polymorphisms in the Promoter Region of the beta-2 Adrenergic Receptor Are Associated with the Early Response of Acute Lymphoblastic Leukemia to Chemotherapy," Blood (2004): 1959-1959.

De Riva A, et al., "Noncognate interaction with MHC class II molecules is essential for maintenance of T cell metabolism to establish optimal memory CD4 T cell function," J Immunol. May 1, 2007;178(9):5488-95.

Kirberg J, et al., Peripheral T cell survival requires continual ligation of the T cell receptor to major histocompatibility complex—encoded molecules. Journal of Experimental Medicine. Oct. 20, 1997;186(8):1269-75.

Wu et al., "A functional T-cell receptor signaling pathway is required for p95vav activity," Mol Cell Biol. Aug. 1995:15(8):4337-46.

Brandt CS, et al., "The B7 family member B7-H6 is a tumor cell ligand for the activating natural killer cell receptor NKp30 in humans," J Exp Med. Jul. 6, 2009;206(7):1495-503.

Martinius HO. Prakinishe Untersuchungen zur Gentherapie der HIV-infektion mit dem retroviralen Vektor M87o ) Preclinical examinations on gentherapy of HIV infecton with the retroviral vector M870). (Thesis) Goethe University Frankfurt; 2007.

Gobbi M, et al., "Functional behaviour and immunological pheno-type of circulating B lymphocytes in multiple myeloma. Studies with pokeweed mitogen" Clin Exp Immunology. Dec. 1984;58(3):625-30.

* cited by examiner

EX  TM  CYP wtNKp30

NKp30-CD3ζ

NKp30-CD28-CD3ζ

EX: extracellular domain
TM: transmembrane domain
CYP: cytoplasmic domain

NKp30

FcRγ

CD3ζ

ITAM

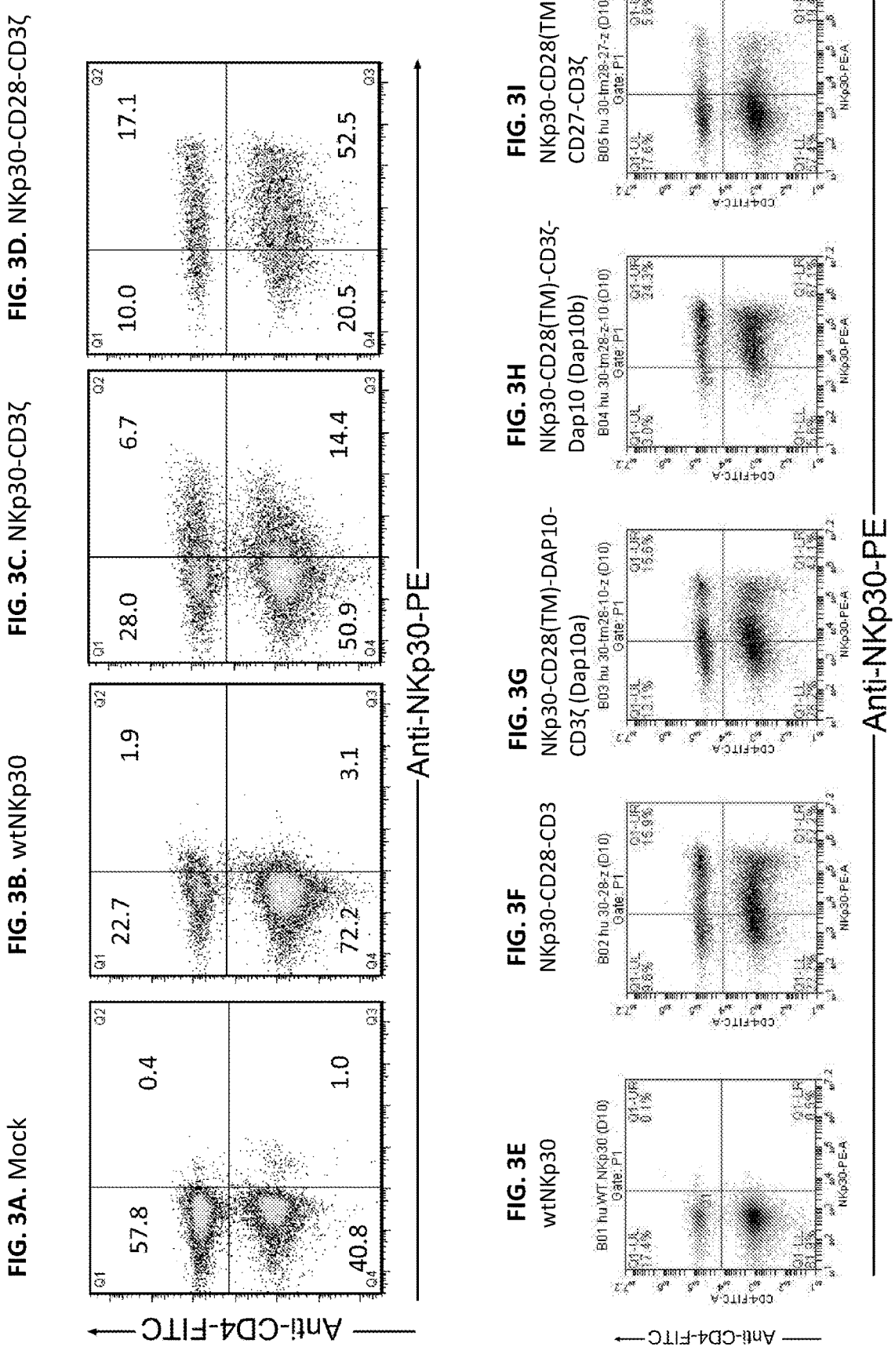

NKp30-mIgG2a-APC

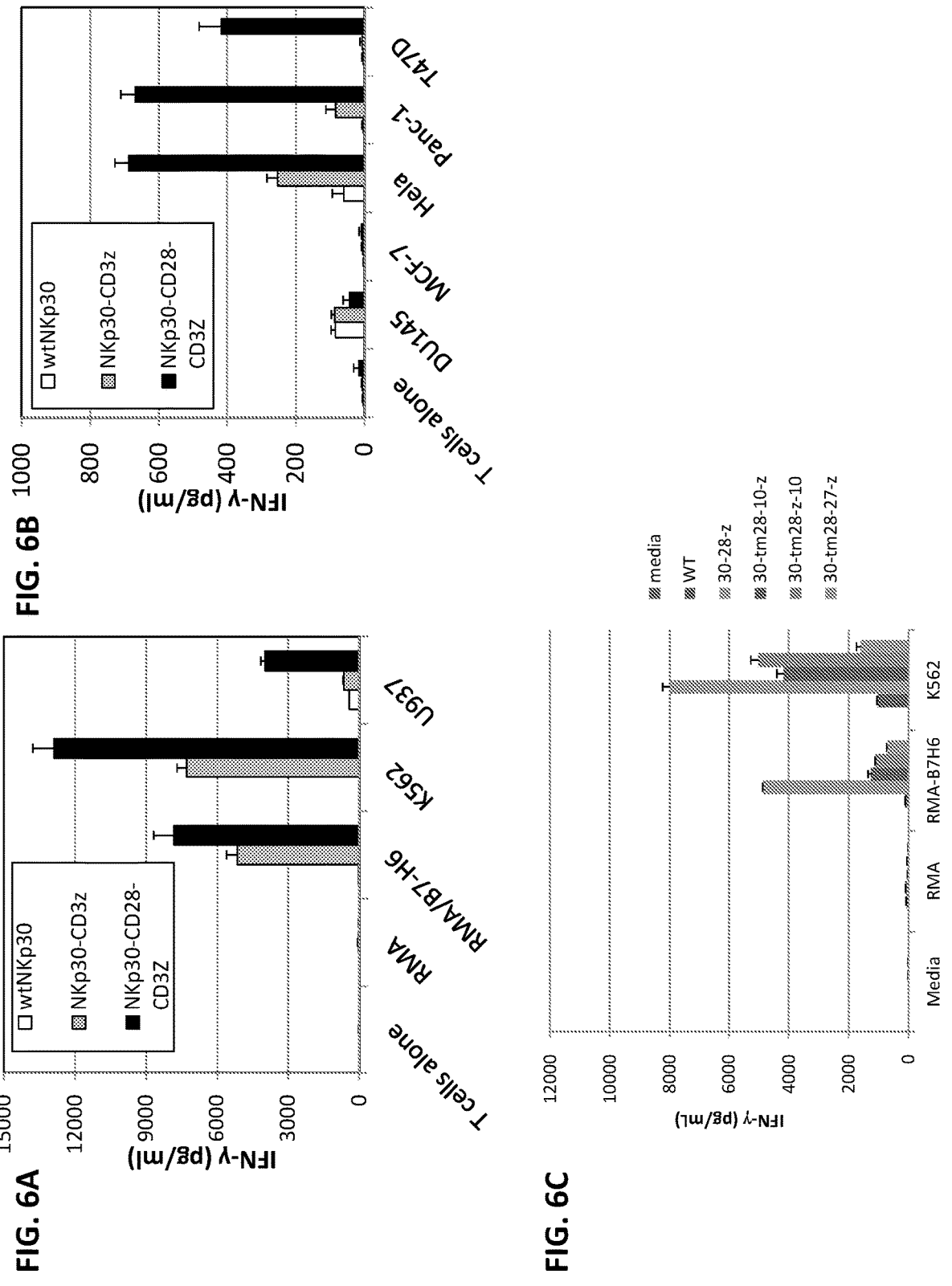

NKp30-Cd28-3ζ     NKp30-CD3ζ     wtNKp30     Mock

Anti-NKp30-PE

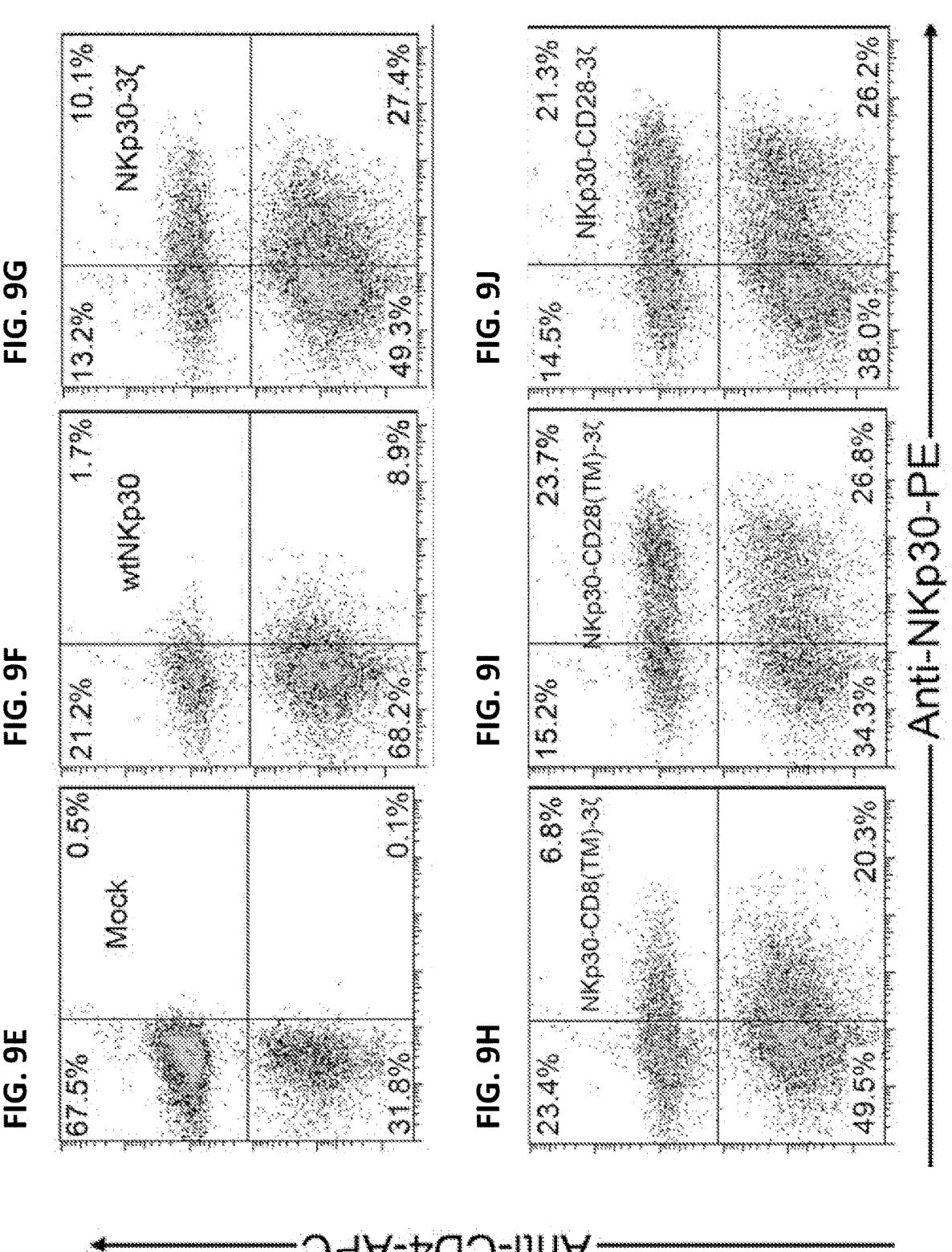

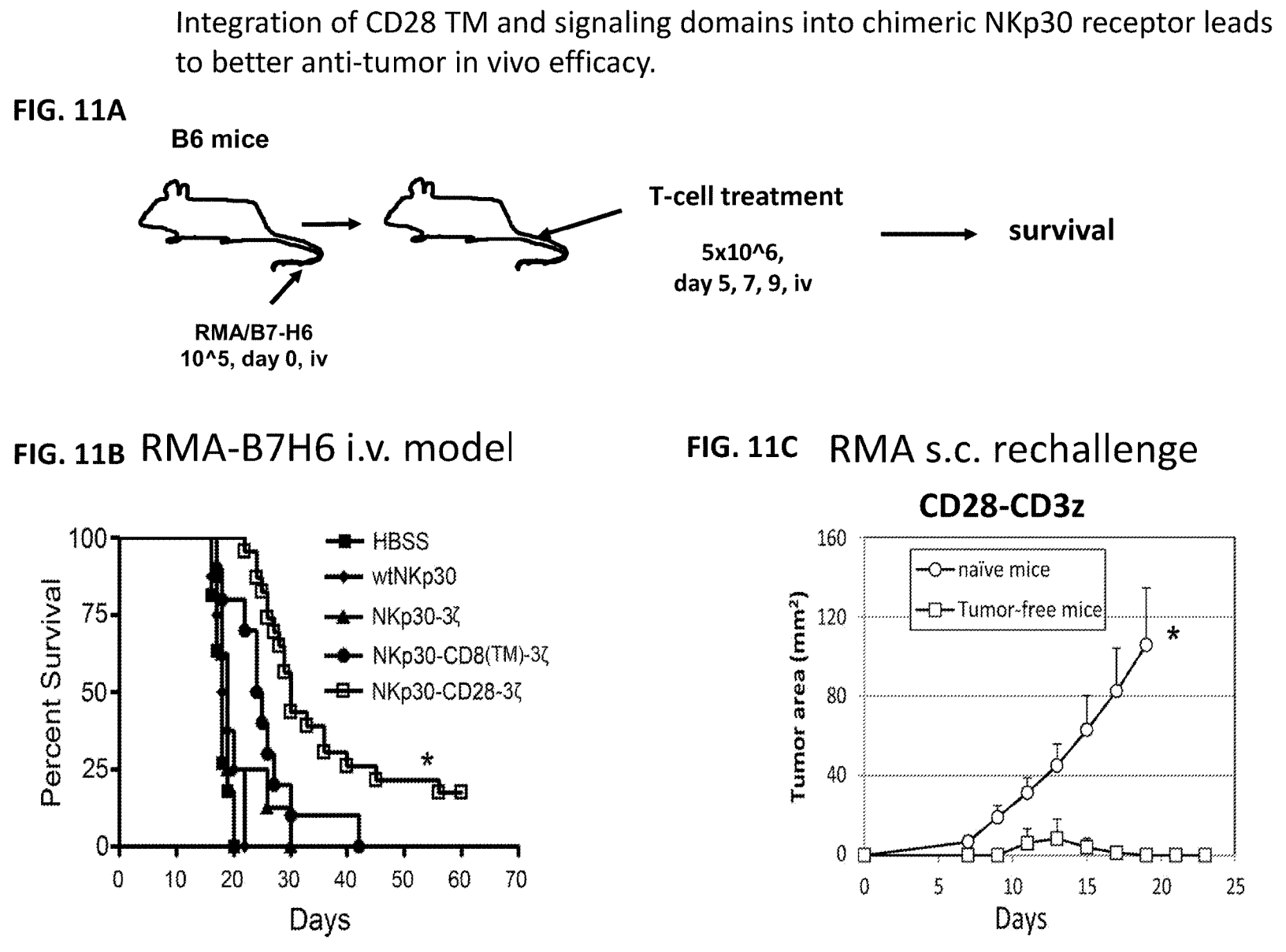

Integration of CD28 TM and signaling domains into chimeric NKp30 receptor leads to better anti-tumor in vivo efficacy.

FIG. 11A

B6 mice

T-cell treatment

5x10^6, day 5, 7, 9, iv

→ survival

RMA/B7-H6 10^5, day 0, iv

FIG. 11C RMA s.c. rechallenge

CD28-CD3z naïve mice
Tumor-free mice

Tumor area (mm²)

Days

FIG. 11B RMA-B7H6 i.v. model

HBSS
wtNKp30
NKp30-3ζ
NKp30-CD8(TM)-3ζ
NKp30-CD28-3ζ

Percent Survival

Days

Chimeric NKp30 Receptor Constructs

All fragments are human genes

FIG. 15. wtNKp30 (SEQ ID NO: 59)

| | |
|---|---|
| Signal peptide | MAWMLLLILIMVHPGSCA |
| NKp30 extracellular domain | LWVSQPPEIRTLEGSSAFLPCSFNASQGRLAIGSVTWFRDEVVPGKEVRNGTPEFRGRLAPLASSRFLHDHQAELHIRDVRGHDASIYVCRVEVLGLGVGTGNGTRLVVEKEHPQLG |
| NKp30 TM domain | AGTVLLLRAGFYAVSFLSVAV |
| NKp30 CYP domain | GSTVYYQGKCLTWKGPRRQLPAVVPAPLPPPCGSSAHLLPPVPGG |

FIG. 16. NKp30-ζ (SEQ ID NO: 60)

| | |
|---|---|
| Signal peptide | MAWMLLLILIMVHPGSCA |
| NKp30 extracellular domain | LWVSQPPEIRTLEGSSAFLPCSFNASQGRLAIGSVTWFRDEVVPGKEVRNGTPEFRGRLAPLASSRFLHDHQAELHIRDVRGHDASIYVCRVEVLGLGVGTGNGTRLVVEKEHPQLG |
| CD3ζ TM domain | ASLCYLLDGILFIYGVILTALFL |
| CD3ζ CYP domain | RVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR |

FIG. 17. NKp30-CD28-ζ (SEQ ID NO: 61)

| | |
|---|---|
| Signal peptide | MAWMLLLILIMVHPGSCA |
| NKp30 extracellular domain | LWVSQPPEIRTLEGSSAFLPCSFNASQGRLAIGSVTWFRDEVVPGKEVRNGTPEFRGRLAPLASSRFLHDHQAELHIRDVRGHDASIYVCRVEVLGLGVGTGNGTRLVVEKEHPQLG |
| CD28 TM+CYP domain | ASFWVLVVVGGVLACYSLLVTVAFIIFWVRSKRSRLLHSDYMNMTPRRPGPTRKHYQPYAPPRDFAAYRSKL |
| CD3ζ CYP domain | RVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR |

FIG. 18. NKp30-CD28(TM)-ζ (SEQ ID NO: 62)

| | |
|---|---|
| Signal peptide | MAWMLLLILIMVHPGSCA |
| NKp30 extracellular domain | LWVSQPPEIRTLEGSSAFLPCSFNASQGRLAIGSVTWFRDEVVPGKEVRNGTPEFRGRLAPLASSRFLHDHQAELHIRDVRGHDASIYVCRVEVLGLGVGTGNGTRLVVEKEHPQLG |
| CD28 TM domain | ASFWVLVVVGGVLACYSLLVTVAFIIFWVRSKKL |
| CD3ζ CYP domain | RVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR |

FIG. 19. NKp30-CD8-ζ (SEQ ID NO: 63)

| Signal peptide | MAWMLLLILIMVHPGSCA |
| NKp30 extracellular domain | LWVSQPPEIRTLEGSSAFLPCSFNASQG RLAIGSVTWFRDEVVPGKEVRNGTPEF RGRLAPLASSRFLHDHQAELHIRDVRG HDASIYVCRVEVLGLGVGTGNGTRLV VEKEHPQLG |
| CD8 TM domain | ASIYIWAPLAGTCGVLLLSLVITKL |
| CD3ζ CYP domain | RVKFSRSADAPAYQQGQNQLYNELNL GRREEYDVLDKRRGRDPEMGGKPQRR KNPQEGLYNELQKDKMAEAYSEIGMK GERRRGKGHDGLYQGLSTATKDTYDA LHMQALPPR |

FIG. 20. 30-tm28-10-3ζ protein sequence (SEQ ID NO: 65)

| NKp30 signal peptide and EC | MAWMLLLILIMVHPGSCALWVSQPPEI RTLEGSSAFLPCSFNASQGRLAIGSVT WFRDEVVPGKEVRNGTPEFRGRLAPL ASSRFLHDHQAELHIRDVRGHDASIYV CRVEVLGLGVGTGNGTRLVVEKEHPQ LG |
| Linker (NheI) | AS |
| CD28 TM | FWVLVVVGGVLACYSLLVTVAFIIFWV RSKRS |
| Dap10 CYP | LCARPRRSPAQEDGKVYINMPGRG |
| Linker (HindIII) | KL |
| CD3ζ CYP | RVKFSRSADAPAYQQGQNQLYNELNL GRREEYDVLDKRRGRDPEMGGKPRRK NPQEGLYNELQKDKMAEAYSEIGMKG ERRRGKGHDGLYQGLSTATKDTYDAL HMQALPPR |

FIG. 22. 30-tm28-27-3ζ protein sequence (SEQ ID NO: 69)

| Region | Sequence |
|---|---|
| NKp30 signal peptide and EC | MAWMLLLLILIMVHPGSCALWVSQPPEI RTLEGSSAFLPCSFNASQGRLAIGSVT WFRDEVVPGKEVRNGTPEFRGRLAPL ASSRFLHDHQAELHIRDVRGHDASIYV CRVEVLGLGVGTGNGTRLVVEKEHPQ LG |
| Linker (NheI) | AS |
| CD28 TM | FWVLVVVGGVLACYSLLVTVAFIIFWV RSKRS |
| Linker (XhoI) | LE |
| CD27 CYP | QRRKYRSNKGESPVEPAEPCRYSCPRE EEGSTIPIQEDYRKPEPACSP |
| Linker (HindIII) | KL |
| CD3ζ CYP | RVKFSRSADAPAYQQGQNQLYNELNL GRREEYDVLDKRRGRDPEMGGKPRRK NPQEGLYNELQKDKMAEAYSEIGMKG ERRRGKGHDGLYQGLSTATKDTYDAL HMQALPPR |

FIG. 21. 30-tm28-3ζ-10 protein sequence (SEQ ID NO: 67)

| Region | Sequence |
|---|---|
| NKp30 signal peptide and EC | MAWMLLLLILIMVHPGSCALWVSQPPEI RTLEGSSAFLPCSFNASQGRLAIGSVT WFRDEVVPGKEVRNGTPEFRGRLAPL ASSRFLHDHQAELHIRDVRGHDASIYV CRVEVLGLGVGTGNGTRLVVEKEHPQ LG |
| Linker (NheI) | AS |
| CD28 TM | FWVLVVVGGVLACYSLLVTVAFIIFWV RSKRS |
| Linker (HindIII) | KL |
| CD3ζ CYP | RVKFSRSADAPAYQQGQNQLYNELNL GRREEYDVLDKRRGRDPEMGGKPRRK NPQEGLYNELQKDKMAEAYSEIGMKG ERRRGKGHDGLYQGLSTATKDTYDAL HMQALPPR |
| Dap10 CYP | LCARPRRSPAQEDGKVYINMPGRG |

SEQUENCE LISTING

```
Sequence total quantity: 128
SEQ ID NO: 1              moltype = AA  length = 164
FEATURE                   Location/Qualifiers
source                    1..164
                          mol_type = protein
                          organism = Homo sapiens
SEQUENCE: 1
MKWKALFTAA ILQAQLPITE AQSFGLLDPK LCYLLDGILF IYGVILTALF LRVKFSRSAD   60
APAYQQGQNQ LYNELNLGRR EEYDVLDKRR GRDPEMGGKP QRRKNPQEGL YNELQKDKMA  120
EAYSEIGMKG ERRRGKGHDG LYQGLSTATK DTYDALHMQA LPPR                   164

SEQ ID NO: 2              moltype = AA  length = 21
FEATURE                   Location/Qualifiers
source                    1..21
                          mol_type = protein
                          organism = Homo sapiens
SEQUENCE: 2
MKWKALFTAA ILQAQLPITE A                                             21

SEQ ID NO: 3              moltype = AA  length = 143
FEATURE                   Location/Qualifiers
source                    1..143
                          mol_type = protein
                          organism = Homo sapiens
SEQUENCE: 3
QSFGLLDPKL CYLLDGILFI YGVILTALFL RVKFSRSADA PAYQQGQNQL YNELNLGRRE   60
EYDVLDKRRG RDPEMGGKPQ RRKNPQEGLY NELQKDKMAE AYSEIGMKGE RRRGKGHDGL  120
YQGLSTATKD TYDALHMQAL PPR                                          143
```

```
SEQ ID NO: 4            moltype = AA  length = 21
FEATURE                 Location/Qualifiers
source                  1..21
                        mol_type = protein
                        organism = Homo sapiens
SEQUENCE: 4
LCYLLDGILF IYGVILTALF L                                        21

SEQ ID NO: 5            moltype = AA  length = 113
FEATURE                 Location/Qualifiers
source                  1..113
                        mol_type = protein
                        organism = Homo sapiens
SEQUENCE: 5
RVKFSRSADA PAYQQGQNQL YNELNLGRRE EYDVLDKRRG RDPEMGGKPQ RRKNPQEGLY  60
NELQKDKMAE AYSEIGMKGE RRRGKGHDGL YQGLSTATKD TYDALHMQAL PPR         113

SEQ ID NO: 6            moltype = AA  length = 163
FEATURE                 Location/Qualifiers
source                  1..163
                        mol_type = protein
                        organism = Homo sapiens
SEQUENCE: 6
MKWKALFTAA ILQAQLPITE AQSFGLLDPK LCYLLDGILF IYGVILTALF LRVKFSRSAD  60
APAYQQGQNQ LYNELNLGRR EEYDVLDKRR GRDPEMGGKP RRKNPQEGLY NELQKDKMAE  120
AYSEIGMKGE RRRGKGHDGL YQGLSTATKD TYDALHMQAL PPR                    163

SEQ ID NO: 7            moltype = AA  length = 15
FEATURE                 Location/Qualifiers
source                  1..15
                        mol_type = protein
                        organism = Homo sapiens
SEQUENCE: 7
MKWKALFTAA ILQAQ                                               15

SEQ ID NO: 8            moltype = AA  length = 146
FEATURE                 Location/Qualifiers
source                  1..146
                        mol_type = protein
                        organism = Homo sapiens
SEQUENCE: 8
LPITEAQSFG LLDPKLCYLL DGILFIYGVI LTALFLRVKF SRSADAPAYQ QGQNQLYNEL  60
NLGRREEYDV LDKRRGRDPE MGGKPRRKNP QEGLYNELQK DKMAEAYSEI GMKGERRRGK  120
GHDGLYQGLS TATKDTYDAL HMQALP                                   146

SEQ ID NO: 9            moltype = AA  length = 21
FEATURE                 Location/Qualifiers
source                  1..21
                        mol_type = protein
                        organism = Homo sapiens
SEQUENCE: 9
LCYLLDGILF IYGVILTALF L                                        21

SEQ ID NO: 10           moltype = AA  length = 112
FEATURE                 Location/Qualifiers
source                  1..112
                        mol_type = protein
                        organism = Homo sapiens
SEQUENCE: 10
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR         112

SEQ ID NO: 11           moltype = AA  length = 201
FEATURE                 Location/Qualifiers
source                  1..201
                        mol_type = protein
                        organism = Homo sapiens
SEQUENCE: 11
MAWMLLLILI MVHPGSCALW VSQPPEIRTL EGSSAFLPCS FNASQGRLAI GSVTWFRDEV  60
VPGKEVRNGT PEFRGRLAPL ASSRFLHDHQ AELHIRDVRG HDASIYVCRV EVLGLGVGTG  120
NGTRLVVEKE HPQLGAGTVL LLRAGFYAVS FLSVAVGSTV YYQGKCLTWK GPRRQLPAVV  180
PAPLPPPCGS SAHLLPPVPG G                                        201

SEQ ID NO: 12           moltype = AA  length = 21
FEATURE                 Location/Qualifiers
source                  1..21
                        mol_type = protein
                        organism = Homo sapiens
```

```
SEQUENCE: 12
AGTVLLLRAG FYAVSFLSVA V                                            21

SEQ ID NO: 13            moltype = AA   length = 45
FEATURE                  Location/Qualifiers
source                   1..45
                         mol_type = protein
                         organism = Homo sapiens
SEQUENCE: 13
GSTVYYQGKC LTWKGPRRQL PAVVPAPLPP PCGSSAHLLP PVPGG                  45

SEQ ID NO: 14            moltype = AA   length = 18
FEATURE                  Location/Qualifiers
source                   1..18
                         mol_type = protein
                         organism = Homo sapiens
SEQUENCE: 14
MAWMLLLILI MVHPGSCA                                                18

SEQ ID NO: 15            moltype = AA   length = 117
FEATURE                  Location/Qualifiers
source                   1..117
                         mol_type = protein
                         organism = Homo sapiens
SEQUENCE: 15
LWVSQPPEIR TLEGSSAFLP CSFNASQGRL AIGSVTWFRD EVVPGKEVRN GTPEFRGRLA  60
PLASSRFLHD HQAELHIRDV RGHDASIYVC RVEVLGLGVG TGNGTRLVVE KEHPQLG     117

SEQ ID NO: 16            moltype = AA   length = 177
FEATURE                  Location/Qualifiers
source                   1..177
                         mol_type = protein
                         organism = Homo sapiens
SEQUENCE: 16
MAWMLLLILI MVHPGSCALW VSQPPEIRTL EGSSAFLPCS FNASQGRLAI GSVTWFRDEV  60
VPGKEVRNGT PEFRGRLAPL ASSRFLHDHQ AELHIRDVRG HDASIYVCRV EVLGLGVGTG  120
NGTRLVVEKE HPQLGAGTVL LLRAGFYAVS FLSVAVGSTV YYQGKYAKST LSGFPQL     177

SEQ ID NO: 17            moltype = AA   length = 21
FEATURE                  Location/Qualifiers
source                   1..21
                         mol_type = protein
                         organism = Homo sapiens
SEQUENCE: 17
AGTVLLLRAG FYAVSFLSVA V                                            21

SEQ ID NO: 18            moltype = AA   length = 18
FEATURE                  Location/Qualifiers
source                   1..18
                         mol_type = protein
                         organism = Homo sapiens
SEQUENCE: 18
MAWMLLLILI MVHPGSCA                                                18

SEQ ID NO: 19            moltype = AA   length = 117
FEATURE                  Location/Qualifiers
source                   1..117
                         mol_type = protein
                         organism = Homo sapiens
SEQUENCE: 19
LWVSQPPEIR TLEGSSAFLP CSFNASQGRL AIGSVTWFRD EVVPGKEVRN GTPEFRGRLA  60
PLASSRFLHD HQAELHIRDV RGHDASIYVC RVEVLGLGVG TGNGTRLVVE KEHPQLG     117

SEQ ID NO: 20            moltype = AA   length = 21
FEATURE                  Location/Qualifiers
source                   1..21
                         mol_type = protein
                         organism = Homo sapiens
SEQUENCE: 20
GSTVYYQGKY AKSTLSGFPQ L                                            21

SEQ ID NO: 21            moltype = AA   length = 190
FEATURE                  Location/Qualifiers
source                   1..190
                         mol_type = protein
                         organism = Homo sapiens
SEQUENCE: 21
MAWMLLLILI MVHPGSCALW VSQPPEIRTL EGSSAFLPCS FNASQGRLAI GSVTWFRDEV  60
VPGKEVRNGT PEFRGRLAPL ASSRFLHDHQ AELHIRDVRG HDASIYVCRV EVLGLGVGTG  120
```

```
NGTRLVVEKE HPQLGAGTVL LLRAGFYAVS FLSVAVGSTV YYQGKCHCHM GTHCHSSDGP   180
RGVIPEPRCP                                                         190

SEQ ID NO: 22            moltype = AA  length = 21
FEATURE                  Location/Qualifiers
source                   1..21
                         mol_type = protein
                         organism = Homo sapiens
SEQUENCE: 22
AGTVLLLRAG FYAVSFLSVA V                                            21

SEQ ID NO: 23            moltype = AA  length = 18
FEATURE                  Location/Qualifiers
source                   1..18
                         mol_type = protein
                         organism = Homo sapiens
SEQUENCE: 23
MAWMLLLILI MVHPGSCA                                                18

SEQ ID NO: 24            moltype = AA  length = 117
FEATURE                  Location/Qualifiers
source                   1..117
                         mol_type = protein
                         organism = Homo sapiens
SEQUENCE: 24
LWVSQPPEIR TLEGSSAFLP CSFNASQGRL AIGSVTWFRD EVVPGKEVRN GTPEFRGRLA   60
PLASSRFLHD HQAELHIRDV RGHDASIYVC RVEVLGLGVG TGNGTRLVVE KEHPQLG      117

SEQ ID NO: 25            moltype = AA  length = 34
FEATURE                  Location/Qualifiers
source                   1..34
                         mol_type = protein
                         organism = Homo sapiens
SEQUENCE: 25
GSTVYYQGKC HCHMGTHCHS SDGPRGVIPE PRCP                              34

SEQ ID NO: 26            moltype = AA  length = 123
FEATURE                  Location/Qualifiers
source                   1..123
                         mol_type = protein
                         organism = Homo sapiens
SEQUENCE: 26
MLRLLLALNL FPSIQVTGNK ILVKQSPMLV AYDNAVNLSW KHLCPSPLFP GPSKPFWVLV   60
VVGGVLACYS LLVTVAFIIF WVRSKRSRLL HSDYMNMTPR RPGPTRKHYQ PYAPPRDFAA   120
YRS                                                                123

SEQ ID NO: 27            moltype = AA  length = 101
FEATURE                  Location/Qualifiers
source                   1..101
                         mol_type = protein
                         organism = Homo sapiens
SEQUENCE: 27
MLRLLLALNL FPSIQVTGKH LCPSPLFPGP SKPFWVLVVV GGVLACYSLL VTVAFIIFWV   60
RSKRSRLLHS DYMNMTPRRP GPTRKHYQPY APPRDFAAYR S                      101

SEQ ID NO: 28            moltype = AA  length = 30
FEATURE                  Location/Qualifiers
source                   1..30
                         mol_type = protein
                         organism = Homo sapiens
SEQUENCE: 28
FWVLVVVGGV LACYSLLVTV AFIIFWVRSK                                   30

SEQ ID NO: 29            moltype = AA  length = 38
FEATURE                  Location/Qualifiers
source                   1..38
                         mol_type = protein
                         organism = Homo sapiens
SEQUENCE: 29
RSRLLHSDYM NMTPRRPGPT RKHYQPYAPP RDFAAYRS                          38

SEQ ID NO: 30            moltype = AA  length = 32
FEATURE                  Location/Qualifiers
source                   1..32
                         mol_type = protein
                         organism = Homo sapiens
SEQUENCE: 30
FWVLVVVGGV LACYSLLVTV AFIIFWVRSK RS                                32
```

-continued

```
SEQ ID NO: 31              moltype = AA   length = 80
FEATURE                    Location/Qualifiers
source                     1..80
                           mol_type = protein
                           organism = Homo sapiens
SEQUENCE: 31
MLRLLLALNL FPSIQVTGNK ILVKQSPMLV AYDNAVNLSY NEKSNGTIIH VKGKHLCPSP  60
LFPGPSKPYA PPRDFAAYRS                                              80

SEQ ID NO: 32              moltype = AA   length = 235
FEATURE                    Location/Qualifiers
source                     1..235
                           mol_type = protein
                           organism = Homo sapiens
SEQUENCE: 32
MALPVTALLL PLALLLHAAR PSQFRVSPLD RTWNLGETVE LKCQVLLSNP TSGCSWLFQP  60
RGAAASPTFL LYLSQNKPKA AEGLDTQRFS GKRLGDTFVL TLSDFRRENE GYYFCSALSN  120
SIMYFSHFVP VFLPAKPTTT PAPRPPTPAP TIASQPLSLR PEACRPAAGG AVHTRGLDFA  180
CDIYIWAPLA GTCGVLLLSL VITLYCNHRN RRRVCKCPRP VVKSGDKPSL SARYV       235

SEQ ID NO: 33              moltype = AA   length = 21
FEATURE                    Location/Qualifiers
source                     1..21
                           mol_type = protein
                           organism = Homo sapiens
SEQUENCE: 33
MALPVTALLL PLALLLHAAR P                                            21

SEQ ID NO: 34              moltype = AA   length = 214
FEATURE                    Location/Qualifiers
source                     1..214
                           mol_type = protein
                           organism = Homo sapiens
SEQUENCE: 34
SQFRVSPLDR TWNLGETVEL KCQVLLSNPT SGCSWLFQPR GAAASPTFLL YLSQNKPKAA  60
EGLDTQRFSG KRLGDTFVLT LSDFRRENEG YYFCSALSNS IMYFSHFVPV FLPAKPTTTP  120
APRPPTPAPT IASQPLSLRP EACRPAAGGA VHTRGLDFAC DIYIWAPLAG TCGVLLLSLV  180
ITLYCNHRNR RRVCKCPRPV VKSGDKPSLS ARYV                             214

SEQ ID NO: 35              moltype = AA   length = 21
FEATURE                    Location/Qualifiers
source                     1..21
                           mol_type = protein
                           organism = Homo sapiens
SEQUENCE: 35
IYIWAPLAGT CGVLLLSLVI T                                            21

SEQ ID NO: 36              moltype = AA   length = 198
FEATURE                    Location/Qualifiers
source                     1..198
                           mol_type = protein
                           organism = Homo sapiens
SEQUENCE: 36
MALPVTALLL PLALLLHAAR PSQFRVSPLD RTWNLGETVE LKCQVLLSNP TSGCSWLFQP  60
RGAAASPTFL LYLSQNKPKA AEGLDTQRFS GKRLGDTFVL TLSDFRRENE GYYFCSALSN  120
SIMYFSHFVP VFLPAKPTTT PAPRPPTPAP TIASQPLSLR PEACRPAAGG AGNRRRVCKC  180
PRPVVKSGDK PSLSARYV                                               198

SEQ ID NO: 37              moltype = AA   length = 93
FEATURE                    Location/Qualifiers
source                     1..93
                           mol_type = protein
                           organism = Homo sapiens
SEQUENCE: 37
MIHLGHILFL LLLPVAAAQT TPGERSSLPA FYPGTSGSCS GCGSLSLPLL AGLVAADAVA  60
SLLIVGAVFL CARPRRSPAQ EDGKVYINMP GRG                               93

SEQ ID NO: 38              moltype = AA   length = 19
FEATURE                    Location/Qualifiers
source                     1..19
                           mol_type = protein
                           organism = Homo sapiens
SEQUENCE: 38
MIHLGHILFL LLLPVAAAQ                                               19

SEQ ID NO: 39              moltype = AA   length = 74
FEATURE                    Location/Qualifiers
source                     1..74
                           mol_type = protein
```

-continued

```
                          organism = Homo sapiens
SEQUENCE: 39
TTPGERSSLP AFYPGTSGSC SGCGSLSLPL LAGLVAADAV ASLLIVGAVF LCARPRRSPA    60
QEDGKVYINM PGRG                                                      74

SEQ ID NO: 40             moltype = AA  length = 21
FEATURE                   Location/Qualifiers
source                    1..21
                          mol_type = protein
                          organism = Homo sapiens
SEQUENCE: 40
LLAGLVAADA VASLLIVGAV F                                              21

SEQ ID NO: 41             moltype = AA  length = 24
FEATURE                   Location/Qualifiers
source                    1..24
                          mol_type = protein
                          organism = Homo sapiens
SEQUENCE: 41
LCARPRRSPA QEDGKVYINM PGRG                                           24

SEQ ID NO: 42             moltype = AA  length = 92
FEATURE                   Location/Qualifiers
source                    1..92
                          mol_type = protein
                          organism = Homo sapiens
SEQUENCE: 42
MIHLGHILFL LLLPVAAAQT TPGERSSLPA FYPGTSGSCS GCGSLSLPLL AGLVAADAVA    60
SLLIVGAVFL CARPRRSPAQ DGKVYINMPG RG                                  92

SEQ ID NO: 43             moltype = AA  length = 19
FEATURE                   Location/Qualifiers
source                    1..19
                          mol_type = protein
                          organism = Homo sapiens
SEQUENCE: 43
MIHLGHILFL LLLPVAAAQ                                                 19

SEQ ID NO: 44             moltype = AA  length = 73
FEATURE                   Location/Qualifiers
source                    1..73
                          mol_type = protein
                          organism = Homo sapiens
SEQUENCE: 44
TTPGERSSLP AFYPGTSGSC SGCGSLSLPL LAGLVAADAV ASLLIVGAVF LCARPRRSPA    60
QDGKVYINMP GRG                                                       73

SEQ ID NO: 45             moltype = AA  length = 21
FEATURE                   Location/Qualifiers
source                    1..21
                          mol_type = protein
                          organism = Homo sapiens
SEQUENCE: 45
LLAGLVAADA VASLLIVGAV F                                              21

SEQ ID NO: 46             moltype = AA  length = 113
FEATURE                   Location/Qualifiers
source                    1..113
                          mol_type = protein
                          organism = Homo sapiens
SEQUENCE: 46
MGGLEPCSRL LLLPLLLAVS GLRPVQAQAQ SDCSCSTVSP GVLAGIVMGD LVLTVLIALA    60
VYFLGRLVPR GRGAAEAATR KQRITETESP YQELQGQRSD VYSDLNTQRP YYK          113

SEQ ID NO: 47             moltype = AA  length = 21
FEATURE                   Location/Qualifiers
source                    1..21
                          mol_type = protein
                          organism = Homo sapiens
SEQUENCE: 47
GVLAGIVMGD LVLTVLIALA V                                              21

SEQ ID NO: 48             moltype = AA  length = 112
FEATURE                   Location/Qualifiers
source                    1..112
                          mol_type = protein
                          organism = Homo sapiens
SEQUENCE: 48
MGGLEPCSRL LLLPLLLAVS GLRPVQAQAQ SDCSCSTVSP GVLAGIVMGD LVLTVLIALA    60
```

```
VYFLGRLVPR GRGAAEATRK QRITETESPY QELQGQRSDV YSDLNTQRPY YK                     112

SEQ ID NO: 49          moltype = AA  length = 21
FEATURE                Location/Qualifiers
source                 1..21
                       mol_type = protein
                       organism = Homo sapiens
SEQUENCE: 49
GVLAGIVMGD LVLTVLIALA V                                                       21

SEQ ID NO: 50          moltype = AA  length = 102
FEATURE                Location/Qualifiers
source                 1..102
                       mol_type = protein
                       organism = Homo sapiens
SEQUENCE: 50
MGGLEPCSRL LLLPLLLAVS DCSCSTVSPG VLAGIVMGDL VLTVLIALAV YFLGRLVPRG             60
RGAAEAATRK QRITETESPY QELQGQRSDV YSDLNTQRPY YK                                102

SEQ ID NO: 51          moltype = AA  length = 101
FEATURE                Location/Qualifiers
source                 1..101
                       mol_type = protein
                       organism = Homo sapiens
SEQUENCE: 51
MGGLEPCSRL LLLPLLLAVS DCSCSTVSPG VLAGIVMGDL VLTVLIALAV YFLGRLVPRG             60
RGAAEATRKQ RITETESPYQ ELQGQRSDVY SDLNTQRPYY K                                 101

SEQ ID NO: 52          moltype = AA  length = 260
FEATURE                Location/Qualifiers
source                 1..260
                       mol_type = protein
                       organism = Homo sapiens
SEQUENCE: 52
MARPHPWWLC VLGTLVGLSA TPAPKSCPER HYWAQGKLCC QMCEPGTFLV KDCDQHRKAA             60
QCDPCIPGVS FSPDHHTRPH CESCRHCNSG LLVRNCTITA NAECACRNGW QCRDKECTEC             120
DPLPNPSLTA RSSQALSPHP QPTHLPYVSE MLEARTAGHM QTLADFRQLP ARTLSTHWPP             180
QRSLCSSDFI RILVIFSGMF LVFTLAGALF LHQRRKYRSN KGESPVEPAE PCRYSCPREE             240
EGSTIPIQED YRKPEPACSP                                                         260

SEQ ID NO: 53          moltype = AA  length = 21
FEATURE                Location/Qualifiers
source                 1..21
                       mol_type = protein
                       organism = Homo sapiens
SEQUENCE: 53
ILVIFSGMFL VFTLAGALFL H                                                       21

SEQ ID NO: 54          moltype = AA  length = 48
FEATURE                Location/Qualifiers
source                 1..48
                       mol_type = protein
                       organism = Homo sapiens
SEQUENCE: 54
QRRKYRSNKG ESPVEPAEPC RYSCPREEG STIPIQEDYR KPEPACSP                          48

SEQ ID NO: 55          moltype = AA  length = 255
FEATURE                Location/Qualifiers
source                 1..255
                       mol_type = protein
                       organism = Homo sapiens
SEQUENCE: 55
MGNSCYNIVA TLLLVLNFER TRSLQDPCSN CPAGTFCDNN RNQICSPCPP NSFSSAGGQR             60
TCDICRQCKG VFRTRKECSS TSNAECDCTP GFHCLGAGCS MCEQDCKQGQ ELTKKGCKDC             120
CFGTFNDQKR GICRPWTNCS LDGKSVLVNG TKERDVVCGP SPADLSPGAS SVTPPAPARE             180
PGHSPQIISF FLALTSTALL FLLFFLTLRF SVVKRGRKKL LYIFKQPFMR PVQTTQEEDG             240
CSCRFPEEEE GGCEL                                                              255

SEQ ID NO: 56          moltype = AA  length = 27
FEATURE                Location/Qualifiers
source                 1..27
                       mol_type = protein
                       organism = Homo sapiens
SEQUENCE: 56
IISFFLALTS TALLFLLFFL TLRFSVV                                                 27

SEQ ID NO: 57          moltype = AA  length = 277
FEATURE                Location/Qualifiers
source                 1..277
```

```
                              mol_type = protein
                              organism = Homo sapiens
SEQUENCE: 57
MCVGARRLGR GPCAALLLLG LGLSTVTGLH CVGDTYPSND RCCHECRPGN GMVSRCSRSQ      60
NTVCRPCGPG FYNDVVSSKP CKPCTWCNLR SGSERKQLCT ATQDTVCRCR AGTQPLDSYK     120
PGVDCAPCPP GHFSPGDNQA CKPWTNCTLA GKHTLQPASN SSDAICEDRD PPATQPQETQ     180
GPPARPITVQ PTEAWPRTSQ GPSTRPVEVP GGRAVAAILG LGLVLGLLGP LAILLALYLL     240
RRDQRLPPDA HKPPGGGSFR TPIQEEQADA HSTLAKI                             277

SEQ ID NO: 58            moltype = AA   length = 21
FEATURE                 Location/Qualifiers
source                  1..21
                        mol_type = protein
                        organism = Homo sapiens
SEQUENCE: 58
VAAILGLGLV LGLLGPLAIL L                                                21

SEQ ID NO: 59            moltype = AA   length = 201
FEATURE                 Location/Qualifiers
REGION                  1..201
                        note = Chimeric receptor
source                  1..201
                        mol_type = protein
                        organism = synthetic construct
SEQUENCE: 59
MAWMLLLILI MVHPGSCALW VSQPPEIRTL EGSSAFLPCS FNASQGRLAI GSVTWFRDEV      60
VPGKEVRNGT PEFRGRLAPL ASSRFLHDHQ AELHIRDVRG HDASIYVCRV EVLGLGVGTG     120
NGTRLVVEKE HPQLGAGTVL LLRAGFYAVS FLSVAVGSTV YYQGKCLTWK GPRRQLPAVV     180
PAPLPPPCGS SAHLLPPVPG G                                               201

SEQ ID NO: 60            moltype = AA   length = 271
FEATURE                 Location/Qualifiers
REGION                  1..271
                        note = Chimeric receptor
source                  1..271
                        mol_type = protein
                        organism = synthetic construct
SEQUENCE: 60
MAWMLLLILI MVHPGSCALW VSQPPEIRTL EGSSAFLPCS FNASQGRLAI GSVTWFRDEV      60
VPGKEVRNGT PEFRGRLAPL ASSRFLHDHQ AELHIRDVRG HDASIYVCRV EVLGLGVGTG     120
NGTRLVVEKE HPQLGASLCY LLDGILFIYG VILTALFLRV KFSRSADAPA YQQGQNQLYN     180
ELNLGRREEY DVLDKRRGRD PEMGGKPQRR KNPQEGLYNE LQKDKMAEAY SEIGMKGERR     240
RGKGHDGLYQ GLSTATKDTY DALHMQALPP R                                    271

SEQ ID NO: 61            moltype = AA   length = 320
FEATURE                 Location/Qualifiers
REGION                  1..320
                        note = Chimeric receptor
source                  1..320
                        mol_type = protein
                        organism = synthetic construct
SEQUENCE: 61
MAWMLLLILI MVHPGSCALW VSQPPEIRTL EGSSAFLPCS FNASQGRLAI GSVTWFRDEV      60
VPGKEVRNGT PEFRGRLAPL ASSRFLHDHQ AELHIRDVRG HDASIYVCRV EVLGLGVGTG     120
NGTRLVVEKE HPQLGASFWV LVVVGGVLAC YSLLVTVAFI IFWVRSKRSR LLHSDYMNMT     180
PRRPGPTRKH YQPYAPPRDF AAYRSKLRVK FSRSADAPAY QQGQNQLYNE LNLGRREEYD     240
VLDKRRGRDP EMGGKPQRRK NPQEGLYNEL QKDKMAEAYS EIGMKGERRR GKGHDGLYQG     300
LSTATKDTYD ALHMQALPPR                                                320

SEQ ID NO: 62            moltype = AA   length = 282
FEATURE                 Location/Qualifiers
REGION                  1..282
                        note = Chimeric receptor
source                  1..282
                        mol_type = protein
                        organism = synthetic construct
SEQUENCE: 62
MAWMLLLILI MVHPGSCALW VSQPPEIRTL EGSSAFLPCS FNASQGRLAI GSVTWFRDEV      60
VPGKEVRNGT PEFRGRLAPL ASSRFLHDHQ AELHIRDVRG HDASIYVCRV EVLGLGVGTG     120
NGTRLVVEKE HPQLGASFWV LVVVGGVLAC YSLLVTVAFI IFWVRSKKLR VKFSRSADAP     180
AYQQGQNQLY NELNLGRREE YDVLDKRRGR DPEMGGKPQR RKNPQEGLYN ELQKDKMAEA     240
YSEIGMKGER RRGKGHDGLY QGLSTATKDT YDALHMQALP PR                        282

SEQ ID NO: 63            moltype = AA   length = 273
FEATURE                 Location/Qualifiers
REGION                  1..273
                        note = Chimeric receptor
source                  1..273
                        mol_type = protein
```

```
                         organism = synthetic construct
SEQUENCE: 63
MAWMLLLILI MVHPGSCALW VSQPPEIRTL EGSSAFLPCS FNASQGRLAI GSVTWFRDEV    60
VPGKEVRNGT PEFRGRLAPL ASSRFLHDHQ AELHIRDVRG HDASIYVCRV EVLGLGVGTG   120
NGTRLVVEKE HPQLGASIYI WAPLAGTCGV LLLSLVITKL RVKFSRSADA PAYQQGQNQL   180
YNELNLGRRE EYDVLDKRRG RDPEMGGKPQ RRKNPQEGLY NELQKDKMAE AYSEIGMKGE   240
RRRGKGHDGL YQGLSTATKD TYDALHMQAL PPR                                273

SEQ ID NO: 64            moltype = DNA   length = 924
FEATURE                  Location/Qualifiers
misc_feature             1..924
                         note = Chimeric receptor
source                   1..924
                         mol_type = other DNA
                         organism = synthetic construct SEQUENCE: 64
atggcctgga tgctgttgct catcttgatc atggtccatc caggatcctg tgctctctgg    60
gtgtcccagc cccctgagat tcgtaccctg gaaggatcct ctgccttcct gccctgctcc   120
ttcaatgcca gccaagggag actggccatt ggctccgtca cgtggttccg agatgaggtg   180
gttccaggga aggaggtgag gaatggaacc ccagagttca ggggccgcct ggccccactt   240
gcttcttccc gtttcctcca tgaccaccag gctgagctgc acatccggga cgtgcgaggc   300
catgacgcca gcatctacgt gtgcagagtg gaggtgctgg ccttggtgt cgggacaggg   360
aatgggactc ggctggtggt ggagaaagaa catcctcagc taggggctag cttttgggtg   420
ctggtggtgg ttggtggagt cctggcttgc tatagcttgc tagtaacagt ggcctttatt   480
attttctggg tgaggagtaa gaggagcctg tgcgcacgcc cacgccgcag ccccgcccaa   540
gaagatggca aagtctacat caacatgcca ggcaggggca agcttagagt gaagttcagc   600
aggagcgcag acgcccccgc gtaccagcag ggccagaacc agctctataa cgagctcaat   660
ctaggacgaa gagaggagta cgatgttttg gacaagagac gtggccggga ccctgagatg   720
gggggaaagc cgagaaggaa gaaccctcag gaaggcctgt acaatgaact gcagaaagat   780
aagatggcgg aggcctacag tgagattggg atgaaaggcg agcgccggag gggcaagggg   840
cacgatggcc tttaccaggg tctcagtaca gccaccaagg acacctacga cgcccttcac   900
atgcaggccc tgccccctcg ctaa                                          924

SEQ ID NO: 65            moltype = AA   length = 307
FEATURE                  Location/Qualifiers
REGION                   1..307
                         note = Chimeric receptor
source                   1..307
                         mol_type = protein
                         organism = synthetic construct SEQUENCE: 65
MAWMLLLILI MVHPGSCALW VSQPPEIRTL EGSSAFLPCS FNASQGRLAI GSVTWFRDEV    60
VPGKEVRNGT PEFRGRLAPL ASSRFLHDHQ AELHIRDVRG HDASIYVCRV EVLGLGVGTG   120
NGTRLVVEKE HPQLGASFWV LVVVGGVLAC YSLLVTVAFI IFWVRSKRSL CARPRRSPAQ   180
EDGKVYINMP GRGKLRVKFS RSADAPAYQQ GQNQLYNELN LGRREEYDVL DKRRGRDPEM   240
GGKPRRKNPQ EGLYNELQKD KMAEAYSEIG MKGERRRGKG HDGLYQGLST ATKDTYDALH   300
MQALPPR                                                             307

SEQ ID NO: 66            moltype = DNA   length = 924
FEATURE                  Location/Qualifiers
misc_feature             1..924
                         note = Chimeric receptor
source                   1..924
                         mol_type = other DNA
                         organism = synthetic construct SEQUENCE: 66
atggcctgga tgctgttgct catcttgatc atggtccatc caggatcctg tgctctctgg    60
gtgtcccagc cccctgagat tcgtaccctg gaaggatcct ctgccttcct gccctgctcc   120
ttcaatgcca gccaagggag actggccatt ggctccgtca cgtggttccg agatgaggtg   180
gttccaggga aggaggtgag gaatggaacc ccagagttca ggggccgcct ggccccactt   240
gcttcttccc gtttcctcca tgaccaccag gctgagctgc acatccggga cgtgcgaggc   300
catgacgcca gcatctacgt gtgcagagtg gaggtgctgg ccttggtgt cgggacaggg   360
aatgggactc ggctggtggt ggagaaagaa catcctcagc taggggctag cttttgggtg   420
ctggtggtgg ttggtggagt cctggcttgc tatagcttgc tagtaacagt ggcctttatt   480
attttctggg tgaggagtaa gaggagcaag cttagagtga agttcagcag gagcgcagac   540
gcccccgcgt accagcaggg ccagaaccag ctctataacg agctcaatct aggacgaaga   600
gaggagtacg atgttttgga caagagacgt ggccgggacc ctgagatggg gggaaagccg   660
agaaggaaga accctcagga aggcctgtac aatgaactgc agaaagataa gatggcggag   720
gcctacagtg agattgggat gaaaggcgag cgccggaggg gcaagggcga tggcctttac   780
cagggtctca gtacagccac caaggacacc tacgacgccc ttcacatgca ggccctgccc   840
ccctcgccct gtgcgcacgc ccacgccgc agcccgccc aagaagatgg caaagtctac   900
atcaacatgc caggcagggg ctga                                          924

SEQ ID NO: 67            moltype = AA   length = 307
FEATURE                  Location/Qualifiers
REGION                   1..307
                         note = Chimeric receptor
source                   1..307
                         mol_type = protein
```

```
                          organism = synthetic construct
SEQUENCE: 67
MAWMLLLILI MVHPGSCALW VSQPPEIRTL EGSSAFLPCS FNASQGRLAI GSVTWFRDEV    60
VPGKEVRNGT PEFRGRLAPL ASSRFLHDHQ AELHIRDVRG HDASIYVCRV EVLGLGVGTG   120
NGTRLVVEKE HPQLGASFWV LVVVGGVLAC YSLLVTVAFI IFWVRSKRSK LRVKFSRSAD   180
APAYQQGQNQ LYNELNLGRR EEYDVLDKRR GRDPEMGGKP RRKNPQEGLY NELQKDKMAE   240
AYSEIGMKGE RRRGKGHDGL YQGLSTATKD TYDALHMQAL PPRLCARPRR SPAQEDGKVY   300
INMPGRG                                                            307

SEQ ID NO: 68              moltype = DNA   length = 1002
FEATURE                    Location/Qualifiers
misc_feature               1..1002
                           note = Chimeric receptor
source                     1..1002
                           mol_type = other DNA
                           organism = synthetic construct
SEQUENCE: 68
atggcctgga tgctgttgct catcttgatc atggtccatc caggatcctg tgctctctgg    60
gtgtcccagc ccctgagat tcgtaccctg gaaggatcct ctgccttcct gccctgctcc   120
ttcaatgcca gccaagggag actgccatt ggctccgtca cgtggttccg agatgaggtg   180
gttccaggga aggaggtgag gaatggaacc ccagagttca ggggccgcct ggccccactt   240
gcttcttccc gtttcctcca tgaccaccag gctgagctgc acatccggga cgtgcgaggc   300
catgacgcca gcatctacgt gtgcagagtc gaggtgctgg gccttggtgt cgggacaggg   360
aatgggactc ggctggtggt ggagaaagaa catcctcagc tagggctag cttttgggtg   420
ctggtggtg ttggtggagt cctggcttgc tatagcttgc tagtaacagt ggcctttatt    480
attttctggg tgaggagtaa gaggagcctc gagcaacgaa ggaaatatag atcaaacaaa   540
ggagaaagtc ctgtggagcc tgcagagcct tgtcgttaca gctgccccag ggaggaggag   600
ggcagcacca tccccatcca ggaggattac cgaaaaccgg agcctgcctg ctcccccaag   660
cttagagtga agttcagcag gagcgcagac gcccccgcgt accagcaggg ccagaaccag   720
ctctataacg agctcaatct aggacgaaga gaggagtac atgtttttgga caagagacgt   780
ggccgggacc ctgagatggg gggaaagccg agaaggaaga accctcagga aggcctgtac   840
aatgaactgc agaaagataa gatggcggag gcctacagtg agattgggat gaaaggcgag   900
cgccggaggg gcaggggca cgatggcctt taccagggtc tcagtacagc caccaaggac   960
acctacgacg cccttcacat gcaggccctg ccccctcgct aa                     1002

SEQ ID NO: 69              moltype = AA   length = 333
FEATURE                    Location/Qualifiers
REGION                     1..333
                           note = Chimeric receptor
source                     1..333
                           mol_type = protein
                           organism = synthetic construct
SEQUENCE: 69
MAWMLLLILI MVHPGSCALW VSQPPEIRTL EGSSAFLPCS FNASQGRLAI GSVTWFRDEV    60
VPGKEVRNGT PEFRGRLAPL ASSRFLHDHQ AELHIRDVRG HDASIYVCRV EVLGLGVGTG   120
NGTRLVVEKE HPQLGASFWV LVVVGGVLAC YSLLVTVAFI IFWVRSKRSL EQRRKYRSNK   180
GESPVEPAEP CRYSCPREEE GSTIPIQEDY RKPEPACSPK LRVKFSRSAD APAYQQGQNQ   240
LYNELNLGRR EEYDVLDKRR GRDPEMGGKP RRKNPQEGLY NELQKDKMAE AYSEIGMKGE   300
RRRGKGHDGL YQGLSTATKD TYDALHMQAL PPR                                333

SEQ ID NO: 70              moltype = DNA   length = 25
FEATURE                    Location/Qualifiers
source                     1..25
                           mol_type = unassigned DNA
                           organism = Homo sapiens
SEQUENCE: 70
agtgcgagga gattcggcag cttat                                         25

SEQ ID NO: 71              moltype = DNA   length = 25
FEATURE                    Location/Qualifiers
source                     1..25
                           mol_type = unassigned DNA
                           organism = Homo sapiens
SEQUENCE: 71
gcgaggagat tcggcagctt atttc                                         25

SEQ ID NO: 72              moltype = DNA   length = 25
FEATURE                    Location/Qualifiers
source                     1..25
                           mol_type = unassigned DNA
                           organism = Homo sapiens
SEQUENCE: 72
ccaccatcct ctatgagatc ttgct                                         25

SEQ ID NO: 73              moltype = DNA   length = 25
FEATURE                    Location/Qualifiers
source                     1..25
                           mol_type = unassigned DNA
                           organism = Homo sapiens
```

-continued

```
SEQUENCE: 73
tcctctatga gatcttgcta gggaa                                                   25

SEQ ID NO: 74           moltype = DNA   length = 25
FEATURE                 Location/Qualifiers
source                  1..25
                        mol_type = unassigned DNA
                        organism = Homo sapiens
SEQUENCE: 74
tctatggctt caactggcta gggtg                                                   25

SEQ ID NO: 75           moltype = DNA   length = 25
FEATURE                 Location/Qualifiers
source                  1..25
                        mol_type = unassigned DNA
                        organism = Homo sapiens
SEQUENCE: 75
caggtagagg ccttgtccac ctaat                                                   25

SEQ ID NO: 76           moltype = DNA   length = 25
FEATURE                 Location/Qualifiers
source                  1..25
                        mol_type = unassigned DNA
                        organism = Homo sapiens
SEQUENCE: 76
gcagcagaca ctgcttctta cttct                                                   25

SEQ ID NO: 77           moltype = DNA   length = 25
FEATURE                 Location/Qualifiers
source                  1..25
                        mol_type = unassigned DNA
                        organism = Homo sapiens
SEQUENCE: 77
gacactgctt cttacttctg tgcta                                                   25

SEQ ID NO: 78           moltype = DNA   length = 25
FEATURE                 Location/Qualifiers
source                  1..25
                        mol_type = unassigned DNA
                        organism = Homo sapiens
SEQUENCE: 78
cctctgcctc ttatcagttg gcgtt                                                   25

SEQ ID NO: 79           moltype = DNA   length = 25
FEATURE                 Location/Qualifiers
source                  1..25
                        mol_type = unassigned DNA
                        organism = Homo sapiens
SEQUENCE: 79
gagcaaagtg gttattatgt ctgct                                                   25

SEQ ID NO: 80           moltype = DNA   length = 25
FEATURE                 Location/Qualifiers
source                  1..25
                        mol_type = unassigned DNA
                        organism = Homo sapiens
SEQUENCE: 80
aagcaaacca gaagatgcga acttt                                                   25

SEQ ID NO: 81           moltype = DNA   length = 25
FEATURE                 Location/Qualifiers
source                  1..25
                        mol_type = unassigned DNA
                        organism = Homo sapiens
SEQUENCE: 81
gacctgtatt ctggcctgaa tcaga                                                   25

SEQ ID NO: 82           moltype = DNA   length = 21
FEATURE                 Location/Qualifiers
source                  1..21
                        mol_type = unassigned DNA
                        organism = Homo sapiens
SEQUENCE: 82
ggcctctgcc tcttatcagt t                                                       21

SEQ ID NO: 83           moltype = DNA   length = 21
FEATURE                 Location/Qualifiers
source                  1..21
                        mol_type = unassigned DNA
```

```
                           organism = Homo sapiens
SEQUENCE: 83
gcctctgcct cttatcagtt g                                                        21

SEQ ID NO: 84           moltype = DNA   length = 21
FEATURE                 Location/Qualifiers
source                  1..21
                        mol_type = unassigned DNA
                        organism = Homo sapiens
SEQUENCE: 84
gcctcttatc agttggcgtt t                                                        21

SEQ ID NO: 85           moltype = DNA   length = 21
FEATURE                 Location/Qualifiers
source                  1..21
                        mol_type = unassigned DNA
                        organism = Homo sapiens
SEQUENCE: 85
aggatcacct gtcactgaag g                                                        21

SEQ ID NO: 86           moltype = DNA   length = 21
FEATURE                 Location/Qualifiers
source                  1..21
                        mol_type = unassigned DNA
                        organism = Homo sapiens
SEQUENCE: 86
ggatcacctg tcactgaagg a                                                        21

SEQ ID NO: 87           moltype = DNA   length = 21
FEATURE                 Location/Qualifiers
source                  1..21
                        mol_type = unassigned DNA
                        organism = Homo sapiens
SEQUENCE: 87
gaattggagc aaagtggtta t                                                        21

SEQ ID NO: 88           moltype = DNA   length = 21
FEATURE                 Location/Qualifiers
source                  1..21
                        mol_type = unassigned DNA
                        organism = Homo sapiens
SEQUENCE: 88
ggagcaaagt ggttattatg t                                                        21

SEQ ID NO: 89           moltype = DNA   length = 21
FEATURE                 Location/Qualifiers
source                  1..21
                        mol_type = unassigned DNA
                        organism = Homo sapiens
SEQUENCE: 89
gcaaaccaga agatgcgaac t                                                        21

SEQ ID NO: 90           moltype = DNA   length = 21
FEATURE                 Location/Qualifiers
source                  1..21
                        mol_type = unassigned DNA
                        organism = Homo sapiens
SEQUENCE: 90
acctgtattc tggcctgaat c                                                        21

SEQ ID NO: 91           moltype = DNA   length = 21
FEATURE                 Location/Qualifiers
source                  1..21
                        mol_type = unassigned DNA
                        organism = Homo sapiens
SEQUENCE: 91
gcctgaatca gagacgcatc t                                                        21

SEQ ID NO: 92           moltype = DNA   length = 29
FEATURE                 Location/Qualifiers
source                  1..29
                        mol_type = unassigned DNA
                        organism = Homo sapiens
SEQUENCE: 92
ctgaaatact atggcaacac aatgataaa                                                29

SEQ ID NO: 93           moltype = DNA   length = 29
FEATURE                 Location/Qualifiers
source                  1..29
```

-continued

```
                              mol_type = unassigned DNA
                              organism = Homo sapiens
SEQUENCE: 93
aaacataggc agtgatgagg atcacctgt                                        29

SEQ ID NO: 94              moltype = DNA   length = 29
FEATURE                    Location/Qualifiers
source                     1..29
                           mol_type = unassigned DNA
                           organism = Homo sapiens
SEQUENCE: 94
attgtcatag tggacatctg catcactgg                                        29

SEQ ID NO: 95              moltype = DNA   length = 29
FEATURE                    Location/Qualifiers
source                     1..29
                           mol_type = unassigned DNA
                           organism = Homo sapiens
SEQUENCE: 95
ctgtattctg gcctgaatca gagacgcat                                        29

SEQ ID NO: 96              moltype = DNA   length = 21
FEATURE                    Location/Qualifiers
source                     1..21
                           mol_type = unassigned DNA
                           organism = Homo sapiens
SEQUENCE: 96
gatacctata gaggaacttg a                                                21

SEQ ID NO: 97              moltype = DNA   length = 21
FEATURE                    Location/Qualifiers
source                     1..21
                           mol_type = unassigned DNA
                           organism = Homo sapiens
SEQUENCE: 97
gacagagtgt ttgtgaattg c                                                21

SEQ ID NO: 98              moltype = DNA   length = 21
FEATURE                    Location/Qualifiers
source                     1..21
                           mol_type = unassigned DNA
                           organism = Homo sapiens
SEQUENCE: 98
gaacactgct ctcagacatt a                                                21

SEQ ID NO: 99              moltype = DNA   length = 21
FEATURE                    Location/Qualifiers
source                     1..21
                           mol_type = unassigned DNA
                           organism = Homo sapiens
SEQUENCE: 99
ggacccacga ggaatatata g                                                21

SEQ ID NO: 100             moltype = DNA   length = 21
FEATURE                    Location/Qualifiers
source                     1..21
                           mol_type = unassigned DNA
                           organism = Homo sapiens
SEQUENCE: 100
ggtgtaatgg gacagatata t                                                21

SEQ ID NO: 101             moltype = DNA   length = 21
FEATURE                    Location/Qualifiers
source                     1..21
                           mol_type = unassigned DNA
                           organism = Homo sapiens
SEQUENCE: 101
gcaagttcat tatcgaatgt g                                                21

SEQ ID NO: 102             moltype = DNA   length = 21
FEATURE                    Location/Qualifiers
source                     1..21
                           mol_type = unassigned DNA
                           organism = Homo sapiens
SEQUENCE: 102
ggctggcatc attgtcactg a                                                21

SEQ ID NO: 103             moltype = DNA   length = 21
FEATURE                    Location/Qualifiers
```

-continued

```
source                  1..21
                        mol_type = unassigned DNA
                        organism = Homo sapiens
SEQUENCE: 103
gctggcatca ttgtcactga t                                         21

SEQ ID NO: 104          moltype = DNA   length = 21
FEATURE                 Location/Qualifiers
source                  1..21
                        mol_type = unassigned DNA
                        organism = Homo sapiens
SEQUENCE: 104
gcatcattgt cactgatgtc a                                         21

SEQ ID NO: 105          moltype = DNA   length = 21
FEATURE                 Location/Qualifiers
source                  1..21
                        mol_type = unassigned DNA
                        organism = Homo sapiens
SEQUENCE: 105
gctttgggag tcttctgctt t                                         21

SEQ ID NO: 106          moltype = DNA   length = 29
FEATURE                 Location/Qualifiers
source                  1..29
                        mol_type = unassigned DNA
                        organism = Homo sapiens
SEQUENCE: 106
tggaacatag cacgtttctc tctggcctg                                 29

SEQ ID NO: 107          moltype = DNA   length = 29
FEATURE                 Location/Qualifiers
source                  1..29
                        mol_type = unassigned DNA
                        organism = Homo sapiens
SEQUENCE: 107
ctgctctcag acattacaag actggacct                                 29

SEQ ID NO: 108          moltype = DNA   length = 29
FEATURE                 Location/Qualifiers
source                  1..29
                        mol_type = unassigned DNA
                        organism = Homo sapiens
SEQUENCE: 108
accgtggctg gcatcattgt cactgatgt                                 29

SEQ ID NO: 109          moltype = DNA   length = 29
FEATURE                 Location/Qualifiers
source                  1..29
                        mol_type = unassigned DNA
                        organism = Homo sapiens
SEQUENCE: 109
tgatgctcag tacagccacc ttggaggaa                                 29

SEQ ID NO: 110          moltype = DNA   length = 21
FEATURE                 Location/Qualifiers
source                  1..21
                        mol_type = unassigned DNA
                        organism = Homo sapiens
SEQUENCE: 110
ggctatcatt cttcttcaag g                                         21

SEQ ID NO: 111          moltype = DNA   length = 21
FEATURE                 Location/Qualifiers
source                  1..21
                        mol_type = unassigned DNA
                        organism = Homo sapiens
SEQUENCE: 111
gcccagtcaa tcaaaggaaa c                                         21

SEQ ID NO: 112          moltype = DNA   length = 21
FEATURE                 Location/Qualifiers
source                  1..21
                        mol_type = unassigned DNA
                        organism = Homo sapiens
SEQUENCE: 112
ggttaaggtg tatgactatc a                                         21

SEQ ID NO: 113          moltype = DNA   length = 21
```

-continued

```
FEATURE              Location/Qualifiers
source               1..21
                     mol_type = unassigned DNA
                     organism = Homo sapiens
SEQUENCE: 113
ggttcggtac ttctgacttg t                                          21

SEQ ID NO: 114       moltype = DNA  length = 21
FEATURE              Location/Qualifiers
source               1..21
                     mol_type = unassigned DNA
                     organism = Homo sapiens
SEQUENCE: 114
gaatgtgtca gaactgcatt g                                          21

SEQ ID NO: 115       moltype = DNA  length = 21
FEATURE              Location/Qualifiers
source               1..21
                     mol_type = unassigned DNA
                     organism = Homo sapiens
SEQUENCE: 115
gcagccacca tatctggctt t                                          21

SEQ ID NO: 116       moltype = DNA  length = 21
FEATURE              Location/Qualifiers
source               1..21
                     mol_type = unassigned DNA
                     organism = Homo sapiens
SEQUENCE: 116
ggctttctct ttgctgaaat c                                          21

SEQ ID NO: 117       moltype = DNA  length = 21
FEATURE              Location/Qualifiers
source               1..21
                     mol_type = unassigned DNA
                     organism = Homo sapiens
SEQUENCE: 117
gctttctctt tgctgaaatc g                                          21

SEQ ID NO: 118       moltype = DNA  length = 21
FEATURE              Location/Qualifiers
source               1..21
                     mol_type = unassigned DNA
                     organism = Homo sapiens
SEQUENCE: 118
gccaccttca aggaaaccag t                                          21

SEQ ID NO: 119       moltype = DNA  length = 21
FEATURE              Location/Qualifiers
source               1..21
                     mol_type = unassigned DNA
                     organism = Homo sapiens
SEQUENCE: 119
gaaaccagtt gaggaggaat t                                          21

SEQ ID NO: 120       moltype = DNA  length = 29
FEATURE              Location/Qualifiers
source               1..29
                     mol_type = unassigned DNA
                     organism = Homo sapiens
SEQUENCE: 120
ggctttctct ttgctgaaat cgtcagcat                                  29

SEQ ID NO: 121       moltype = DNA  length = 29
FEATURE              Location/Qualifiers
source               1..29
                     mol_type = unassigned DNA
                     organism = Homo sapiens
SEQUENCE: 121
aggatggagt tcgccagtcg agagcttca                                  29

SEQ ID NO: 122       moltype = DNA  length = 29
FEATURE              Location/Qualifiers
source               1..29
                     mol_type = unassigned DNA
                     organism = Homo sapiens
SEQUENCE: 122
cctcaaggat cgagaagatg accagtaca                                  29
```

-continued

```
SEQ ID NO: 123          moltype = DNA   length = 29
FEATURE                 Location/Qualifiers
source                  1..29
                        mol_type = unassigned DNA
                        organism = Homo sapiens
SEQUENCE: 123
tacagccacc ttcaaggaaa ccagttgag                                      29

SEQ ID NO: 124          moltype = DNA   length = 816
FEATURE                 Location/Qualifiers
misc_feature            1..816
                        note = Chimeric receptor
source                  1..816
                        mol_type = other DNA
                        organism = synthetic construct
SEQUENCE: 124
atggcctgga tgctgttgct catcttgatc atggtccatc caggatcctg tgctctctgg   60
gtgtcccagc ccctgagat tcgtaccctg gaaggatcct ctgccttcct gccctgctcc   120
ttcaatgcca gccaagggag actggccatt ggctccgtca cgtggttccg agatgaggtg   180
gttccaggga aggaggtgag gaatggaacc ccagagttca ggggccgcct ggccccactt   240
gcttcttccc gtttcctcca tgaccaccag gctgagctgc acatccggga cgtgcgaggc   300
catgacgcca gcatctacgt gtgcagagtg gaggtgctgg gccttggtgt cgggacaggc   360
aatgggactc ggctggtggt ggagaaagaa catcctcagc taggggctag cctctgctac   420
ctgctggatg gaatcctctt catctatggt gtcattctca ctgccttgtt cctgagagtg   480
aagttcagca ggagcgcaga cgcccccgcg taccagcagg gccagaacca gctctataac   540
gagctcaatc taggacgaag agaggagtac gatgttttgg acaagagacg tggccgggac   600
cctgagatgg ggggaaagcc gcagagaagg aagaaccctc aggaaggcct gtacaatgaa   660
ctgcagaaag ataagatggc ggaggcctac agtgagattg ggatgaaagg cgagcgccgg   720
aggggcaagg ggcacgatgg cctttaccag ggtctcagta cagccaccaa ggacacctac   780
gacgcccttc acatgcaggc cctgccccct cgctaa                             816

SEQ ID NO: 125          moltype = DNA   length = 963
FEATURE                 Location/Qualifiers
misc_feature            1..963
                        note = Chimeric receptor
source                  1..963
                        mol_type = other DNA
                        organism = synthetic construct
SEQUENCE: 125
atggcctgga tgctgttgct catcttgatc atggtccatc caggatcctg tgctctctgg   60
gtgtcccagc ccctgagat tcgtaccctg gaaggatcct ctgccttcct gccctgctcc   120
ttcaatgcca gccaagggag actggccatt ggctccgtca cgtggttccg agatgaggtg   180
gttccaggga aggaggtgag gaatggaacc ccagagttca ggggccgcct ggccccactt   240
gcttcttccc gtttcctcca tgaccaccag gctgagctgc acatccggga cgtgcgaggc   300
catgacgcca gcatctacgt gtgcagagtg gaggtgctgg gccttggtgt cgggacaggc   360
aatgggactc ggctggtggt ggagaaagaa catcctcagc taggggctag cttttgggtg   420
ctggtggagt ttggtggagt cctggcttgc tatagcttgc tagtaacagt ggcctttatt   480
attttctggg tgaggagtaa gaggagcagg ctcctgcaca gtgactacat gaacatgact   540
ccccgccgcc ccgggcccac ccgcaagcat taccagccct atgccccacc acgcgacttc   600
gcagcctatc gctccaagct tagagtgaag ttcagcagga gcgcagacgc ccccgcgtac   660
cagcaggcc agaaccagct ctataacgag ctcaatctag gacgaagaga ggagtacgat   720
gttttggaca agagacgtgg ccgggaccct gagatggggg gaaagccgca gagaaggaag   780
aaccctcagg aaggcctgta caatgaactg cagaaagata agatggcgga ggcctacagt   840
gagattggga tgaaaggcga gcgccggagg gcaagggggc acgatggcct ttaccagggt   900
ctcagtacag ccaccaagga cacctacgac gcccttcaca tgcaggccct gccccctcgc   960
taa                                                                 963

SEQ ID NO: 126          moltype = DNA   length = 849
FEATURE                 Location/Qualifiers
misc_feature            1..849
                        note = Chimeric receptor
source                  1..849
                        mol_type = other DNA
                        organism = synthetic construct
SEQUENCE: 126
atggcctgga tgctgttgct catcttgatc atggtccatc caggatcctg tgctctctgg   60
gtgtcccagc ccctgagat tcgtaccctg gaaggatcct ctgccttcct gccctgctcc   120
ttcaatgcca gccaagggag actggccatt ggctccgtca cgtggttccg agatgaggtg   180
gttccaggga aggaggtgag gaatggaacc ccagagttca ggggccgcct ggccccactt   240
gcttcttccc gtttcctcca tgaccaccag gctgagctgc acatccggga cgtgcgaggc   300
catgacgcca gcatctacgt gtgcagagtg gaggtgctgg gccttggtgt cgggacaggc   360
aatgggactc ggctggtggt ggagaaagaa catcctcagc taggggctag cttttgggtg   420
ctggtggtgg ttggtggagt cctggcttgc tatagcttgc tagtaacagt ggcctttatt   480
attttctggg tgaggagtaa gaagcttaga gtgaagttca gcaggagcgc agacgcccc   540
gcgtaccagc agggccagaa ccagctctat aacgagctca atctaggacg aagagaggag   600
tacgatgttt tggacaagag acgtggccgg gaccctgaga tggggggaaa gccgcagaga   660
aggaagaacc tcaggaagg cctgtacaat gaactgcaga aagataagat ggcggaggcc   720
tacagtgaga ttgggatgaa aggcgagcgc cggagggggca aggggcacga tggcctttac   780
cagggtctca gtacagccac caaggacacc tacgacgccc ttcacatgca ggccctgccc   840
```

-continued

```
cctcgctaa                                                     849

SEQ ID NO: 127         moltype = DNA  length = 819
FEATURE                Location/Qualifiers
misc_feature           1..819
                       note = Chimeric receptor
source                 1..819
                       mol_type = other DNA
                       organism = synthetic construct
SEQUENCE: 127
atggcctgga tgctgttgct catcttgatc atggtccatc caggatcctg tgctctctgg  60
gtgtcccagc cccctgagat tcgtaccctg gaaggatcct ctgccttcct gccctgctcc 120
ttcaatgcca gccaagggag actggccatt ggctccgtca cgtggttccg agatgaggtg 180
gttccaggga aggaggtgag gaatggaacc ccagagttca ggggccgcct ggccccactt 240
gcttcttccc gtttcctcca tgaccaccag gctgagctgc acatccggga cgtgcgaggc 300
catgacgcca gcatctacgt gtgcagagtg gaggtgctgg gccttggtgt cgggacaggg 360
aatgggactc ggctggtggt ggagaaagaa catcctcagc taggggctag catctacatc 420
tgggcgccct tggccgggac ttgtggggtc cttctcctgt cactggttat caccaagctt 480
agagtgaagt tcagcaggag cgcagacgcc cccgcgtacc agcagggcca gaaccagctc 540
tataacgagc tcaatctagg acgaagagag gagtacgatg ttttggacaa gagacgtggc 600
cgggaccctg agatgggggg aaagccgaga aggaagaacc ctcaggaagg cctgtacaat 660
gaactgcaga aagataagat ggcggaggcc tacagtgaga ttgggatgaa aggcgagcgc 720
cggaggggca aggggcacga tggcctttac caggtctca gtacagccac caaggacacc 780
tacgacgccc ttcacatgca ggccctgccc cctcgctaa                          819

SEQ ID NO: 128         moltype = AA  length = 19
FEATURE                Location/Qualifiers
source                 1..19
                       mol_type = protein
                       organism = synthetic construct
REPEAT                 8..15
                       note = 6-8 Xaa residues represent any naturally occurring
                        amino acid residue
VARIANT                1
                       note = Asp or Glu
MOD_RES                4
                       note = Phosphotyrosine (ITAM motif)
VARIANT                7
                       note = Ile or Leu
MOD_RES                16
                       note = Phosphotyrosine (ITAM motif)
VARIANT                19
                       note = Ile or Leu
VARIANT                2
                       note = any naturally occuring amino acid residue
VARIANT                3
                       note = any naturally occuring amino acid residue
VARIANT                5
                       note = any naturally occuring amino acid residue
VARIANT                6
                       note = any naturally occuring amino acid residue
VARIANT                17
                       note = any naturally occuring amino acid residue
VARIANT                18
                       note = any naturally occuring amino acid residue
SEQUENCE: 128
DXXYXXIXXX XXXXXYXXI                                           19
```

NUCLEIC ACID ENCODING NKP30 RECEPTOR TARGETED THERAPEUTICS

CROSS-REFERENCE TO RELATED APPLICATIONS

This application is a divisional of U.S. application Ser. No. 16/882,800, filed May 26, 2020, now U.S. Pat. No. 11,872,248, which is a divisional of U.S. application Ser. No. 15/830,605, filed Dec. 4, 2017, now U.S. Pat. No. 10,682,378, which is a divisional of U.S. application Ser. No. 14/342,060, filed Nov. 24, 2014, now U.S. Pat. No. 9,833,476, which is a U.S. Nat'l Phase application of Int'l Appl. No. PCT/US2012/053511, filed Aug. 31, 2012, which claims priority to U.S. Provisional Appl. No. 61/529,410, filed Aug. 31, 2011, all of which are incorporated by reference in their entireties herein.

STATEMENT REGARDING FEDERALLY SPONSORED RESEARCH OR DEVELOPMENT

This invention was made with government support under contract number CA 130911 awarded by the National Institutes of Health. The government has certain rights in the invention.

SEQUENCE LISTING DISCLOSURE

The contents of the electronic sequence listing (11483070001205.xml; size: 135,659 bytes; and Date of Creation: Aug. 5, 2025) is herein incorporated by reference in its entirety.

BACKGROUND

Field

The present disclosure is directed to T cells that express chimeric NKp30 receptors ("chimeric NKp30 T cells"), methods of making and using chimeric NKp30 T cells, and methods of using these chimeric NKp30 T cells to address diseases and disorders. In one aspect, the disclosure broadly relates to chimeric NKp30 T cells, isolated populations thereof, and compositions comprising the same. In another aspect, said chimeric NKp30 T cells are further designed to express a functional non-TCR receptor. The disclosure also pertains to methods of making said chimeric NKp30 T cells, and methods of reducing or ameliorating, or preventing or treating, diseases and disorders, especially cancers, using said chimeric NKp30 T cells, populations thereof, or compositions comprising the same.

Description of Related Art

The global burden of cancer doubled between 1975 and 2000, and cancer is expected to become the leading cause of death worldwide by 2010. According to the American Cancer Society, it is projected to double again by 2020 and to triple by 2030. Thus, there is a need for more effective therapies to treat various forms of cancer. Ideally, any cancer therapy should be effective (at killing cancerous cells), targeted (i.e. selective, to avoid killing healthy cells), permanent (to avoid relapse and metastasis), and affordable. Today's standards of care for most cancers fall short in some or all of these criteria.

T cells, especially cytotoxic T cells, play important roles in anti-tumor immunity (Rossing and Brenner (2004) Mol.

Ther. 10:5-18). Adoptive transfer of tumor-specific T cells into patients provides a means to treat cancer (Sadelain, et al. (2003) Nat. Rev. Cancer 3:35-45). However, the traditional approaches for obtaining large numbers of tumor-specific T cells are time-consuming, laborious and sometimes difficult because the average frequency of antigen-specific T cells in periphery is extremely low (Rosenberg (2001) Nature 411:380-384; Ho, et al. (2003) Cancer Cell 3:431-437; Crowley, et al. (1990) Cancer Res. 50:492-498). In addition, isolation and expansion of T cells that retain their antigen specificity and function can also be a challenging task (Sadelain, et al. (2003) supra). Genetic modification of primary T cells with tumor-specific immunoreceptors, such as full-length T cell receptors or chimeric T cell receptor molecules can be used for redirecting T cells against tumor cells (Stevens, et al. (1995) J. Immunol. 154:762-771; Oelke, et al. (2003) Nat. Med. 9:619-624; Stancovski, et al. (1993) J. Immunol. 151:6577-6582; Clay, et al. (1999) J. Immunol. 163:507-153). This strategy avoids the limitation of low frequency of antigen-specific T cells, allowing for facilitated expansion of tumor-specific T cells to therapeutic doses.

Natural killer (NK) cells are innate effector cells serving as a first line of defense against certain viral infections and tumors (Biron, at al. (1999) Annu. Rev. Immunol. 17:189-220; Trinchieri (1989) Adv. Immunol. 47:187-376). They have also been implicated in the rejection of allogeneic bone marrow transplants (Lanier (1995) Curr. Opin. Immunol. 7:626-631; Yu, et al. (1992) Annu. Rev. Immunol. 10:189-214). Innate effector cells recognize and eliminate their targets with fast kinetics, without prior sensitization. Therefore, NK cells need to sense if cells are transformed, infected, or stressed to discriminate between abnormal and healthy tissues. According to the missing self phenomenon (Karre, et al. (1986) Nature (London) 319:675-678), NK cells accomplish this by looking for and eliminating cells with aberrant major histocompatibility complex (MHC) class I expression; a concept validated by showing that NK cells are responsible for the rejection of the MHC class I-deficient lymphoma cell line RMA-S, but not its parental MHC class I-positive line RMA.

Natural killer (NK) cells can also attack tumor and virally infected cells in the absence of MHC restriction, utilizing a combination of signals from activating and inhibitory receptors. One group of activating NK receptors are natural cytotoxicity receptors (NCRs), which include NKp46 (NCR1), NKp44 (NCR2) and NKp30 (also called natural cytotoxicity receptor 3 (NCR3) or CD337). These receptors are exclusively expressed on NK cells, which play important roles in NK-mediated tumor cell-killing.

NKp30 is an activating NK receptor that is involved in the NK-mediated killing of tumor cells. NKp30 recognizes ligands on tumor cells and dendritic cells. These ligands are highly expressed on a subset of tumor cells, but not most other normal cells. There is some evidence that some subsets of dendritic cells may express these ligands in vitro. In laboratory mice, NKp30 is a pseudogene. NKp30 has been further described in the literature including Brandt et al., J Exp Med. 2009 Jul. 6; 206(7):1495-503; Byrd et al., PLoS One. 2007 Dec. 19; 2(12):e1339; and Delahaye et al., Nat Med. 2011 June; 17(6):700-7, each of which is incorporated by reference herein in its entirety.

Two cellular NKp30 receptor ligands have been identified: BAT3 and B7-H6. BAT3 is a nuclear protein, which is involved in the interaction with P53 and induction of apoptosis after stress such as DNA damage. B7-H6 is a recently identified B7 family member. Structures of an NKp30 ligand binding site and an NKp30-B7-H6 complex have been reported in the literature (Li et al., J Exp Med. 2011 Apr. 11; 208(4):703-14; Joyce et al., Proc Natl Acad Sci USA. 2011 Apr. 12; 108(15):6223-8). Unlike BAT3, B7-H6 is expressed on the surface of tumor cells, but not normal cells. Thus, the NKp30 receptor-NKp30 ligand system provides a relatively specific system for immune cells to recognize tumor cells.

NKp30 associates with CD3ζ and FcRγ for signal transduction. A recent study shows that there exist three isoforms of NKp30 (i.e., A, B and C), which differs in signaling capacity in NK cells (Delahaye et al., Nat Med. 2011 June; 17(6):700-7). Isoforms A and B were reported to efficiently interact with CD3 and are associated with good prognosis of gastrointestinal stromal tumors, whereas isoform C poorly associate with CD3ζ and linked to poor prognosis. Specifically, isoform A was demonstrated to associate with CD3ζ upon NKp30 cross-linking, whereas isoform B was demonstrated to constitutively associate with CD3ζ.

Inhibitory receptors specific for MHC class I molecules have been identified in mice and humans. The human killer cell Ig-like receptors (KIR) recognize HLA-A, -B, or -C; the murine Ly49 receptors recognize H-2K or H-2D; and the mouse and human CD94/NKG2 receptors are specific for Qalb or HLA-E, respectively (Long (1999) Annu. Rev. Immunol. 17:875-904; Lanier (1998) Annu. Rev. Immunol. 16:359-393; Vance, et al. (1998) J. Exp. Med. 188:1841-1848).

Activating NK cell receptors specific for classic MHC class I molecules, nonclassic MHC class I molecules or MHC class I-related molecules have been described (Bakker, et al. (2000) Hum. Immunol. 61:18-27). One such receptor is NKG2D (natural killer cell group 2D) which is a C-type lectin-like receptor expressed on NK cells, γδ-TcR+ T cells, and CD8+ αβ-TcR+ T cells (Bauer, et al. (1999) Science 285:727-730). NKG2D is associated with the transmembrane adapter protein DAPI0 (Wu, et al. (1999) Science 285:730-732), whose cytoplasmic domain binds to the p85 subunit of the PI-3 kinase.

In humans, two families of ligands for NKG2D have been described (Bahram (2000) Adv. Immunol. 76:1-60; Cerwenka and Lanier (2001) Immunol. Rev. 181:158-169). NKG2D binds to the polymorphic MHC class I chain-related molecules (MIC)-A and MICB (Bauer, et al. (1999) supra). These are expressed on many human tumor cell lines, on several freshly isolated tumor specimens, and at low levels on gut epithelium (Groh, et al. (1999) Proc. Natl. Acad. Sci. USA 96:6879-6884). NKG2D also binds to another family of ligands designated the UL binding proteins (ULBP)-1, -2, -3, and -4 molecules (Cosman, et al. (2001) Immunity 14:123-133; Kubin, et al. (2001) Eur. J. Immunol. 31:1428-1437; Conejo-Garcia, J. R., F. Benencia, et al. (2003). "Letal, A tumor-associated NKG2D immunoreceptor ligand, induces activation and expansion of effector immune cells." Cancer Biol Ther 2(4): 446-451). Although similar to class I MHC molecules in their α1 and α2 domains, the genes encoding these proteins are not localized within the MHC. Like MIC (Groh, et al. (1996) supra), the ULBP molecules do not associate with P2-microglobulin or bind peptides. The known murine NKG2D-binding repertoire encompasses the retinoic acid early inducible-1 gene products (RAE-I) and the related H60 minor histocompatibility antigen (Cerwenka, et al. (2000) Immunity 12:721-727; Diefenbach, et al. (2000) Nat. Immunol. 1:119-126). RAE-I and H60 were identified as ligands for mouse NKG2D by expression cloning these cDNA from a mouse transformed lung cell line (Cerwenka, et al. (2000) supra). Transcripts of RAE-I are rare in adult tissues but abundant in the embryo and on many mouse tumor cell lines, indicating that these are oncofetal antigens.

Recombinant receptors containing an cytoplasmic domain for activating T cells and an extracellular antigen-binding domain, which is typically a single-chain fragment of a monoclonal antibody and is specific for a tumor-specific antigen, have been reported for targeting tumors for destruction. See, e.g., U.S. Pat. No. 6,410,319.

Baba et al. ((2000) Hum. Immunol. 61:1202-18) disclose KIR2DL1-CD3ζ chain chimeric proteins. Further, WO 02/068615 (which describes prior work by the present inventors) suggests fusion proteins of NKG2D containing the external domain of NKG2D with a distinct DAP10 interacting domain or with cytoplasmic domains derived from other signaling molecules, for example CD28, for use in engineering cells that respond to NKG2D ligands and potentially create a system with enhanced signaling capabilities.

Brandt et al., J Exp Med. 2009 Jul. 6; 206(7):1495-503 discloses use of IL-2-producing DO11.10 mouse T cell hybridoma expressing a chimeric receptors (in which the intracytoplasmic domain of mouse CD3ζ was fused either to the extracellular portion of NKp30 or NKp46) as reporter constructs in assays to evaluate recognition of ligands which were measured by detecting IL-2 secretion. However, the reference does not report introduction of these constructs into normal T cells or therapeutic use of these constructs (e.g., for treatment of cancer).

U.S. Pat. No. 5,359,046 discloses a chimeric DNA sequence encoding a membrane bound protein, wherein the chimeric DNA comprises a DNA sequence encoding a signal sequence which directs the membrane bound protein to the surface membrane; a DNA sequence encoding a non-MHC restricted extracellular binding domain of a surface membrane protein selected from the group consisting of CD4, CD8, IgG and single-chain antibody that binds specifically to at least one ligand, wherein said ligand is a protein on the surface of a cell or a viral protein; a transmembrane domain from a protein selected from the group consisting of CD4, CD8, IgG, single-chain antibody, the CD3ζ chain, the CD3γ chain, the CD3δ chain and the CD3ε chain; and a cytoplasmic signal-transducing domain of a protein that activates an intracellular messenger system selected from the group consisting of the CD3ζ chain, the CD3γ chain, the CD3δ chain and the CD3ε chain, wherein the extracellular domain and cytoplasmic domain are not naturally joined together and the cytoplasmic domain is not naturally joined to an extracellular ligand-binding domain, and when the chimeric DNA is expressed as a membrane bound protein in a selected host cell under conditions suitable for expression, the membrane bound protein initiates signaling in the host cell.

Cellular immunotherapy has been shown to result in specific tumor elimination and has the potential to provide specific and effective cancer therapy (Ho, W. Y. et al. 2003. *Cancer Cell* 3:1318-1328; Morris, E. C. et al. 2003. *Clin. Exp. Immunol.* 131:1-7; Rosenberg, S. A. 2001. *Nature* 411:380-384; Boon, T. and P. van der Bruggen. 1996. *J. Exp. Med.* 183:725-729). T cells have often been the effector cells of choice for cancer immunotherapy due to their selective recognition and powerful effector mechanisms. T cells recognize specific peptides derived from internal cellular proteins in the context of self-major histocompatibility complex (MHC) using their T cell receptors (TCR).

WO/2006/036445 (and its U.S. counterpart, now patented as U.S. Pat. No. 7,924,298) discloses a chimeric receptor protein comprising a C-type lectin-like natural killer cell receptor, or a protein associated therewith, fused to an immune signaling receptor having an immunoreceptor tyrosine-based activation motif for reducing or eliminating a tumor. To the N-terminus of the C-type lectin-like NK cell receptor is fused an immune signaling receptor having an immunoreceptor tyrosine-based activation motif (ITAM), (Asp/Glu)-Xaa-Xaa-Tyr*-Xaa-Xaa-(Ile/Leu)-Xaa$_{6-8}$-Tyr*-Xaa-Xaa-(Ile/Leu) which is involved in the activation of cellular responses via immune receptors. Similarly, when employing a protein associated with a C-type lectin-like NK cell receptor, an immune signaling receptor can be fused to the C-terminus of said protein. That publication additionally discloses that suitable immune signaling receptors for use in the chimeric receptor include, but are not limited to, the ζ chain of the T-cell receptor, the eta chain which differs from the ζ chain only in its most C-terminal exon as a result of alternative splicing of the ζ mRNA, the δ, γ and ε chains of the T-cell receptor (CD3ζ chains) and the 7 subunit of the FcRI receptor. That publication further discloses that the immune signaling receptor may be CD3ζ e.g., GENBANK accession number NM_198053), or human Fcs receptor-γ chain (e.g., GENBANK accession number M33195) or the cytoplasmic domain or a splicing variant thereof. Further exemplary chimeric receptors described in that publication include is a fusion between NKG2D and CD3ζ or DAP10 and CD3ζ.

It is recognized in the art that the TCR complex associates in precise fashion by the formation of dimers and association of these dimers (TCR-α/β, CD3-γ/ε, CD3-δ/ε, and CD3ζ dimer) into one TCR complex that can be exported to the cell surface. The inability of any of these complexes to form properly can inhibit TCR assembly and expression (Call, M. E. et al., (2007) Nature Rev. Immunol., 7:841-850; Call, M. E. et al., (2005) Annu. Rev. Immunol., 23:101-125).

Particular amino acid residues in the respective TCR chains have been identified as important for proper dimer formation and TCR assembly. In particular, for TCR-α, these key amino acids in the transmembrane portion are arginine (for association with CD3ζ) and lysine (for association with the CD3-ε/δ dimer). For TCR-β, the key amino acid in the transmembrane portion is a lysine (for association with CD3-ε/γ dimer). For CD3-γ, the key amino acid in the transmembrane portion is a glutamic acid. For CD3-8, the key amino acid in the transmembrane portion is an aspartic acid. For CD3-ε, the key amino acid in the transmembrane portion is an aspartic acid. For CD3ζ, the key amino acid in the transmembrane portion is an aspartic acid (Call, M. E. et al., (2007) Nature Rev. Immunol., 7:841-850; Call, M. E. et al., (2005) Annu. Rev. Immunol., 23:101-125).

Peptides derived from altered or mutated proteins in tumors can be recognized by specific TCRs. Several key studies have led to the identification of antigens associated with specific tumors that have been able to induce effective cytotoxic T lymphocyte (CTL) responses in patients (Ribas, A. et al. 2003. J. Clin. Oncol. 21:2415-2432). T cell effector mechanisms include the ability to kill tumor cells directly and the production of cytokines that activate other host immune cells and change the local tumor microenvironment. Theoretically, T cells could identify and destroy a tumor cell expressing a single mutated peptide. Adoptive immunotherapy with CTL clones specific for MARTI or gp100 with low dose IL-2 has been effective in reduction or stabilization of tumor burden in some patients (Yee, C. et al. 2002. Proc. Natl. Acad. Sci. USA 99:16168-16173). Other approaches use T cells with a defined anti-tumor receptor. These approaches include genetically modifying CTLs with new antigen-specific T cell receptors that recognize tumor peptides and MHC, chimeric antigen receptors (CARs) derived from single chain antibody fragments (scFv) coupled to an appropriate signaling element, or the use of chimeric NK cell receptors (Ho, W. Y. et al. 2003. Cancer Cell 3:431-437; Eshhar, Z. et al. 1993. Proc. Natl. Acad. Sci. USA 90:720-724; Maher, J. and E. T. Davies. 2004. Br. J. Cancer 91:817-821; Zhang, T. et al. 2005. Blood 106:1544-1551).

Additional disclosures generally related to the field of cell-based therapies and chimeric NK receptors include WO/2011/05936, WO/2006/036445, U.S. patent application publication no. 2002/0039576, U.S. patent application publication no. 2006/0166314, U.S. provisional patent applications No. 61/255,980, filed Oct. 29, 2009, 60/612,836 filed Sep. 24, 2004, 60/681,782, filed May 17, 2005, Anderson et al. (2004) Blood 104:1565-1573, and Maeda et al. (2005) Blood 106:749-755, each of which is hereby incorporated by reference herein in its entirety.

BRIEF SUMMARY

Many human cancer cells naturally express NKp30 ligands. To harness the NKp30 receptor-ligand interaction for cancer therapy, we have created chimeric NKp30 (chNKp30) receptors by linking human NKp30 to a variety of other protein domains, including human CD3ζ, CD28, Dap10, CD27, and CD8, that allow for stable protein expression and enhanced or altered signal transduction in T cells.

The examples below demonstrate that treatment with chNKp30-expressing T cells promoted survival and tumor eradication in mice bearing a tumor that expressed an NKp30 ligand. Additionally, the treatment elicited the hosts to generate memory responses against similar tumors lacking NKp30 ligand expression, such that mice that survived the first tumor were also completely resistant to the tumor re-challenge.

Without intent to be limited by theory, it is believed that these memory responses may be mediated by "epitope spreading," wherein initial targeting of NKp30 ligands by the chNKp3o-expressing T cells is thought to lead to tumor cell death, followed by efficient presentation of tumor antigens by professional APCs (such as DCs), probably as a result of the presence of proinflammatory cytokines (e.g., IFNγ, TNF-α, and GM-CSF) and chemokines. Cross-priming of host T cells by these APCs may further lead to expansion of polyclonal tumor-specific T cells (i.e., epitope spreading). Due to these memory responses, it is predicted that tumors would be less able to evade immune surveillance through selection of tumor cells bearing mutations or deletions of targeted antigens (Swann et al., J. Clin. Invest. 117: 1137-1146; Kim et al., Immunology 121: 1-14). Thus, the methods of the present disclosure can induce polyclonal tumor-specific T cells that will minimize the chances for tumor cells to "escape," increasing the efficacy of the treatment and reducing the likelihood of recurrent tumor disease.

More specifically, the examples below demonstrate that chimeric NKp30 molecules can be expressed by viral transduction in human T cells and allow these cells to recognize tumor cells that express an NKp30 ligand, B7-H6. The chimeric NKp30 expressing T cells kill these tumor cells and secrete cytokines (e.g., IFN-γ), but not when cultured with ligand-deficient tumor cells.

These chimeric receptors were also expressed in murine T cells and lead to in vitro killing and cytokine release in the presence of ligand-expressing tumor cells. In addition, these murine T cells expressing chimeric human NKp30 constructs were demonstrated to remove ligand-expressing tumors in vivo and increase survival of mice bearing a ligand-expressing lymphoma. Several of these mice become long-term survivors. These survivors were resistant to a tumor re-challenge with a similar, but ligand-deficient, lymphoma. These data show that this chimeric NKp30 receptor T cell treatment can lead to tumor eradication and suggest induction of long-term tumor immunity in the treated animals. Thus, chimeric NKp30 receptors may be a viable therapy for the treatment of tumors that express NKp30 ligands.

In summary, a chNKp30 receptor can be used to redirect T cells against NKp30 ligand-expressing tumors. Incorporation of a CD28-signaling domain into chimeric NKp30 receptors can stimulate both primary and costimulatory signals for enhanced antitumor activities. NKp30 can recognize its ligands on several different types of tumor cells, and this study demonstrates a potential broad therapeutic usefulness of this chNKp30 CAR approach for the treatment of cancer.

We additionally envision a portion of DAP10, or other proteins (such as DAP12) to enhance the function of NKp30. In addition, we have also created chimeric molecules that contain NKp30 fused to more than one of these other protein signaling domains. These combinations create new receptors with novel and unexpected signaling properties, including cellular cytotoxicity and cytokine production. The properties of the various chimeric NKp30 molecules have been empirically determined.

The present disclosure also relates to a method for reducing or eliminating tumors. The method involves introducing into an isolated T cell of a patient (or an allogeneic T cell, e.g., obtained from a compatible donor) having or suspected of having or at risk for developing a tumor a nucleic acid construct containing a first nucleic acid sequence comprising a promoter operably linked to a second nucleic acid sequence encoding a chimeric receptor protein as described in the preceding paragraphs, e.g., comprising an NKp30 extracellular domain linked to a variety of other protein domains, including domains of CD3ζ, CD28, CD8, DAP10, and/or CD27. The T cell is subsequently introduced back into the patient so that the chimeric receptor is expressed on the surface of the T cell to activate anti-tumor immunity in the patent thereby reducing or eliminating the tumor.

BRIEF DESCRIPTION OF THE DRAWINGS

FIGS. 3A-I shows the level of surface expression of chimeric NKp30 receptors on human T cells for the constructs illustrated in FIG. 2 and additional constructs. Surface expression was analyzed by flow cytometry using labeled anti-NKp30 and anti-CD4 mAbs (the latter identifies CD4-positive T cells). Results are shown for mock-transfected cells (FIG. 3A); wild-type (i.e., non-chimeric) NKp30 transfected cells (FIG. 3B); chimeric NKp30-CD3ζ transfected cells (FIG. 3C); chimeric NKp30-CD28-CD3ζ transfected cells (FIG. 3D); wild-type (i.e., non-chimeric) NKp30 transfected cells (FIG. 3E); chimeric NKp30-CD28-CD3 transfected cells (FIG. 3F); NKp30-CD28(TM)-DAP10-CD3ζ transfected cells (FIG. 3G); NKp30-CD28(TM)-CD3ζ-Dap10 transfected (FIG. 3H); and NKp30-CD28 (TM)-CD27-CD3ζ (FIG. 3I). The results generally indicate robust surface expression of the chimeric constructs, except that the level of detected surface expression was somewhat lower for 30-tm28-27-z than the other constructs. In contrast, retroviral transduction of human T cells with wtNKp30 gene did not lead to significant surface expression.

FIGS. 6A-E illustrates production of IFN-γ after co-culture of transfected T cells with NKp30 ligand-positive cells but not with ligand-negative cells (or T cells alone). FIGS. 6A-B show that NKp30-CD3ζ+ (grey bars, middle bar in each group) and NKp30-CD28-CD3ζ+ T (black bars, rightmost bar in each group) cells produced significant amounts of IFN-γ, indicating that these chimeric NKp30- modified T cells could functionally recognize NKp30 ligand-bearing tumor cells. In contrast, wild-type NKp30-modified T cells (FIG. 6A, white bars, left bar in each group) did not show any significant response to the stimulation by NKp30-ligand positive cells. FIG. 6C illustrates IFN-γ production after co-culture with T cells that were mock-transfected, transfected with wild-type NKp30, NKp30-CD28-CD3ζ, NKp30-CD28(TM)-DAP10-CD3ζ, NKp30-CD28 (TM)-CD3ζ-Dap10, and NKp30-CD28(TM)-CD27-CD3ζ (leftmost through rightmost bars in each group, respectively). IFN-γ production was highest in the cultures containing NKp30-CD28-CD3ζ transfected T cells. FIGS. 6D-E further illustrate that NKp30 chimeric antigen receptor-modified T cells respond to NKp30 ligand-positive cells by producing IFN-γ. Five to seven days after retroviral transduction, NKp30 chimeric antigen receptor-modified T cells (100,000 cells) were cocultured with either irradiated or mitomycin C-treated tumor cells for 24 h. Suspension tumor cells (100,000 cells) (D) and adherent tumor cells (25,000 cells) (F) were used. RMA and MCF-7 cells were used as negative controls. IFN-γ amounts in the supernatants were analyzed with ELISA. Results are shown as mean+/−SD. Asterisks (*) indicate p<0.05.

In FIG. 7A, NKp30-CD3ζ+ (black bars, middle bar in each group) or NKp30-CD28-CD3ζ+ (diagonal hatched bars, rightmost bar in each group) T cells lysed NKp30 ligand-positive cells (RMA/B7-H6, K562, U937, HeLa, Panc-1, A375, and T47D) but not ligand-negative cells (cell line RMA) indicating that these chimeric NKp30-modified T cells could functionally recognize NKp30 ligand-bearing tumor cells in a specific manner. In contrast, a far lower percentage of tumor cells were lysed in the presence of wild-type NKp30-modified T cells (FIG. 7A, light gray bars, left bar in each group). NKp30-CD28-CD3ζ+ killed a greater percentage of NKp30 ligand-positive tumor cells than NKp30-CD3ζ. Results are shown for triplicate experiments (mean+/−SD). Similarly, in FIG. 7B, the T cells expressing the 30-28-z, 30-tm28-10-z, 30-tm28-z-10, and 30-tm28-27-z constructs lysed NKp30 ligand-positive cells (RMA-B7H6 and K562) but not the negative control RMA cell (which lacks B7H6 expression), whereas far fewer tumor cells were lysed in the presence of T cells expressing wild-type NKp30. FIG. 7B legend: constructs in each group of bars, in order from left to right, were: NKp30, 30-28-z, 30-tm28-10-z, 30-tm28-z-10, and 30-tm28-27-z.

FIGS. 9E-J further exemplifies chimeric human NKp30 expression on mouse cells. Human NKp30 expression on mouse T cells 7 d after transduction. NKp30 expression was detected using the PE-conjugated anti-NKp30 mAb in combination with the anti-mouse CD4-FITC mAb. CD42 T cells are CD8+ T cells. The data are representative of three experiments. Expression levels are shown for mock-transfected cells (FIG. 9E); wild-type (i.e., non-chimeric) NKp30 transfected cells (FIG. 9F); chimeric NKp30-CD3ζ transfected cells (FIG. 9G); chimeric NKp30-CD8(TM)-CD3ζ transfected cells (FIG. 9H); chimeric NKp30-CD28(TM)-CD3ζ transfected cells (FIG. 9I), and chimeric NKp30-CD28-CD3ζ transfected cells (FIG. 9J).

FIGS. 11A-C. Integration of CD28 TM and signaling domains into chimeric NKp30 receptor leads to long-term survival in tumor-bearing mice treated with these T cells in vivo. Mouse T cells transduced with chimeric NKp30 enhanced survival of mice injected with lymphoma cells, specifically RMA/B7-H6 that express the NKp30 ligand B7-H6 (schematically illustrated in FIG. 11A). Integration of CD28 TM and signaling domains into chimeric NKp30 receptor was demonstrated to lead to better anti-tumor in vivo efficacy. RMA/B7-H6 cells (105) were administered i.v. on day 0. On day 5, 7 and 9, tumor-bearing mice were injected with T cells (5×10⁶) that were modified to express wtNKp30 (◆), NKp30-CD3ζ (▲), NKp30-CD8-CD3ζ (●) and NKp30-CD28-CD3ζ (□), respectively (FIG. 11B). Injection with a saline solution (HBSS) was used as negative control. Data are presented in Kaplan-Meier survival curves. Additionally, surviving mice gained ligand-independent tumor resistance. Long-term survivors were re-challenged with a similar, but ligand-deficient, lymphoma, specifically RMA cells that had not been transformed with the B7-H6 construct. Overall survival was determined, and none of the re-challenged mice had tumor growth by the end of the study period, whereas naïve mice did (FIG. 11C).

Figures 12A, 12B:
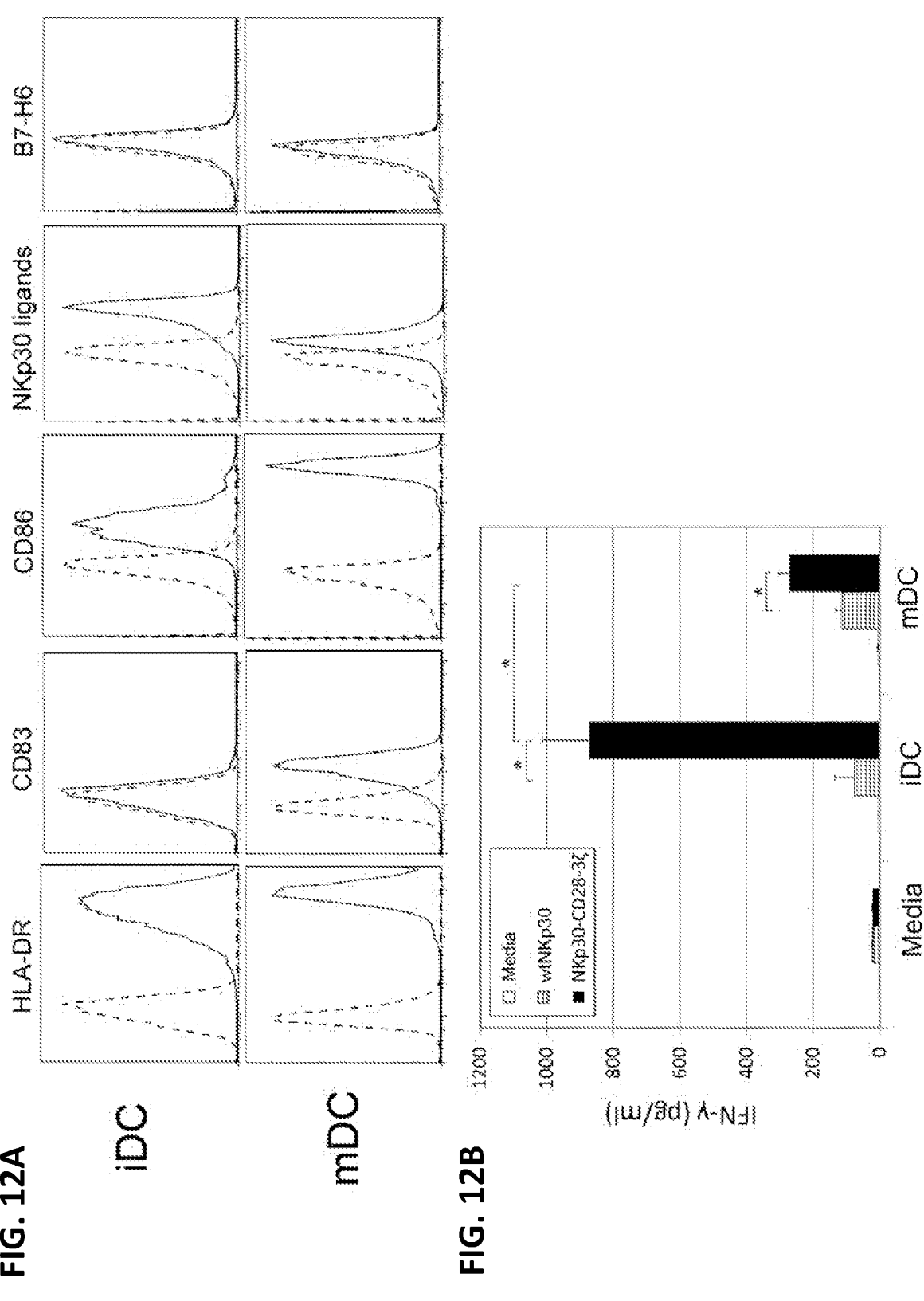

FIGS. 12A-B. Human dendritic cells ("DCs") bind to NKp30 and can stimulate autologous NKp30-CD28-3ζ-modified T cells to produce IFN-γ. (A) The cell surface phenotype and binding to NKp30 of PBMC-derived human DCs (both iDCs and mDCs) was determined by flow cytometry. Specific mAb or NKp30-Ig as indicated (solid line) or an isotype control Ab staining (dashed line) is shown. (B) Five to seven days after retroviral transduction, NKp30 chimeric antigen receptor-modified T cells ($10^5$ cells) were cocultured with either iDCs or mDCs at a ratio of 5:1 (T/DC) for 24 h. IFN-γ amounts in the supernatants were determined by ELISA. Results shown (mean+SD) are representative of two experiments. Asterisk (*) indicates p<0.05. As further discussed infra, because NKp30 ligands can be expressed by human dendritic cells, these results help confirm that the methods and compositions of the present disclosure may be useful to prevent or treat diseases where elimination of dendritic cells may be helpful, such as autoimmune diseases or rejection of transplanted organs.

Figures 13A, 13B, 13C:
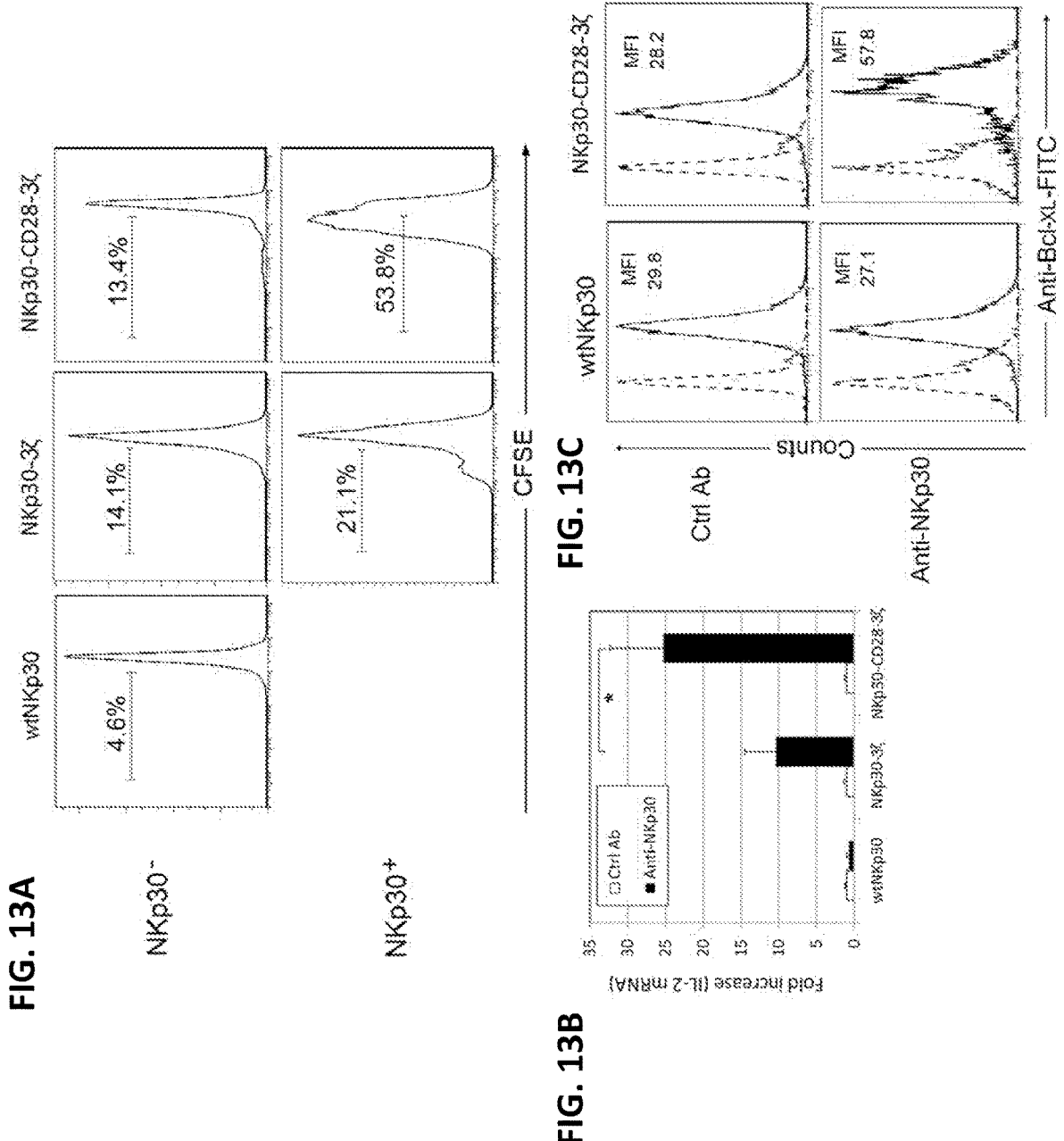

FIGS. 13A-B. Engagement of NKp30-CD28-3ζ receptor led to increased T cell proliferation and upregulation of IL-2 and Bcl-$x_L$. (A) NKp30 receptor (either wtNKp30 or chimeric NKp30)-modified human T cells were labeled with CFSE, as described in the examples below, and cocultured with HeLa cells (100,000 cells, NKp30 ligand-positive) in the presence of a small amount of IL-2 (25 U/ml) for 3 d. Analysis of T cell proliferation (i.e., CFSE dilution) was performed on both NKp30+ (FL4) and NKp30– cells within the same mixed T cell population by flow cytometry. (B) NKp30-modified T cells (250,000 cells) were cultured in anti-NKp30 mAb (4 µg)-coated 24-well plates for 24 h. Mouse IgG was used as a negative control. IL-2 gene expression was determined by real-time PCR, as described in the examples below. Results are shown as fold increase, in which the IL-2 gene expression in the control mAb-treated T cells was normalized to 1. Data are presented as mean+/–SD from two independent experiments. (C) Twenty-four hours after cross-linking with immobilized anti-NKp30 mAbs, as described in the examples below, T cells were collected. Bcl-$x_L$ expression was determined by flow cytometry after intracellular staining with anti-Bcl-$x_L$-FITC (solid line) or isotype control mAbs (dashed line). Asterisk (*) indicates p<0.05.

Figure 14:
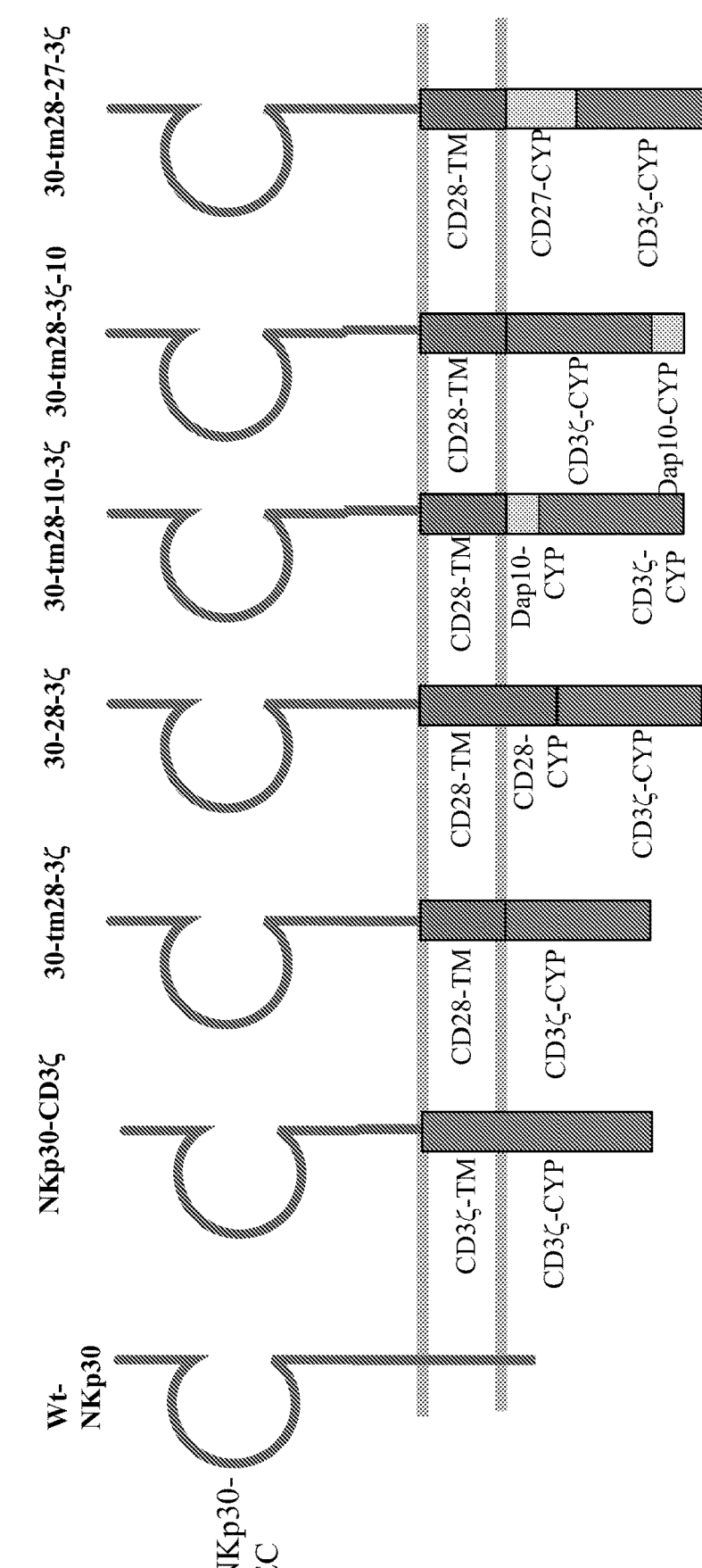

FIG. 14 schematically illustrates additional exemplary chimeric NKp30 receptor constructs. The two horizontal lines represent a cell membrane, with the portion above both lines corresponding to the extracellular domain (NKp30 extracellular domain in each Illustrated construct), the portion between the horizontal lines corresponding to the transmembrane domain (e.g., CD3ζ transmembrane domain or CD28 domain in the illustrated construct, though other transmembrane domains are also used in exemplary embodiments, e.g., a CD8 transmembrane domain in the construct shown in FIG. 19); and the portion below both horizontal lines including the one or more activation domain(s) (e.g., the cytoplasmic domains of CD3ζ, CD28, DAP10, CD27, and combinations thereof. Illustrated constructs include wild-type NKp30 (Wt-NKp30); NKp30-CD3ζ, containing the NKp30 extracellular domain and CD3ζ transmembrane and cytoplasmic domains; 30-tm28-3ζ (also referred to herein as NKp30-CD28(TM)-CD3ζ); 30-28-3ζ (also referred to herein as NKp30-CD28-CD3ζ); 30-tm28-10-3ζ (also referred to herein as NKp30-CD28(TM)-DAP10-CD3ζ); 30-tm28-3ζ-10 (also referred to herein as NKp30-

CD28(TM)-CD3ζ-Dap10); and 30-tm28-27-3ζ (also referred to herein as NKp30-CD28(TM)-CD27-CD3ζ.

FIG. 15 provides a polypeptide sequence of a wild-type human NKp30 and illustrates domains thereof.

FIGS. 16-22 provide polypeptide sequences of chimeric NKp30 receptors, and exemplary polynucleotide sequences are shown below. In these figures, the labels "TM" or "TM domain" refer to transmembrane domain sequences; the labels "EC" or "EC domain" refer to extracellular sequences (e.g., NKp30 ligand-binding domain sequences) and "CYP" or "CYP domain" refer to cytoplasmic domain sequences (which include signaling domains of the identified polypeptides). The identified polypeptides refer to the wild-type sequences from which the respective domains were derived.

FIG. 16 provides the polypeptide sequence of an NKp30-CD3ζ (also referred to herein as NKp30-CD3z or NKp30-C or NKp30-3z) construct comprising a signal peptide and extracellular domain of NKp30, and a transmembrane and cytoplasmic domain of CD3ζ. An exemplary coding sequence of this NKp30-CD3ζ construct is:

(SEQ ID NO: 124)
```
ATGGCCTGGATGCTGTTGCTCATCTTGATCATGGTCCATCCAGGATCCTG

TGCTCTCTGGGTGTCCCAGCCCCCTGAGATTCGTACCCTGGAAGGATCCT

CTGCCTTCCTGCCCTGCTCCTTCAATGCCAGCCAAGGGAGACTGGCCATT

GGCTCCGTCACGTGGTTCCGAGATGAGGTGGTTCCAGGGAAGGAGGTGAG

GAATGGAACCCCAGAGTTCAGGGGCCGCCTGGCCCCACTTGCTTCTTCCC

GTTTCCTCCATGACCACCAGGCTGAGCTGCACATCCGGGACGTGCGAGGC

CATGACGCCAGCATCTACGTGTGCAGAGTGGAGGTGCTGGGCCTTGGTGT

CGGGACAGGGAATGGGACTCGGCTGGTGGTGGAGAAAGAACATCCTCAGC

TAGGGGCTAGCCTCTGCTACCTGCTGGATGGAATCCTCTTCATCTATGGT

GTCATTCTCACTGCCTTGTTCCTGAGAGTGAAGTTCAGCAGGAGCGCAGA

CGCCCCCGCGTACCAGCAGGGCCAGAACCAGCTCTATAACGAGCTCAATC

TAGGACGAAGAGAGGAGTACGATGTTTTGGACAAGAGACGTGGCCGGGAC

CCTGAGATGGGGGGAAAGCCGCAGAGAAGGAAGAACCCTCAGGAAGGCCT

GTACAATGAACTGCAGAAAGATAAGATGGCGGAGGCCTACAGTGAGATTG

GGATGAAAGGCGAGCGCCGGAGGGGCAAGGGGCACGATGGCCTTTACCAG

GGTCTCAGTACAGCCACCAAGGACACCTACGACGCCCTTCACATGCAGGC

CCTGCCCCCTCGC.
```

FIG. 17 provides the polypeptide sequence of an NKp30-CD28-CD3ζ (also referred to herein as NKp30-CD28-CD3, 30-28-z, 30-28-3ζ, NKp30-CD28-CD3z, or NKp30-CD28-ζ) construct comprising a signal peptide and extracellular domain of NKp30, a transmembrane and cytoplasmic domain of CD28, and a further cytoplasmic domain of CD3ζ. An exemplary coding sequence of this NKp30-CD28-CD3ζ construct is:

(SEQ ID NO: 125)
```
ATGGCCTGGATGCTGTTGCTCATCTTGATCATGGTCCATCCAGGATCCTG

TGCTCTCTGGGTGTCCCAGCCCCCTGAGATTCGTACCCTGGAAGGATCCT

CTGCCTTCCTGCCCTGCTCCTTCAATGCCAGCCAAGGGAGACTGGCCATT
```

-continued

```
GGCTCCGTCACGTGGTTCCGAGATGAGGTGGTTCCAGGGAAGGAGGTGAG

GAATGGAACCCCAGAGTTCAGGGGCCGCCTGGCCCCACTTGCTTCTTCCC

GTTTCCTCCATGACCACCAGGCTGAGCTGCACATCCGGGACGTGCGAGGC

CATGACGCCAGCATCTACGTGTGCAGAGTGGAGGTGCTGGGCCTTGGTGT

CGGGACAGGGAATGGGACTCGGCTGGTGGTGGAGAAAGAACATCCTCAGC

TAGGGGCTAGCTTTTGGGTGCTGGTGGTGGTTGGTGGAGTCCTGGCTTGC

TATAGCTTGCTAGTAACAGTGGCCTTTATTATTTTCTGGGTGAGGAGTAA

GAGGAGCAGGCTCCTGCACAGTGACTACATGAACATGACTCCCCGCCGCC

CCGGGCCCACCCGCAAGCATTACCAGCCCTATGCCCCACCACGCGACTTC

GCAGCCTATCGCTCCAAGCTTAGAGTGAAGTTCAGCAGGAGCGCAGACGC

CCCCGCGTACCAGCAGGGCCAGAACCAGCTCTATAACGAGCTCAATCTAG

GACGAAGAGAGGAGTACGATGTTTTGGACAAGAGACGTGGCCGGGACCCT

GAGATGGGGGGAAAGCCGCAGAGAAGGAAGAACCCTCAGGAAGGCCTGTA

CAATGAACTGCAGAAAGATAAGATGGCGGAGGCCTACAGTGAGATTGGGA

TGAAAGGCGAGCGCCGGAGGGGCAAGGGGCACGATGGCCTACCAGGGTCT

CAGTACAGCCACCAAGGACACCTACGACGCCCTTCACATGCAGGCCCTGC

CCCCTCGC.
```

FIG. 18 provides the polypeptide sequence of an NKp30-CD28(TM)-CD3ζ (also referred to herein as NKp30-CD28 (TM)-ζ or 30-tm28-3ζ) construct comprising a signal peptide and extracellular domain of NKp30, and a transmembrane and cytoplasmic domain of CD3ζ. An exemplary coding sequence of this NKp30-CD28(TM)-CD3 construct is:

```
                                        (SEQ ID NO: 126)
ATGGCCTGGATGCTGTTGCTCATCTTGATCATGGTCCATCCAGGATCCTG

TGCTCTCTGGGTGTCCCAGCCCCCTGAGATTCGTACCCTGGAAGGATCCT

CTGCCTTCCTGCCCTGCTCCTTCAATGCCAGCCAAGGGAGACTGGCCATT

GGCTCCGTCACGTGGTTCCGAGATGAGGTGGTTCCAGGGAAGGAGGTGAG

GAATGGAACCCCAGAGTTCAGGGGCCGCCTGGCCCCACTTGCTTCTTCCC

GTTTCCTCCATGACCACCAGGCTGAGCTGCACATCCGGGACGTGCGAGGC

CATGACGCCAGCATCTACGTGTGCAGAGTGGAGGTGCTGGGCCTTGGTGT

CGGGACAGGGAATGGGACTCGGCTGGTGGTGGAGAAAGAACATCCTCAGC

TAGGGGCTAGCTTTTGGGTGCTGGTGGTGGTTGGTGGAGTCCTGGCTTGC

TATAGCTTGCTAGTAACAGTGGCCTTTATTATTTTCTGGGTGAGGAGTAA

GAAGCTTAGAGTGAAGTTCAGCAGGAGCGCAGACGCCCCCGCGTACCAGC

AGGGCCAGAACCAGCTCTATAACGAGCTCAATCTAGGACGAAGAGAGGAG

TACGATGTTTTGGACAAGAGACGTGGCCGGGACCCTGAGATGGGGGGAAA

GCCGCAGAGAAGGAAGAACCCTCAGGAAGGCCTGTACAATGAACTGCAGA

AAGATAAGATGGCGGAGGCCTACAGTGAGATTGGGATGAAAGGCGAGCGC

CGGAGGGGCAAGGGGCACGATGGCCTTTACCAGGGTCTCAGTACAGCCAC

CAAGGACACCTACGACGCCCTTCACATGCAGGCCCTGCCCCCTCGC.
```

FIG. 19 provides the polypeptide sequence of an NKp30-CD8-CD3ζ (also referred to herein as NKp30-CD8-ζ or NKp30-CD8(TM)-3ζ) construct comprising a signal peptide and extracellular domain of NKp30, a transmembrane domain of CD8, and a cytoplasmic domain of CD3ζ. An exemplary coding sequence of this NKp30-CD8-CD3ζ construct is:

```
                                        (SEQ ID NO: 127)
ATGGCCTGGATGCTGTTGCTCATCTTGATCATGGTCCATCCAGGATCCTG

TGCTCTCTGGGTGTCCCAGCCCCCTGAGATTCGTACCCTGGAAGGATCCT

CTGCCTTCCTGCCCTGCTCCTTCAATGCCAGCCAAGGGAGACTGGCCATT

GGCTCCGTCACGTGGTTCCGAGATGAGGTGGTTCCAGGGAAGGAGGTGAG

GAATGGAACCCCAGAGTTCAGGGGCCGCCTGGCCCCACTTGCTTCTTCCC

GTTTCCTCCATGACCACCAGGCTGAGCTGCACATCCGGGACGTGCGAGGC

CATGACGCCAGCATCTACGTGTGCAGAGTGGAGGTGCTGGGCCTTGGTGT

CGGGACAGGGAATGGGACTCGGCTGGTGGTGGAGAAAGAACATCCTCAGC

TAGGGGCTAGCATCTACATCTGGGCGCCCTTGGCCGGGACTTGTGGGGTC

CTTCTCCTGTCACTGGTTATCACCAAGCTTAGAGTGAAGTTCAGCAGGAG

CGCAGACGCCCCCGCGTACCAGCAGGGCCAGAACCAGCTCTATAACGAGC

TCAATCTAGGACGAAGAGAGGAGTACGATGTTTTGGACAAGAGACGTGGC

CGGGACCCTGAGATGGGGGGAAAGCCGAGAAGGAAGAACCCTCAGGAAGG

CCTGTACAATGAACTGCAGAAAGATAAGATGGCGGAGGCCTACAGTGAGA

TTGGGATGAAAGGCGAGCGCCGGAGGGGCAAGGGGCACGATGGCCTTTAC

CAGGGTCTCAGTACAGCCACCAAGGACACCTACGACGCCCTTCACATGCA

GGCCCTGCCCCCTCGCTAA.
```

FIG. 20 provides the polypeptide sequence of a NKp30-CD28(TM)-DAP10-CD3ζ (also referred to herein as 30-tm28-10-3z, Dap10a, 30-tm28-10-7, or 30-tm28-10-3ζ) construct comprising a signal peptide and extracellular domain of NKp30, transmembrane domain of CD28, cytoplasmic domain of Dap10, and a cytoplasmic domain of CD3ζ. An exemplary coding sequence of this NKp30-CD28 (TM)-DAP10-CD3ζ construct is:

```
                                        (SEQ ID NO: 64)
ATGGCCTGGATGCTGTTGCTCATCTTGATCATGGTCCATCCAGGATCCTG

TGCTCTCTGGGTGTCCCAGCCCCCTGAGATTCGTACCCTGGAAGGATCCT

CTGCCTTCCTGCCCTGCTCCTTCAATGCCAGCCAAGGGAGACTGGCCATT

GGCTCCGTCACGTGGTTCCGAGATGAGGTGGTTCCAGGGAAGGAGGTGAG

GAATGGAACCCCAGAGTTCAGGGGCCGCCTGGCCCCACTTGCTTCTTCCC

GTTTCCTCCATGACCACCAGGCTGAGCTGCACATCCGGGACGTGCGAGGC

CATGACGCCAGCATCTACGTGTGCAGAGTGGAGGTGCTGGGCCTTGGTGT

CGGGACAGGGAATGGGACTCGGCTGGTGGTGGAGAAAGAACATCCTCAGC

TAGGGGCTAGCTTTTGGGTGCTGGTGGTGGTTGGTGGAGTCCTGGCTTGC

TATAGCTTGCTAGTAACAGTGGCCTTTATTATTTTCTGGGTGAGGAGTAA

GAGGAGCCTGTGCGCACGCCCACGCCGCAGCCCCGCCCAAGAAGATGGCA

AAGTCTACATCAACATGCCAGGCAGGGGCAAGCTTAGAGTGAAGTTCAGC

AGGAGCGCAGACGCCCCCGCGTACCAGCAGGGCCAGAACCAGCTCTATAA
```

-continued

```
CGAGCTCAATCTAGGACGAAGAGAGGAGTACGATGTTTTGGACAAGAGAC

GTGGCCGGGACCCTGAGATGGGGGGAAAGCCGAGAAGGAAGAACCCTCAG

GAAGGCCTGTACAATGAACTGCAGAAAGATAAGATGGCGGAGGCCTACAG

TGAGATTGGGATGAAAGGCGAGCGCCGGAGGGGCAAGGGGCACGATGGCC

TTTACCAGGGTCTCAGTACAGCCACCAAGGACACCTACGACGCCCTTCAC

ATGCAGGCCCTGCCCCCTCGC.
```

FIG. 21 provides the polypeptide sequence of a NKp30-CD28(TM)-CD3ζ-Dap10 (also referred to herein as 30-tm28-3z-10, Dap10b, 30-tm28-z-10, or 30-tm28-3ζ-10) construct construct comprising a signal peptide and extracellular domain of NKp30, transmembrane domain of CD28, a cytoplasmic domain of CD3ζ, and a cytoplasmic domain of Dap10. An exemplary coding sequence of this NKp30-CD28(TM)-CD3ζ-Dap10 construct is:

```
                                       (SEQ ID NO: 66)
ATGGCCTGGATGCTGTTGCTCATCTTGATCATGGTCCATCCAGGATCCTG

TGCTCTCTGGGTGTCCCAGCCCCCTGAGATTCGTACCCTGGAAGGATCCT

CTGCCTTCCTGCCCTGCTCCTTCAATGCCAGCCAAGGGAGACTGGCCATT

GGCTCCGTCACGTGGTTCCGAGATGAGGTGGTTCCAGGGAAGGAGGTGAG

GAATGGAACCCCAGAGTTCAGGGGCCGCCTGGCCCCACTTGCTTCTTCCC

GTTTCCTCCATGACCACCAGGCTGAGCTGCACATCCGGGACGTGCGAGGC

CATGACGCCAGCATCTACGTGTGCAGAGTGGAGGTGCTGGGCCTTGGTGT

CGGGACAGGGAATGGGACTCGGCTGGTGGTGGAGAAAGAACATCCTCAGC

TAGGGGCTAGCTTTTGGGTGCTGGTGGTGGTTGGTGGAGTCCTGGCTTGC

TATAGCTTGCTAGTAACAGTGGCCTTTATTATTTTCTGGGTGAGGAGTAA

GAGGAGCAAGCTTAGAGTGAAGTTCAGCAGGAGCGCAGACGCCCCCGCGT

ACCAGCAGGGCCAGAACCAGCTCTATAACGAGCTCAATCTAGGACGAAGA

GAGGAGTACGATGTTTTGGACAAGAGACGTGGCCGGGACCCTGAGATGGG

GGGAAAGCCGAGAAGGAAGAACCCTCAGGAAGGCCTGTACAATGAACTGC

AGAAAGATAAGATGGCGGAGGCCTACAGTGAGATTGGGATGAAAGGCGAG

CGCCGGAGGGGCAAGGGGCACGATGGCCTTTACCAGGGTCTCAGTACAGC

CACCAAGGACACCTACGACGCCCTTCACATGCAGGCCCTGCCCCCTCGCC

TGTGCGCACGCCCACGCCGCAGCCCCGCCCAAGAAGATGGCAAAGTCTAC

ATCAACATGCCAGGCAGGGGC.
```

FIG. 22 provides the polypeptide sequence of a NKp30-CD28(TM)-CD27-CD3ζ (also referred to herein as 30-tm28-27-3z, 30-tm28-27-z, or 30-tm28-27-3ζ) construct comprising a signal peptide and extracellular domain of NKp30, transmembrane domain of CD28, a cytoplasmic domain of CD27, and a cytoplasmic domain of CD3ζ. An exemplary coding sequence of this NKp30-CD28(TM)-CD3ζ-Dap10 construct is:

```
                                       (SEQ ID NO: 68)
ATGGCCTGGATGCTGTTGCTCATCTTGATCATGGTCCATCCAGGATCCTG

TGCTCTCTGGGTGTCCCAGCCCCCTGAGATTCGTACCCTGGAAGGATCCT
```

-continued

```
CTGCCTTCCTGCCCTGCTCCTTCAATGCCAGCCAAGGGAGACTGGCCATT

GGCTCCGTCACGTGGTTCCGAGATGAGGTGGTTCCAGGGAAGGAGGTGAG

GAATGGAACCCCAGAGTTCAGGGGCCGCCTGGCCCCACTTGCTTCTTCCC

GTTTCCTCCATGACCACCAGGCTGAGCTGCACATCCGGGACGTGCGAGGC

CATGACGCCAGCATCTACGTGTGCAGAGTGGAGGTGCTGGGCCTTGGTGT

CGGGACAGGGAATGGGACTCGGCTGGTGGTGGAGAAAGAACATCCTCAGC

TAGGGGCTAGCTTTTGGGTGCTGGTGGTGGTTGGTGGAGTCCTGGCTTGC

TATAGCTTGCTAGTAACAGTGGCCTTTATTATTTTCTGGGTGAGGAGTAA

GAGGAGCCTCGAGCAACGAAGGAAATATAGATCAAACAAAGGAGAAAGTC

CTGTGGAGCCTGCAGAGCCTTGTCGTTACAGCTGCCCCAGGGAGGAGGAG

GGCAGCACCATCCCCATCCAGGAGGATTACCGAAAACCGGAGCCTGCCTG

CTCCCCCAAGCTTAGAGTGAAGTTCAGCAGGAGCGCAGACGCCCCCGCGT

ACCAGCAGGGCCAGAACCAGCTCTATAACGAGCTCAATCTAGGACGAAGA

GAGGAGTACGATGTTTTGGACAAGAGACGTGGCCGGGACCCTGAGATGGG

GGGAAAGCCGAGAAGGAAGAACCCTCAGGAAGGCCTGTACAATGAACTGC

AGAAAGATAAGATGGCGGAGGCCTACAGTGAGATTGGGATGAAAGGCGAG

CGCCGGAGGGGCAAGGGGCACGATGGCCTTTACCAGGGTCTCAGTACAGC

CACCAAGGACACCTACGACGCCCTTCACATGCAGGCCCTGCCCCCTCGC.
```

DETAILED DESCRIPTION OF PREFERRED EMBODIMENTS

NKp30 is a natural cytotoxicity receptor that is expressed on NK cells and recognizes B7-H6, which is expressed on several types of tumors but few normal cells. To target effector T cells against B7-H6+ tumors, we developed several chimeric antigen receptors based on NKp30, including receptors that contain the CD28- and/or CD3γ-signaling domains with the transmembrane domains from CD3γ, CD28, or CD8α. Chimeric NKp30-expressing T cells responded to B7-H6+ tumor cells. T cells expressing NKp30 chimeric antigen receptors (CARs) produced IFN-γ and killed B7-H6 ligand-expressing tumor cells; this response was dependent upon ligand expression on target cells but not on MHC expression. PBMC-derived dendritic cells also express NKp30 ligands, including immature dendritic cells, and they stimulated NKp30 CAR-bearing T cells to produce IFN-γ, but to a lesser extent. The addition of a CD28–signaling domain significantly enhanced the activity of the NKp30 CAR in a PI3K-dependent manner.

Adoptive transfer of T cells expressing a chimeric NKp30 receptor containing a CD28-signaling domain inhibited the growth of a B7-H6-expressing murine lymphoma (RMA/B7-H6) in vivo. Moreover, mice that remained tumor-free were resistant to a subsequent challenge with the wild-type RMA tumor cells, suggesting the generation of immunity against other tumor antigens. These results demonstrates the specificity and therapeutic potential of adoptive immunotherapy with NKp30 chimeric antigen receptor-expressing T cells against B7-H6+ tumor cells in vivo.

The present disclosure relates to a chimeric receptor molecule comprising an NKp30 extracellular domain expressed on the surface of a T cell to activate killing of a tumor cell. Nucleic acid sequences encoding the chimeric receptor molecule are introduced into a patient's T-cells (or compatible T cells, e.g., an allogeneic T cell obtained from a compatible donor or a cell bank) and T-cells that express the chimeric receptor molecule are subsequently introduced into the patient. In this manner, the chimeric receptor molecules provide a means for the patient's own immune cells to recognize and destroy tumor cells, activate anti-tumor immunity, and establish long-term, specific, anti-tumor responses for treating tumors or preventing re-growth of dormant or residual tumor cells.

By way of illustration, human chimeric receptor molecules composed of an NKp30 extracellular domain in combination with transmembrane and/or cytoplasmic domains of CD3ζ and/or CD28 were generated and expressed in human T-cells. Specifically, a gene encoding a chimeric receptor comprising the extracellular domain of human NKp30 and transmembrane and cytoplasmic domains of human CD3ζ (NKp30-CD3ζ receptor) was generated. A gene encoding a chimeric receptor comprising the extracellular domain of human NKp30, the transmembrane domain of CD28, and cytoplasmic domain of human CD3ζ NKp30-CD28-CD3ζ receptor) was also generated. As described further in the examples below, these chimeric NKp30 genes were introduced into human T cells ex vivo by retroviral transduction, and were shown to be efficiently surface-expressed. Moreover, T cells expressing these chimeric NKp30 receptors ("chimeric NKp30 T cells") were demonstrated to be specifically activated by and lysed NKp30 ligand-positive tumor cells. The same (human) chimeric NKp30 genes were introduced into mouse T cells ex vivo by retroviral transduction and were demonstrated to be surface-expressed by mouse cells as well, and transduced mouse cells were specifically activated by and lysed NKp30 ligand-positive tumor cells. Moreover, the transduced mouse T cells increased survival of mice injected with NKp30-ligand expressing tumor cells. Several mice became long-term survivors that were resistant to a tumor re-challenge with a similar, but NKp30 ligand-deficient, lymphoma. These results indicate that this chimeric T cell treatment can lead to tumor eradication and suggest induction of long-term tumor immunity in the animals.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

"Allogeneic T cell" refers to a T cell from a donor having a tissue that is not genetically identical to the recipient. The T cell may have an HLA type that partially or fully matches the recipient or does not match the recipient. In some instances allogeneic transplant donors may be related (usually a closely HLA matched sibling), syngeneic (a monozygotic 'identical' twin of the patient) or unrelated (donor who is not related and found to have very close degree of HLA matching). The HLA genes fall in two categories (Type I and Type I). In general, mismatches of the Type-I genes (i.e. HLA-A, HLA-B, or HLA-C) increase the risk of graft rejection. A mismatch of an HLA Type II gene (i.e. HLA-DR, or HLA-DQB1) increases the risk of graft-versus-host disease.

In the context of the present disclosure, a T cell progenitor refers to any cell that may give rise to a T cell including but not limited to adult and embryonic stem cells, induced stem cells, hematopoietic stem cells (e.g., CD34+ hematopoietic stem cells), thymocytes, and T lymphocyte-restricted progenitors typically found in the thymus. Additional exemplary T cell progenitors include thymocytes in the double negative stages (each negative for both CD4 and CD8), such as the double negative 1 stage (Lineage-CD44+CD25-CD117+), double negative 2 stage (Lineage-CD44+CD25+CD117+), double negative 3 stage (Lineage-CD44−CD25+), double negative 4 stage (Lineage-CD44−CD25−), double positive stage (CD4+CD8+) and/or single positive stage (CD4+CD8− or CD4−CD8+).

In the context of the present disclosure, a "bank of tissue matched chimeric NKp30 T cells" refers to different compositions each containing T cells of a specific HLA allotype which express a chimeric NKp30 receptor according to the present disclosure. Ideally this bank will comprise compositions containing T cells of a wide range of different HLA types that are representative of the human population. Such a bank of engineered chimeric NKp30 T cells will be useful as it will facilitate the availability of T cells suitable for use in different recipients, such as cancer patients.

As used herein. CD3ζ (CD3ζ) refers to human polypeptide or polynucleotide (or orthologs in other species if the context so indicates) having exemplary sequences as follows. Two CD3 transcript variants have been reported. One transcript variant, CD3ζ transcript variant 1, has Genbank accession number NM_198053 (polynucleotide), encoding the polypeptide CD3ζ chain isoform 1 precursor (NP_0.932170.1) having the sequence:

```
                                      (SEQ ID NO: 1)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTATK

DTYDALHMQALPPR
``` which is annotated as comprising a signal peptide (residues 1-21, i.e., MKWKALFTAAILQAQLPITEA (SEQ ID NO: 2)) and a mature peptide (residues 22-164, i.e., QSFGLL-DPKLCYLLDGILFIYGVILTALFLRVKFSRSADAPA-YQQGQNQLYNELNLGRRE EYDVLDKRR-GRDPEMGGKPQRRKNPQEGLYNELQKDKMAEAYSEI-GMKGERRRGKG HDGLYQGLSTATKDTYDALHMQALPPR (SEQ ID NO: 3)), and is further annotated as comprising a transmembrane region (residues 31-51, i.e., LCYLLDGILFIYGVILTALFL (SEQ ID NO: 4)) and additionally includes the cytoplasmic domain sequence

```
                                      (SEQ ID NO: 5)
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR.
```

A second transcript variant, CD3ζ transcript variant 2, has Genbank accession number NM_000734.3 (polynucleotide), encoding the polypeptide CD3ζ chain isoform 2 precursor (NP_000725.1) having the sequence:

```
                                          (SEQ ID NO: 6)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKD

TYDALHMQALPPR
``` which is annotated as comprising a signal peptide (residues 1-21, i.e., MKWKALFTAAILQAQ (SEQ ID NO: 7)) and a mature peptide (residues 22-164, i.e., LPITEAQSFGLL-DPKLCYLLDGILFIYGVILTALFLRVKFSRSADAPA-YQQGQNQLYNELN LGRREEYDVLDKRR-GRDPEMGGKPRRKNPQEGLYNELQKDKMAEAYSEI GMKGERRR GKGHDGLYQGLSTATKDTY-DALHMQALP (SEQ ID NO: 8)), and is further annotated as comprising a transmembrane region (residues 31-51, i.e., LCYLLDGILFIYGVILTALFL (SEQ ID NO: 9)) and additionally includes the cytoplasmic domain sequence

```
                                         (SEQ ID NO: 10)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.
```

As used herein, NKp30 refers to human polypeptide or polynucleotide (or orthologs in other species if the context so indicates) having exemplary sequences as follows. Three NKp30 isoforms have been reported. A human NKp30 isoform A gene has Genbank accession number NP_667341.1 having the sequence: MAWMLLLIL-IMVHPGSCALWVSQPPEIRTLEGSSAFLPCSF-NASQGRLAIGSVTWFRDEV VPGKEVRNGTPEFRGR-LAPLASSRFLHDHQAELHIRDVRGHDASIYVCRVEV LGLGVGT GNGTRLVVEKEHPQLGAGTVLLL-RAGFYAVSFLSVAVGSTVYYQGKCLTWKGPRRQLP AVVPAPLPPPCGSSAHLLPPVPGG (SEQ ID NO: 11) which is annotated as comprising a transmembrane region (residues 136-156, i.e., AGTVLLLRAGFYAVSFLSVAV (SEQ ID NO: 12)) and includes a cytoplasmic domain having the sequence GSTVYYQGKCLTWKGPRRQL-PAVVPAPLPPPCGSSAHLLPPVPGG (SEQ ID NO: 13)) and additionally includes the signal peptide sequence MAWMLLLILIMVHPGSCA (SEQ ID NO: 14) and an extracellular domain having the sequence

```
                                         (SEQ ID NO: 15)
LWVSQPPEIRTLEGSSAFLPCSFNASQGRLAIGSVTWFRDEVVPGKEVRN

GTPEFRGRLAPLASSRFLHDHQAELHIRDVRGHDASIYVCRVEVLGLGVG

TGNGTRLVVEKEHPQLG.
```

A second transcript variant, human NKp30 isoform B gene has Genbank accession number NP_001138938.1 having the sequence: MAWMLLLILIMVHPGSCALWVSQP-PEIRTLEGSSAFLPCSFNASQGRLAIGSVTWFRDEV VPGKEVRNGTPEFRGRLAPLASSRFLHDHQAEL-HIRDVRGHDASIYVCRVEVLGLGVGT GNGTRLVVEKEHPQLGAGTVLLLRAGFYAVSFLSVA-VGSTVYYQGKYAKSTLSGFPQL (SEQ ID NO: 16)

which is annotated as comprising the same transmembrane region sequence as isoform A (residues 136-156, i.e., AGTVLLLRAGFYAVSFLSVAV (SEQ ID NO: 17)) and includes the signal peptide sequence MAWMLLLIL-IMVHPGSCA (SEQ ID NO: 18), extracellular domain sequence LWVSQPPEIRTLEGSSAFLPCSFNASQGR-LAIGSVTWFRDEVVPGKEVRNGTPEFRGRLA PLASSRFLHDHQAEL-HIRDVRGHDASIYVCRVEVLGLGVGTGNGTRLVVEK EHPQLG (SEQ ID NO: 19), and cytoplasmic domain sequence GSTVYYQGKYAKSTLSGFPQL (SEQ ID NO: 20).

A third transcript variant, human NKp30 isoform C gene has Genbank accession number NP_001138939.1 having the sequence: MAWMLLLILIMVHPGSCALWVSQP-PEIRTLEGSSAFLPCSFNASQGRLAIGSVTWFRDEV VPGKEVRNGTPEFRGRLAPLASSRFLHDHQAEL-HIRDVRGHDASIYVCRVEVLGLGVGT GNGTRLVVEKEHPQLGAGTVLLLRAGFYAVSFLSVA-VGSTVYYQGKCHCHMGTHCHS SDGPRGVIPEPRCP (SEQ ID NO: 21) which contains the same sequence region sequence as isoforms A and B which is likewise expected to function as a transmembrane sequence (residues 136-156, i.e., AGTVLLLRAGFYAVSFLSVAV (SEQ ID NO: 22)) and includes the signal peptide sequence MAWMLLLIL-IMVHPGSCA (SEQ ID NO: 23), extracellular domain sequence LWVSQPPEIRTLEGSSAFLPCSFNASQGR-LAIGSVTWFRDEVVPGKEVRNGTPEFRGRLA PLASSRFLHDHQAEL-HIRDVRGHDASIYVCRVEVLGLGVGTGNGTRLVVE KEHPQLG (SEQ ID NO: 24) and cytoplasmic domain sequence

```
                                         (SEQ ID NO: 25)
GSTVYYQGKCHCHMGTHCHSSDGPRGVIPEPRCP.
```

As used herein, CD28 refers to human polypeptide or polynucleotide (or orthologs in other species if the context so indicates) having exemplary sequences as follows. Three human CD28 transcript variants have been reported. One transcript variant, human CD28 isoform 1, has Genbank accession number AF222341_1 having the sequence:

```
                                         (SEQ ID NO: 26)
MLRLLLALNLFPSIQVTGNKILVKQSPMLVAYDNAVNLSWKHLCPSPLFP

GPSKPFWVLVVVGGVLACYSLLVTVAFIIFWVRSKRSRLLHSDYMNMTPR

RPGPTRKHYQPYAPPRDFAAYRS.
```

A second transcript variant, human CD28 isoform 2, has Genbank accession number AAF33793.1 having the sequence:

```
                                         (SEQ ID NO: 27)
MLRLLLALNLFPSIQVTGKHLCPSPLFPGPSKPFWVLVVVGGVLACYSLL

VTVAFIIFWVRSKRSRLLHSDYMNMTPRRPGPTRKHYQPYAPPRDFAAYR

S.
```

CD28 isoforms 2 and 3 each include the transmembrane sequence FWVLVVVGGVLACYSLLVTVAFIIFWVRSK (SEQ ID NO: 28) and cytoplasmic domain sequence RSRLLHSDYMNMTPRRPGPTRKHYQPYAPPRD-FAAYRS (SEQ ID NO: 29). In exemplary embodiments, the transmembrane sequence may include adjacent sequences annotated as part of another domain, e.g., an exemplary transmembrane sequence is

```
                                        (SEQ ID NO: 30)
    FWVLVVVGGVLACYSLLVTVAFIIFWVRSKRS.
```

A third transcript variant, human CD28 isoform 3, has Genbank accession number AAF33794.1 having the sequence:

```
                                        (SEQ ID NO: 31)
MLRLLLALNLFPSIQVTGNKILVKQSPMLVAYDNAVNLSYNEKSNGTII

HVKGKHLCPSPLFPGPSKPYAPPRDFAAYRS.
```

As used herein, CD8 refers to human polypeptide or polynucleotide (or orthologs in other species if the context so indicates) having exemplary sequences as follows. Two human CD8 transcript variants have been reported. One transcript variant, CD8 α chain isoform 1 precursor, has Genbank accession number NP_001759.3 having the sequence:

```
                                        (SEQ ID NO: 32)
MALPVTALLLPLALLLHAARPSQFRVSPLDRTWNLGETVELKCQVLLSN

PTSGCSWLFQPRGAAASPTFLLYLSQNKPKAAEGLDTQRFSGKRLGDTF

VLTLSDFRRENEGYYFCSALSNSIMYFSHFVPVFLPAKPTTTPAPRPPT

PAPTIASQPLSLRPEACRPAAGGAVHTRGLDFACDIYIWAPLAGTCGVL

LLSLVITLYCNHRNRRRVCKCPRPVVKSGDKPSLSARYV
``` which is annotated as comprising a signal peptide (residues 1-21, i.e., MALPVTALLLPLALLLHAARP (SEQ ID NO: 33)) and a mature peptide (residues 22-235, i.e., SQFRVSPL-DRTWNLGETVELKCQVLLSNPTSGCSWLFQPR-GAAASPTFLLYLSQNKPKA AEGLDTQRFSGKRLGDTFVLTLSDFRREN-EGYYFCSALSNSIMYFSHFVPVFLPAKFTT PAPRPPTPAPTIASQPLSLRPEACR-PAAGGAVHTRGLDFACDIYI-WAPLAGTCGVLLLSLV ITLYCNHRNRRRVCK-CPRPVVKSGDKPSLSARYV (SEQ ID NO: 34)), and is further annotated as comprising a transmembrane region (residues 183-203, i.e.,

```
                                        (SEQ ID NO: 35))
        IYIWAPLAGTCGVLLLSLVIT.
```

A second transcript variant, CD8 α chain isoform 2 precursor, has Genbank accession number NP_741969.1 has the sequence

```
                                        (SEQ ID NO: 36)
MALPVTALLLPLALLLHAARPSQFRVSPLDRTWNLGETVELKCQVLLSNP

TSGCSWLFQPRGAAASPTFLLYLSQNKPKAAEGLDTQRFSGKRLGDTFVL

TLSDFRRENEGYYFCSALSNSIMYFSHFVPVFLPAKPTTTPAPRPPTPAP

TIASQPLSLRPEACRPAAGGAGNRRRVCKCPRPVVKSGDKPSLSARYV
``` which contains the same sequence annotated as a signal peptide in isoform 1 (residues 1-21) which is likewise expected to function as a signal peptide, with the remaining residues (i.e., residues 22-198) likewise expected to correspond to the mature polypeptide.

As used herein, DAP10 refers to human polypeptide or polynucleotide (or orthologs in other species if the context so indicates) having exemplary sequences as follows. Two human DAP10 transcript variants have been reported. One transcript variant, human DAP10 isoform 1 precursor (hematopoietic cell signal transducer isoform 1 precursor) has Genbank accession number NP_055081.1 having the sequence:

```
                                        (SEQ ID NO: 37)
MIHLGHILFLLLLPVAAAQTTPGERSSLPAFYPGTSGSCSGCGSLSLPLL

AGLVAADAVASLLIVGAVFLCARPRRSPAQEDGKVYINMPGRG
``` which is annotated as comprising a signal peptide (residues 1-19, i.e., MIHLGHILFLLLLPVAAAQ (SEQ ID NO: 38)) and a mature peptide (residues 20-93, i.e., TTPGERSSLPAFYPGTSGSCSGCGSLSLPL-LAGLVAADAVASLLIVGAVFLCARPRRSPA QEDGKVYINMPGRG (SEQ ID NO: 39)), and is further annotated as comprising a transmembrane region (residues 49-69, i.e., LLAGLVAADAVASL-LIVGAVF (SEQ ID NO: 40)) and additionally includes the cytoplasmic domain sequence

```
                                        (SEQ ID NO: 41)
        LCARPRRSPAQEDGKVYINMPGRG.
```

A second transcript variant, DAP10 isoform 2 precursor (hematopoietic cell signal transducer isoform 2 precursor) has Genbank accession number NP_001007470.1 having the sequence:

```
                                        (SEQ ID NO: 42)
MIHLGHILFLLLLPVAAAQTTPGERSSLPAFYPGTSGSCSGCGSLSLPLL

AGLVAADAVASLLIVGAVFLCARPRRSPAQDGKVYINMPGRG
``` which is annotated as comprising a signal peptide (residues 1-19, i.e., MIHLGHILFLLLLPVAAAQ (SEQ ID NO: 43)) and a mature peptide (residues 20-92, i.e TTPGERSSLPAFYPGTSGSCSGCGSLSLPL-LAGLVAADAVASLLIVGAVFLCARPRRSPA QDGKVYINMPGRG (SEQ ID NO: 44)), and is further annotated as comprising a transmembrane region (residues 49-69, i.e., LLAGLVAADAVASLLIVGAVF (SEQ ID NO: 45)).

As used herein, DAP12 refers to human polypeptide or polynucleotide (or orthologs in other species if the context so indicates) having exemplary sequences as follows. Four human DAP12 transcript variants have been reported. One transcript variant, human DAP12 isoform 1 precursor (TYRO protein tyrosine kinase-binding protein isoform 1 precursor) has Genbank accession number NP_003323.1 having the sequence:

```
                                        (SEQ ID NO: 46)
MGGLEPCSRLLLLPLLLAVSGLRPVQAQAQSDCSCSTVSPGVLAGIVMGD

LVLTVLIALAVYFLGRLVPRGRGAAEAATRKQRITETESPYQELQGQRSD

VYSDLNTQRPYYK
``` which is annotated as comprising a signal peptide (residues 1-27) and a mature peptide (residues 28-113), and is further annotated as comprising a transmembrane region (residues 41-61, i.e., GVLA-GIVMGDLVLTVLIALAV (SEQ ID NO: 47)).

A second transcript variant, human DAP12 isoform 2 precursor (TYRO protein tyrosine kinase-binding protein isoform 2 precursor) has Genbank accession number NP_937758.1 having the sequence:

```
                                        (SEQ ID NO: 48)
MGGGLEPCSRLLLLPLLLAVSGLRPVQAQAQSDCSCSTVSPGVLAGIVMGD

LVLTVLIALAVYFLGRLVPRGRGAAEAATRKQRITETESPYQELQGQRSDV

YSDLNTQRPYYK
``` which is annotated as comprising a signal peptide (residues 1-27) and a mature peptide (residues 28-112), and is further annotated as comprising a transmembrane region (residues 41-61, i.e., GVLA-GIVMGDLVLTVLIALAV (SEQ ID NO: 49)).

A third transcript variant, human DAP12 isoform 3 precursor (TYRO protein tyrosine kinase-binding protein isoform 3 precursor) has Genbank accession number NP_001166985.1 having the sequence:

```
                                        (SEQ ID NO: 50)
MGGGLEPCSRLLLLPLLLAVSDCSCSTVSPGVLAGIVMGDLVLTVLIALAV

YFLGRLVPRGRGAAEAATRKQRITETESPYQELQGQRSDVYSDLNTQRPY

YK
``` which is annotated as comprising a signal peptide (residues 1-24) and a mature peptide (residues 25-102).

A fourth transcript variant, human DAP12 isoform 4 precursor (TYRO protein tyrosine kinase-binding protein isoform 4 precursor) has Genbank accession number NP_001166986.1 having the sequence:

```
                                        (SEQ ID NO: 51)
MGGGLEPCSRLLLLPLLLAVSDCSCSTVSPGVLAGIVMGDLVLTVLIALAV

YFLGRLVPRGRGAAEATRKQRITETESPYQELQGQRSDVYSDLNTQRPYY

K
``` which is annotated as comprising a signal peptide (residues 1-24) and a mature peptide (residues 25-101).

As used herein, CD27 refers to human polypeptide or polynucleotide (or orthologs in other species if the context so indicates) having exemplary sequences as follows. CD27 antigen precursor (also identified in Genbank as "T-cell activation antigen" and "CD27 molecule") has Genbank accession numbers NP_001233, AAH12160, and AAA58411, each having the sequence:

```
                                        (SEQ ID NO: 52)
MARPHPWWLCVLGTLVGLSATPAPKSCPERHYWAQGKLCCQMCEPGTFLV

KDCDQHRKAAQCDPCIPGVSFSPDHHTRPHCESCRHCNSGLLVRNCTITA

NAECACRNGWQCRDKECTECDPLPNPSLTARSSQALSPHPQPTHLPYVSE

MLEARTAGHMQTLADFRQLPARTLSTHWPPQRSLCSSDFIRILVIFSGMF

LVFTLAGALFLHQRRKYRSNKGESPVEPAEPCRYSCPREEEGSTIPIQED

YRKPEPACSP
``` for which exemplary coding sequences include or contained in Genbank Accession Nos. BC012160.1, M63928.1, and NM_001242.4.

CD27 (NP_001233) is annotated as comprising a signal peptide (residues 1-20) and a mature peptide (residues 21-260), and is further annotated as including a transmembrane region (residues 192-212, i.e., ILVIFSGMFLVFTL-AGALFLH (SEQ ID NO: 53)) and additionally includes the cytoplasmic domain sequence

```
                                        (SEQ ID NO: 54)
QRRKYRSNKGESPVEPAEPCRYSCPREEEGSTIPIQEDYRKPEPACSP.
```

As used herein, 41BB (also known as tumor necrosis factor receptor superfamily member 9, TNFRSF9, 4-1BB, CD137, CDw137, or ILA) refers to human polypeptides or polynucleotides (or orthologs in other species if the context so indicates) having exemplary sequences as follows. Tumor necrosis factor receptor superfamily member 9 precursor has Genbank accession number NP_001552.2, having the sequence:

```
                                        (SEQ ID NO: 55)
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCEL
```

(for which an exemplary coding sequence is contained in NM_001561.5) which polypeptide is annotated as including a signal peptide (residues 1-17) and mature peptide (residues 18-255) and is additionally annotated as including a transmembrane region (residues 187-213, i.e., HSFFLALTSTALLFLLFFLTLRFSVV (SEQ ID NO: 56)).

As used herein, OX40 (also known as tumor necrosis factor receptor superfamily member 4 precursor; ACT35; CD134; TXGP1L) refers to human polypeptides or polynucleotides (or orthologs in other species if the context so indicates) having exemplary sequences as follows. Tumor necrosis factor receptor superfamily member 4 precursor has Genbank accession number NP_003318.1, having the sequence:

```
                                        (SEQ ID NO: 57)
MCVGARRLGRGPCAALLLLGLGLSTVTGLHCVGDTYPSNDRCCHECRPGN

GMVSRCSRSQNTVCRPCGPGFYNDVVSSKPCKPCTWCNLRSGSERKQLCT

ATQDTVCRCRAGTQPLDSYKPGVDCAPCPPGHFSPGDNQACKPWTNCTLA

GKHTLQPASNSSDAICEDRDPPATQPQETQGPPARPITVQPTEAWPRTSQ

GPSTRPVEVPGGRAVAAILGLGLVLGLLGPLAILLALYLLRRDQRLPPDA

HKPPGGGSFRTPIQEEQADAHSTLAKI
```

(for which an exemplary coding sequence is contained in NM_003327.3) which polypeptide is annotated as including a signal peptide (residues 1-28) and mature peptide (residues 29-277) and is additionally annotated as including a transmembrane region (residues 215-235, i.e., VAAILGLGLVLGLLGPLAILL (SEQ ID NO: 58)).

It will be appreciated by those of ordinary skill in the art that the endpoints of the above-identified domains can be altered within the scope of the present disclosure, for example by extending or truncating one or both endpoints, e.g, by up to plus or minus five amino acids and optionally substituting an omitted portion of a domain with a suitable linker (such as an engineered or artificial sequence or a functionally similar sequence drawn from the same approximate region of a homologous protein).

In the context of the present disclosure, Chimeric NKp30 refers to a polypeptide (or coding polynucleotide) comprising the ligand-binding domain of NKp30 and at least one transmembrane domain and at least one signaling domain, wherein at least one domain is a domain a polypeptide other than NKp30. Exemplary transmembrane domains comprise the transmembrane domain of the polypeptides NKp30, CD28, CD8, CD3ζ, DAP10, CD27, and DAP12, preferably CD28, CD8, or CD3ζ, and most preferably CD28. Exemplary signaling domains comprises the signaling domain (e.g., cytoplasmic domains) of a polypeptide selected from the group consisting: NKp30, CD28, CD8, CD3ζ, DAP10, CD27, and DAP12, such as CD28 and/or CD3ζ.

In the context of the present disclosure, a "therapeutically effective amount" is identified by one of skill in the art as being an amount of chimeric NKp30 T cells that, when administered to a patient, alleviates the signs and or symptoms of the disease (e.g., cancer, infection, or autoimmune diseases). The actual amount to be administered can be determined based on studies done either in vitro or in vivo where the chimeric NKp30 T cells exhibit pharmacological activity against disease. For example, the chimeric NKp30 T cells may inhibit tumor cell growth either in vitro or in vivo and the amount of chimeric NKp30 T cells that inhibits such growth is identified as a therapeutically effective amount.

In the context of the present disclosure, the words "chimeric," "chimera" and the phrases "chimeric gene" and "chimeric polypeptide" and the like refer to a gene comprising an in-frame fusion between coding sequences of different polypeptides or portions of polypeptides, or the protein produced by translation thereof. Preferred chimeras comprise complete domains of different proteins, e.g., comprising one or more of each of extracellular, transmembrane, and cytoplasmic domains, wherein each domain is independently selected.

In the context of the present disclosure, the phrase "chimeric NKp30 T cells" or similar phrases refer to a T cell, which may be an isolated T cell, which expresses a chimeric NKp30 receptor. Optionally, a chimeric NKp30 T cell may also be TCR-deficient T cell, and/or may recombinantly express one or more additional receptors to initiate signaling to T cells.

The terms "purified," "substantially purified," and "isolated" as used herein refer to the state of being free of other, dissimilar compounds with which the compound is normally associated in its natural state, so that the "purified," "substantially purified," and "isolated" subject comprises at least 0.5%, 1%, 5%, 10%, or 20%, and most preferably at least 50% or 75% of the mass, by weight, of a given sample. In one preferred embodiment, these terms refer to the compound comprising at least 95% of the mass, by weight, of a given sample. As used herein, the terms "purified," "substantially purified," and "isolated," when referring to a nucleic acid or protein, also refers to a state of purification or concentration different than that which occurs naturally in the mammalian, especially human body. Any degree of purification or concentration greater than that which occurs naturally in the mammalian, especially human, body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

The term "nucleic acid" or "nucleic acid sequence" refers to a deoxyribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones (see e.g., Oligonucleotides and Analogues, a Practical Approach, ed. F. Eckstein, Oxford Univ. Press (1991); Antisense Strategies, Annals of the N.Y. Academy of Sciences, Vol. 600, Eds. Baserga et al. (NYAS 1992); Milligan J. Med. Chem. 36:1923-1937 (1993); Antisense Research and Applications (1993, CRC Press), Mata, Toxicol. Appl. Pharmacol. 144:189-197 (1997); Strauss-Soukup, Biochemistry 36:8692-8698 (1997); Samstag, Antisense Nucleic Acid Drug Dev, 6:153-156 (1996)) (47-53).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues (Batzer et al, Nucleic Acid Res., 19:5081 (1991); Ohtsuka et al., J. Biol. Chem., 260:2605-2608 (1985); Rossolini et al., Mol. Cell. Probes, 8:91-98 (1994)) (54-56). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "plasma membrane translocation domain" or simply "translocation domain" means a polypeptide domain that, when incorporated into a polypeptide coding sequence, can with greater efficiency "chaperone" or "translocate" the hybrid ("fusion") protein to the cell plasma membrane than without the domain.

The term "signaling domain" refers to a portion of a receptor, costimulatory molecule, or other polypeptide that help effect the functional activities of a cell, e.g., a T cell. More specifically, a signaling domain may enhance (or inhibit) the functional activities of a T cell, such as the production of Th1 cytokines, cytotoxicity, in vivo persistence, proliferation, and IFN-g production. Exemplary signaling domains include the cytoplasmic domains of NKp30, CD28, CD8, CD3ζ, DAP10, CD27, 41BB, OX40, or DAP12, as well as fragments, homologs, variants, analogs, conservatively modified variants, mimetics, and/or chimeras thereof.

The "translocation domain," "ligand-binding domain," and chimeric receptors compositions described herein also include "analogs," or "conservative variants" and "mimetics" (or "peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions (such as deletions from one or both ends of a domain, e.g., deletion of up to five amino acids) of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein, which encodes a polypeptide, also describes every possible silent variation of the nucleic acid. One of skill will recognize that each codon in a nucleic acid (except AUG, which is ordinarily the only codon for methionine, and TOO, which is ordinarily the only codon for tryptophan) can be modified to yield a functionally identical molecule. Accordingly, each silent variation of a nucleic acid, which encodes a polypeptide, is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gin/asn; gly/asp; gly/ala or pro; his/asn or gin; ile/leu or val; leu/ile or val; lys/arg or gln or glu; met/leu or tyr or lie; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (T), Leucine (L), Methionine (M), Valine (V); and 6) Phenylalanine (F), Tyrosine (Y), Tryptophan (W); (see also, e.g., Creighton, Proteins, W.H. Freeman and Company (1984); Schultz and Schimer, Principles of Protein Structure, Springer-Verlag (1979)) (57-58). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The term "mimetic" and "peptidomimetic" refer to a synthetic chemical compound that has substantially the same structural and/or functional characteristics of the polypeptides, e.g., translocation domains, ligand-binding domains, or chimeric receptors. The mimetic can be either entirely composed of synthetic, non-natural analogs of amino acids, or may be chimeric molecules of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides which are conservative variants, routine experimentation will determine whether a mimetic's structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a β turn, γ turn, β sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(—O)—CH 2- and —C(—O)—NH—), aminomethylene (CH2-NH), ethylene, olefin (CH—CH), ether (CH 2-O), thioether (CH2-S), tetrazole (CN 4), thiazole, retroamide, thioamide, or ester (see, e.g., Spatola, Chemistry and Biochemistry of Amino Acids, Peptides and Proteins, Vol. 7, pp 267-357, "Peptide Backbone Modifications," Marcell Dekker, NY (1983)) (157). A polypeptide can also be characterized as a mimetic by containing all or some non-natural residues in place of naturally occurring amino acid residues; non-natural residues are well described in the scientific and patent literature.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein). Typically, "heterologous nucleic acid" refers to a sequence that originates from a source foreign to an intended host cell or, if from the same source, is modified from its original form. A heterologous nucleic acid in a host cell can comprise a nucleic acid that is endogenous to the particular host cell but has been modified, for example by mutagenesis or by isolation from native cis-regulatory sequences. A heterologous nucleic acid also includes non-naturally occurring multiple copies of a native nucleotide sequence. A heterologous nucleic acid can also comprise a nucleic acid that is incorporated into a host cell's nucleic acids at a position wherein such nucleic acids are not ordinarily found.

The term "complementary sequences," as used herein, indicates two nucleotide sequences that comprise anti-parallel nucleotide sequences capable of pairing with one another upon formation of hydrogen bonds between base pairs. As used herein, the term "complementary sequences" means nucleotide sequences which are substantially complementary, as can be assessed by the same nucleotide comparison methods set forth below, or is defined as being capable of hybridizing to the nucleic acid segment in question under relatively stringent conditions such as those described herein. A particular example of a complementary nucleic acid segment is an antisense oligonucleotide.

The term "gene" refers broadly to any segment of DNA associated with a biological function. A gene encompasses sequences including but not limited to a coding sequence, a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The term "operatively linked," as used herein, refers to a functional combination between a promoter region and a nucleotide sequence such that the transcription of the nucleotide sequence is controlled and regulated by the promoter region. Techniques for operatively linking a promoter region to a nucleotide sequence are known in the art.

The term "vector" is used herein to refer to a nucleic acid molecule having nucleotide sequences that enable its replication in a host cell. A vector can also include nucleotide sequences to permit ligation of nucleotide sequences within the vector, wherein such nucleotide sequences are also replicated in a host cell. Representative vectors include plasmids, cosmids, and viral vectors.

The term "construct," as used herein to describe a type of construct comprising an expression construct, refers to a vector further comprising a nucleotide sequence operatively inserted with the vector, such that the nucleotide sequence is recombinantly expressed.

The terms "recombinantly expressed" or "recombinantly produced" are used interchangeably to refer generally to the process by which a polypeptide encoded by a recombinant nucleic acid is produced.

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions.

An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" also encompass the ligation of nucleic acids having various coding regions or domains or promoter sequences from different sources into an expression cassette or vector for expression of, e.g., inducible or constitutive expression of a fusion protein comprising a translocation domain and a nucleic acid sequence amplified using a primer.

The term "autoimmunity" or "autoimmune disease or condition" herein An "autoimmune disease" herein is a disease or disorder arising from and directed against an individual's own tissues or a co-segregate or manifestation thereof or resulting condition therefrom. Examples of auto-immune diseases or disorders include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, non-granulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type I, and rapidly progressive GN, allergic conditions, allergic reaction, eczema including allergic or atopic eczema, asthma such as asthma bronchiale, bronchial asthma, and auto-immune asthma, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis); or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barre syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AGED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia greata, CREST syndrome (calcinosis, Raynaud's phenomenon, esophageal dysmotility, sclerodactyl), and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Pelty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, hemo-globinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antibodies, non-malignant thymoma, vitiligo, SCID and Epstein-Barr virus-associated diseases, acquired immune deficiency syndrome (AIDS), parasitic diseases such as Lesihmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

The term "about", as used herein when referring to a measurable value such as a percentage of sequence identity (e.g., when comparing nucleotide and amino acid sequences as described herein below), a nucleotide or protein length, an amount of binding, etc. is meant to encompass variations of ±20% or ±10%, more preferably ±5%, even more preferably ±1, and still more preferably ±9% from the specified amount, as such variations are appropriate to perform a disclosed method or otherwise carry out an embodiment of the present disclosure.

The term "substantially identical", is used herein to describe a degree of similarity between nucleotide sequences, and refers to two or more sequences that have at least about least about 60%, preferably at least about 70%, more preferably at least about 80%, more preferably about 90% to 99%, still more preferably about 95% to about 99%, and most preferably about 99% nucleotide identify, when compared and aligned for maximum correspondence, as measured using one of the following sequence comparison algorithms or by visual inspection. Preferably, the substantial identity exists in nucleotide sequences of at least about 100 residues, more preferably in nucleotide sequences of at least about 150 residues, and most preferably in nucleotide sequences comprising a full length coding sequence. The term "full length" is used herein to refer to a complete open reading frame encoding a polypeptide, as described further herein. Methods of determining percentage identity are well known in the art. Preferably, percentage identity is determined using the Smith-Waterman alignment algorithm.

In one aspect, substantially identical sequences can be polymorphic sequences. The term "polymorphic" refers to the occurrence of two or more genetically determined alternative sequences or alleles in a population. An allelic difference can be as small as one base pair.

In another aspect, substantially identical sequences can comprise mutagenized sequences, including sequences comprising silent mutations. A mutation can comprise one or more residue changes, a deletion of residues, or an insertion of additional residues.

Another indication that two nucleotide sequences are substantially identical is that the two molecules hybridize specifically to or hybridize substantially to each other under stringent conditions. In the context of nucleic acid hybridization, two nucleic acid sequences being compared can be designated a "probe" and a "target." A "probe" is a reference nucleic acid molecule, and a "target" is a test nucleic acid molecule, often found within a heterogeneous population of nucleic acid molecules. A "target sequence" is synonymous with a "test sequence."

The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" and "stringent hybridization wash conditions" refer to conditions under which a probe will hybridize to its target subsequence, typically in a complex mixture of nucleic acids but to no other sequences. Stringent conditions are sequence-dependent and will be different in different circumstances. Longer sequences hybridize specifically at higher temperatures. An extensive guide to the hybridization of nucleic acids is that in Tigssen, Techniques in Biochemistry and Molecular Biology—Hybridization With Nucleic Probes, "Overview of principles of hybridization and the strategy of nucleic acid assays." (1973) Generally, highly stringent hybridization and wash conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium).

Stringent conditions will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the additional of destabilizing agents such as formamide. For selective or specific hybridization, a positive signal is at least two times background, optionally 10 times background hybridization. Exemplary stringent hybridization conditions are: 50% formamide, 5×SSC, and 1% SDS, incubating at 42° C. or 5×SSC, 1% SDS, incubating at 65° C. The hybridization and wash steps effected in said exemplary stringent hybridization conditions are each effected for at least 1, 2, 5, 10, 15, 30, 60, or more minutes. Preferably, the wash and hybridization steps are each effected for at least 5 minutes, and more preferably, 10 minutes, 15 minutes, or more than 15 minutes.

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook et al., eds. (1989) Molecular Cloning: A Laboratory Manual, Cold Spring Harbor Laboratory Press, Cold Spring Harbor, N.Y. for a description of SSC buffer. Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4× to 6×SSC at 40° C. For short probes (e.g., about 10 to 50 nucleotides), stringent conditions typically involve salt concentrations of less than about 1 M Na+ ion, typically about 0.01 to 1 M Na+ ion concentration (or other salts) at pH 7.0-8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

Nucleic acids that do not hybridize to each other under stringent conditions are still substantially related if the polypeptides that they encode are substantially related. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. Preferably, the wash and hybridization steps are each effected for at least 5 minutes. A positive hybridization is at least twice background. Those of ordinary skill will readily recognize that alternative hybridization and wash conditions can be utilized to provide conditions of similar stringency.

In the context of the present disclosure, by a "TCR-deficient T cell", or a similar phrase is intended an isolated T cell(s) that lacks expression of a functional TCR, is internally capable of inhibiting its own TCR production, or produces a TCR that is defective in function so that the T cell cannot mediate effector functions triggered through TCR recognition, and further wherein progeny of said T cell(s) may also be reasonably expected to be internally capable of inhibiting their own TCR production. Internal capability is important in the context of therapy where TCR turnover timescales (~hours) are much faster than demonstrable efficacy timescales (days-months), i.e., internal capability is required to maintain the desired phenotype during the therapeutic period. This may e.g., be accomplished by different means (for example, as described in WO2011059836), e.g., by engineering a T cell such that it does not express any functional TCR on its cell surface, or by engineering the T cell such that it does not express one or more of the subunits that comprise a functional TCR and therefore does not produce a functional TCR or by engineering a T cell such that it produces very little functional TCR on its surface, or which expresses a substantially impaired TCR, e.g. by engineering the T cell to express mutated or truncated forms of one or more of the subunits that comprise the TCR, thereby rendering the T cell incapable of expressing a functional TCR or resulting in a cell that expresses a substantially impaired TCR. The different subunits that comprise a functional TCR are known in the art (see, e.g., WO2011059836). Whether a cell expresses a functional TCR may be determined using known assay methods such as are known in the art (Id). By a "substantially impaired TCR" it is meant that this TCR will not substantially elicit an adverse immune reaction in a host, e.g., a GVHD reaction. As further described in WO2011059836, optionally these TCR-deficient cells may be engineered to comprise other mutations or transgenes that e.g., mutations or transgenes that affect T cell growth or proliferation, result in expression or absence of expression of a desired gene or gene construct. e.g., another receptor or a cytokine or other immunomodulatory or therapeutic polypeptide or a selectable marker such as a dominant selectable marker gene, e.g., DHFR or neomycin transferase. For example, a TCR-deficient T cell may express a chimeric NKp30 of the present disclosure.

A "pharmaceutical composition" refers to a chemical or biological composition suitable for administration to a mammal. Such compositions may be specifically formulated for administration via one or more of a number of routes, including but not limited to buccal, intraarterial, intracardial, intracerebroventricular, intradermal, intramuscular, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, liquid, gel, drops, or other means of administration.

As used herein, a nucleic acid construct or nucleic acid sequence is intended to mean a DNA molecule which can be transformed or introduced into a T cell and be transcribed and translated to produce a product (e.g., a chimeric receptor or a suicide protein).

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (Gateway® Technology; Invitrogen, Carlsbad California). If such sites do not exist, the synthetic oligonucleotide adapters or linkers are used in accordance with conventional practice.

The present disclosure contemplates compositions and methods for reducing or ameliorating, or preventing or treating, diseases or conditions such as cancer and infectious disease. In a non-limiting embodiment, the compositions are based on the concept of providing an allogeneic source of isolated human T cells, namely chimeric NKp30 T cells, which can be manufactured in advance of patient need and inexpensively. The ability to create a single therapeutic product at a single site using processes that are well controlled is attractive in terms of both cost and quality considerations. The change from an autologous to an allogeneic source for T cells offers significant advantages. For example, it has been estimated that a single healthy donor could supply T cells sufficient to treat dozens of patients after transduction and expansion.

As is well known to one of skill in the art, various methods are readily available for isolating allogeneic T cells from a subject, for example, using cell surface marker expression or using commercially available kits (e.g., ISO-CELL™ from Pierce, Rockford, Ill.).

While not necessary for most therapeutic usages of the subject chimeric NKp30 T cells, in some instances it may be desirable to remove some or all of the donor T cells from the host shortly after they have mediated their anti-tumor effect. This may be facilitated by engineering the T cells to express additional receptors or markers that facilitate their removal and/or identification in the host such as GFP, suicide genes, and the like. This is not expected to compromise efficacy as it has previously been shown that donor T cells do not need to remain long in the host for a long-term anti-tumor effect to be initiated (Zhang, T., et al. 2007. Cancer Res. 67:11029-11036; Barber, A. et al. 2008. *J. Immunol.* 180:72-78).

In one embodiment of the present disclosure, nucleic acid constructs introduced into engineered T cells further contains a suicide gene such as thymidine kinase (TK) of the HSV virus (herpes virus) type I (Bonini, et al. (1997) Science 276:1719-1724), a Fas-based "artificial suicide gene" (Thomis, et al. (2001) Blood 97:1249-1257), or *E. coli* cytosine deaminase gene which are activated by ganciclovir, AP1903, or 5-fluorocytosine, respectively. The suicide gene is advantageously included in the nucleic acid construct of the present disclosure to provide for the opportunity to ablate the transduced T cells in case of toxicity and to destroy the chimeric construct once a tumor has been reduced or eliminated. The use of suicide genes for eliminating transformed or transduced cells is well-known in the art. For example, Bonini, et al. ((1997) Science 276:1719-1724) teach that donor lymphocytes transduced with the HSV-TK suicide gene provide antitumor activity in patients for up to one year and elimination of the transduced cells is achieved using ganciclovir. Further, Gonzalez, et al. ((2004) J. Gene Med. 6:704-711) describe the targeting of neuroblastoma with cytotoxic T lymphocyte clones genetically modified to express a chimeric scFvFc:£ immunoreceptor specific for an epitope on L1-CAM, wherein the construct further expresses the hygromycin thymidine kinase (HyTK) suicide gene to eliminate the transgenic clones.

It is contemplated that the suicide gene can be expressed from the same promoter as the chimeric NKp30, or from a different promoter. Generally, however, nucleic acid sequences encoding the suicide protein and chimeric NKp30 reside on the same construct or vector. Expression of the suicide gene from the same promoter as the chimeric NKp30 can be accomplished using any well-known internal ribosome entry site (IRES). Suitable IRES sequences which can be used in the nucleic acid construct of the present disclosure include, but are not limited to, IRES from EMCV, c-myc, FGF-2, poliovirus and HTLV-1. By way of illustration only, a nucleic acid construct for expressing a chimeric receptor can have the following structure: promoter→chimeric receptor→IRES→suicide gene. Alternatively, the suicide gene can be expressed from a different promoter than that of the chimeric receptor (e.g., promoter 1→chimeric receptor-→promoter 2→suicide gene).

Because of the broad application of T cells for cell therapies, and the improved nature of the T cells of the invention, the present disclosure encompasses any method or composition wherein T cells are therapeutically desirable. Such compositions and methods include those for reducing or ameliorating, or preventing or treating cancer, infection, autoimmune diseases, or other diseases or conditions that are based on the use of T cells derived from an allogeneic source that express a chimeric NKp30.

As indicated, further embodiments of the present disclosure embrace recombinant expression of receptors in said chimeric NKp30 T cells, such as chimeric NKG2D, chimeric Fv domains, NKG2D, or any other receptor to initiate signals to T cells, thereby creating potent, specific effector T cells. One of skill in the art can select the appropriate receptor to be expressed by the T cell based on the disease to be treated. For example, receptors that can be expressed by the T cell for treatment of cancer would include any receptor to a ligand that has been identified on cancer cells. Such receptors include, but are not limited to, NKG2A, NKG2C, NKG2F, LLT1, AICL, CD26, NKRP1, NKp44, NKp46, CD244 (2B4), DNAM-1, and NKp80.

In an exemplary embodiment, the modified T cells do not express a functional T cell receptor (TCR). In this embodiment, the T cells are TCR-deficient in the expression of a functional TCR. These cells can function as a platform to allow the expression of other targeting receptors (such as chimeric NKp30 as described herein) that may be useful in specific diseases, while retaining the effector functions of T cells, albeit without a functioning TCR.

In an exemplary embodiment, the chimeric NKp30 T cells may comprise one or more additional receptors. Such additional receptors include, but not limited to, chimeric receptors comprising a ligand binding domain obtained from NK2D, NKG2A, NKG2C, NKG2F, LLT1, AICL, CD26, NKRP1, NKp44, NKp46, CD244 (2B4), DNAM-1, and NKp80, or an anti-tumor antibody such as anti-Her2neu or anti-EGFR, and a signaling domain obtained from CD3ζ, DAP10, CD28, 41BB, CD27, and CD40L. In one embodiment of the present disclosure, the chimeric receptor may bind B7-H6, BAT3, Her2neu, EGFR, mesothelin, CD38, CD20, CD19, PSA, MUC1, MUC2, MUC3A, MUC3B, MUC4, MUC5AC, MUC5B, MUC6, MUC7, MUC8, MUC12, MUC13, MUC15, MUC16, MUC17, MUC19, MUC20, estrogen receptor, progesterone receptor, or RON. In additional exemplary embodiments of the present disclosure, the chimeric receptor may bind MIC-A, MIC-B, or one or more members of the ULBP/RAET1 family including ULBP1, ULBP2, ULBP3, ULBP4, ULBP5, and ULBP6.

In the methods of the present disclosure a patient suffering from cancer, infection, or autoimmune disease is administered a therapeutically effective amount of a composition comprising said chimeric NKp30 T cells. In another embodiment of the present disclosure, a therapeutically effective amount of a composition comprising said chimeric NKp30 T cells is administered to prevent, treat, or reduce cancer, infection, or autoimmune diseases.

Methods of Producing TCR-Deficient T-Cells

The chimeric NKp30 T cells may further be a TCR-deficient (i.e., stably lacking expression of a functional TCR). Removal of TCR function may advantageously provide "universal" cell products, which can be stored for future therapy of any patient.

As is further described in WO/2011/05936, TCR-deficient T-cells may be produced using a variety of approaches. T cells internalize, sort, and degrade the entire T cell receptor as a complex, with a half-life of about 10 hours in resting T cells and 3 hours in stimulated T cells (von Essen, M. et al. 2004. *J. Immunol.* 173:384-393). Proper functioning of the TCR complex requires the proper stoichiometric ratio of the proteins that compose the TCR complex. TCR function is though to require two functioning TCR C proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

In one embodiment, TCR expression is eliminated using small-hairpin RNAs (shRNAs) that target nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR. Even though some TCR complexes can be recycled to the cell surface, the shRNA will prevent new production of TCR proteins resulting in degradation and removal of the entire TCR complex, resulting in the production of a Tcell having a stable deficiency in functional TCR expression.

Expression of shRNAs in primary T cells can be achieved using any conventional expression system, e.g., a lentiviral expression system. Although lentiviruses are useful for targeting resting primary T cells, not all T cells will express the shRNAs. Some of these T cells may not express sufficient amounts of the shRNAs to allow enough inhibition of TCR expression to alter the functional activity of the T cell. Thus, T cells that retain moderate to high TCR expression after viral transduction can be removed, e.g., by cell sorting or separation techniques, so that the remaining T cells are deficient in cell surface TCR or CD3, enabling the expansion of an isolated population of Tcells deficient in expression of functional TCR or CD3.

In a non-limiting embodiment, exemplary targeting shRNAs have been designed for key components of the TCR complex as set forth below (Table 4).

TABLE 1

| Target | Target base | shRNA Sequence | GC % | SEQ ID NO: |
|---|---|---|---|---|
| TCR-β | 18[a] | AGTGCGAGGAGATTCGGCAGCTTAT | 52 | 70 |
| | 21[a] | GCGAGGAGATTCGGCAGCTTATTTC | 52 | 71 |
| | 48[a] | CCACCATCCTCTATGAGATCTTGCT | 48 | 72 |
| | 54[a] | TCCTCTATGAGATCTTGCTAGGGAA | 44 | 73 |
| TCR-α | 3[b] | TCTATGGCTTCAACTGGCTAGGGTG | 52 | 74 |
| | 76[b] | CAGGTAGAGGCCTTGTCCACCTAAT | 52 | 75 |
| | 01[b] | GCAGCAGACACTGCTTCTTACTTCT | 48 | 76 |
| | 07[b] | GACACTGCTTCTTACTTCTGTGCTA | 44 | 77 |
| CD3-ε | 89[c] | CCTCTGCCTCTTATCAGTTGGCGTT | 52 | 78 |
| | 27[c] | GAGCAAAGTGGTTATTATGTCTGCT | 40 | 79 |
| | 62[c] | AAGCAAACCAGAAGATGCGAACTTT | 40 | 80 |
| | 45 | GACCTGTATTCTGGCCTGAATCAGA | 48 | 81 |
| | | GGCCTCTGCCTCTTATCAGTT | 52 | 82 |
| | | GCCTCTGCCTCTTATCAGTTG | 52 | 83 |
| | | GCCTCTTATCAGTTGGCGTTT | 48 | 84 |
| | | AGGATCACCTGTCACTGAAGG | 52 | 85 |
| | | GGATCACCTGTCACTGAAGGA | 52 | 86 |
| | | GAATTGGAGCAAAGTGGTTAT | 38 | 87 |
| | | GGAGCAAAGTGGTTATTATGT | 38 | 88 |
| | | GCAAACCAGAAGATGCGAACT | 48 | 89 |
| | | ACCTGTATTCTGGCCTGAATC | 48 | 90 |
| | | GCCTGAATCAGAGACGCATCT | 52 | 91 |
| | | CTGAAATACTATGGCAACACAATGATAAA | 31 | 92 |
| | | AAACATAGGCAGTGATGAGGATCACCTGT | 45 | 93 |
| | | ATTGTCATAGTGGACATCTGCATCACTGG | 45 | 94 |
| | | CTGTATTCTGGCCTGAATCAGAGACGCAT | 48 | 95 |
| CD3-δ[d] | | GATACCTATAGAGGAACTTGA | 38 | 96 |
| | | GACAGAGTGTTTGTGAATTGC | 43 | 97 |
| | | GAACACTGCTCTCAGACATTA | 43 | 98 |
| | | GGACCCACGAGGAATATATAG | 48 | 99 |
| | | GGTGTAATGGGACAGATATAT | 38 | 100 |
| | | GCAAGTTCATTATCGAATGTG | 38 | 101 |
| | | GGCTGGCATCATTGTCACTGA | 52 | 102 |
| | | GCTGGCATCATTGTCACTGAT | 48 | 103 |
| | | GCATCATTGTCACTGATGTCA | 43 | 104 |
| | | GCTTTGGGAGTCTTCTGCTTT | 48 | 105 |
| | | TGGAACATAGCACGTTTCTCTCTGGCCTG | 52 | 106 |
| | | CTGCTCTCAGACATTACAAGACTGGACCT | 48 | 107 |
| | | ACCGTGGCTGGCATCATTGTCACTGATGT | 52 | 108 |
| | | TGATGCTCAGTACAGCCACCTTGGAGGAA | 52 | 109 |
| CD3-γ[e] | | GGCTATCATTCTTCTTCAAGG | 43 | 110 |
| | | GCCCAGTCAATCAAAGGAAAC | 48 | 111 |
| | | GGTTAAGGTGTATGACTATCA | 38 | 112 |
| | | GGTTCGGTACTTCTGACTTGT | 48 | 113 |
| | | GAATGTGTCAGAACTGCATTG | 43 | 114 |
| | | GCAGCCACCATATCTGGCTTT | 52 | 115 |
| | | GGCTTTCTCTTTGCTGAAATC | 43 | 116 |
| | | GCTTTCTCTTTGCTGAAATCG | 43 | 117 |
| | | GCCACCTTCAAGGAAACCAGT | 52 | 118 |
| | | GAAACCAGTTGAGGAGGAATT | 43 | 119 |
| | | GGCTTTCTCTTTGCTGAAATCGTCAGCAT | 45 | 120 |
| | | AGGATGGAGTTCGCCAGTCGAGAGCTTCA | 55 | 121 |
| | | CCTCAAGGATCGAGAAGATGACCAGTACA | 48 | 122 |
| | | TACAGCCACCTTCAAGGAAACCAGTTGAG | 48 | 123 |

[a]With reference to Accession No. EU030678.
[b]With reference to Accession No. AY247834.
[c]With reference to Accession No. NM_000733.
[d]With reference to Accession No. NM_000732.
[e]With reference to Accession No. NM_000073.

TCR-α, TCR-β, TCR-γ, TCR-δ, CD3-γ, CD3-δ, CD3-ε, or CD3ζ mRNAs can be targeted separately or together using a variety of targeting shRNAs. The TCR-β and TCR-α chains are composed of variable and constant portions. Several targeting shRNAs have been designed for the constant portions of these TCR/CD3 sequences. One or a combination of shRNAs can be used for each molecular target to identify the most efficient inhibitor of TCR expression. Using established protocols, each shRNA construct is cloned into, e.g., a pLko.1 plasmid, with expression controlled by a promoter routinely used in the art, e.g., the U6p promoter. The resulting construct can be screened and confirmed for accuracy by sequencing. The shRNA expression plasmid can then be transfected into any suitable host cell (e.g., 293T), together with a packaging plasmid and an envelope plasmid for packaging. Primary human peripheral blood mononuclear cells (PBMCs) are isolated from healthy donors and activated with low dose soluble anti-CD3 and 25 U/ml rhuIL-2 for 48 hours. Although it is not required to activate T cells for lentiviral transduction, transduction works more efficiently and allows the cells to continue to expand in IL-2. The activated cells are washed and transduced, e.g., using a 1 hour spin-fection at 30° C., followed by a 7 hour resting period.

In another embodiment, over-expression of a dominant-negative inhibitor protein is capable of interrupting TCR expression or function. In this embodiment, a minigene that incorporates part, or all, of a polynucleotide encoding for one of the TCR components (e.g., TCR-α, TCR-β, CD3-γ, CD3-δ, CD3-ε, or CD3ζ) is prepared, but is modified so that: (1) it lacks key signaling motifs (e.g. an ITAM) required for protein function; (2) is modified so it does not associate properly with its other natural TCR components; or (3) can associate properly but does not bind ligands (e.g. a truncated TCRβ minigene).

These minigenes may also encode a portion of a protein that serves as a means to identify the over-expressed minigene. For example, polynucleotides encoding a truncated CD19 protein, which contains the binding site for anti-CD19 mAbs, can be operably linked to the minigene so that the resulting cell that expresses the minigene will express the encoded protein and can be identified with anti-CD19 mAbs. This identification enables one to determine the extent of minigene expression and isolate cells expressing this protein (and thus lack a functional TCR).

In one embodiment, over-expression of a minigene lacking a signaling motif(s) lead to a TCR complex that cannot signal properly when the TCR is engaged by its MHC-peptide ligand on an opposing cell. In a non-limiting embodiment, high expression of this minigene (and the encoded polypeptide) outcompetes the natural complete protein when the TCR components associate, resulting in a TCR complex that cannot signal. In another embodiment, the minigene comprises, or alternatively consists of, a polynucleotide encoding full or partial CD3ζ, CD3-γ, CD3-δ, or CD3-ε polypeptides lacking the ITAM motifs required for signaling. The CD3ζ protein contains three ITAM motifs in the cytoplasmic portion, and in one embodiment, removal of one or more of these through truncation or mutation inhibits proper TCR signaling in any complexes where this modified protein is incorporated. The construct may incorporate MM or other signaling motifs, which are known to alter cell signaling and promote inhibitory signals through the recruitment of phosphatases such as SHP1 and SHP2.

In another embodiment, over-expression of a minigene is modified so that the encoded polypeptide can associate with some, but not all, of its natural partners, creating competition with the normal protein for those associating proteins. In another non-limiting hypothesis, high level expression of the minigene (and the encoded polypeptide) outcompetes the natural partner proteins and prevents assembly of a functional TCR complex, which requires all components to associate in the proper ratios and protein-protein interactions. In another embodiment, minigenes comprise, or alternatively consist of, all or part of the polynucleotides encoding full-length proteins (e.g., TCR-α, TCR-β, CD3-γ, CD3-δ, CD3-ε, or CD3ζ, but containing selected deletions in the sequence coding for amino acids in the transmembrane portion of the protein that are known to be required for assembly with other TCR/CD3 proteins.

In a preferred embodiment, selected deletions in the sequence coding for amino acids in the transmembrane portion of the protein known to be required for assembly with other TCR/CD3 proteins include, but are not limited to: the arginine residue at position S in the TCR-α transmembrane region; the lysine residue at position 10 in the TCR-α transmembrane region; the lysine residue at position 9 in the TCR-β transmembrane region; the glutamic acid residue in the transmembrane region of CD3-γ; the aspartic acid residue in the transmembrane region of CD3-δ-ε; the aspartic acid residue in the transmembrane region of CD3-s; and the aspartic acid residue in the transmembrane region of CD3ζ.

Over-expression of a truncated TCR-α, TCR-β, TCR-γ, or TCR-δ protein results in a TCR complex that cannot bind to MHC-peptide ligands, and thus will not function to activate the T cell. In another embodiment, minigenes comprise, or alternatively consist of, polynucleotides encoding the entire cytoplasmic and transmembrane portions of these proteins and portions of the extracellular region, but lacks polynucleotides encoding all or part of the first extracellular domain (i.e., the most outer domain containing the ligand binding site). In a preferred embodiment, said minigene polynucleotides do not encode Vα and Vβ polypeptides of the TCR-α and TCR-β chains. In one embodiment, the minigene polynucleotides may be operably linked to polynucleotides encoding a protein epitope tag (e.g. CD19), thereby allowing mAb identification of cells expressing these genes.

In another embodiment, the chimeric NKp30 T cells may be TCR-deficient and may express an additional functional, non-TCR receptor, including those described below under the heading "additional receptors."

In another embodiment, these minigenes can be expressed using a strong viral promoter, such as the 5'LTR of a retrovirus, or a CMV or SV40 promoter. Typically, this promoter is immediately upstream of the minigene and leads to a high expression of the minigene mRNA. In another embodiment, the construct encodes a second polynucleotide sequence under the same promoter (using for example an IRES DNA sequence between) or another promoter. This second polynucleotide sequence may encode for a functional non-TCR receptor providing specificity for the T cell, such as a chimeric NKp30 of the present disclosure. Additional examples of this polynucleotide include, but are not limited to, chimeric NKG2D, chimeric NKp30, chimeric NKp46, chimeric anti-CD19, or chimeric anti-Her2neu. In a further embodiment, promoter-minigenes are constructed into a retroviral or other suitable expression plasmid and transfected or transduced directly into T cells using standard methods (Zhang, T. et al., (2006) Cancer Res., 66(11) 5927-5933; Barber, A. et al., (2007) Cancer Res., 67(10): 5003-5008).

After viral transduction and expansion using any of the methods discussed previously, any T cells that still express TCR/CD3 are removed using anti-CD3 mAbs and magnetic beads using Miltenyi selection columns as previously described (Barber, A. et al., (2007) Cancer Res., 67(10): 5003-5008). The T cells are subsequently washed and cultured in IL-2 (50 U/ml) for 3 to 7 days to allow expansion of the effector cells in a similar manner as for use of the cells in vivo.

The expression of TCR αβ and CD3 can be evaluated by flow cytometry and quantitative real-time PCR (QRT-PCR). Expression of TCR-α, TCR-β, CD3ε, CD3ζ, and GAPDH (as a control) mRNA can be analyzed by QRT-PCR using an ABI7300 real-time PCR instrument and gene-specific TAQMAN® primers using methods similar to those used in Sentman, C. L. et al. ((2004) *J. Immunol.* 173:6760-6766). Changes in cell surface expression can be determined using antibodies specific for TCR-α, TCR-β, CD3ε, CD8, CD4, CD5, and CD45.

It is possible that a single shRNA species may not sufficiently inhibit TCR expression on the cell surface. In this case, multiple TCR shRNAs may be used simultaneously to target multiple components of the TCR complex. Each component is required for TCR complex assembly at the cell surface, so a loss of one of these proteins can result in loss of TCR expression at the cell surface. While some or even all TCR expression may remain, it is the receptor function which determines whether the receptor induces an immune response. The functional deficiency, rather than complete cell surface absence, is the critical measure. In general, the lower the TCR expression, the less likely sufficient TCR cross-linking can occur to lead to T cell activation via the TCR complex. While particular embodiments embrace the targeting of TCR-α, TCR-β, and CD3-ε, other components of the TCR complex, such as CD3-γ, CD3-δ, or CD3ζ, can also be targeted.

The primary aim of removing the TCR from the cell surface is to prevent the activation of the T cell to incompatible MHC alleles. To determine whether the reduction in TCR expression with each shRNA or minigene construct is sufficient to alter T cell function, the T cells can be tested for: (1) cell survival in vitro; (2) proliferation in the presence of mitomycin C-treated allogeneic PBMCs; and (3) cytokine production in response to allogeneic PBMCs, anti-CD3 mAbs, or anti-TCR mAbs.

To test cell survival, transduced T cells are propagated in complete RPMI medium with rhuIL-2 (25-50 U/ml). Cells are plated at similar densities at the start of culture and a sample may be removed for cell counting and viability daily for 7 or more days. To determine whether the T cells express sufficient TCR to induce a response against allogeneic cells, transduced or control T cells are cultured with mitomycin C-treated allogeneic or syngeneic PBMCs. The T cells are preloaded with CFSE, which is a cell permeable dye that divides equally between daughter cells after division. The extent of cell division can be readily determined by flow cytometry. Another hallmark of T cell activation is production of cytokines. To determine whether each shRNA construct inhibits T cell function, transduced T cells are cultured with anti-CD3 mAbs (2 ng/ml to 5000 ng/ml). After 24 hours, cell-free supernatants are collected and the amount of TL-2 and IFN-γ produced is quantified by ELISA. PMA/ionomycin are used as a positive control to stimulate the T cells and T cells alone are used as a negative control.

It is possible that removal of TCR-α or TCR-β components may allow the preferential expansion of TCR-γ/δT cells. These T cells are quite rare in the blood, however the presence of these cells can be determined with anti-TCR-γ/δ antibodies. If there is an outgrowth of these cells, the targeting of CD3-ε, which is required for cell surface expression of both TCR-α/β and TCR-γ/δ at the cell surface, can be used. Both IL-2 and IFN-γ are key effector cytokines that drive T cell expansion and macrophage activation. Therefore, reduced production of these cytokines is a sign of a functional defect. It is also possible to measure changes in other cytokines, such as TNF-α. Any reduction in T cell survival upon elimination of TCR expression can be determined by culturing the T cells with PBMCs, which better reflects the in vivo environment and provides support for T cell survival.

Additional Receptors

Further embodiments embrace recombinant expression of additional receptors in said chimeric NKp30 T cells. Exemplary additional receptors include chNKG2D, chimeric Fv domains, NKG2D, or any other receptor to initiate signals to T cells, thereby creating potent, specific effector T cells. One of skill in the art can select the appropriate receptor to be expressed by the chimeric NKp30 T cells based on the disease to be treated. For example, receptors that can be expressed by the chimeric NKp30 T cells for treatment of cancer would include any receptor to a ligand that has been identified on cancer cells. Such receptors include, but are not limited to, NKG2D (GENBANK accession number BC039836), NKG2A (GENBANK accession number AF461812), NKG2C (GENBANK accession number AJ001684), NKG2F, LLT1, AICL, CD26, NKRP1, NKp30 (e.g., GENBANK accession number AB055881), NKp44 (e.g., GENBANK accession number AJ225109), NKp46 (e.g., GENBANK accession number AJ001383), CD244 (2B4), DNAM-1, and NKp80.

In another embodiment, such additional receptors include, but not limited to, chimeric receptors comprising a ligand binding domain obtained from NKG2D, NKG2A, NKG2C, NKG2F, LLT1, AICL, CD26, NKRP1, NKp30, NKp44, NKp46, CD244 (2B4), DNAM-1, and NKp80, or an anti-tumor antibody, such as anti-Her2neu and anti-EGFR, and a signaling domain obtained from CD3ζ (e.g., GENBANK accession number NM_198053), DAP10 (e.g., GENBANK accession number AF072845), CD28, 41BB, CD27, and/or CD40L.

In a further embodiment, the additional chimeric receptor binds MIC-A, MIC-B, Her2neu, EGFR, mesothelin, CD38, CD20, CD19, PSA, MUC1, MUC2, MUC3A, MUC3B, MUC4, MUC5AC, MUC5B, MUC6, MUC7, MUC8, MUC12, MUC13, MUC15, MUC16, MUC17, MUC19, MUC20, estrogen receptor, progesterone receptor, RON, or one or more members of the ULBP/RAET1 family including ULBP1, ULBP2, ULBP3, ULBP4, ULBP5, and ULBP6.

By way of illustration only, a chimeric NKp30 may be co-expressed with an additional receptor via one or more viral vectors. To achieve co-expression in one vector, expression of the chimeric NKp30 T cells and additional receptor may be driven by identical or different promoters. In another embodiment, if an IRES sequence is used to separate the genetic elements then only one promoter is used.

A C-type lectin-like NK cell receptor protein particularly suitable for use in exemplary additional chimeric receptors includes a receptor expressed on the surface of natural killer cells, wherein upon binding to its cognate ligand(s) it alters NK cell activation. The receptor may work alone or in concert with other molecules. Ligands for these receptors are generally expressed on the surface of one or more tumor cell types, e.g., tumors associated with cancers of the colon, lung, breast, kidney, ovary, cervix, and prostate; melanomas; myelomas; leukemias; and lymphomas (Wu, et al. (2004) J. Clin. Invest. 114:60-568; Groh, et al. (1999) Proc. Natl. Acad. Sci. USA 96:6879-6884; Pende, et al. (2001) Eur. J. Immunol. 31:1076-1086) and are not widely expressed on the surface of cells of normal tissues. Examples of such ligands include, but are not limited to, MIC-A, MIC-B, heat shock proteins, ULBP binding proteins (e.g., ULPBs 1-4), and non-classical HLA molecules such as HLA-E and HLA-G, whereas classical MHC molecules such as HLA-A, HLA-B, or HLA-C and alleles thereof are not generally considered strong ligands of the C-type lectin-like NK cell receptor protein. C-type lectin-like NK cell receptors which bind these ligands generally have a type II protein structure, wherein the N-terminal end of the protein is cytoplasmic. In addition to any NK cell receptors previously listed above, further exemplary NK cell receptors of this type include, but are not limited to, Dectin-1 (GENBANK accession number AJ312373 or AJ312372), Mast cell function-associated antigen (GENBANK accession number AF097358), HNKR-PIA (GENBANK accession number U11276), LLT1 (GENBANK accession number AF133299), CD69 (GENBANK accession number NM_001781), CD69 homolog, CD72 (GENBANK accession number NM_001782), CD94 (GENBANK accession number NM_002262 or NM_007334), KLRF1 (GENBANK accession number NM_016523), Oxidised LDL receptor (GENBANK accession number NM_002543), CLEC-1, CLEC-2 (GENBANK accession number NM_016509), NKG2D (GENBANK accession number BC039836), NKG2C (GENBANK accession number AJ001684), NKG2A (GENBANK accession number AF461812), NKG2E (GENBANK accession number AF461157), WUGSC:H_DJ0701016.2, or Myeloid DAP12-associating lectin (MDL-1; GENBANK accession number AJ271684). In an exemplary embodiment, the NK cell receptor is human NKG2D or human NKG2C.

Similar type I receptors which would be useful in the chimeric receptor include NKp46 (GENBANK accession number AJ001383), NKp30 (including GENBANK accession number AB055881), or NKp44 (GENBANK accession number AJ225109).

As an alternative to the C-type lectin-like NK cell receptor protein, a protein associated with a C-type lectin-like NK cell receptor protein can be used in the additional chimeric receptor protein. In general, proteins associated with C-type lectin-like NK cell receptor am defined as proteins that interact with the receptor and transduce signals therefrom. Suitable human proteins which function in this manner further include, but are not limited to, DAP10 (e.g., GENBANK accession number AF072845), DAP12 (e.g., GENBANK accession number AF019562) and FcRγ.

To the N-terminus of the C-type lectin-like NK cell receptor may be fused an immune signaling receptor having an immunoreceptor tyrosine-based activation motif (ITAM), (Asp/Glu)-Xaa-Xaa-Tyr*-Xaa-Xaa-(Ile/Leu)-Xaa$_{6-8}$-Tyr*-Xaa-Xaa-(Ile/Leu) (SEQ ID NO:128) which is involved in the activation of cellular responses via immune receptors. Similarly, when employing a protein associated with a C-type lectin-like NK cell receptor, an immune signaling receptor can be fused to the C-terminus of said protein. Suitable immune signaling receptors for use in the chimeric receptor include, but are not limited to. the ~ chain of the T-cell receptor, the eta chain which differs from the ζ chain only in its most C-terminal exon as a result of alternative splicing of the ζ mRNA, the δ, γ and ε chains of the T-cell receptor (CD3 chains) and they subunit of the FcR1 receptor. In particular embodiments, in addition to immune signaling receptors identified previously, the immune signaling receptor is CD3ζ (e.g., GENBANK accession number NM_198053), or human Fcs receptor-γ chain (e.g., GENBANK accession number M33195) or the cytoplasmic domain or a splicing variant thereof.

In particular embodiments, said additional receptor may be a chimeric receptor fusion between NKG2D and CD3ζ, or DAP10 and CD3ζ.

As will be appreciated by one of skill in the art, in some instances, a few amino acids at the ends of the C-type lectin-like natural killer cell receptor (or protein associated therewith) or immune signaling receptor can be deleted, usually not more than 10, more usually not more than 5 residues. Also, it may be desirable to introduce a small number of amino acids at the borders, usually not more than 10, more usually not more than 5 residues. The deletion or insertion of amino acids will usually be as a result of the needs of the construction, providing for convenient restriction sites, ease of manipulation, improvement in levels of expression, or the like. In addition, the substitution of one or more amino acids with a different amino acid can occur for similar reasons, usually not substituting more than about five amino acids in any one domain.

Additional Exemplary Chimeric NKp30 Receptors

By way of illustration, human chimeric receptor molecules composed of an NKp30 extracellular domain in combination with transmembrane and/or cytoplasmic domains of CD3ζ and/or CD28 were generated and expressed in human T-cells. Specifically, a gene encoding a chimeric receptor comprising the extracellular domain of human NKp30 and transmembrane and cytoplasmic domains of human CD3ζ (NKp30-CD3ζ receptor) was generated. A gene encoding a chimeric receptor comprising the extracellular domain of human NKp30, the transmembrane domain of CD28, and cytoplasmic domain of human CD3ζ (NKp30-CD28-CD3ζ receptor) was also generated.

The CD3ζ chain is type I protein with the C-terminus in the cytoplasm (Weissman, et al. (1988) Proc. Natl. Acad. Sci. USA 85:9709-9713). To generate a chimeric NKG2D-CD3ζ fusion protein, an initiation codon ATG may be placed ahead of the coding sequence for the cytoplasmic region of the CD3ζ chain (without a stop codon TAA). Upon expression, the orientation of the CD3ζ portion is reversed inside the cells.

Expression Constructs

In the nucleic acid construct encoding the chimeric NKp30 receptor of the present disclosure, typically a promoter is operably linked to the nucleic acid sequence encoding the chimeric receptor, i.e., they are positioned so as to promote transcription of the messenger RNA from the DNA encoding the chimeric receptor. The promoter can be of genomic origin or synthetically generated. A variety of promoters for use in T cells are well-known in the art (e.g., the CD4 promoter disclosed by Marodon, et al. (2003) Blood 101(9):3416-23). The promoter can be constitutive or inducible, where induction is associated with the specific cell type or a specific level of maturation. Alternatively, a number of well-known viral promoters are also suitable. Additional exemplary promoters include the β-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The sequence of the open reading frame encoding the chimeric NKp30 receptor of the present disclosure can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns may stabilize the mRNA or provide T cell-specific expression (Barthel and Goldfeld (2003) J. Immunol. 171(7):3612-9). Also, it may be further advantageous to use endogenous or exogenous non-coding regions to stabilize the mRNA.

For expression of the chimeric NKp30 receptor of the present disclosure, the naturally occurring or endogenous transcriptional initiation region of the nucleic acid sequence encoding N-terminal component of the chimeric receptor can be used to generate the chimeric receptor in the target host. Alternatively, an exogenous transcriptional initiation region can be used which allows for constitutive or inducible expression, wherein expression can be controlled depending upon the target host, the level of expression desired, the nature of the target host, and the like.

Likewise, the signal sequence directing the chimeric NKp30 receptor to the surface membrane can be the endogenous signal sequence of N-terminal component of the chimeric receptor. Optionally, in some instances, it may be desirable to exchange this sequence for a different signal sequence. However, the signal sequence selected typically should be compatible with the secretory pathway of T cells so that the chimeric receptor is presented on the surface of the T cell.

Similarly, a termination region can be provided by the naturally occurring or endogenous transcriptional termination region of the nucleic acid sequence encoding the C-terminal component of the chimeric NKp30 receptor. Alternatively, the termination region can be derived from a different source. For the most part, the source of the termination region is generally not considered to be critical to the expression of a recombinant protein and a wide variety of termination regions can be employed without adversely affecting expression.

The chimeric construct, which encodes the chimeric receptor can be prepared in conventional ways. Since, for the most part, natural sequences are employed, the natural genes can be isolated and manipulated so as to allow for the proper joining of the various components. For example, the nucleic acid sequences encoding the proteins of the chimeric receptor can be isolated by employing the polymerase chain reaction (PCR), using appropriate primers which result in amplification of the desired portions of the genes. Alternatively, restriction digests of cloned genes can be used to generate the chimeric construct. In either case, the sequences can be selected to facilitate assembly of the desired chimera, e.g., by provide for restriction sites which are blunt-ended, or have complementary overlaps.

The various manipulations for preparing the chimeric construct can be carried out in vitro and in particular embodiments the chimeric construct is introduced into vectors for cloning and expression in an appropriate host using standard transformation or transfection methods. Thus, after each manipulation, the resulting construct from joining of the DNA sequences can be cloned, the vector isolated, and the sequence screened to insure that the sequence encodes the desired chimeric receptor. The sequence can be screened by restriction analysis, sequencing, or the like.

It is contemplated that the chimeric construct can be introduced into T cells as naked DNA or in a suitable vector. Methods of stably transfecting T cells by electroporation using naked DNA are known in the art. See, e.g., U.S. Pat. No. 6,410,319. Naked DNA generally refers to the DNA encoding a chimeric receptor of the present disclosure contained in a plasmid expression vector in proper orientation for expression. Advantageously, the use of naked DNA can reduce the time required to produce T cells expressing the chimeric receptor of the present disclosure.

Alternatively, a viral vector (e.g., a retroviral vector, adenoviral vector, adeno-associated viral vector, or lentiviral vector) can be used to introduce the chimeric construct into T cells. Preferred vectors for use in accordance with the method of the present disclosure are non-replicating in the subject's T cells. A large number of vectors are known which are based on viruses, where the copy number of the virus maintained in the cell is low enough to maintain the viability of the cell. Illustrative vectors include the pFB-neo vectors (STRATAGENE™) as well as vectors based on HIV, SV40, EBV, HSV or BPV. Once it is established that the transfected or transduced T cell is capable of expressing the chimeric receptor as a surface membrane protein with the desired regulation and at a desired level, it can be determined whether the chimeric receptor is functional in the host cell to provide for the desired signal induction (e.g., production of IFN-γ, TNF-β, GM-CSF upon stimulation with the appropriate ligand).

Primary human PBMCs can be isolated from healthy donors and activated with low-dose soluble anti-CD3 and rhuIL-2, anti-CD3/anti-CD28 beads and rhuIL-2, or irradiated antigen presenting cells and rhuIL-2. Although it is not required to activate T cells for lentiviral transduction, transduction is more efficient and the cells continue to expand in IL-2. The activated cells may be washed and transduced as described herein, followed by a resting period. The cells may be washed and cultured in IL-2 for 3 to 7 days to allow expansion of the effector cells in a similar manner as for use of the cells in vivo.

The expression of TCRαβ, CD3, and NKG2D can be evaluated by flow cytometry and quantitative real-time PCR (QRT-PCR). The number of CD4+ and CD8+ T cells can also be determined. Overall cell numbers and the percentage of chimeric NKp30 T cells can be determined by flow cytometry. Vector-only transduced cells can also be included as controls.

After viral transduction and expansion, the chimeric NKp30 T cells can be separated by mAbs with magnetic beads over Miltenyi columns and identified and isolated. For example, chimeric NKp30 T cells expression can be verified by flow cytometry using anti-NKp30 mAbs or QRT-PCR using specific primers for the chimeric NKp30 T cells receptor. Function of these chimeric NKp30 T cells can be determined by culturing the cells with tumor cells that express NKp30 ligand(s). T cell proliferation and cytokine production (IFN-γ and IL-2) can be determined by flow cytometry and ELISA, respectively.

Another hallmark of T cell activation is production of cytokines. To determine whether chimeric NKp30 T cells induce T cell activation, the T cells may be co-cultured with syngeneic PBMCs or with tumor cells that do (or do not) express NKp30 ligand(s). After a period of incubation, such as 24 hours, cell-free supernatants may be collected and the amount of IL-2 and IFN-γ produced is quantified by ELISA. T cells alone and culture with ligand-deficient cells can be used as a negative control.

Subsequently, the transduced T cells may be reintroduced or administered to the subject to activate anti-tumor responses in said subject. To facilitate administration, the transduced T cells according to the present disclosure can be made into a pharmaceutical composition or made implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed which does not render ineffectual the cells expressing the chimeric receptor. Thus, desirably the transduced T cells can be made into a pharmaceutical composition containing a balanced salt solution, preferably Hanks' balanced salt solution, or normal saline.

Methods of Ameliorating or Reducing Symptoms of, or Treating, or Preventing, Diseases and Disorders Using Chimeric NKp30 T Cells The present disclosure is also directed to methods of reducing or ameliorating, or preventing or treating, diseases and disorders using the chimeric NKp30 T cells described herein, isolated populations thereof, or therapeutic compositions comprising the same. In one embodiment, the chimeric NKp30 T cells described herein, isolated populations thereof, or therapeutic compositions comprising the same are used to reduce or ameliorate, or prevent or treat cancer, infection, or autoimmune disease. Additional exemplary diseases and disorders that may potentially be reduced, ameliorated, prevented, and/or treated using the methods and compositions of the present disclosure can be identified by those of skill in the art and may include (by way of non-limiting examples) graft versus host disease (GVHD), transplantation rejection, one or more autoimmune disorders, or radiation sickness. For example, because NKp30 ligands can be expressed by human dendritic cells, it is further contemplated that the methods and compositions of the present disclosure may be useful to prevent or treat diseases where elimination of dendritic cells may be helpful, such as autoimmune diseases or rejection of transplanted organs.

Preferably, the cancer expresses at least one NKp30 ligand (e.g., B7-H6), and more preferably expresses a sufficiently high level of at least one NKp30 ligand to activate the chimeric NKp30 T cells of the present disclosure. Though some cancers may not express an NKp30 ligand, expression of NKp30 ligands have been reported in cell lines from many cancers, including leukemia, lymphomas, cervical cancer, gastric sarcoma, breast cancer, pancreatic cancer, melanoma, and prostate cancer. Optionally, the methods of the present disclosure may include a step of determining susceptibility of the cancer to a therapy disclosed herein, e.g., by detecting expression of one or more NKp30 ligands on cancer cells.

In addition to the illustrative chimeric NKp30 T cells described herein, it is contemplated that chimeric NKp30 T cells can be modified or developed to express additional functional receptors useful in treatment of diseases such as cancer, infection, or autoimmune diseases, as described previously. Briefly, the treatment methods of the present disclosure contemplate the use of chimeric NKp30 T cells expressing additional receptors, such as chNKG2D, chimeric Fv domains, NKG2D, or any other receptor to initiate signals to T cells, thereby creating potent, specific effector T cells. One of skill in the art can select the appropriate receptor to be expressed by T cell based on the disease to be treated. For example, receptors that can be expressed by the chimeric NKp30 T cells for treatment of cancer would include any receptor that binds to a ligand that has been identified on cancer cells. Such receptors include, but are not limited to, NKG2D, NKG2A, NKG2C, NKG2F, LLT1, AICL, CD26, NKRP1, NKp30, NKp44, NKp46, CD244 (2B4), DNAM-1, and NKp80.

In another embodiment, such receptors include, but not limited to, chimeric receptors comprising a ligand binding domain obtained from NKG2D, NKG2A, NKG2C, NKG2F, LLT1, AICL, CD26, NKRP1, NKp30, NKp44, NKp46, CD244 (2B4), DNAM-1, and NKp80, or an anti-tumor antibody such as anti-Her2neu and anti-EGFR, and a signaling domain obtained from CD3ζ, DAP10, CD28, 41BB, CD27, and CD40L.

In a further embodiment, the additional receptor binds MIC-A, MIC-B, Her2neu, EGFR, mesothelin, CD38, CD20, CD19, PSA, MUC1, MUC2, MUC3A, MUC3B, MUC4, MUC5AC, MUC5B, MUC6, MUC7, MUC8, MUC12, MUC13, MUC15, MUC16, MUC17, MUC19, MUC20, estrogen receptor, progesterone receptor, RON, or one or more members of the ULBP/RAET1 family including ULBP1, ULBP2, ULBP3, ULBP4, ULBP5, and ULBP6.

Efficacy of the compositions of the present disclosure can be demonstrated in the most appropriate in vivo model system depending on the type of drug product being developed. The medical literature provides detailed disclosure on the advantages and uses of a wide variety of such models. For example, there are many different types of cancer models that are used routinely to examine the pharmacological activity of drugs against cancer such as xenograft mouse models (e.g., Mattern, J. et al. 1988. *Cancer Metastasis Rev.* 7:263-284; Macor, P. et al. 2008. Curr. Pharm. Des. 14:2023-2039) or even the inhibition of tumor cell growth in vitro. In the case of GVHD, there are models in mice of both acute GVHD (e.g., He, S. et al. 2008. *J. Immunol.* 181:7581-7592) and chronic GVHD (e.g., Xiao, Z. Y. et al. 2007. *Life Sci.* 81:1403-1410).

Once the compositions of the present disclosure have been shown to be effective in vivo in animals, clinical studies may be designed based on the doses shown to be safe and effective in animals. One of skill in the art can design such clinical studies using standard protocols as described in textbooks such as Spilker (2000. *Guide to Clinical Trials.* Lippincott Williams & Wilkins: Philadelphia).

Administration

In one embodiment of the present disclosure, the chimeric NKp30 T cells are administered to a recipient subject at an amount of between about $10^6$ to $10^{11}$ cells. In a preferred embodiment of the present disclosure, the chimeric NKp30 T cells are administered to a recipient subject at an amount of between $10^8$ to $10^9$ cells. In a preferred embodiment of the present disclosure, the chimeric NKp30 T cells are administered to a recipient subject with a frequency of once every twenty-six weeks or less, such as once every sixteen weeks or less, once every eight weeks or less, or once every four weeks or less.

These values provide general guidance of the range of transduced T cells to be utilized by the practitioner upon optimizing the method of the present disclosure for practice. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on inter-individual differences in pharmacokinetics, drug disposition, and metabolism. One skilled in the art readily can make any necessary adjustments in accordance with the exigencies of the particular situation.

A person of skill in the art would be able to determine an effective dosage and frequency of administration based on teachings in the art or through routine experimentation, for example guided by the disclosure herein and the teachings in Goodman, L. S., Gilman, A., Brunton, L. L., Lazo, J. S., & Parker, K. L. (2006). Goodman & Gilman's the pharmacological basis of therapeutics. New York: McGraw-Hill; Howland, R. D., Mycek, M. J., Harvey, R. A., Champe, P. C., & Mycek, M. J. (2006). Pharmacology. Lippincott's illustrated reviews. Philadelphia: Lippincott Williams & Wilkins; and Golan, D. E. (2008). Principles of pharmacology: the pathophysiologic basis of drug therapy. Philadelphia, Pa., [etc.]: Lippincott Williams & Wilkins. The dosing schedule can be based on well-established cell-based therapies (see, e.g., Topalian and Rosenberg (1987) Acta Haematol. 78 Suppl 1:75-6; U.S. Pat. No. 4,690,915) or an alternate continuous infusion strategy can be employed.

In another embodiment of the present disclosure, the chimeric NKp30 T cells are administered to a subject in a pharmaceutical formulation.

In one embodiment of the present disclosure, the chimeric NKp30 T cells may be optionally administered in combination with one or more active agents. Such active agents include analgesic, antipyretic, anti-inflammatory, antibiotic, antiviral, and anti-cytokine agents. Active agents include agonists, antagonists, and modulators of TNF-$\alpha$, IL-2, IL-4, IL-6, IL-10, IL-12, IL-13, IL-18, IFN-$\alpha$, IFN-$\gamma$, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors. Active agents also include 2-Arylpropionic acids, Aceclofenac, Acemetacin, Acetylsalicylic acid (Aspirin), Alclofenac, Alminoprofen, Amoxiprin, Ampyrone, Arylalkanoic acids, Azapropazone, Benorylate/Benorilate, Benoxaprofen, Bromfenac, Carprofen, Celecoxib, Choline magnesium salicylate, Clofezone, COX-2 inhibitors, Dexibuprofen, Dexketoprofen, Diclofenac, Diflunisal, Droxicam, Ethenzamide, Etodolac, Etoricoxib, Faislamine, fenamic acids, Fenbufen, Fenoprofen, Flufenamic acid, Flunoxaprofen, Flurbiprofen, Ibuprofen, Ibuproxam, Indometacin, Indoprofen, Kebuzone, Ketoprofen, Ketorolac, Lornoxicam, Loxoprofen, Lumiracoxib, Magnesium salicylate, Meclofenamic acid, Mefenamic acid, Meloxicam, Metamizole, Methyl salicylate, Mofebutazone, Nabumetone, Naproxen, N-Arylanthranilic acids, Nerve Growth Factor (NGF), Oxametacin, Oxaprozin, Oxicams, Oxyphenbutazone, Parecoxib, Phenazone, Phenylbutazone, Phenylbutazone, Piroxicam, Pirprofen, profens, Proglumetacin, Pyrazolidine derivatives, Rofecoxib, Salicyl salicylate, Salicylamide, Salicylates, Sulfinpyrazone, Sulindac, Suprofen, Tenoxicam, Tiaprofenic acid, Tolfenamic acid, Tolmetin, and Valdecoxib.

Antibiotics include Amikacin, Aminoglycosides, Amoxicillin, Ampicillin, Ansamycins, Arsphenamine, Azithromycin, Azlocillin, Aztreonam, Bacitracin, Carbacephem, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftazidime, Ceftibuten, Ceftizoxime, Ceftobiprole, Ceftriaxone, Cefuroxime, Cephalosporins, Chloramphenicol, Cilastatin, Ciprofloxacin, Clarithromycin, Clindamycin, Cloxacillin, Colistin, Co-trimoxazole, Dalfopristin, Demeclocycline, Dicloxacillin, Dirithromycin, Doripenem, Doxycycline, Enoxacin, Ertapenem, Erythromycin, Ethambutol, Flucloxacillin, Fosfomycin, Furazolidone, Fusidic acid, Gatifloxacin, Geldanamycin, Gentamicin, Glycopeptides, Herbimycin, Imipenem, Isoniazid, Kanamycin, Levofloxacin, Lincomycin, Linezolid, Lomefloxacin, Loracarbef, Macrolides, Mafenide, Meropenem, Meticillin, Metronidazole, Mezlocillin, Minocycline, Monobactams, Moxifloxacin, Mupirocin, Nafcillin, Neomycin, Netilmicin, Nitrofurantoin, Norfloxacin, Ofloxacin, Oxacillin, Oxytetracycline, Paromomycin, Penicillin, Penicillins, Piperacillin, Platensimycin, Polymyxin B, Polypeptides, Prontosil, Pyrazinamide, Quinolones, Quinupristin, Rifampicin, Rifampin, Roxithromycin, Spectinomycin, Streptomycin, Sulfacetamide, Sulfamethizole, Sulfanilimide, Sulfasalazine, Sulfisoxazole, Sulfonamides, Teicoplanin, Telithromycin, Tetracycline, Tetracyclines, Ticarcillin, Tinidazole, Tobramycin, Trimethoprim, Trimethoprim-Sulfamethoxazole, Troleandomycin, Trovafloxacin, and Vancomycin.

Active agents also include Aldosterone, Beclometasone, Betamethasone, Corticosteroids, Cortisol, Cortisone acetate, Deoxycorticosterone acetate, Dexamethasone, Fludrocortisone acetate, Glucocorticoids, Hydrocortisone, Methylprednisolone, Prednisolone, Prednisone, Steroids, and Triamcinolone. Any suitable combination of these active agents is also contemplated.

A "pharmaceutical excipient" or a "pharmaceutically acceptable excipient" is a carrier, usually a liquid, in which an active therapeutic agent is formulated. In one embodiment of the present disclosure, the active therapeutic agent is a population of chimeric NKp30 T cells. In one embodiment of the present disclosure, the active therapeutic agent is a population of chimeric NKp30 T cells that are TCR-deficient. The excipient generally does not provide any pharmacological activity to the formulation, though it may provide chemical and/or biological stability. Exemplary formulations can be found, for example, in Remington's Pharmaceutical Sciences, 19s Ed., Grennaro, A., Ed., 1995 which is incorporated by reference.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the present disclosure is contemplated. Supplementary active compounds can also be incorporated into the compositions.

In a particularly preferred embodiment of the present disclosure, appropriate carriers include, but are not limited to, Hank's Balanced Salt Solution (HBSS), Phosphate Buffered Saline (PBS), or any freezing medium having for example, 10% DMSO and 90% human serum.

Pharmaceutical compositions typically must be sterile and stable under the conditions of manufacture and storage (in this context, the term "sterile" does not preclude presence of intended living components, e.g., live T cells or viruses adapted to transduce a chimeric NKp30 receptor of the present disclosure). The composition can be formulated as a solution. The carrier can be a dispersion medium containing, for example, water, saline solution, preservatives, etc.

For each of the recited embodiments, the compounds can be administered by a variety of dosage forms. Any biologically-acceptable dosage form known to persons of ordinary skill in the art, and combinations thereof, are contemplated. Examples of such dosage forms include, without limitation, liquids, solutions, suspensions, emulsions, injectables (including subcutaneous, intramuscular, intravenous, and intradermal), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain teachings related to T-cell receptor deficient T-cell compositions and methods of use thereof were disclosed in U.S. Provisional patent application No. 61/255,980, filed Oct. 29, 2009, the disclosure of which is herein incorporated by reference in its entirety.

Certain teachings related to the production of T cells expressing chimeric receptors and methods of use thereof were disclosed in U.S. patent application publication no. US 2010/0029749, published Feb. 4, 2010, the disclosure of which is herein incorporated by reference in its entirety.

The entire disclosure of each document cited (including patents, patent applications, journal articles, abstracts, manuals, books, or other disclosures) in the present application, including the Background, Detailed Description, and Examples, are each herein incorporated by reference in their entireties.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1: Production of Chimeric NKp30 Human T Cells

Figures 1, 2:
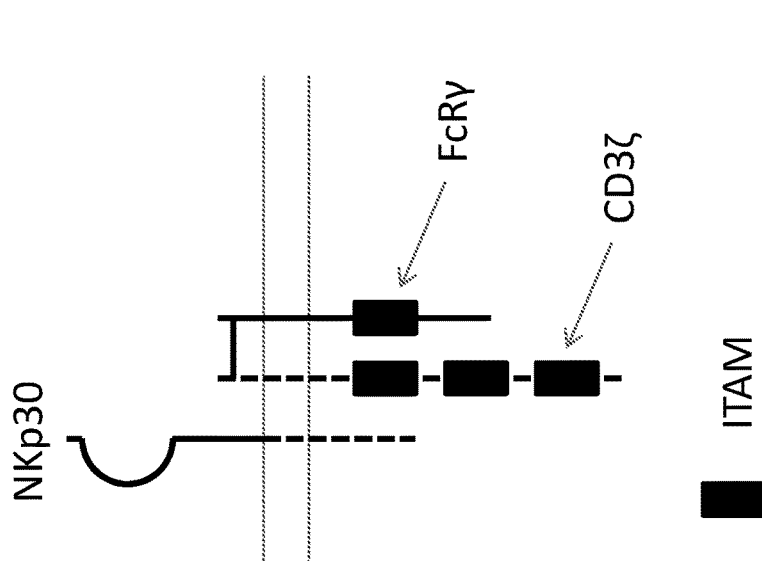
FIG. 1 provides a graphical overview of proteins involved in NKp30 signaling. Ligand-bound NKp30 can activate signaling through CD3ζ and FcRγ. The long horizontal lines represent the cell membrane, with the extracellular space oriented toward the top of the figure. NKp30 interaction with CD3ζ correlates with the NKp30 splice variant isoform, with NKp30 isoform A associating with CD3ζ upon cross-linking, NKp30 isoform B constitutively associating with CD3ζ, and NKp30 isoform C poorly associating with CD3ζ. ITAM: immunoreceptor tyrosine-based activation motif.
FIG. 2 illustrates chimeric NK receptors exemplified herein. Extracellular (EX or EC), transmembrane (TM), and cytoplasmic (CYP) (i.e., intracellular) portions are indicated. Wild-type (WT) and chimeric forms of the receptors are indicated. wtNKp30 indicates the mature wild-type NKp30 polypeptide. NKp30-CD3ζ indicates an NKp30 cytoplasmic domain fused to the transmembrane and cytoplasmic domains of CD3ζ. NKp30-CD28-CD3 indicates an NKp30 cytoplasmic domain fused to the transmembrane and cytoplasmic domains of CD28, and additionally the cytoplasmic domain of CD3ζ. All constructs are human.

Natural killer (NK) cells can attack tumor cells, which are recognized utilizing a combination of signals from activating and inhibitory receptors including NKp30. FIG. 1 provides an graphical overview proteins involved in NKp30 signaling, which include FcRγ and CD3ζ, each of which contain immunoreceptor tyrosine-based activation motif (ITAM) which are involved in the activation of cellular responses via immune receptors.

In an effort to develop a new mechanism for T cells to attack tumor cells and induce host anti-tumor immunity, we genetically modified primary human T cells with chimeric NKp30 receptor containing the (cytoplasmic) CD3ζ and/or CD28 chain signaling domains. Our hypothesis was that the chimeric NKp30-modified T cells would react to NKp30 ligand-positive tumor cells and become fully activated resulting in elimination of the tumor and induction of host anti-tumor immunity. The chimeric NKp30 constructs used in this study are schematically illustrated in IG. 2. Wild-type (WT) NKp30 contains the full-length human NKp30. The NKp30-CD3ζ receptor comprises the extracellular domain of human NKp30 fused to the transmembrane (TM) and signaling domains of human CD3ζ chain as illustrated in FIG. 16. The NKp30-CD28-CD3ζ receptor was constructed by joining the extracellular domain of NKp30 to the TM and cytoplasmic domain of human CD28 and further to the signaling domains of human CD3ζ chain as illustrated in FIG. 17. Due to the nature of dimerization of CD28 molecule, it is thought to be likely that NKp30-CD28-CD3ζ receptor expresses as a dimer.

Surface expression of chimeric NKp30 receptors on human T cells was analyzed by flow cytometry using anti-NKp30 and anti-CD4 mAbs. CD4+ and CD4− populations were clearly discernible in each sample. As expected, mock-transfected cells had little activation (FIG. 3A). Retroviral transduction of human T cells with wild-type (i.e., non-chimeric) NKp30 gene only led to marginal surface expression (FIG. 3B). The chimeric construct NKp30-CD3ζ (FIG. 3C) was expressed on human T cells at efficiency around 20% (i.e., about 20% of the total cell population had staining intensity above a cutoff chosen to indicate positive cell staining, indicated in each panel by a vertical line). The chimeric NKp30-CD28-CD3ζ receptor (FIG. 3D) gave rise to significantly higher surface expression of NKp30 (about 70% of the total cell population).

Example 2: Chimeric NKp30 Human T Cells Specifically Respond to Tumor Cells Expressing NKp30 Ligands This example demonstrates that the NKp30 chimeric T cells described in Example 1 were specifically activated by cells expressing NKp30 ligands.

A panel of human tumor cell lines as well as human PBMCs were screened for the expression of NKp30 ligands on mRNA level by RT-PCR (FIG. 4) using primers specific for the NKp30 ligands BAT3 and B7-H6, as well as a housekeeping gene (GAPDH) as a positive control. All tested human tumor cells had detectable amounts of BAT3 mRNA, whereas B7-H6 expression was readily detected in HeLa, U937, Panc-1, T47D, RPMI8226, K562, and A375 cells, but expression was at lower levels or undetectable in MCF-7, DU145, IM9, U266 and human PBMCs.

Figure 5A:
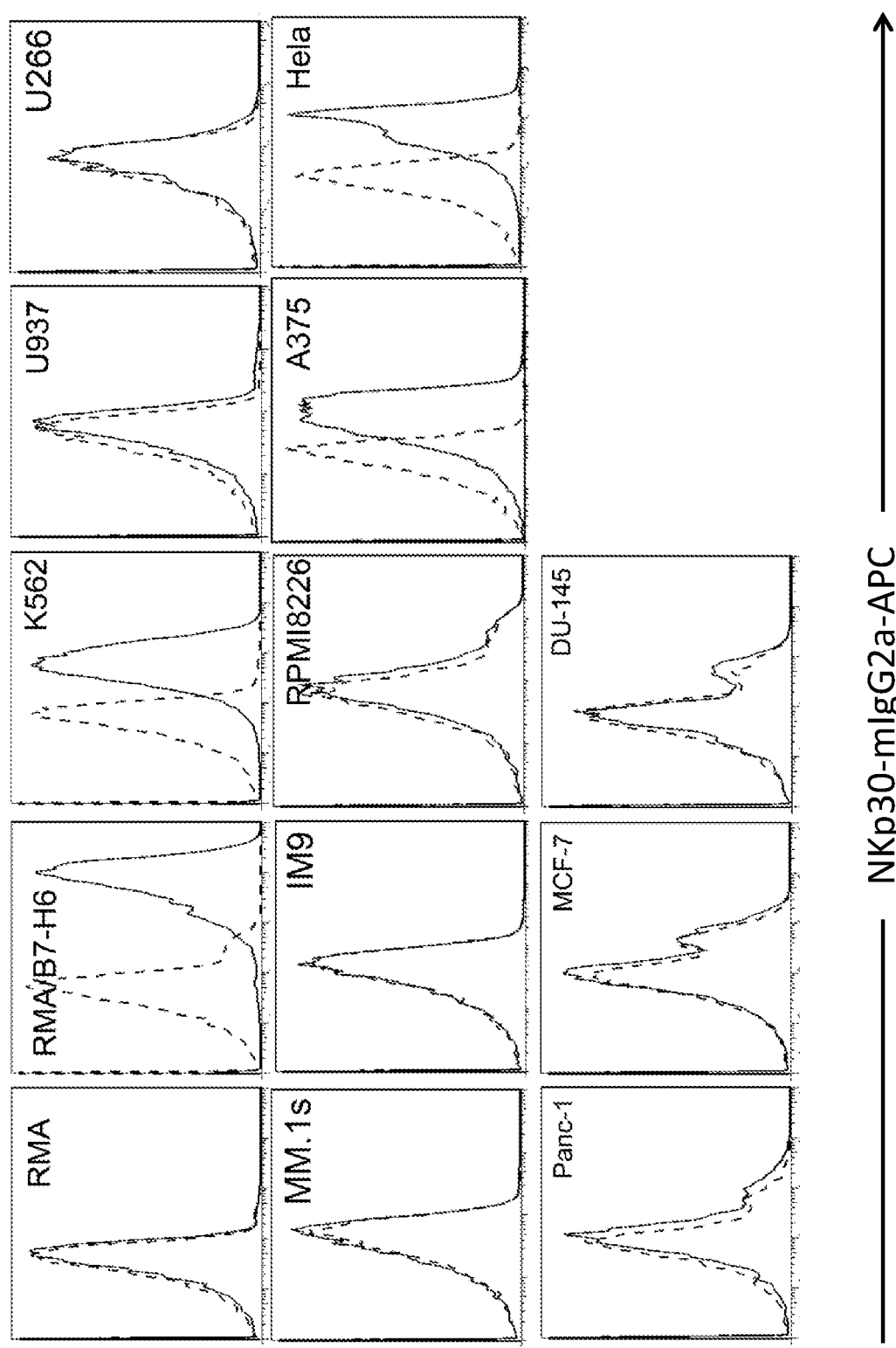
FIG. 5A. Surface expression of NKp30 ligands on tumor cells. K562, A375 and HeLa cells express high amounts of NKp30 ligands, whereas U937, RPMP8226, T47D and Panc-1 cells express marginal levels of NKp30 ligands. Some tumor cells (IM9, MM.1s, MCF-7 and DU145) as well as human PBMCs do not express NKp30 ligands. B7-H6 mRNA amounts are correlated with surface expression of NKp30 ligands, suggesting that B7-H6 is the major surface ligand of NKp30 in the tested tumors.
Figure 5B:
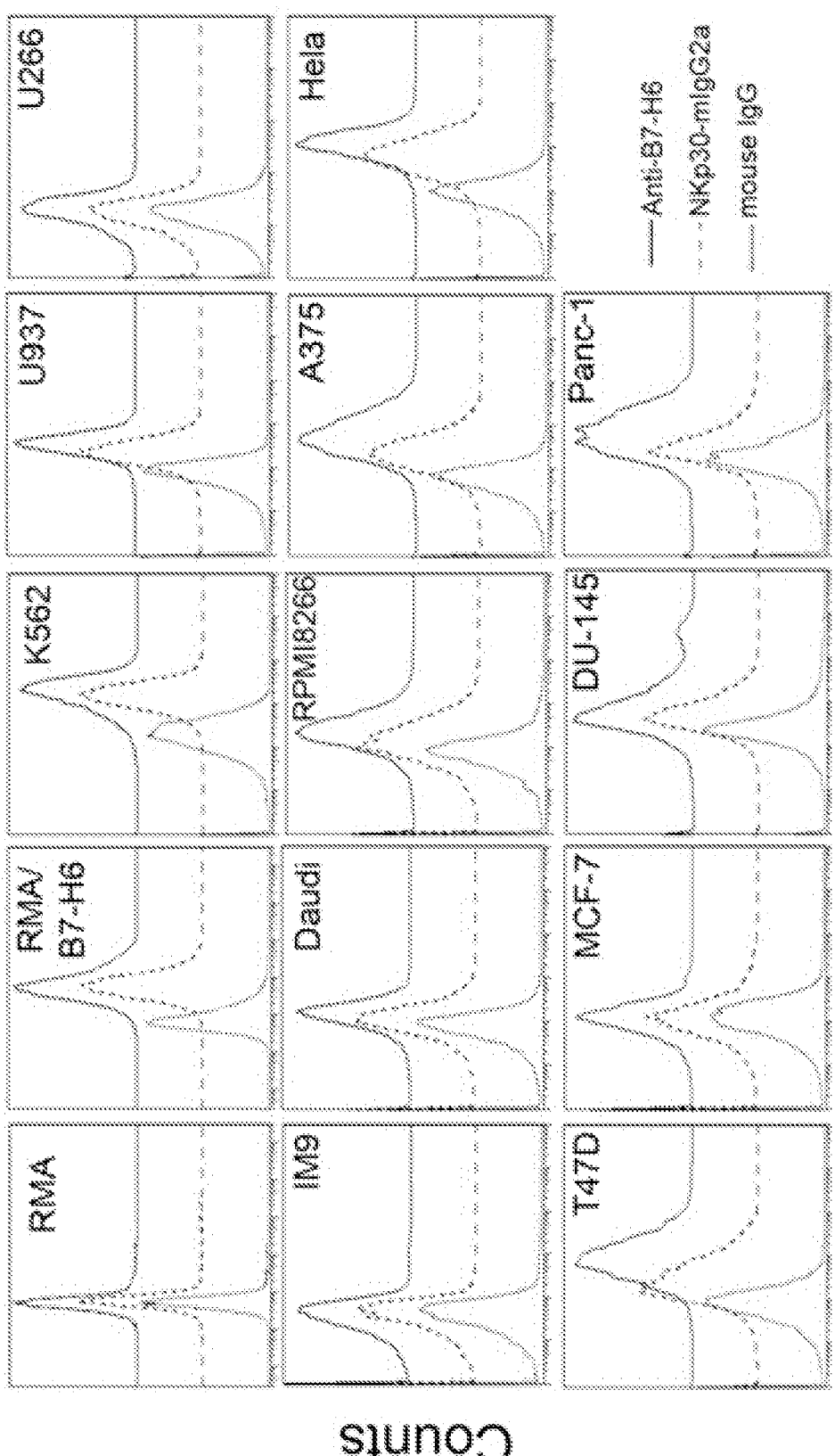
FIG. 5B. NKp30 ligand expression on the surface of human tumor cell lines was measured by flow cytometry using anti-B7-H6 mAbs (solid line) or a soluble NKp30 receptor fused to a mouse IgG2a Fc region (NKp30-mIgG2a; dashed line), followed by staining with allophycocyanin-conjugated goat anti-mouse IgG. Isotype controls are shown as a dotted line.

Surface expression of NKp30 ligands was then determined using a soluble human NKp30-mIgG2a fusion protein, which labels cells that surface-express NKp30 ligands (such as B7-H6). As shown in FIG. 5, K562, A375 and HeLa cells express high amounts of NKp30 ligands, whereas U937, RPMP8226, T47D and Panc-1 cells express marginal levels of NKp30 ligands. Some tumor cells (IM9, MM.1s, MCF-7 and DU145) as well as human PBMCs do not express NKp30 ligands. B7-H6 mRNA amounts are correlated with surface expression of NKp30 ligands, suggesting that B7-H6 is the major surface ligand of NKp30 in the tested tumors. The result is also consistent with prior reports that BAT3 is a nuclear protein, which is usually not expressed on cell surface and therefore would not be expected to trigger NKp30 and be detected in this assay.

The murine lymphoma cell line RMA was also negative for NKp30 binding (FIG. 5, "RMA), however, RMA cells transfected with a B7-H6 construct were positive for NKp30 binding (FIG. 5, "RMA/B7-H6").

Chimeric NKp30-transduced human T cells were then shown to specifically recognize these NKp30 ligand-positive tumor cells and respond by producing IFN-γ. As shown in FIG. 6. NKp30-CD3ζ+ (grey bars, middle bar in each group) or NKp30-CD28-CD3ζ+ (black bars, rightmost bar in each group) T cells produced significant amounts of IFN-γ after co-culture with NKp30 ligand-positive cells but not with ligand-negative cells indicating that these chimeric NKp30-modified T cells could functionally recognize NKp30 ligand-bearing tumor cells. In contrast, wild-type NKp30-modified T cells (white bars, left bar in each group) did not show any significant response to the stimulation by NKp30-ligand positive cells. NKp30-CD28-CD3ζ+ evoked significantly higher production of IFN-γ in the presence of NKp30 ligand-positive tumor cells than NKp30-CD3ζ, especially for cell lines for which the ligand expression was low. The reason for this may be higher amount of surface expression and/or presence of the CD28 co-stimulatory signaling domain of NKp30-CD28-CD3ζ+.

For the experiments shown in FIG. 6 when tumor cells were grown in suspension, co-culture with gene-modified primary human T cells ($10^5$) was performed in round-bottom 96-well plates at a ratio of 1:1, whereas adherent tumor cells ($2.5 \times 10^4$) were co-cultured with T cells in flat-bottom plates. Tumor cells were irradiated (120 Gys) before use. Cell-free supernatants were collected after 24 hr and analyzed for IFN-γ by ELISA using Duoset ELISA kits (R&D systems, Minneapolis, MN).

Figure 7A:
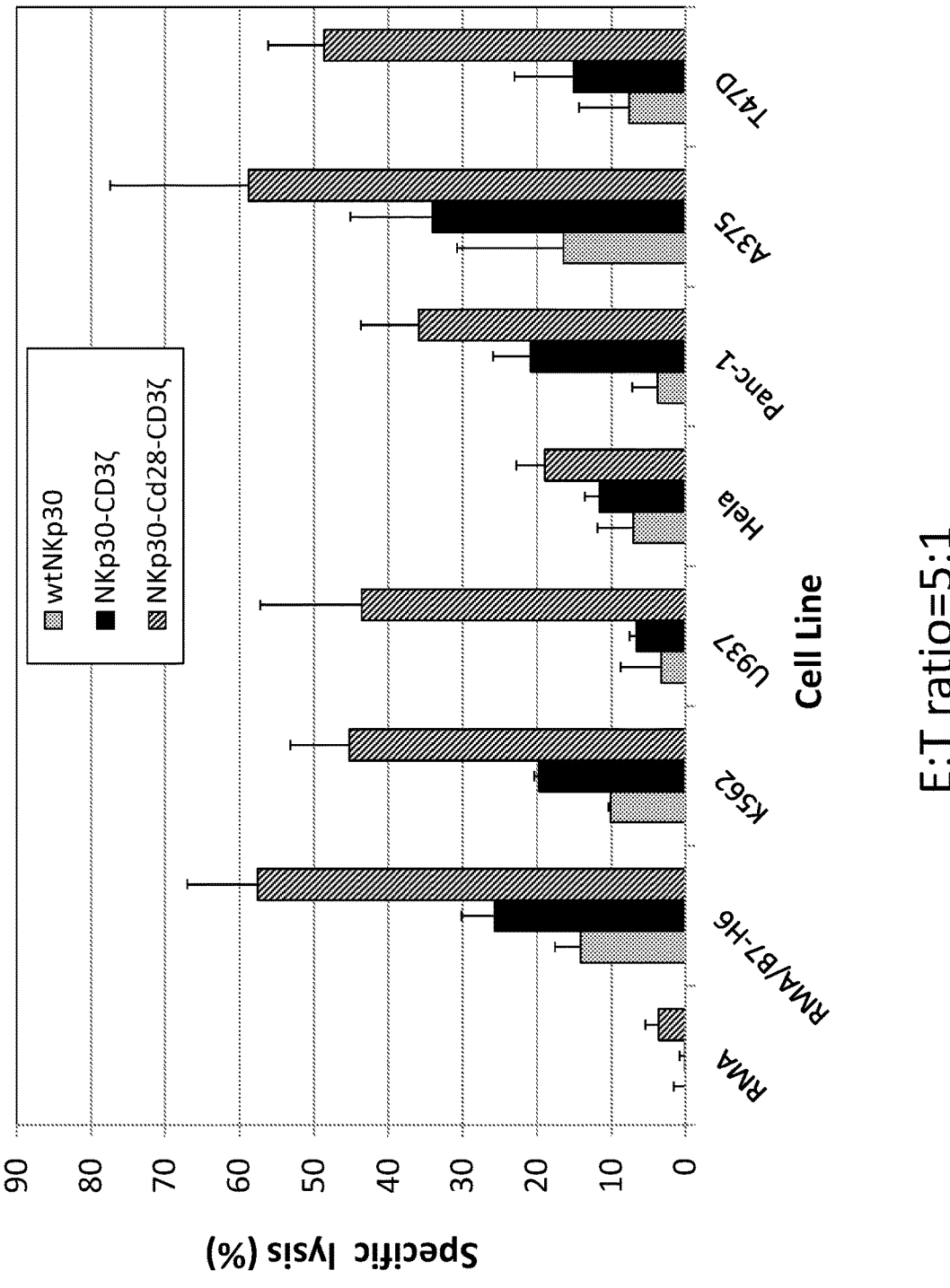
FIGS. 7A-B. Chimeric NKp30-bearing human T cells lysed NKp30-ligand positive tumor cells. Effector T cells derived from human PBMCs were modified with wtNKp30, NKp30-3ζ, or NKp30-CD28-3 ζ and cocultured with tumor cells at a ratio of 5:1 in 5-h LDH-release assays.

Chimeric NKp30-bearing human T cells were then demonstrated to lyse NKp30-ligand positive tumor cells. The cytotoxic activity of chimeric NKp30-modified human T cells against various tumor cell lines was determined using a LDH release assay. NKp30 receptor-modified human T cells were co-cultured with NKp30 ligand-positive RMA/B7-H6 (murine lymphoma), K562, U937, Hela, Panc-1, A375, T47D cells and -negative RMA at E:T ratios of 5:1 for Sh. FIG. 7A shows results of triplicate experiments (mean+/−SD). NKp30-CD3ζ+ (black bars, middle bar in each group) or NKp30-CD28-CD3ζ+ (dark gray bars, rightmost bar in each group) T cells lysed NKp30 ligand-positive cells (RMA/B7-H6, K562, U937, HeLa, Panc-1, A375, and T47D) but not ligand-negative cells (cell line RMA) indicating that these chimeric NKp30-modified T cells could functionally recognize NKp30 ligand-bearing tumor cells in a specific manner. In contrast, a far lower percentage of tumor cells were lysed in the presence of wild-type NKp30-modified T cells (light gray bars, left bar in each group). NKp30-CD28-CD3ζ-+ killed a greater percentage of NKp30 ligand-positive tumor cells than NKp30-CD34.

Figure 8:
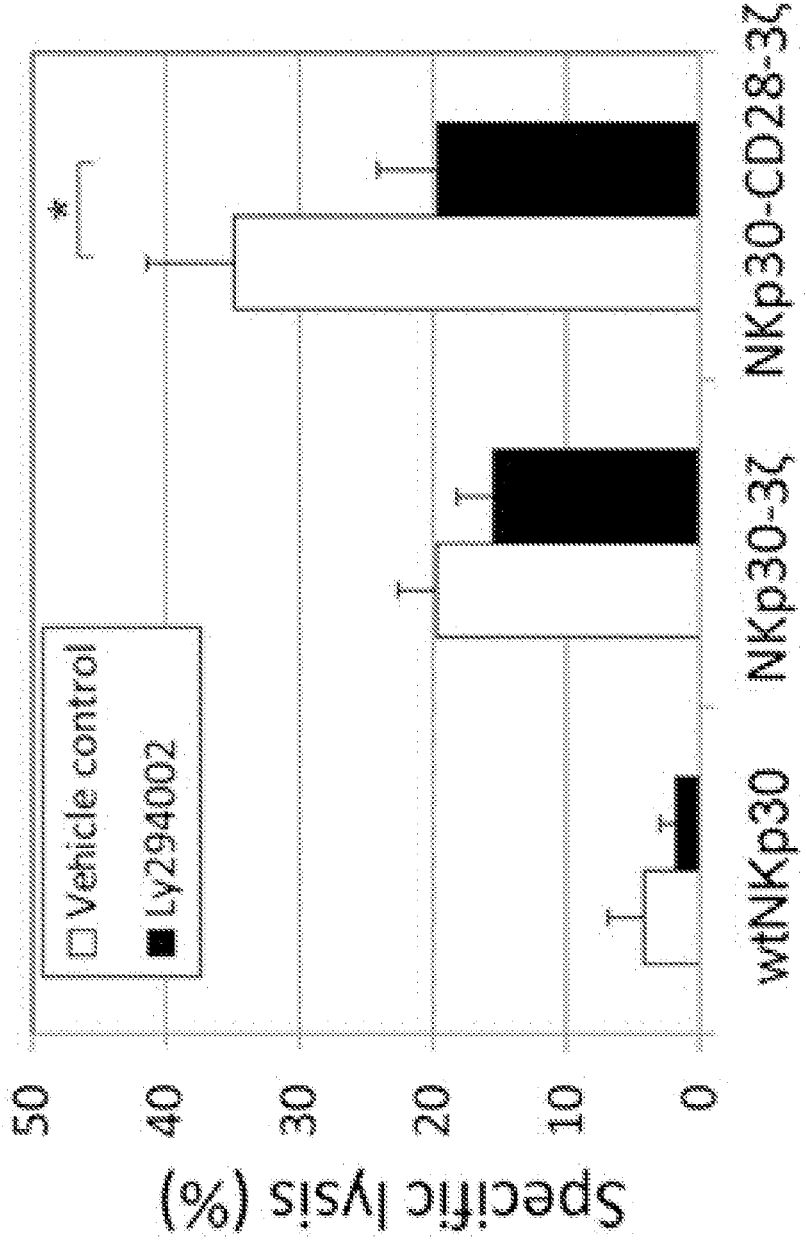
FIG. 8. Shows data indicating that PI3 kinase is involved in NKp30-CD28-CD3ζ-mediated cytotoxicity. Specific lysis was significantly decreased for the chimeric NKp30-CD28-CD3ζ T cells incubated with the Ly294002 inhibitor, indicating that the PI3 kinase plays a role in NKp30-CD28-CD3ζ-mediated cytotoxicity. NKp30-modified effector T cells were incubated with a PI3K inhibitor LY294002 (10 µM) at 37° C. for 1 h before coculture with K562 target cells at a E:T ratio of 5:1 in 5-h LDH-release assays. Vehicle controls are 0.1% DMSO. The data shown are the mean+/−SD of triplicates and are representative of two independent experiments. Asterisk (*) indicates p<0.05.

Cross-linking of CD28 leads to activation of the PI3K pathway. Therefore, we hypothesized that significantly enhanced IFN-γ production and cytotoxicity by T cells after engagement of the NKp30-CD28-3ζ receptor might be due to activation of PI3K. To test whether activation of PI3 kinase pathway plays a role in NKp30-CD28-CD3ζ-mediated cytotoxicity, a PI3K inhibitor LY294002 (10 μM) was pre-incubated with T cells for 1 hr prior to co-culture with tumor cells expressing B7-H6 at an E:T ratio of 3:1. DMSO (0.02%) was used as vesicle control. The cytotoxicity was determined by a 5-hr LDH release assay. Results are shown in mean+SD of triplicates (FIG. 8). *: P<0.05. Specific lysis was significantly decreased for the chimeric NKp30-CD28–CD34 T cells incubated with the Ly294002 inhibitor, indicating that the PI3 kinase plays a role in NKp30-CD28-CD3ζ-mediated cytotoxicity. This was not observed for the chimeric NKp30– CD3ζ T cells. This result was expected because CD28 is thought to induce signals in T cells in a PI3-kinase dependent manner. These results demonstrate that that PI3K is important for enhancement of function when the cytoplasmic part of CD28 is included. Without intent to be limited by theory, it is believed that this construct uses the CD28 induced PI3K signals, such that the PI3K inhibitor decreases cytotoxicity of the NKp30-CD28-CD3ζ receptor to the amount similar to the NKp30-CD3ζ receptor, which lacks the CD28 signaling element. However, irrespective of the mechanism of action, the CD28-containing construct exhibits elevated cytotoxicity (and as shown below, tumor protection) relative to other exemplified constructs.

Example 3: Production of Chimeric NKp30 Mouse T Cells

This example demonstrates that human NKp30 receptors (both wild-type and chimeric) can express on primary mouse T cells. Because NKp30 is a pseudogene in inbred mice, we determined whether chimeric human NKp30 receptors could be expressed on mouse T cells, which allows the testing of in vivo efficacy of chimeric NKp30-modified T cells against NKp30 ligand-positive tumor cells in immunocompetent mouse models. One day after ConA (1 ug/ml) stimulation, mouse spleen cells were transduced with retroviral supernatants containing NKp30 or control viruses. After expansion and G418 selection, mouse T cells were stained with anti-CD4 FITC and anti-NKp30-PE (FIG. 9). Similar to the expression profile observed on human T cells, chimeric NKp30 receptors were expressed on mouse T cells, although the expression of NKp30 observed was slightly lower than with human T cells.

Figures 9A, 9B, 9C, 9D:
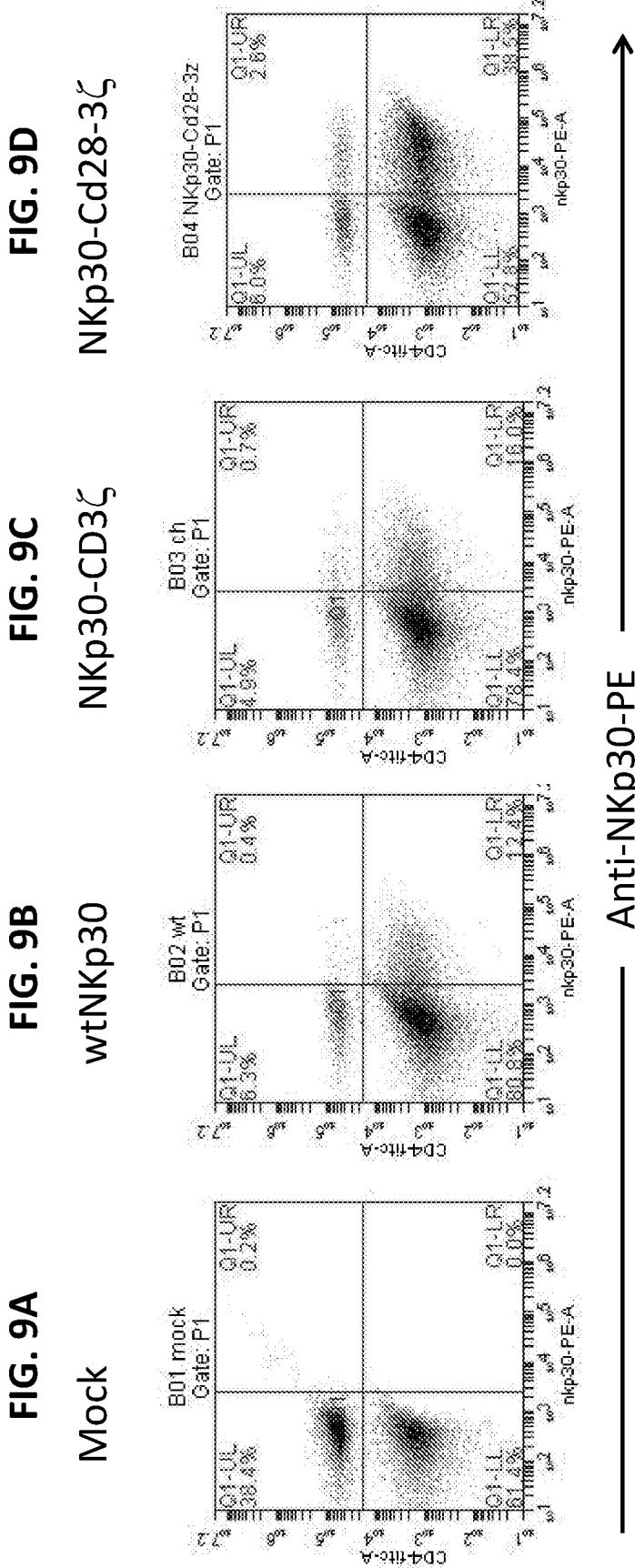
FIGS. 9A-D. NKp30 expression on mouse T cells. Expression levels are shown for mock-transfected cells (FIG. 9A); wild-type (i.e., non-chimeric) NKp30 transfected cells (FIG. 9B); chimeric NKp30-CD3ζ transfected cells (FIG. 9C); and chimeric NKp30-CD28-CD3ζ transfected cells (FIG. 9D).

As expected, mock-transfected cells had low levels of NKp30 signaling (FIG. 9A). Retroviral transduction of mouse T cells with wild-type (i.e., non-chimeric) NKp30 gene only led to expression on about 12.8% of cells (FIG. 3B). The chimeric construct NKp30-CD3ζ (FIG. 3C) was expressed on mouse T cells at efficiency around 16.7% (i.e., about 16.7% of the total cell population had staining intensity above a cutoff chosen to indicate positive cell staining, indicated in each panel by a vertical line). The chimeric NKp30-CD28-CD3ζ receptor (FIG. 9D) gave rise to significantly higher surface expression of NKp30 (about 41.1% of the total cell population).

Example 4: Hunan NKp30 Receptors are Functional in Mouse T Cells

This example demonstrates that chimeric NKp30 mouse T cells specifically respond to tumor cells expressing NKp30 ligands. These results indicate that Human NKp30 Receptors are functional in mouse T cells.

Effector T cells derived from B6 (open), perforin-deficient (Pfp−/−, filled) mice that were modified with NKp30 receptors were co-cultured with RMA or RMA/B7-H6 cells, respectively, at a ratio of 1:1 5-hr LDH release assays. The data are presented as mean±SD of triplicates and are representative results from two independent experiments. The T cells lysed a significantly higher percentage of NKp30 ligand-positive cells (RMA/B7-H6, FIG. 10B) than ligand-negative cells (cell line RMA, FIG. 10A). Specific lysis was substantially decreased with the Pfp−/− cells. These results demonstrated that specific lysis of RMA/B7-H6 by NKp30-modified murine T cells required perforin.

Example 5: Chimeric Human NKp30 Receptors Leads to Better Anti-Tumor In Vivo Efficacy and Enhanced Mouse Survival in a Murine B7-H6+ Lymphoma Model In this example, mouse T cells transduced with chimeric NKp30 were shown to enhance survival of mice injected with lymphoma cells, specifically RMA/B7-H6 that express the NKp30 ligand B7-H6 (schematically illustrated in FIG. 11A). Integration of CD28 TM and signaling domains into chimeric NKp30 receptor was demonstrated to lead to better anti-tumor in vivo efficacy. RMA/B7-H6 cells ($10^5$) were administered i.v. on day 0. On day 5, 7 and 9, tumor-bearing mice were injected with T cells ($5 \times 10^6$) that were modified to express wtNKp30 (◆), NKp30-CD3ζ (▲), NKp30-CD8-CD3ζ (●) and NKp30-CD28-CD3ζ (□), respectively (FIG. 11B). Injection with a saline solution (HBSS) was used as negative control. Data are presented in Kaplan-Meier survival curves.

Previous results had shown that i.v. injection of RMA cells leads to systemic lymphoma in B6 mice (Zhang et al., Cancer Res. 67: 11029-11036). The present results demonstrate that although B7-H6 is a human molecule, its expression did not significantly alter the growth of RMA cells. Intravenous administration of 0 RMA/B7-H6 cells led to the development of systemic lymphoma, with a median survival of 18 d, which is the typical growth for a similar dose of RMA tumor cells in B6 mice (Zhang et al., Cancer Res. 67: 11029-11036).

Survival curves were similar for mice injected with saline or T cells transduced with wtNKp30 (with no mice surviving past about 20-22 days) indicating that wENKp30 T cells had little or no beneficial effect. Additionally, although wtNKp30, NKp30-3ζ, and NKp30-CD8(TM)-3ζ allowed T cells to respond to RMA/B7-H6 cells in vitro, the murine T cells modified with these receptors showed little effect on the survival of tumor-bearing mice in this aggressive lymphoma model.

Slight improvements in survival were obtained with NKp30-CD3ζ T cells, particularly for the final 25% of surviving mice, with some mice surviving for up to about 30 days. Further improvements in survival were obtained with NKp30-CD8-CD3ζ T cells, with some mice surviving for up to about 42 days. However, the greatest improvements in survival were observed with NKp30-CD28-CD3ζ T cells. Treatment with NKp30-CD28-3ζ+ T cells significantly improved median survival from 18 to 30 d, with approximately 20% of the population (4 out of 23 mice) surviving to the end of the experiment (60 days). Several of these mice become long-term survivors, indicating that treatment with this chimeric NKp30 T cell resulted in tumor eradication.

Example 6: Chimeric NKp30-CD28-CD3ζ T Cells Confer Long-Term Tumor Resistance In the preceding example, several of the mice treated with NKp30-CD28-CD3ζ T cells became long-term survivors subsequent to injection with lymphoma cells. The lymphoma cells were RMA cells transformed with a B7-H6 construct (RMA/B7-H6).

To determine whether this chimeric NKp30 T cell resulted in NKp30-independent tumor immunity, long-term survivors were re-challenged with a similar, but ligand-deficient, lymphoma, specifically RMA cells that had not been transformed with the B7-H6 construct. These survivors were indeed resistant to the tumor re-challenge. Overall survival was determined, and none of the re-challenged mice had tumor growth by the end of the study period, whereas naïve mice did (FIG. 11C). These results show that this chimeric T cell treatment can lead to tumor eradication and suggest induction of long-term tumor immunity can be acquired.

Because ligand-negative tumor cells could selectively grow out after CAR T cell therapy, it would be beneficial if treatment with NKp30-CD28-3ζ+ T cells induced host immunity against other tumor antigens. These results demonstrate that adoptive transfer of NKp30-CD28-3ζ+ T cells may allow hosts to generate immunological memory against RMA tumor antigens. In addition, we observed that NKp30-CD28-3ζ+ T cells persisted longer than did either NKp30-3ζ+ or NKp30-CD8(TM)-34+ T cells (data not shown), which correlated with their enhanced antitumor efficacy.

Example 7: Additional Exemplary Embodiments of Chimeric NKp30 Receptors

Figures 6D, 6E:
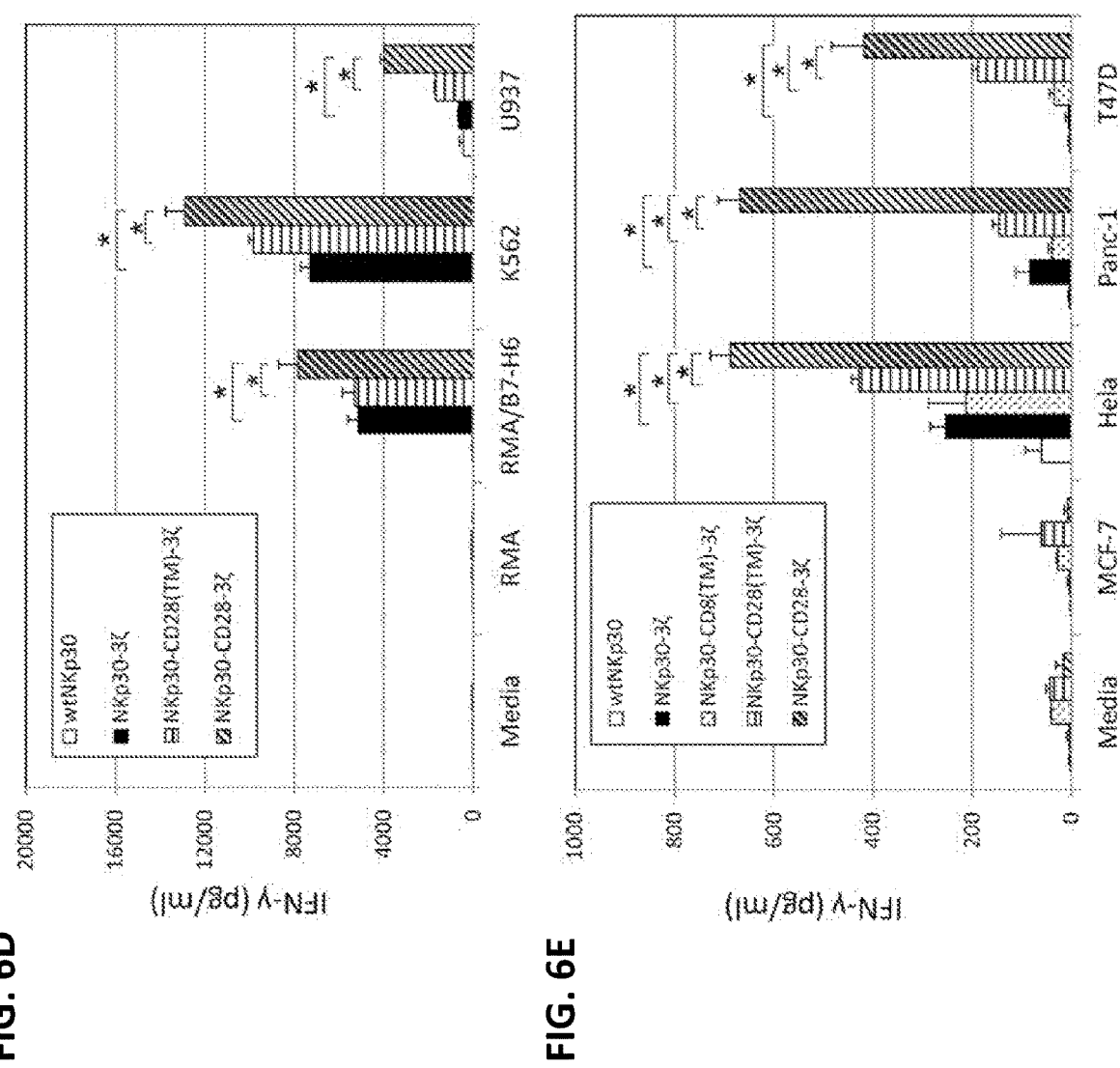
Figure 7B:
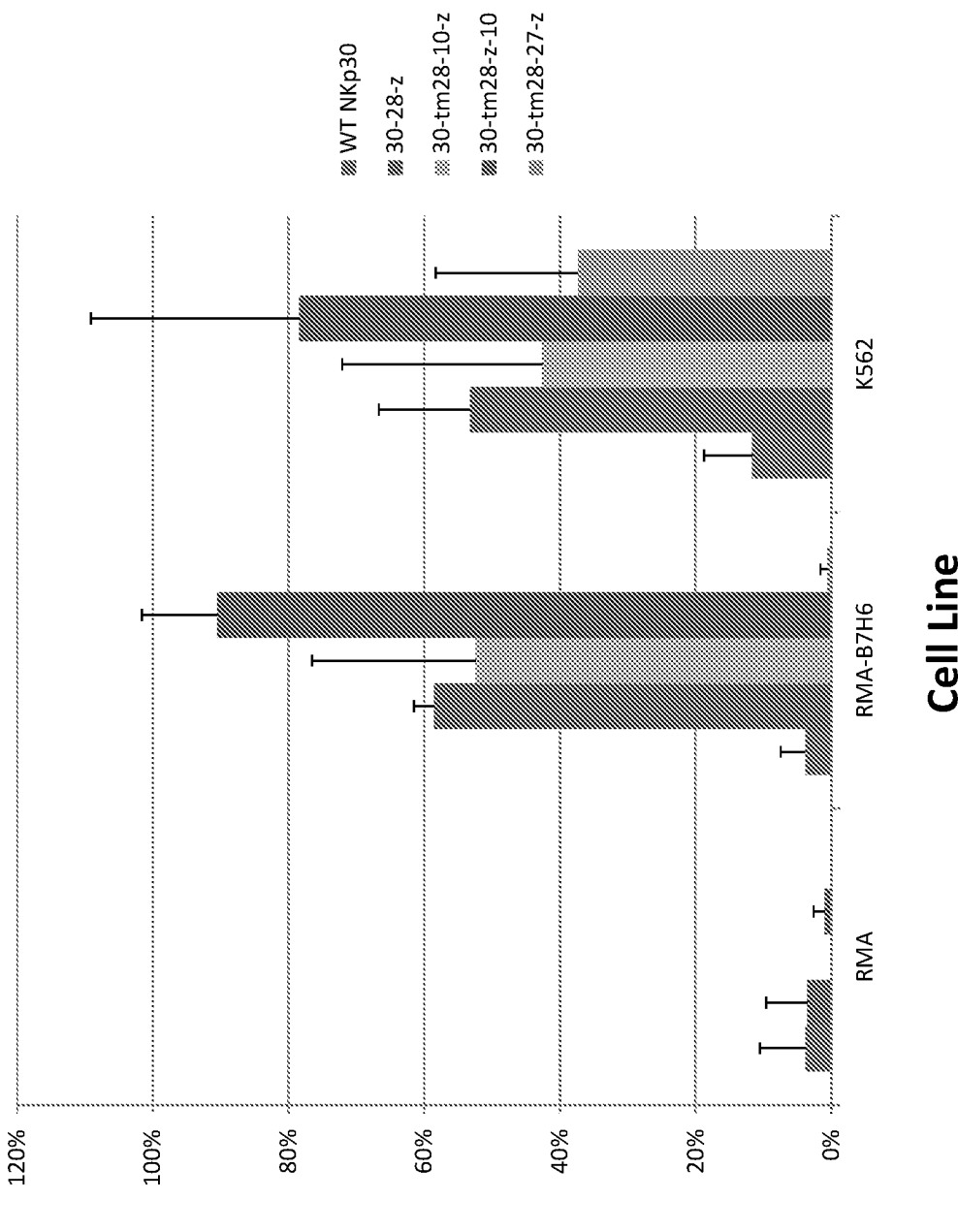

Additional chimeric NKp30 receptors were produced as illustrated in FIGS. 18 and 20-22. These sequences encoding these receptors were introduced into human and/or mouse T cells, and their surface expression was detected (FIGS. 3 and 9). T cells transformed with these constructs were also demonstrated to produce IFN-γ production and cause specific lysis of NKp30 ligand-positive tumor cells (FIGS. 6 and 7). These cells are tested in vitro and/or in vivo for cancer cell killing activity as described above in Examples 5 and 6.

Example 8: Human DCs Express NKp30 Ligands and can Stimulate Chimeric NKp30-Expressing T Cells to Produce IFN-γ

This example shows that PBMC-derived dendritic cells express NKp30 ligands, including immature dendritic cells, and they can stimulate NKp30 CAR-bearing T cells to produce IFN-γ, but to a lesser extent than NKp30 ligand-positive tumor cells.

It is known that NKp30 plays an important role in human NK-DC interactions (Moretta et al., Immunol. Lett. 100: 7-13; Vitale et al., Blood 106: 566-571). At low NK/DC ratios, DCs promote IFN-γ production and cytotoxicity by NK cells in an NKp30-dependent manner (Vitale et al., Blood 106: 566-571; Ferlazzo et al., J. Exp. Med. 195: 343-351), which suggests that DCs express NKp30 ligands. With the use of NKp30-mIg2a, we confirmed that both iDCs and mDCs can bind to soluble NKp30, which is consistent with DCs expressing ligands for NKp30 (FIG. 12A). The level of cell surface staining on iDCs was higher than on mDCs. However, there was no significant expression of B7-H6 on DCs as determined with mAb 47.39, a specific anti-B7-H6 mAb. To determine whether the NKp30 CAR-modified T cells can respond to DCs, T cells were cocultured with either iDCs or mDCs at a 5:1 ratio for 24 h. IFN-γ production (200-800 pg/ml) was observed by NKp30-28-ζ-modified T cells after coculture with DCs (FIG. 12B). Compared with mDCs, iDCs induced higher amounts of IFN-γ, which reflected their greater binding to soluble NKp30.

Example 9: Integration of a CD28 Signal into the NKp30 Chimeric Antigen Receptor Promotes In Vitro T Cell Proliferation It is known that CD28 signals enhance T cell survival and proliferation. To Investigate whether integration of CD28 signaling in the chNKp30 receptor resulted in similar outcomes upon engagement of the NKp30 receptor, CFSE-labeled T cells were cocultured with HeLa cells (NKp30 ligand positive) in the presence of a small amount of IL-2 (25 U/ml) for 3 d. As shown in FIG. 13A, engagement of NKp30-CD28-3ζ-bearing T cells led to more T cell proliferation than did engagement of NKp30-3ζ-bearing T cells. Two important mechanisms through which CD28 signaling promotes T cell survival are through upregulation of IL-2 and an antiapoptotic protein, Bcl-xL. To determine whether NKp30-CD28-3ζ+ T cells upregulated IL-2 and Bcl-xL in response to cross-linking of the chimeric receptor, T cells were cultured in anti-NKp30 mAb-coated wells for 24 h. IL-2 mRNA and Bcl-xL protein were determined using real-time PCR and intracellular staining, respectively. The results show that NKp30-CD28-3ζ+ T cells increased IL-2 expression by 25-fold after receptor crosslinking compared with a 10-fold induction in NKp30-3ζ+ T cells (FIG. 13B). No significant upregulation of IL-2 was observed in wtNKp30-modified T cells cultured under these conditions. Similarly, we observed greater expression of Bcl-xL in NKp30-CD28– 3ζ+ T cells compared with NKp30-3ζ+ T cells (FIG. 13C). These data suggest that NKp30-CD28-3ζ+ T cells can receive a costimulatory signal through CD28 that leads to increased IL-2 and Bcl-xL expression.

Example 10

Figures 3J, 3K, 3L, 3M, 3N, 3O:
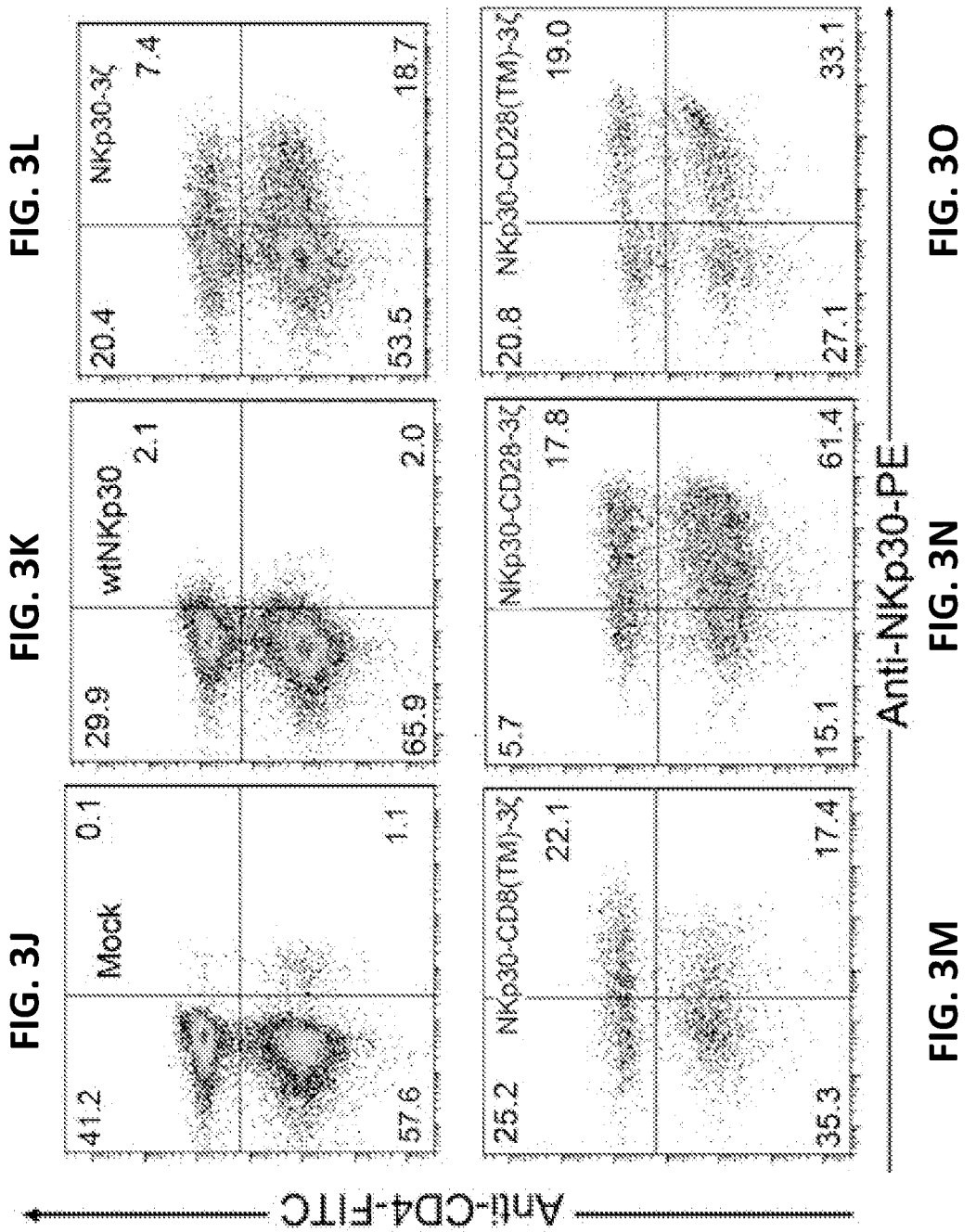
FIGS. 3J-O show NKp30 expression on human T cells 7 d after transduction with NKp30 chimeric antigen receptors (CARs). NKp30 expression was measured using the PE-conjugated anti-NKp30 mAbs in combination with anti-CD4-FITC mAbs. More than 99% of cells were CD3+ T cells (data not shown). CD4– T cells are CD8+ T cells. Results are shown for mock-transfected cells (FIG. 3J); wild-type (i.e., non-chimeric) NKp30 transfected cells (FIG. 3K); chimeric NKp30-CD3ζ transfected cells (FIG. 3L); chimeric NKp30-CD8(TM)-CD3ζ transfected cells (FIG. 3M); chimeric NKp30-CD28-CD3ζ transfected cells (FIG. 3N) and NKp30-CD28(TM)-CD3ζ transfected cells (FIG. 3O). The data are representative of three experiments.

Surface expression of chimeric NKp30 receptors on human T cells was analyzed by flow cytometry using anti-NKp30 and anti-CD4 mAbs. As shown in FIG. 3K, retroviral transduction of human T cells with wtNKp30 gene did not lead to significant surface expression. Insufficient expression of wtNKp30 on the cell surface may be due to an absence of FcgR expression on T cells, which is associated with CD37 and NKp30 on human NK cells. Replacement of the NKp30 TM domain with the CD37 TM domain improved CAR expression. Our results showed that the CD8a TM domain efficiently allows surface expression of chimeric NKp30 receptor on T cell. The human CD28 TM domain also resulted in higher surface expression of chimeric NKp30, with or without the CD28 CYP domain.

Figures 4A, 4B:
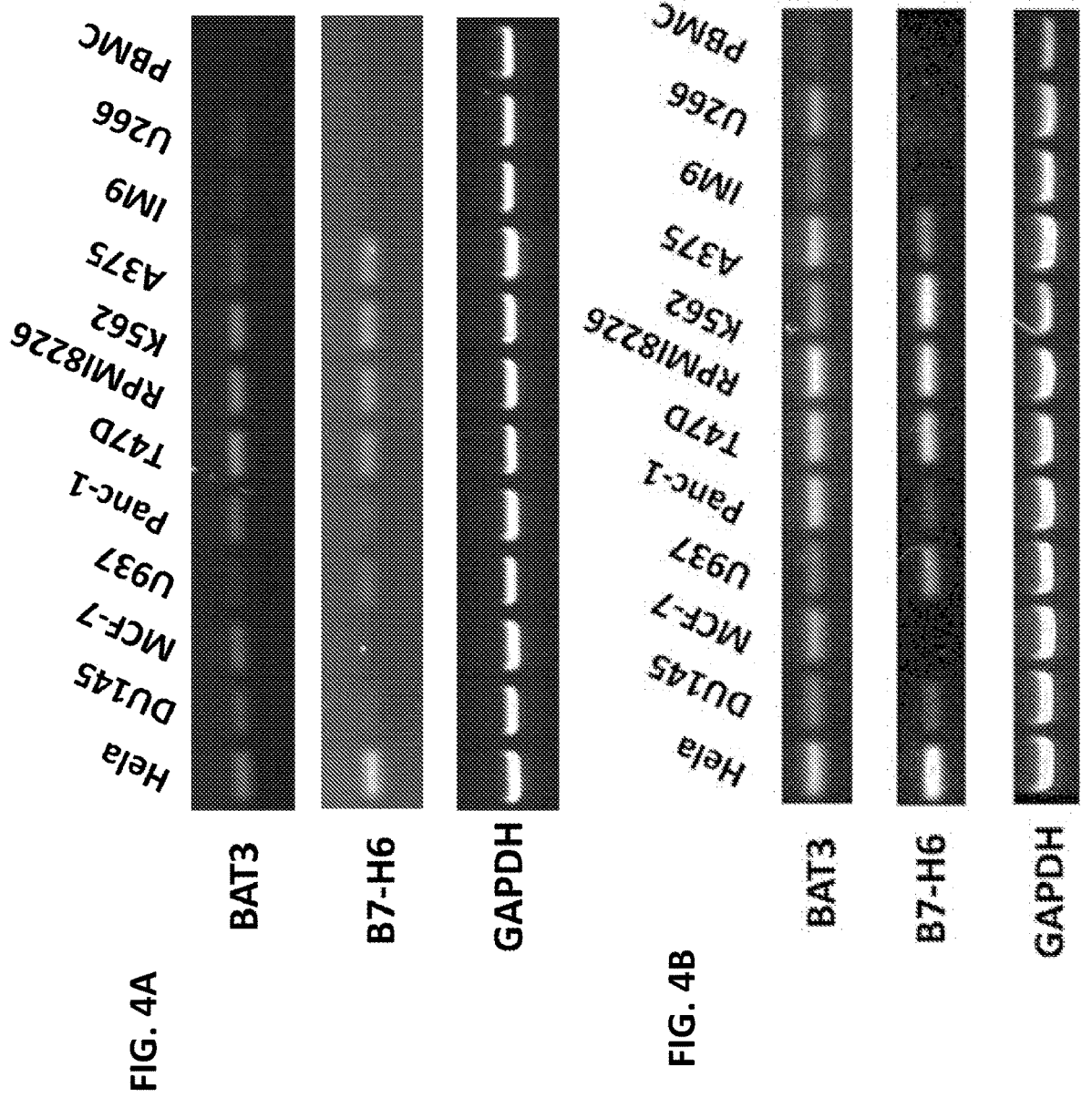
FIGS. 4A-B. Expression of NKp30 ligands on tumor cells and PBMC. Human tumor cell lines as well as human PBMCs were screened for the expression of NKp30 ligand mRNAs by RT-PCR using primers specific for the NKp30 ligands BAT3 and B7-H6, as well as a housekeeping gene (GAPDH) as an internal positive control. All tested human tumor cells had detectable amounts of BAT3 mRNA, whereas B7-H6 expression was readily detected in HeLa, U937, Panc-1, T47D, RPM18226, K562, and A375 cells, but expression was at lower levels or undetectable in MCF-7, DU145, IM9, U266 and human PBMCs.

Chimeric NKp30-Expressing T Cells Produce IFN-γ Upon Coculture with NKp30 Ligand-Positive Tumor Cells A panel of human tumor cell lines was screened for NKp30 ligand expression using a soluble human NKp30-mIgG2a fusion protein and an anti-B7-H6 mAb (called 47.39). As shown in FIG. 4B, K562, A375, HeLa, and T47D cells expressed high amounts of NKp30 ligands, whereas U937, RPMP8226, DU145, and Panc-1 cells expressed low amounts of NKp30 ligands. Some tumor cells (IM9, U266, and MCF-7) did not express NKp30 ligands on the cell surface. All tested human tumor cells have detectable levels of BAT3 mRNA, as detected by RT-PCR (FIG. 4B). In contrast, B7-H6 mRNA levels were correlated to surface expression of NKp30 ligands, suggesting that B7-H6 is the major surface ligand of NKp30 in tumors. The result was also consistent with the fact that BAT3 is a nuclear protein, which is usually not expressed on the cell surface. In addition, RT-PCR results showed that PBMCs lacked the mRNAs of B7-H6 and Bat3 (FIG. 4B).

To determine whether chimeric NKp30-transduced human T cells were able to recognize NKp30 ligand-positive tumor cells, the chimeric NKp30 CAR-bearing T cells were cultured with different tumor cells, and IFN-γ responses measured by ELISA. As shown in FIGS. 6D-E, NKp30-3ζ+, NKp30-CD8(TM)-3ζ+, NKp30-CD28(TIM)-3ζ+, or NKp30-CD28-3ζ+ T cells produced significant amounts of IFN-γ after coculture with NKp30 ligand-positive cells but not when cultured with ligand-negative cells, indicating that these NKp30 CAR-modified T cells could functionally recognize NKp30 ligand-bearing tumor cells. In contrast, wtNKp30-modified T cells did not show any significant response to the stimulation by NKp30 ligand-positive cells. NKp30-CD28-3ζ-expressing T cells produced significantly more IFN-γ than did T cells expressing NKp30-3ζ+, NKp30-CD8(TM)-3ζ+, or NKp30-28 (TM)-3ζ+ in the presence of NKp30 ligand-positive tumor cells, especially when the ligand expression was low. The reason was likely due to higher surface expression of this CAR and/or the presence of the CD28 costimulatory signaling domain in NKp30-CD28-3.

Chimeric NKp30-Bearing Human T Cells Kill NKp30 Ligand-Positive Tumor Cells

Figure 7C:
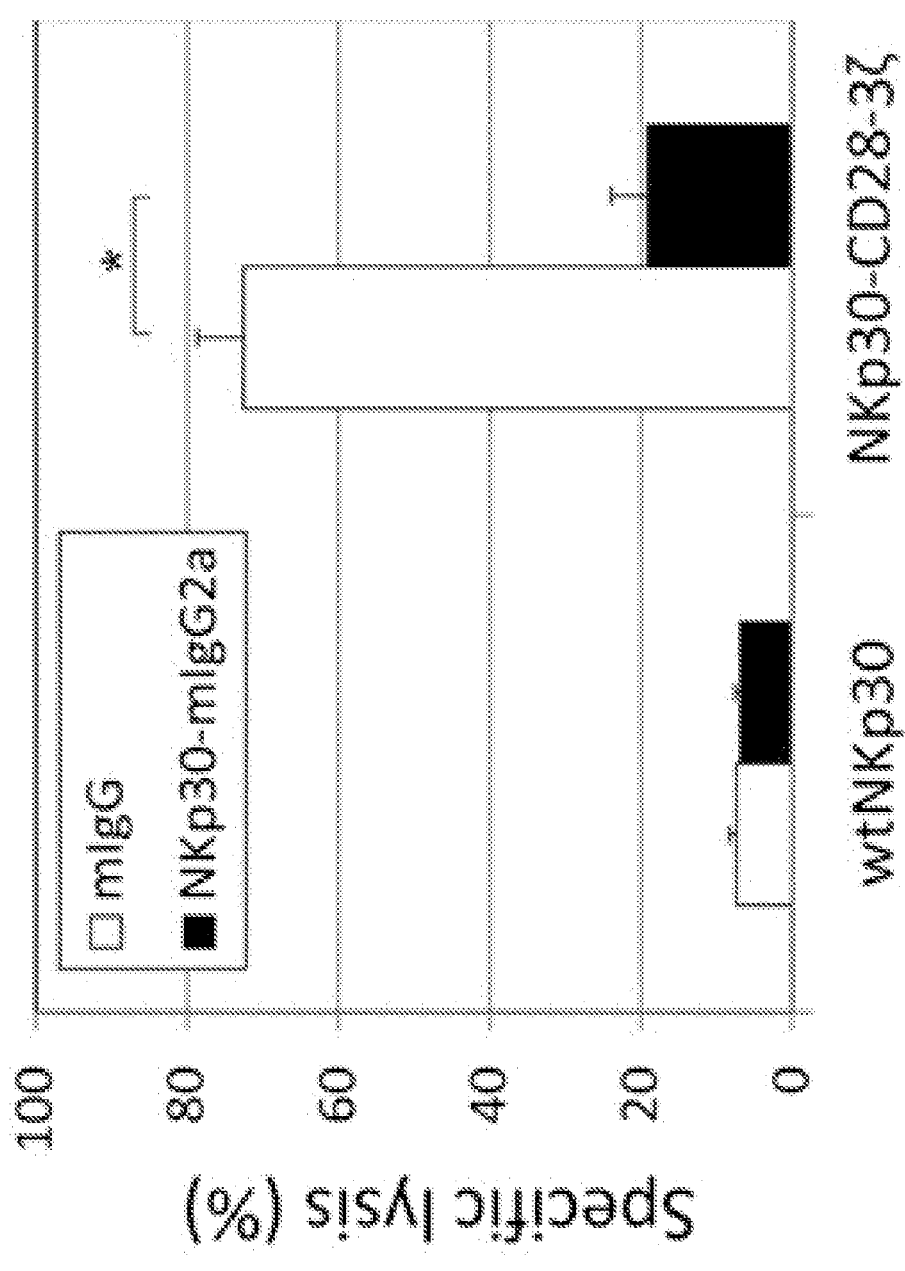
FIG. 7C further illustrates that lysis was mediated by the chimeric NKp30 constructs. NKp30-mIgG2a significantly reduced NKp30-28-3ζ-bearing T cell-mediated cytotoxicity. These results demonstrated that chimeric NKp30-bearing T cells killed ligand-positive tumor cells, and the interaction between chimeric NKp30 receptors and NKp30 ligands was essential for chimeric NKp30-mediated T cell function. Effector T cells modified with wtNKp30 or NKp30-CD28-3ζ were cocultured with target cells K562 in the presence of 10 µg/ml NKp30-mIgG2a or mouse IgG at a ratio of 5:1; the percentage of specific lysis was determined after a 5-h LDH-release assay. The data are presented as mean+/−SD and are representative of two independent experiments.

The cytotoxic activity of chimeric NKp30-modified human T cells against various tumor cell lines was determined. As shown in FIG. 7C, NKp30 CAR-bearing T cells were able to lyse NKp30 ligand-positive target cells (RMA/B7-H6, T47D, Panc-1, A375, K562, and RPMI8226) but not the ligand-negative cell lines RMA and MCF-7 in vitro. Similar to cytokine production, no significant killing was observed when wtNKp30-modified T cells were used. NKp30-CD28-3ζ receptor bestowed T cells with significantly higher lytic activity than did NKp30-3ζ, NKp30-CD8 (TM)-3ζ, or NKp30-CD28(TM)-3ζ. Because RMA/B7-H6 tumor cells lack expression of human MHC class I and II molecules, these data indicate that the chimeric NKp30 receptor-modified T cell-mediated killing of these tumor cells was ligand dependent and MHC independent. To confirm that chimeric NKp30-mediated killing is dependent on the interactions between NKp30 and its ligands, soluble NKp30 (NKp30-mIgG2a) was incubated with K562 target cells prior to the coculture with T cells. As shown in FIG. 7C, NKp30-mIgG2a significantly reduced NKp30-28-3ζ-bearing T cell-mediated cytotoxicity. These results demonstrated that chimeric NKp30-bearing T cells killed ligand-positive tumor cells, and the interaction between chimeric NKp30 receptors and NKp30 ligands was essential for chimeric NKp30-mediated T cell function.

Figures 10A, 10B:
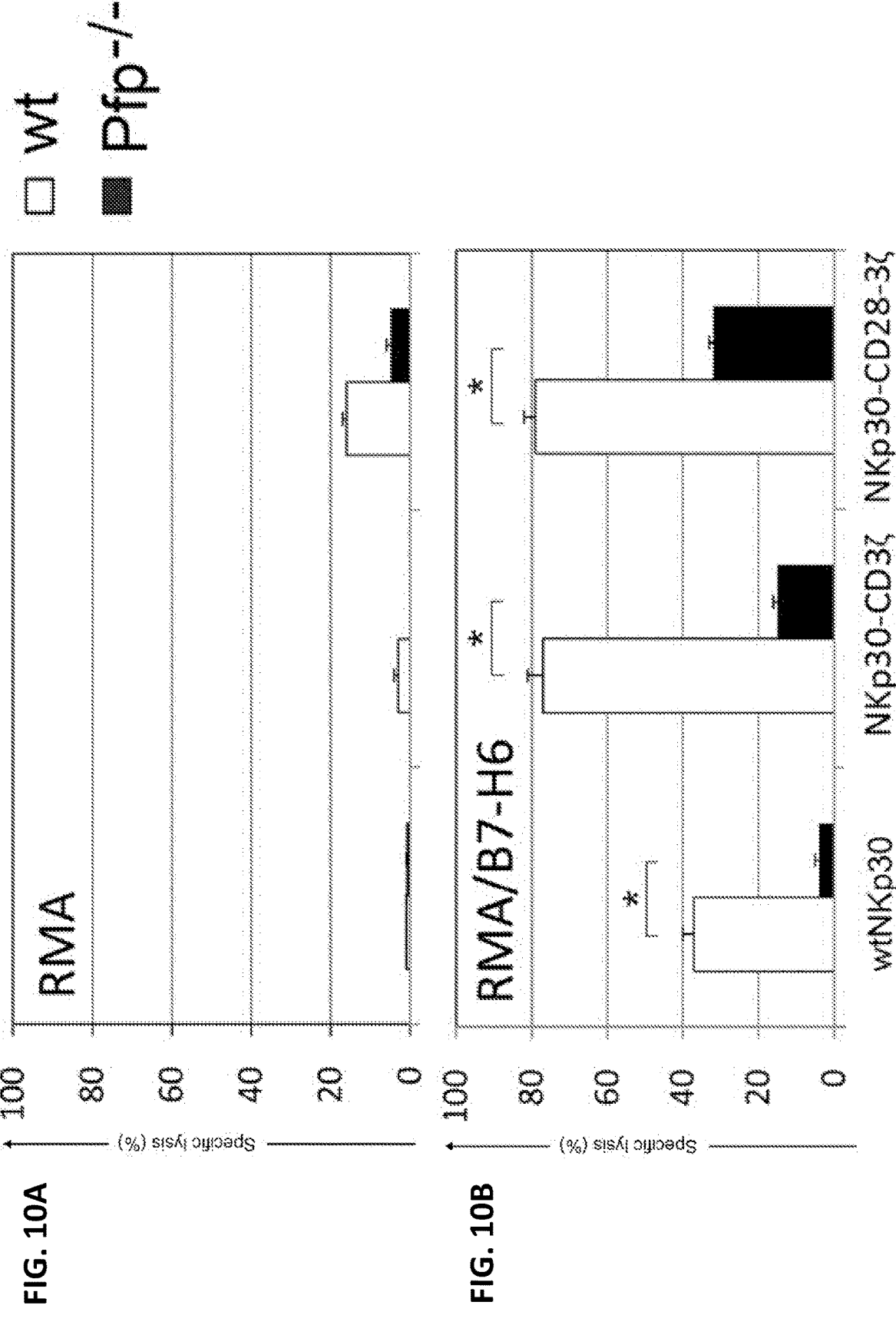
FIGS. 10A-B. Human NKp30 receptors are functional in mouse T cells. Effector T cells derived from B6 (open), perforin-deficient (Pfp−/−, filled) mice that were modified with NKp30 receptors were co-cultured with RMA or RMA/B7-H6 cells at an E:T ratio of 1:1 in 5-h LDH-release assays. The T cells lysed a significantly higher percentage of NKp30 ligand-positive cells (RMA/B7-H6, FIG. 10B) than ligand-negative cells (cell line RMA, FIG. 10A). The data are presented as mean±SD of triplicates and are representative results from two independent experiments (FIGS. 10A and 10B). Specific lysis was substantially decreased with the Pfp−/− cells.
Figure 10C:
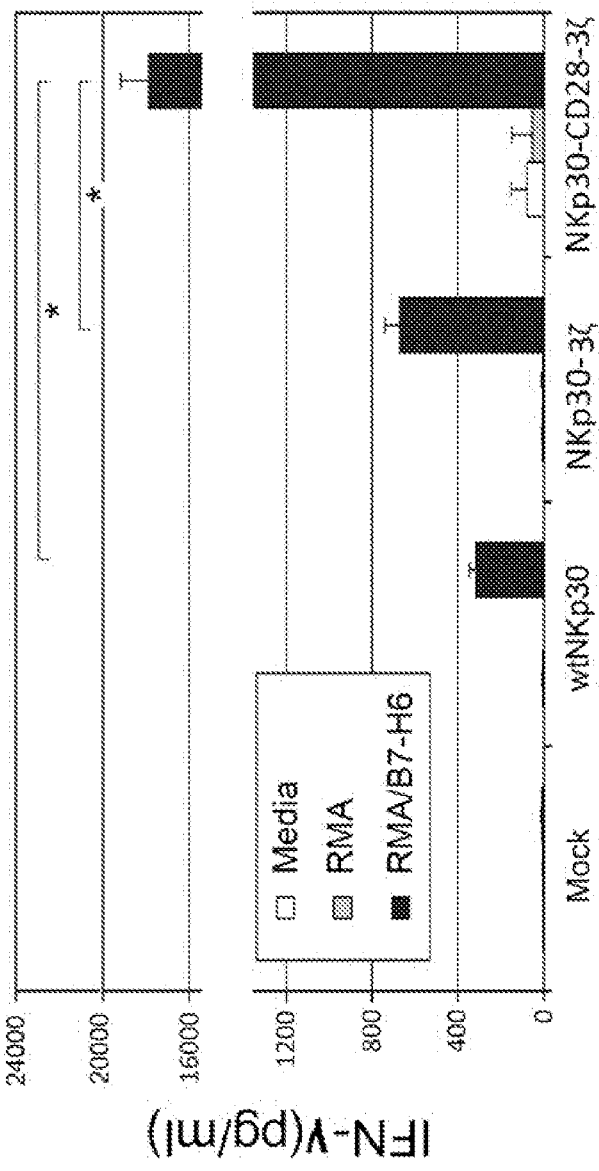
FIG. 10C shows amounts of IFN-γ produced by transduced murine T cells in response to NKp30 ligand-positive cells. Seven days after retroviral transduction, NKp30-modified T cells (100,000 cells) were cocultured with irradiated RMA/B7-H6 cells (100,000 cells) for 24 h. Mouse lymphoma cell line RMA was used as a negative control. IFN-γ amounts in the supernatants were analyzed by ELISA. Results are shown as mean+/−SD.

Adoptive Transfer of NKp30-CD28z+ T Cells Significantly Improves the Survival of RMA/B7-H6 Tumor-Bearing Mice and Induces the Generation of Immunological Memory Because NKp30 is a pseudogene in inbred mice, we determined whether human NKp30 CARs could be expressed on mouse T cells, which allows the testing of in vivo efficacy of chimeric NKp30-modified T cells against NKp30 ligand-positive tumor cells in immunocompetent mouse tumor models. Similar to the expression profile observed on human T cells, NKp30 CARs were expressed on mouse T cells (FIG. 9E-J). All chNKp30-modified murine T cells responded to coculture with RMA/B7-H6 cells, but not with RMA cells, by producing IFN-γ; NKp30-CD28-3ζ-bearing T cells produced more IFN-γ than did NKp30-3ζ-expressing T cells (FIG. 10C). wtNKp30-modified mouse T cells also produced low levels of IFN-γ in response to B7-H6 (FIG. 10C). In addition, chNKp30-modified mouse T cells were highly cytotoxic. Even at an E:T ratio of 1:1, T cells expressing either NKp30-CD28-3 or NKp30-3C receptor killed RMA/B7-H6 cells at an efficiency of 80% (FIG. 10A-B). No significant killing of NKp30 ligand-negative RMA cells was observed. Perforin had a role in the killing process, because NKp30 CAR-modified T cells deficient in perforin showed a significantly reduced ($p < 0.05$) ability to kill RMA/B7-H6 tumor cells.

Methods

Except where indicated otherwise, the experimental results were generally obtained using the methods that follow.

Mice

C57Bl/J6 (B6; wild-type [wt]) mice were purchased from the National Cancer Institute (Frederick, MD). Perforin-deficient mice C57BL/6-Prf1tm1Sdz/J (Pfp2/2) were obtained from The Jackson Laboratory (Bar Harbor, ME). All experiments were conducted according to protocols approved by Dartmouth College's Institutional Animal Care and Use Committee.

Cell Lines and Cell Culture

Bosc23, GP+E86, PT67, K652, U937, HeLa, U266, and Jurkat cell lines were obtained from the American Type Culture Collection (Rockville, MD). Breast cancer cell lines MCF-7 and T47D were provided by Dr. James Direnzo (The Geisel School of Medicine at Dartmouth). Pancreatic cancer cell line Panc-1 was provided by Dr. Murray Korc (School of Medicine, Indiana University, Indianapolis, IN). Prostate cancer cell line DU145 and melanoma cell line A375 were provided by Dr. Marc Ernstoff (The Geisel School of Medicine at Dartmouth). An RMA subline RMA/B7-H6 that expresses an NKp30 ligand, B7-H6, was generated by retroviral transduction using dualtropic retroviral vectors containing the B7-H6 gene, according to our previous protocol (Zhang et al., Blood 106: 1544-1551). Packaging cells Bosc23, GP+E86, and PT67 were grown in DMEM with a high glucose concentration (4.5 g/l), supplemented with 10% heat-inactivated FBS (Atlanta Biologicals, Lawrenceville, GA), 100 U/mi penicillin, 100 sg/ml streptomycin, 1 mM pyruvate, 10 mM HEPES, 0.1 mM nonessential amino acids, and 50 µM 2-ME. All other cell lines were cultured in RPMI 1640 plus the same supplements as in DMEM. Human dendritic cells (DCs) were generated from blood mononuclear cells that were obtained from cell cones from the Dartmouth-Hitchcock Medical Center Blood Donor Center from leukapheresis cell donations. CD14+ cells were selected using magnetic beads (Miltenyi Biotec) and were cultured in six-well plates (5×10$^5$/ml) in 2 ml complete RPMI 1640 media with recombinant human IL-4 (100 ng/ml; PeproTech, Rocky Hill, NJ) and recombinant human GM-CSF (100 ng/ml; PeproTech). On days 4 and 6, 2 ml fresh media with IL-4 and GM-CSF was added to the cultures. On day 8, the nonadherent cells were collected and used as iDCs. To generate mDCs, the media were replaced with fresh media containing LPS (1 µg/ml; Sigma, St. Louis, MO) and CD40L (200 ng/ml; PeproTech) on day 6 for 2 d.

Construction of Chimeric NKp30 Receptors

The full-length human NKp30, CD28, and CD8α cDNAs were purchased from Open Biosystems (Huntsville, AL). Human CD3γ-chain-signaling domain and full-length B7-H6 cDNAs were cloned by RT-PCR using RNAs from Jurkat cells as templates. The chimeric NKp30 constructs used in this study are illustrated in FIGS. 2 and 12. wt NKp30 contains the full-length human NKp30. Chimeric receptor NKp30-3ζ comprises the extracellular domain (aa 1-139) of human NKp30 fused to the TM domain (aa 31-51) and the signaling domains of human CD3γ-chain (aa 52-164). The NKp30-CD8-3ζ receptor was constructed by joining the extracellular domain of NKp30 to the TM domain of human CD8α (aa 183-203) and the signaling domain of CD3γ-chain. The NKp30-CD28-3ζ receptor contains the TM and signaling domains of CD28 (aa 153-220) and the signaling domain of the CD3γ-chain. As a control receptor, NKp30-28(TM)-3ζ is similar to NKp30-CD28-3ζ, except that the CD28-signaling domain was removed. All PCR reactions were performed using a high-fidelity DNA polymerase Phusion (New England BioLabs, Ipswich, MA). All oligonucleotides were synthesized by Sigma-Genosys (The Woodlands, TX). All genes were cloned into a retroviral vector pFB-neo (Stratagene, Palo Alto, CA).

Retroviral Transduction

Production of retroviral vectors and retroviral transduction were performed according to modified protocols, as described previously (Zhang et al., Blood 106: 1544-1551; Zhang et al., Cancer Res. 66: 5927-5933). In brief, transduction of murine primary T cells was conducted using ecotropic viruses collected from vector-transfected GP+E86 cells, whereas dualtropic retroviral viruses generated from vector-transfected PT67 cells were used to infect human primary T cells. Primary T cells from spleens of B6 mice were infected 18-24 h after Con A (1 µg/ml; Sigma) stimulation. Two days postinfection, transduced primary T cells (0.5-1×10$^6$/ml) were selected in RPMI media containing G418 (1 mg/ml) plus 25 U/mi recombinant human IL-2 for three additional days. Viable cells were isolated using His-topaque-1083 (Sigma), washed extensively, and expanded for 2 d without G418 before functional analyses or i.v. injection. Primary human cells were stimulated with anti-CD3 mAb OKT3 (40 ng/ml; eBioscience, San Diego, CA) for 3 d before retroviral transduction. 0418 selection of retrovirally transduced human T cells followed the same procedures for selecting chimeric antigen receptor-transduced murine T cells.

Production of Soluble Human NKp30-mIgG2a Fusion Protein

To make a soluble human NKp30-mIgG2a fusion protein, the extracellular portion of human NKp30 (aa 1-262) was fused to the mouse IgG2a hinge-CH2-CH3 portion. NKp30-mIgG2a gene was cloned into pFB-neo. NKp30-mIgG2a fusion protein was expressed in retroviral vector stably transduced B16F10 cells. The production and purification of NKp30-mIgG2a protein were performed according to previous protocols (Zhang et al., Blood 106: 1544-1551; Zhang et al., Cancer Res. 66: 5927-5933).

Generation of Anti-B7-H6 mAbs

Eight- to twelve-week-old B6 mice were immunized (i.p.) with mitomycin C-treated RMA/B7-H6 cells (5×10$^6$). Two weeks after the initial immunization, mice were boosted with 50 µg recombinant B7-H6 (extracellular domain) prepared from Escherichia coli and IFA (Sigma), three times at weekly intervals. Three days after the last boosting immunization, mice splenocytes were fused to NS1 cells (provided by Dr. William Wade, The Geisel School of Medicine, Dartmouth College) using standard techniques, and hybridoma supernatants were screened for reactivity to both B7-H6-negative and -positive cell lines by flow cytometry. Two clones (47.39 and 127.4; both of the IgG2a subclass) were isolated.

Flow Cytometry

For flow cytometry analysis of NKp30 ligand expression, cells were stained with either NKp30-mIgG2a or anti-B7-H6 mAb, followed by DyLight 649-conjugated goat anti-mouse IgG (BioLegend, San Diego, CA). Cell surface phenotyping of transduced primary T cells was determined by staining with FITC-conjugated anti-CD4 (clone OKT4; BioLegend), PEconjugated anti-NKp30 (clone P30-15; BioLegend) mAbs. The following mAbs were used to analyze the cell surface phenotype of DCs: allophycocyanin-conjugated anti-CD86 (BioLegend), PE-conjugated anti-CD11c (BioLegend), FITC-conjugated anti-CD83 (BioLegend), and FITC conjugated anti-HLA-DR (eBioscience). Intracellular staining of Bcl-xL in T cells was performed using anti-BclxL-FITC (Southern Biotech, Birmingham, AL), based on the protocol described previously (Eriksson et al., J. Leukoc. Biol. 76: 667-675). All samples were preincubated with either FcR block Ab (anti-mouse CD16/CD32, 2.4G2; Bio X Cell, Lebanon, NH) for mouse cells staining or human g globulins (Cohn's fraction, G4386; Sigma) for human cell staining. Cell fluorescence was monitored using an Accuri C6 cytometer. Flow cytometry analysis was performed using either Accuri or FlowJo software.

RT-PCR and Quantitative PCR

Extraction of total RNA and preparation of cDNAs from human tumor cell lines and PBMCs were performed as described (Zhang et al., Cancer Res. 66: 5927-5933). The resulting cDNA, corresponding to 50 ng total RNA, was subjected to PCR amplification in a total volume of 20 ml, including 0.5 mmol/I each primer, 0.2 mmol/I each deoxy-nucleotide triphosphate, and 1 U Taq DNA polymerase (New England BioLabs). The primers used for amplification are shown in Supplemental Table I. The PCR conditions were as follows: 95° C. for 5 min, followed by 30 cycles of 95° C. for 30 s (denaturation), 60° C. for 30 s (annealing), and 72° C. for 30 s (extension), with a 3-min incubation at 72° C. at the end. The PCR products were run on agarose gels and visualized by staining with SYBR Safe (Invitrogen). For quantitative real-time PCR of human IL-2 mRNA, triplicates of cDNA samples from T cells were mixed with SYBR Green Master Mix (Applied Biosystems) and IL-2-specific primers (Supplemental Table I) in a total volume of 25 ml. The reactions were run on a Bio-Rad iCycler. The relative gene expression was calculated as described (Eriksson et al., J. Immunol. 176: 6219-6224). GAPDH gene was used as an internal control. The mean value of relative IL-2 expression in control mAb-treated T cell samples was set as 1.

Cytotoxicity Assay

Cytotoxicity of T cells against target cells was determined by an LDHrelease assay using the CytoTox 96 Non-Radio-active Cytotoxicity Assay kit (Promega, Madison, WI). Specific lysis was determined using the following equation:

percentage of specific lysis=[(experimental−effector spontaneous−target spontaneous)/(target maximum−target spontaneous)]×100. In the cytotoxicity-blocking experiments, K562 target cells were preincubated with a soluble NKp30 receptor, NKp30-mIgG2a (10 sg/ml), for 30 min before coculture with T cells in an LDH-release assay.

Cytokine Production by T Cells

To determine whether chimeric antigen receptor T cells responded to tumor cells with production of IFN-$\gamma$, T cells ($10^5$) were cocultured with suspension tumor cells at an E:T ratio of 1:1 or with adherent tumor cells at an E:T ratio of 1:0.25 ($10^5$:$2.5\times10^4$) in 96-well V-bottom or flat-bottom plates, respectively, for 24 h. Cell-free supernatants were assayed for IFN-$\gamma$ by ELISA using DuoSet ELISA kits (R&D Systems).

Treatment of Lymphoma-Bearing Mice with Chimeric NKp30-Modified T Cells

As a systemic mouse lymphoma model, B6 mice were injected with $10^5$ RMA/B7-H6 cells in 400 ml HBSS via tail veins. For treatment with T cells, mice were administered $5\times10^6$ wt NKp30 (wtNKp30) or chimeric NKp30-modified T cells i.v. starting on day 5 post tumor inoculations. T cell transfer was repeated on days 7 and 9 using T cells from the same T cell preparation that were expanded for additional days in vitro. Mice were monitored closely and sacrificed when they became moribund.

Tumor Rechallenge

Mice that survived for 60 d after initial tumor inoculation without signs of disease were regarded as tumor free and were inoculated s.c. with $10^4$ wt RMA tumor cells on the shaved right flank. Naive B6 mice were used as controls. Tumor size was monitored every 2 d, and mice were sacrificed when tumor burden became excessive.

Statistical Analysis

Differences between groups were analyzed using a Student t test or ANOVA; p values <0.05 were considered significant. Kaplan-Meier survival curves were plotted and analyzed using Prism software (GraphPad Software, San Diego, CA).

What is claimed is:

1. A nucleic acid construct that encodes a chimeric receptor, wherein said nucleic acid construct comprises a promoter operably linked to a nucleic acid sequence that encodes a chimeric NKp30 receptor comprising a NKp30 extracellular domain, a CD28 transmembrane (TM) domain, a DAP10 signaling domain, and a CD3ζ signaling domain.

2. The nucleic acid construct according to claim 1, that encodes a chimeric receptor, wherein the chimeric receptor further comprises an additional signaling domain of a polypeptide selected from the group consisting of NKp30, CD28, CD8, CD3ζ, CD27, 41BB, OX40, and DAP12.

3. The nucleic acid construct according to claim 2, wherein the additional signaling domain is that of NKp30.

4. The nucleic acid construct according to claim 2, wherein the additional signaling domain is that of CD28, CD8, CD3ζ, CD27, 41BB, OX40, or DAP12.

5. The nucleic acid construct according to claim 2, wherein the additional signaling domain is that of CD8.

6. The nucleic acid construct according to claim 2, wherein the additional signaling domain is that of CD3ζ.

7. The nucleic acid construct according to claim 2, wherein the additional signaling domain is that of 4-1BB.

8. The nucleic acid construct according to claim 2, wherein the additional signaling domain is that of OX40.

9. The nucleic acid construct according to claim 2, wherein the additional signaling domain is that of DAP12.

10. A vector comprising the nucleic acid construct of claim 1.

11. A vector comprising the nucleic acid construct of claim 2.

* * * * *